US012746045B2

(12) United States Patent
Gunther et al.

(10) Patent No.: US 12,746,045 B2
(45) Date of Patent: Sep. 29, 2026

(54) TENSION BAND SYSTEMS AND METHODS

(71) Applicants: Stephen B. Gunther, Keswick, VA (US); Jacob Carroll, Memphis, TN (US); Richard Obert, Poway, CA (US)

(72) Inventors: Stephen B. Gunther, Keswick, VA (US); Jacob Carroll, Memphis, TN (US); Richard Obert, Poway, CA (US)

( * ) Notice: Subject to any disclaimer, the term of this patent is extended or adjusted under 35 U.S.C. 154(b) by 0 days.

(21) Appl. No.: 18/999,036

(22) Filed: Dec. 23, 2024

(65) Prior Publication Data

US 2025/0120756 A1 Apr. 17, 2025

Related U.S. Application Data

(63) Continuation-in-part of application No. 17/991,246, filed on Nov. 21, 2022, now Pat. No. 12,171,472, which is a continuation of application No. 17/396,107, filed on Aug. 6, 2021, now Pat. No. 11,504,170.

(60) Provisional application No. 63/561,244, filed on Mar. 4, 2024, provisional application No. 63/065,188, filed on Aug. 13, 2020.

(51) Int. Cl.
*A61B 17/72* (2006.01)
*A61B 17/68* (2006.01)

(52) U.S. Cl.
CPC ...... *A61B 17/7225* (2013.01); *A61B 17/7208* (2013.01); *A61B 2017/681* (2013.01)

(58) Field of Classification Search
CPC . A61B 17/72; A61B 17/7216; A61B 17/7225; A61B 17/7208; A61B 2017/681
USPC .......... 606/62
See application file for complete search history.

(56) References Cited

U.S. PATENT DOCUMENTS

2009/0287213 A1 * 11/2009 Pieske ........ A61B 17/7291 606/62
2009/0306718 A1 * 12/2009 Tipirneni ........ A61B 17/8685 606/264

(Continued)

OTHER PUBLICATIONS

International Search Report and Written Opinion dated May 6, 2025 for corresponding PCT Application No. PCT/US2025/018055.

*Primary Examiner* — Eduardo C Robert
*Assistant Examiner* — Christina Negrellirodriguez
(74) *Attorney, Agent, or Firm* — David Meibos; Maywood IP Law

(57) ABSTRACT

A bone fixation assembly may include an elongate fixation member, first and second cortical fixation elements, and a flexible tensioning element. The elongate fixation member may include a longitudinal passageway, a proximal portion couplable within a first bone fragment, and a distal portion couplable within a second bone fragment to provide relative fixation between the first and second bone fragments. The first and second cortical fixation elements may engage cortical surfaces on the first and second bone fragments. The flexible tensioning element may be pass through the longitudinal passageway, span a bone fracture, and couple intermediate the first and second cortical fixation elements to provide a compression force therebetween. The flexible tensioning may preload the bone fracture in compression to resist tensile force imparted across the bone fracture, thereby maintaining fixation of the first bone fragment relative to the second bone fragment.

19 Claims, 101 Drawing Sheets

(56) References Cited

U.S. PATENT DOCUMENTS

| | | | | |
|---|---|---|---|---|
| 2011/0282346 | A1* | 11/2011 | Pham ................. | A61B 17/1725 606/62 |
| 2014/0228845 | A1* | 8/2014 | Gorsline ............ | A61B 17/7291 606/62 |
| 2015/0351815 | A1 | 12/2015 | Wales et al. | |
| 2020/0000505 | A1* | 1/2020 | Vitale .................. | A61B 17/842 |
| 2023/0092603 | A1 | 3/2023 | Gunther et al. | |
| 2024/0065686 | A1 | 2/2024 | Evans et al. | |

* cited by examiner

TENSION BAND SYSTEMS AND METHODS

CROSS-REFERENCE TO RELATED APPLICATIONS

The present application is a continuation-in-part of U.S. patent application Ser. No. 17/991,246 filed on Nov. 21, 2022, entitled TENSION BAND SYSTEMS AND METHODS, which is a continuation of U.S. patent application Ser. No. 17/396,107 filed on Aug. 6, 2021, entitled TENSION BAND SYSTEMS AND METHODS, which issued on Nov. 22, 2022 as U.S. Pat. No. 11,504,170, which claims priority to U.S. Provisional Patent Application No. 63/065,188 filed on Aug. 13, 2020, entitled TENSION BAND SYSTEMS AND METHODS.

The present application also claims priority to U.S. Provisional Application No. 63/561,244 filed on Mar. 4, 2024, entitled TENSION BAND SYSTEMS AND METHODS.

The foregoing are incorporated by reference as though set forth herein in their entirety.

TECHNICAL FIELD

The present disclosure relates to surgical implants, systems, and methods. More specifically, the present disclosure relates to bone fixation devices, systems, assemblies, and methods for repairing bone fractures.

BACKGROUND

Bone fractures may be reduced and repaired with many different types of orthopedic internal fixation devices, systems, and methods. Two common types of orthopedic internal fixation devices include intramedullary rods and bone plates.

Intramedullary rods and bone plates each have their own particular advantages and disadvantages. For example, intramedullary rods typically require smaller incision sites and have less or no prominence in comparison to bone plates. Both of these characteristics may be desirable from a cosmetic perspective. Intramedullary rods usually cause fewer disturbances to surrounding soft tissues (e.g., less/no soft tissue stripping/irritation) in comparison to bone plates, reducing the risk of complications that may develop after surgery.

On the other hand, a bone plate may provide better structural integrity for certain types of bone fractures. In some instances, a bone plate surgical procedure may also be less difficult to perform in comparison to an intramedullary rod surgical procedure.

In any event, both intramedullary rods and bone plates can be associated with many risks, including, but not limited to: breaking, bone screws that may loosen or pull-out over time, delayed healing or non-unions, infections, subsequent hardware removal issues (e.g., via revision surgery) that may result in bone voids that weaken the bone, etc.

Moreover, certain types of bone fractures may be subject to large tensile or traction forces that tend to "pull apart" a fractured bone, further complicating the bone healing process. Example bone fractures that can experience large tensile forces include, but are not limited to clavicle fractures, olecranon fractures, fibula fractures, patellar fractures, malleolar fractures, etc. In such cases, an intramedullary rod or bone plate alone may not provide an optimal solution for fixation strength and sustained fracture reduction during the bone healing process.

A tension band is another form of orthopedic internal fixation device that may be utilized to help resist tensile forces to increase fixation, reduce bone fractures, and help promote the bone healing process. However, a tension band alone may not provide optimal fixation strength, reduction characteristics, and/or bone healing characteristics in every scenario.

Accordingly, orthopedic fixation devices, systems, and methods that can provide improved fixation, reduction, and bone healing would be desirable.

SUMMARY

The various bone fixation, devices, systems, assemblies and methods of the present disclosure have been developed in response to the present state of the art, and in particular, in response to the problems and needs in the art that have not yet been fully solved by currently available bone fixation, devices, systems, assemblies, and methods. In some embodiments, the bone fixation, devices, systems, assemblies, and methods of the present disclosure may provide improved surgical procedures for repairing bone fractures.

In some embodiments, a bone fixation assembly may include an elongate fixation member, a first cortical fixation element, a second cortical fixation element, and a flexible tensioning element. The elongate fixation member may include a longitudinal passageway formed therethrough, the proximal portion which may rotatably couple within a first bone fragment of a bone, and the distal portion which may couple within a second bone fragment of the bone to provide fixation of the second bone fragment relative to the first bone fragment. The first cortical fixation element may be configured to engage a first cortical surface on the first bone fragment adjacent the proximal portion of the elongate fixation member, and the second cortical fixation element may be configured to engage a second cortical surface on the second bone fragment adjacent the distal portion of the elongate fixation member. The flexible tensioning element may be configured to pass through the longitudinal passageway of the elongate fixation member and couple intermediate the first and second cortical fixation elements to provide a compression force therebetween. The flexible tensioning element passing through the longitudinal passageway of the elongate fixation member may span a bone fracture intermediate the first and second bone fragments. The flexible tensioning element coupled intermediate the first and second cortical fixation elements may also be configured to preload the bone fracture in compression to resist tensile force imparted across the bone fracture, thereby maintaining fixation of the first bone fragment relative to the second bone fragment.

In some embodiments of the bone fixation assembly, the proximal portion of the elongate fixation member may include a proximal helical thread that rotatably couples the proximal portion of the elongate fixation member within the first bone fragment.

In some embodiments of the bone fixation assembly, the proximal portion of the elongate fixation member may include a torque connection feature that may be configured to receive a torque force to rotatably couple the proximal portion of the elongate fixation member within the first bone fragment.

In some embodiments of the bone fixation assembly, the first cortical fixation element may include: a first bone-facing side; a first reverse side opposite the first bone-facing side; a first hole formed through the first cortical fixation element between the first bone-facing side and the first reverse side that may be configured to receive the flexible tensioning element therethrough; a second hole formed through the first cortical fixation element between the first bone-facing side and the first reverse side that may be configured to receive the flexible tensioning element therethrough; and a third hole formed through the first cortical fixation element between the first bone-facing side and the first reverse side that may be configured to receive the flexible tensioning element therethrough.

In some embodiments of the bone fixation assembly, the second cortical fixation element may include: a second bone-facing side; a second reverse side opposite the second bone-facing side; a first passageway formed through the second cortical fixation element between the second bone-facing side and the second reverse side that may be configured to receive the flexible tensioning element therethrough; and a second passageway formed through the second cortical fixation element between the second bone-facing side and the second reverse side that may be configured to receive the flexible tensioning element therethrough.

In some embodiments of the bone fixation assembly, the second cortical fixation element may include a channel formed thereon intermediate the first passageway and the second passageway that may be configured to receive the flexible tensioning element therein.

In some embodiments of the bone fixation assembly, the elongate fixation member may include a fixation element dock formed on the distal portion of the elongate fixation member, and the second cortical fixation element may include a docking surface shaped for reception on the fixation element dock.

In some embodiments, a bone fixation assembly may include an elongate fixation member, a first cortical fixation element, a second cortical fixation element, and a flexible tensioning element. The elongate fixation member may include a longitudinal passageway formed therethrough, the proximal portion which may translatably couple within a first bone fragment of a bone, and the distal portion which may couple within a second bone fragment of the bone to provide fixation of the second bone fragment relative to the first bone fragment. The first cortical fixation element may be configured to engage a first cortical surface on the first bone fragment adjacent the proximal portion of the elongate fixation member, and the second cortical fixation element may be configured to engage a second cortical surface on the second bone fragment adjacent the distal portion of the elongate fixation member. The flexible tensioning element may be configured to pass through the longitudinal passageway of the elongate fixation member and couple intermediate the first and second cortical fixation elements to provide a compression force therebetween. The flexible tensioning element passing through the longitudinal passageway of the elongate fixation member may span a bone fracture intermediate the first and second bone fragments. The flexible tensioning element coupled intermediate the first and second cortical fixation elements may also be configured to preload the bone fracture in compression to resist tensile force imparted across the bone fracture, thereby maintaining fixation of the first bone fragment relative to the second bone fragment.

In some embodiments of the bone fixation assembly, the proximal portion of the elongate fixation member may include one or more proximal anti-rotation features that may translatably couple the proximal portion of the elongate fixation member within the first bone fragment.

In some embodiments of the bone fixation assembly, the proximal portion of the elongate fixation member may include an impact surface that may be configured to receive an impact force to translatably couple the proximal portion of the elongate fixation member within the first bone fragment.

In some embodiments of the bone fixation assembly, the distal portion of the elongate fixation member may include one or more distal anti-rotation features that may translatably couple the distal portion of the elongate fixation member within the second bone fragment.

In some embodiments of the bone fixation assembly, the first cortical fixation element may include: a first bone-facing side; a first reverse side opposite the first bone-facing side; a first hole formed through the first cortical fixation element between the first bone-facing side and the first reverse side that may be configured to receive the flexible tensioning element therethrough; a second hole formed through the first cortical fixation element between the first bone-facing side and the first reverse side that may be configured to receive the flexible tensioning element therethrough; and a third hole formed through the first cortical fixation element between the first bone-facing side and the first reverse side that may be configured to receive the flexible tensioning element therethrough.

In some embodiments of the bone fixation assembly, the second cortical fixation element may include: a second bone-facing side; a second reverse side opposite the second bone-facing side; a first passageway formed through the second cortical fixation element between the second bone-facing side and the second reverse side that may be configured to receive the flexible tensioning element therethrough; and a second passageway formed through the second cortical fixation element between the second bone-facing side and the second reverse side that may be configured to receive the flexible tensioning element therethrough.

In some embodiments of the bone fixation assembly, the elongate fixation member may include a fixation element dock formed on the distal portion of the elongate fixation member, and the second cortical fixation element may include a docking surface shaped for reception on the fixation element dock.

In some embodiments, a bone fixation assembly may include an elongate fixation member, a flexible tensioning element, and a tension locking mechanism. The elongate fixation member may include a longitudinal passageway formed through the elongate fixation member, a proximal portion that may be couplable to a first bone fragment of a bone, and a distal portion that may be couplable to a second bone fragment of the bone to provide fixation of the second bone fragment relative to the first bone fragment. The flexible tensioning element may be configured to pass through the longitudinal passageway and form a loop that spans the first and second bone fragments to secure the elongate fixation member to the bone. The tension locking mechanism may be configured to lock and maintain a selected tension force applied to the flexible tensioning element. The loop spanning the first and second bone fragments may span a bone fracture intermediate the first and second bone fragments, and the selected tension force applied to the flexible tensioning element may be locked and maintained by the tension locking mechanism to preload the bone fracture in compression to resist tensile force imparted across the bone fracture, thereby maintaining fixation of the first bone fragment relative to the second bone fragment.

In some embodiments of the bone fixation assembly, the tension locking mechanism may include a tension chamber formed within the elongate fixation member, a tension chamber locking surface positioned within the tension chamber, a taper bullet receivable within the tension chamber, and a taper bullet locking surface shaped to engage the tension chamber locking surface. The first end of the flexible tensioning element may be configured to couple with the taper bullet. The second end of the flexible tensioning element may be configured to: exit the longitudinal passageway at a distal end of the elongate fixation member; wrap back around the first and second bone fragments to form the loop spanning the first and second bone fragments; enter back into the longitudinal passageway at a proximal end of the elongate fixation member; pass through the tension chamber formed within the elongate fixation member such that the flexible tensioning element becomes trapped between the tension chamber locking surface and the taper bullet locking surface; and exit the longitudinal passageway at the distal end of the elongate fixation member.

In some embodiments of the bone fixation assembly, the second end of the flexible tensioning element may be configured to receive the selected tension force, the first end of the flexible tensioning element may be configured to pull the taper bullet within the tension chamber toward the second end of the elongate fixation member in response to the selected tension force applied to the second end of the flexible tensioning element, and the taper bullet locking surface may be configured to compress the flexible tensioning element against the tension chamber locking surface to lock and maintain the selected tension force applied to the flexible tensioning element.

In some embodiments of the bone fixation assembly, the tension chamber may be formed within at least one of: the proximal portion of the elongate fixation member, the distal portion of the elongate fixation member, and an intermediate portion of the elongate fixation member.

In some embodiments of the bone fixation assembly, the elongate fixation member may also include at least one anchor reception chamber that may be configured to receive at least a portion of a bone anchor therein to provide a secondary lock that maintains the selected tension force applied to the flexible tensioning element.

In some embodiments, the bone anchor may include at least one of: a threaded bone anchor, a compression bone anchor, an anti-rotation bone anchor, a finned anti-rotation bone anchor, and a transverse fastener.

In some embodiments of the bone fixation assembly, the at least one anchor reception chamber may be formed within at least one of: the proximal portion of the elongate fixation member and the distal portion of the elongate fixation member.

These and other features and advantages of the present disclosure will become more fully apparent from the following description and appended claims or may be learned by the practice of the bone fixation, devices, systems, assemblies, and methods set forth hereinafter.

BRIEF DESCRIPTION OF THE DRAWINGS

Exemplary embodiments of the disclosure will become more fully apparent from the following description taken in conjunction with the accompanying drawings. Understanding that these drawings depict only exemplary embodiments and are, therefore, not to be considered limiting of the scope of the present disclosure, the exemplary embodiments of the present disclosure will be described with additional specificity and detail through use of the accompanying drawings in which:

FIG. 39D illustrates a cross-sectional view of the elongate fixation member of FIG. 39C;

FIG. 40A illustrates a distal perspective view of an anti-rotation bone anchor, according to an embodiment of the present disclosure;

FIG. 40B illustrates a proximal perspective view of the anti-rotation bone anchor of FIG. 40A;

FIG. 40C illustrates a side view of the anti-rotation bone anchor of FIG. 40A;

FIG. 40D illustrates a proximal end view of the anti-rotation bone anchor of FIG. 40A;

FIG. 41 illustrates a partially transparent side view of a bone fixation assembly, according to an embodiment of the present disclosure;

FIG. 42 illustrates a close up view of a distal end of the bone fixation assembly of FIG. 41;

FIG. 43 illustrates a close up view of a proximal end of the bone fixation assembly of FIG. 41;

FIG. 44 illustrates a perspective view of the bone fixation assembly of FIG. 41;

FIG. 45 illustrates a transparent anterior perspective view of the bone fixation assembly of FIG. 41 implanted in a bone;

FIG. 46 illustrates a transparent posterior perspective view of the bone fixation assembly of FIG. 41 implanted in the bone;

FIG. 47 illustrates a transparent distal perspective view of the bone fixation assembly of FIG. 41 implanted in the bone;

Figure 39A:
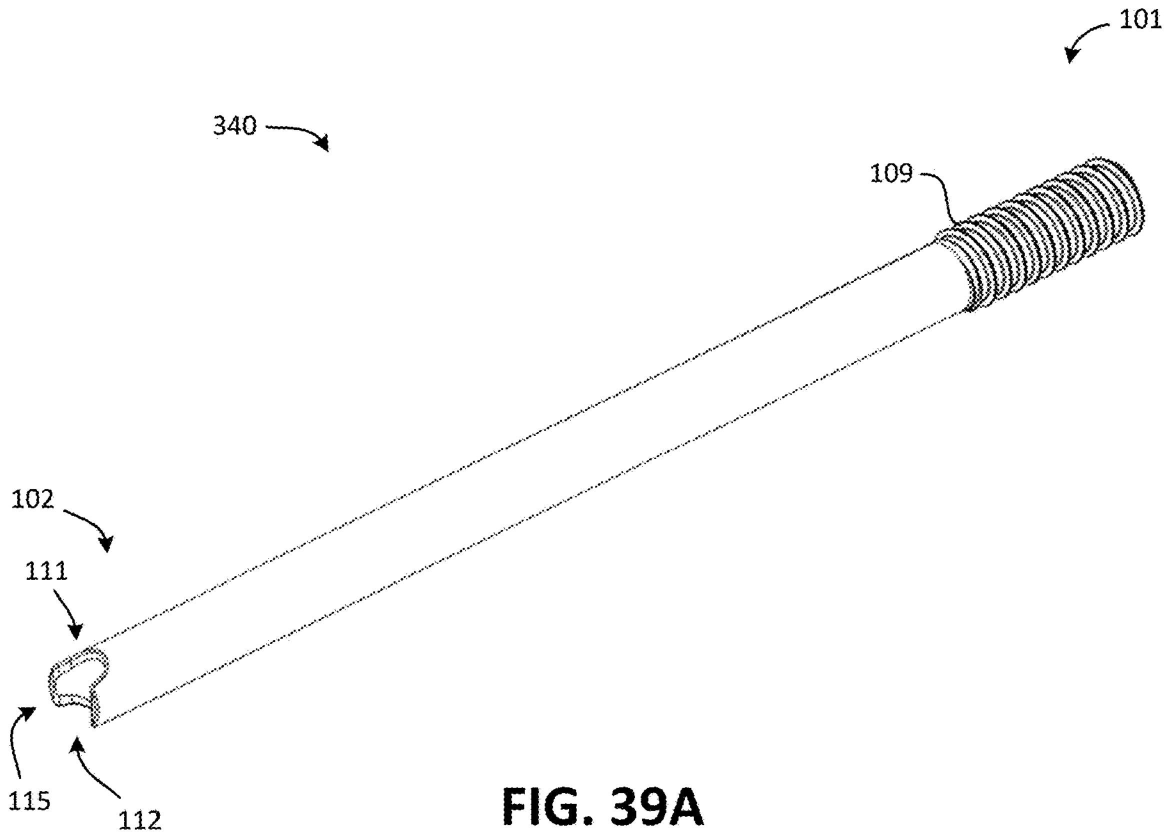
FIG. 39A illustrates a distal perspective view of an elongate fixation member, according to another embodiment of the present disclosure.
Figure 39B:
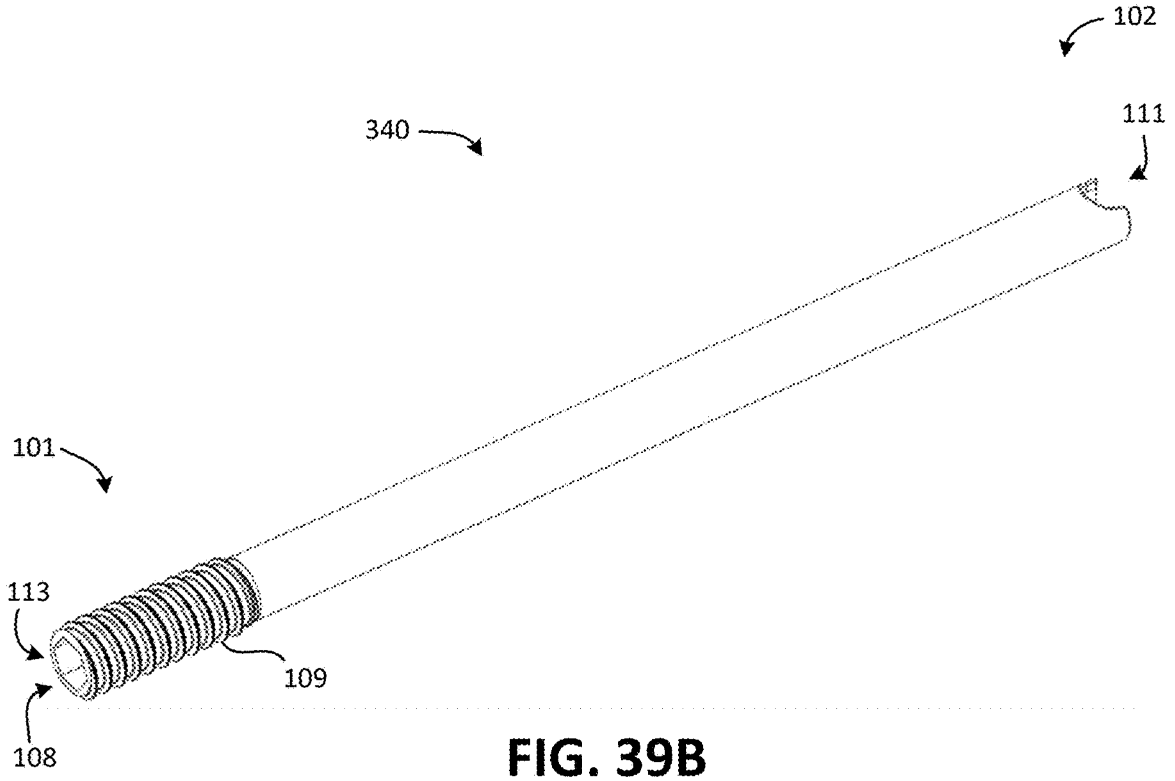
FIG. 39B illustrates a proximal perspective view of the elongate fixation member of FIG. 39A.
Figure 39C:
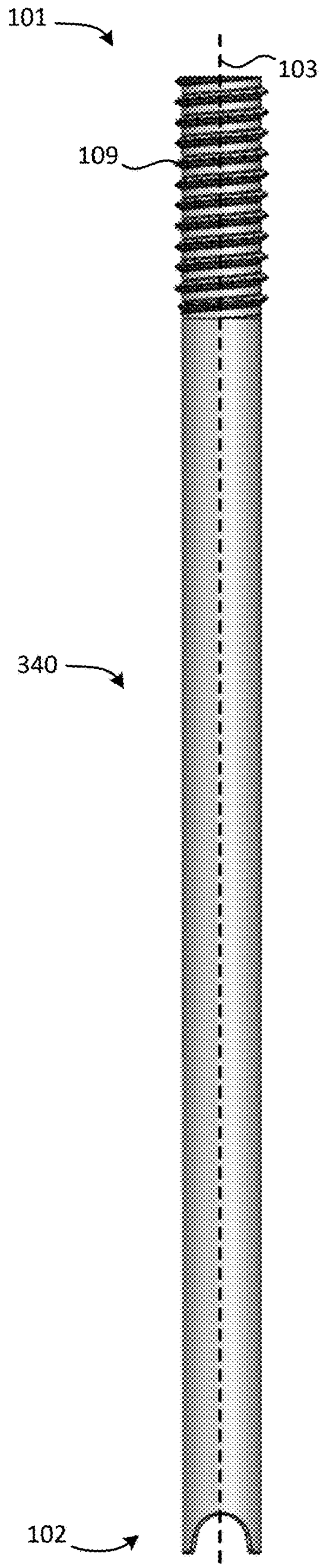
FIG. 39C illustrates a side view of the elongate fixation member of FIG. 39A.
Figure 39D:
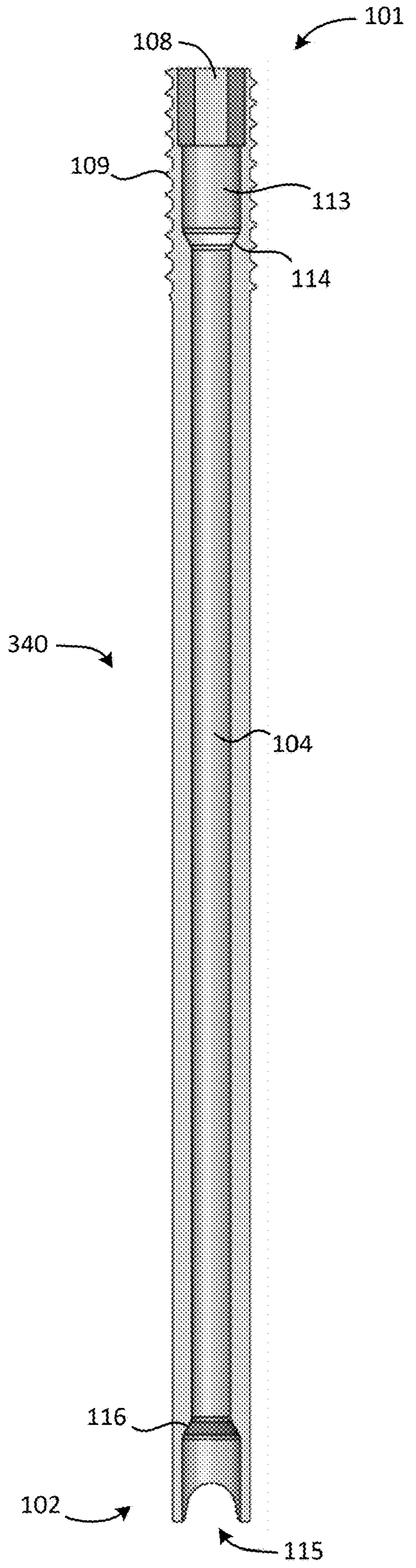
Figure 40A:
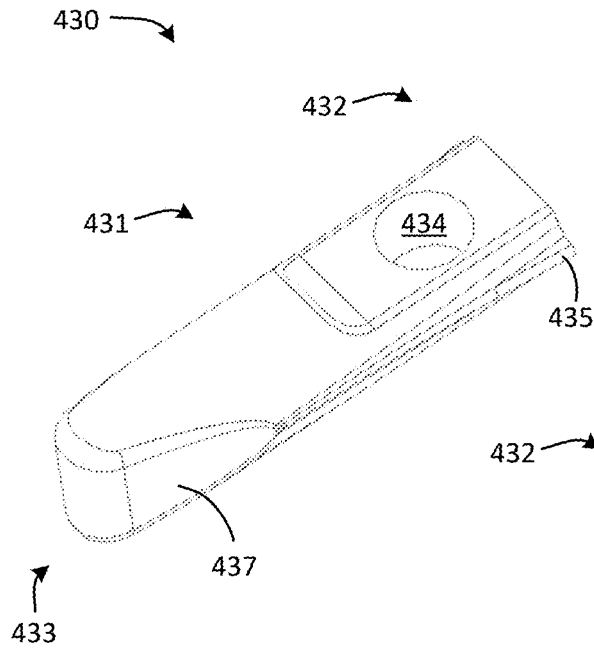
Figure 40B:
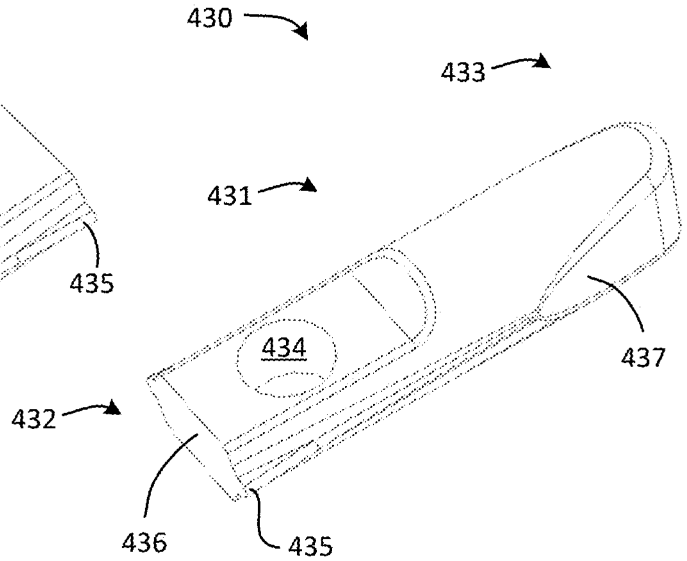
Figure 40C:
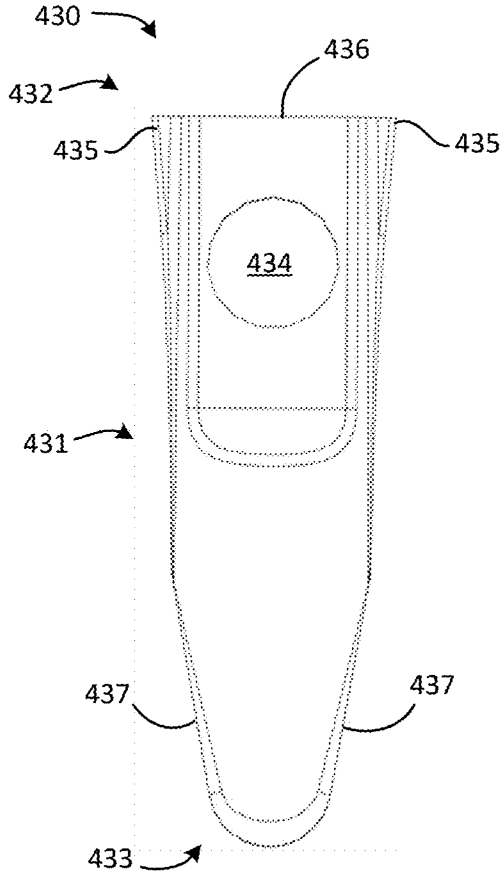
Figure 40D:
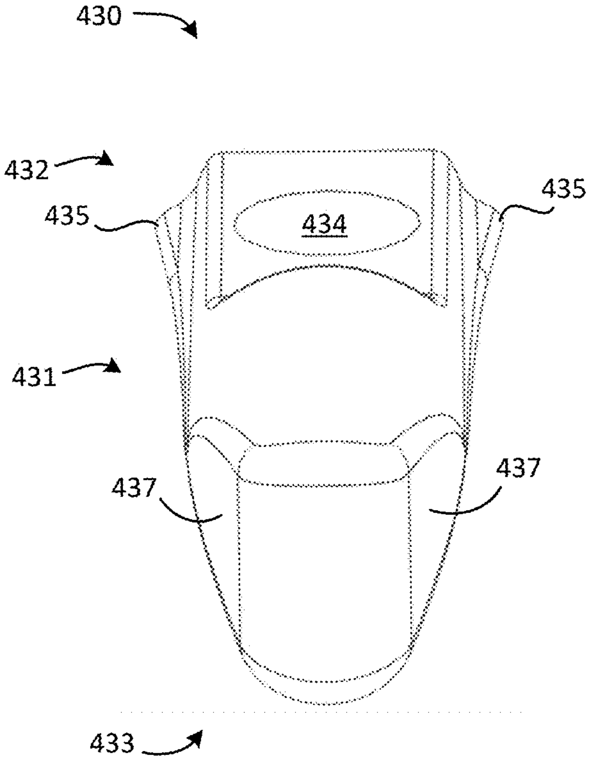
Figure 41:
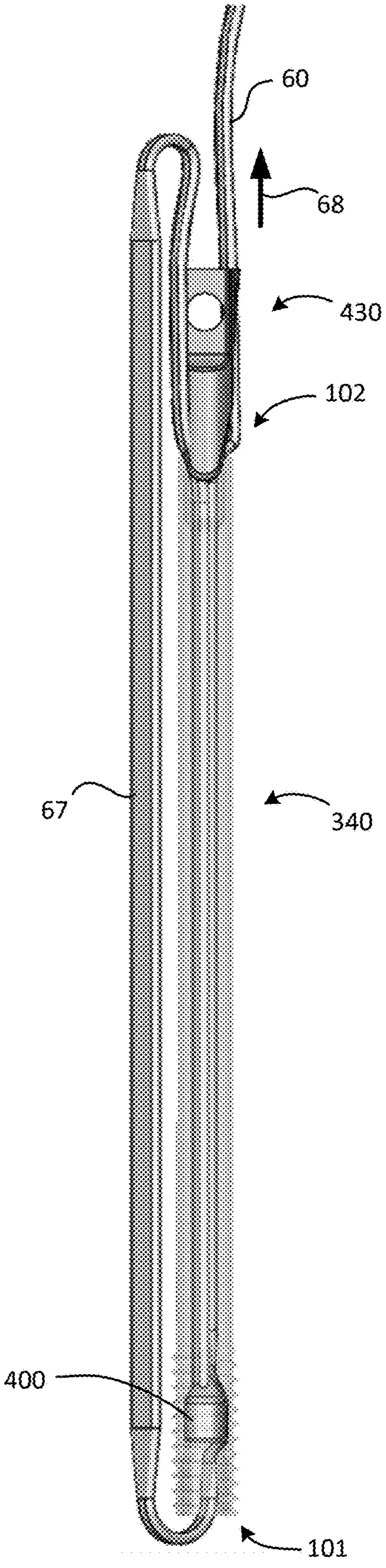
Figure 44:
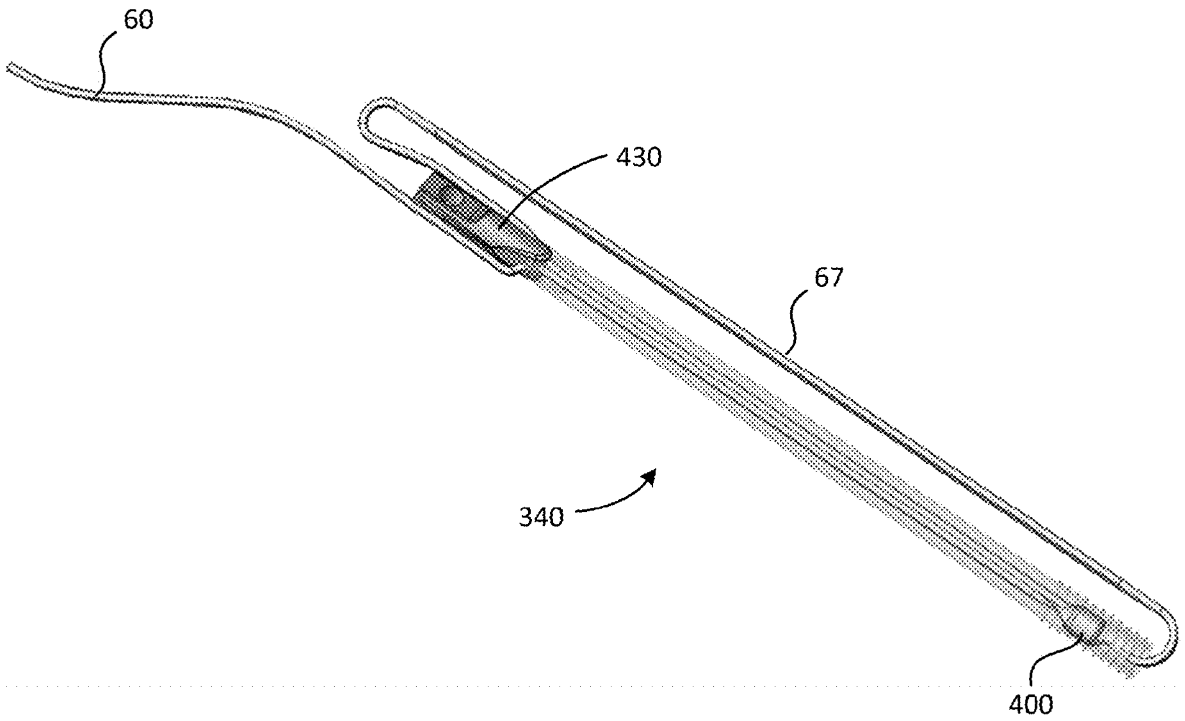
Figure 45:
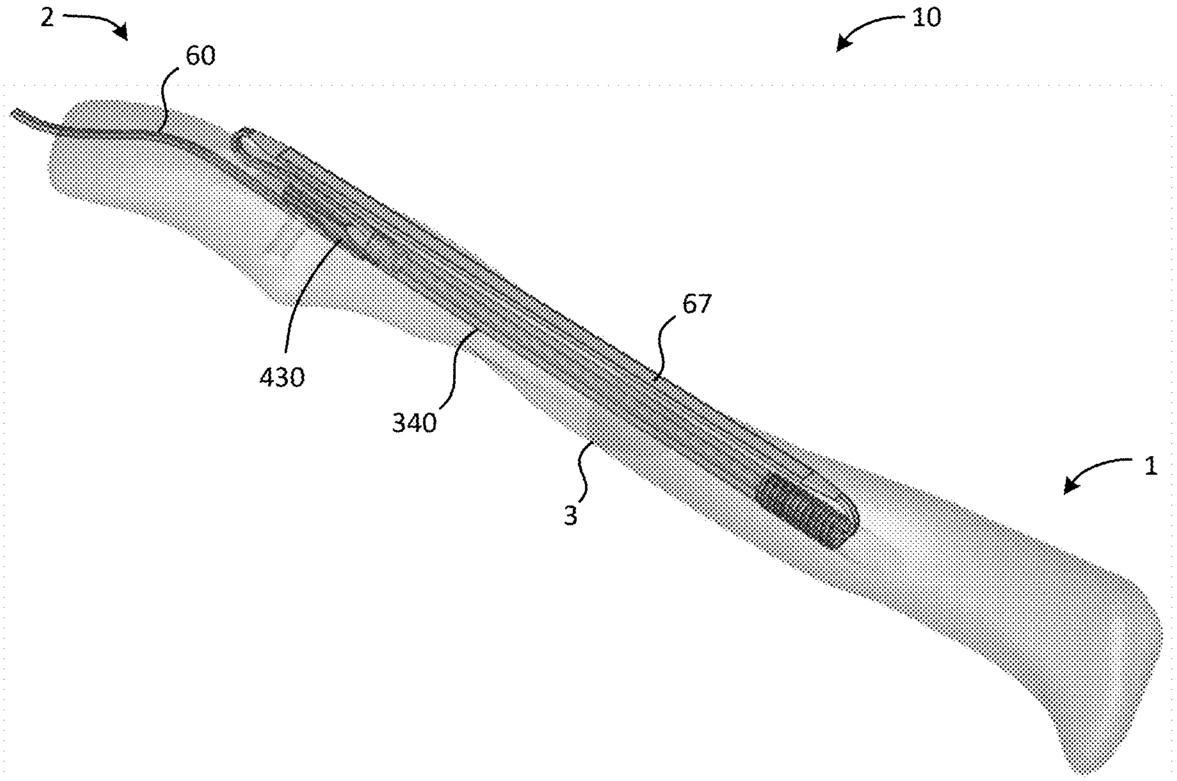
Figure 46:
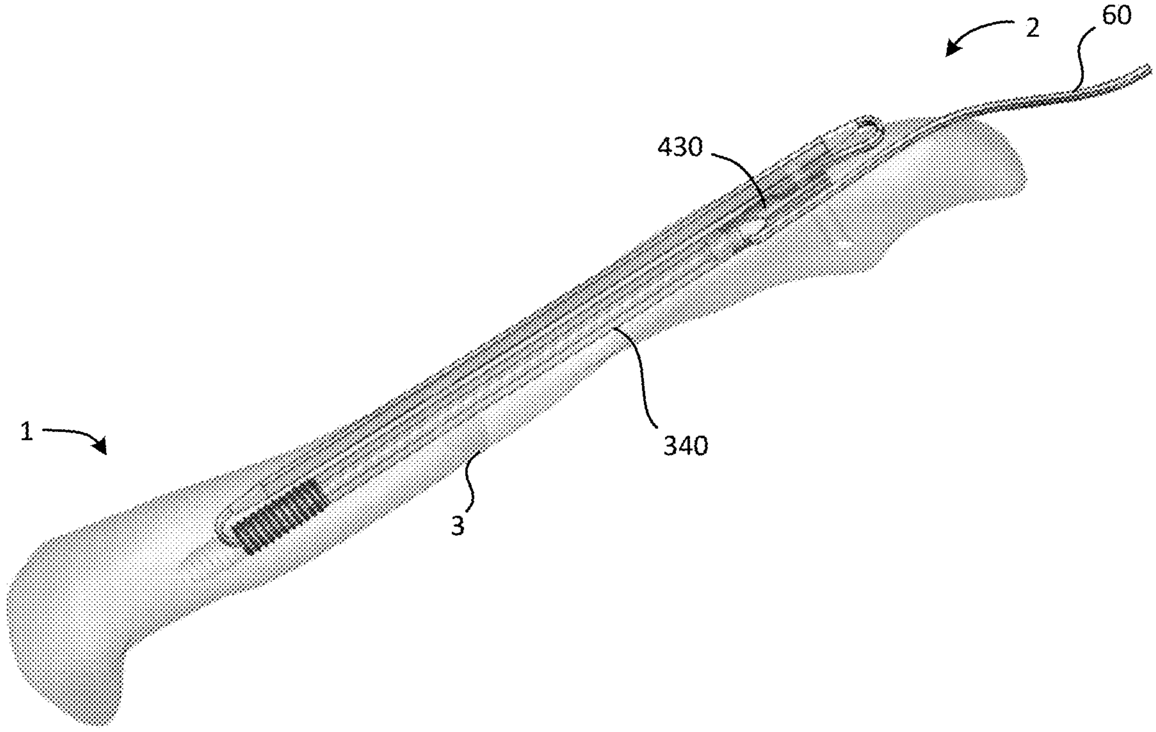
Figure 47:
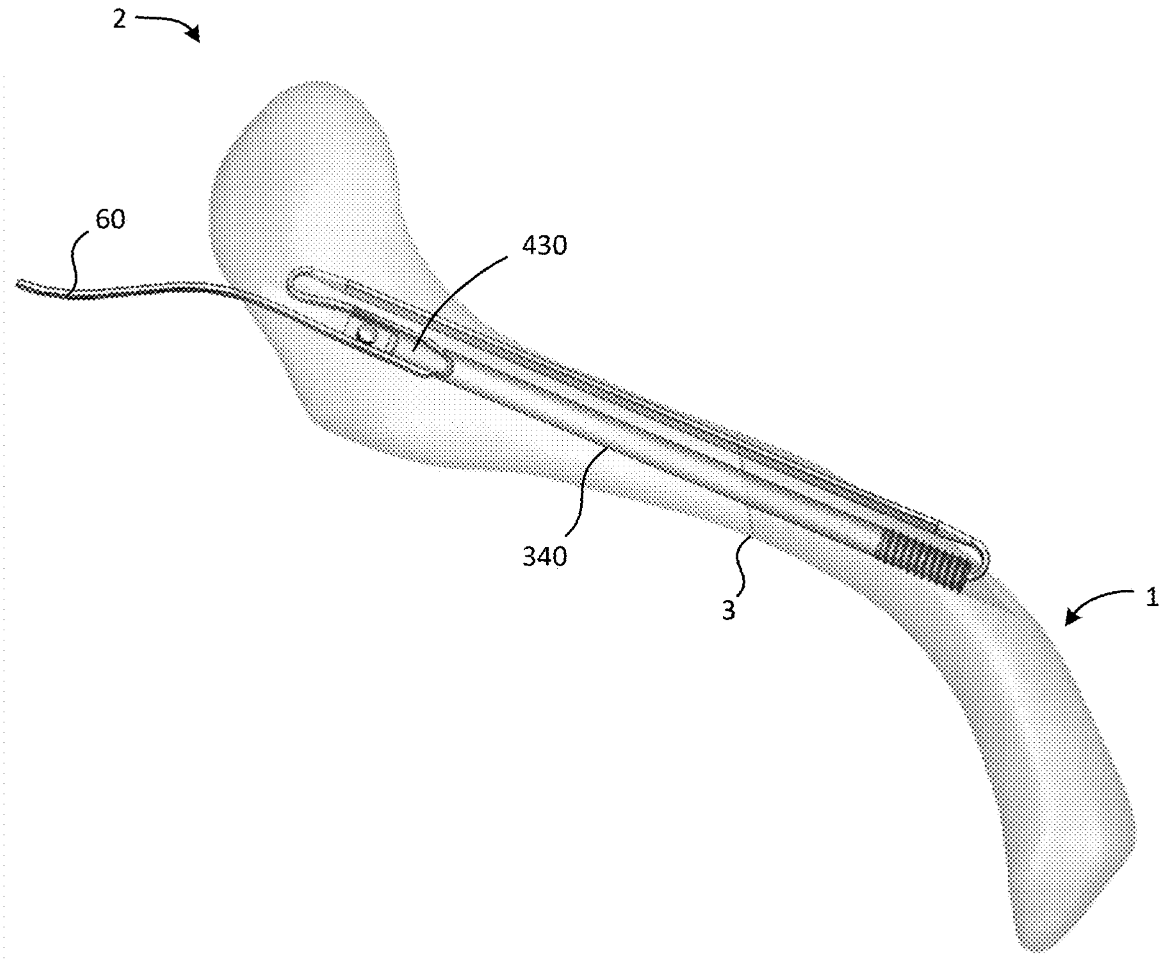
Figure 48:
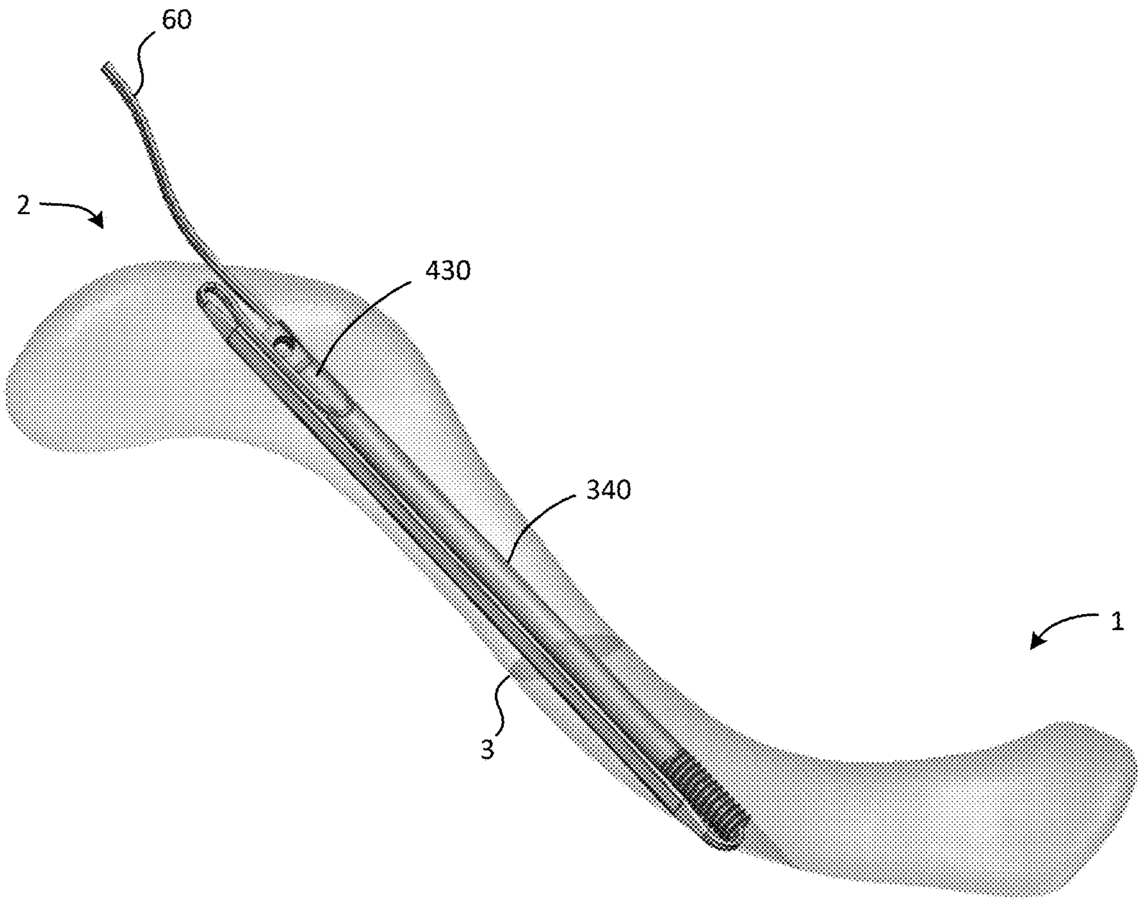
Figure 49:
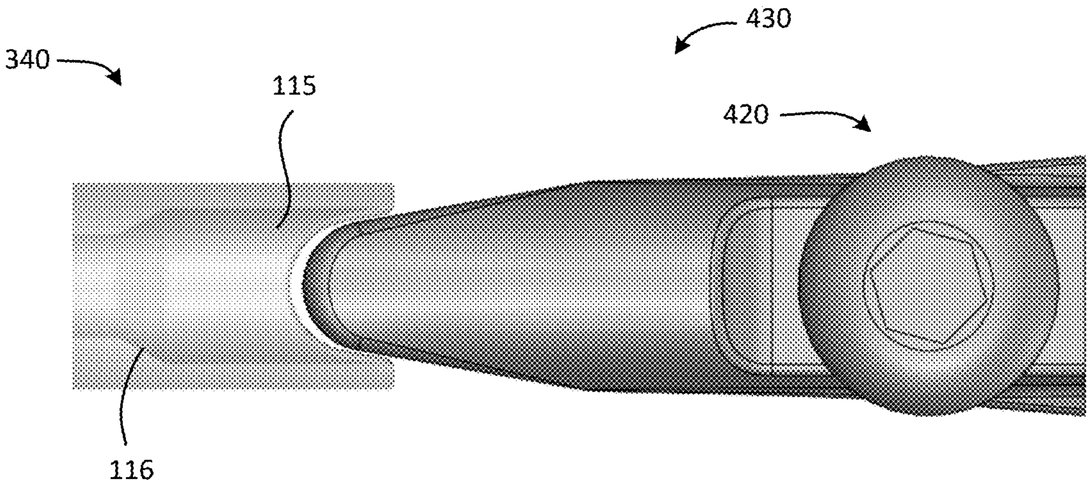
Figure 50:
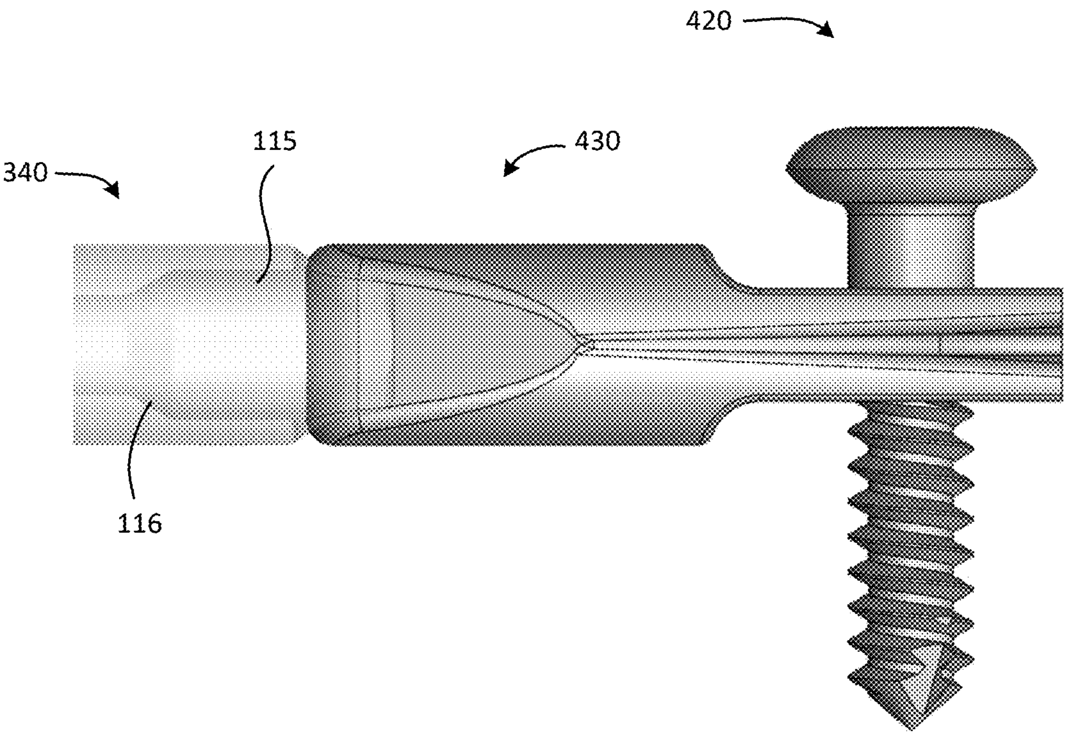
Figure 51:
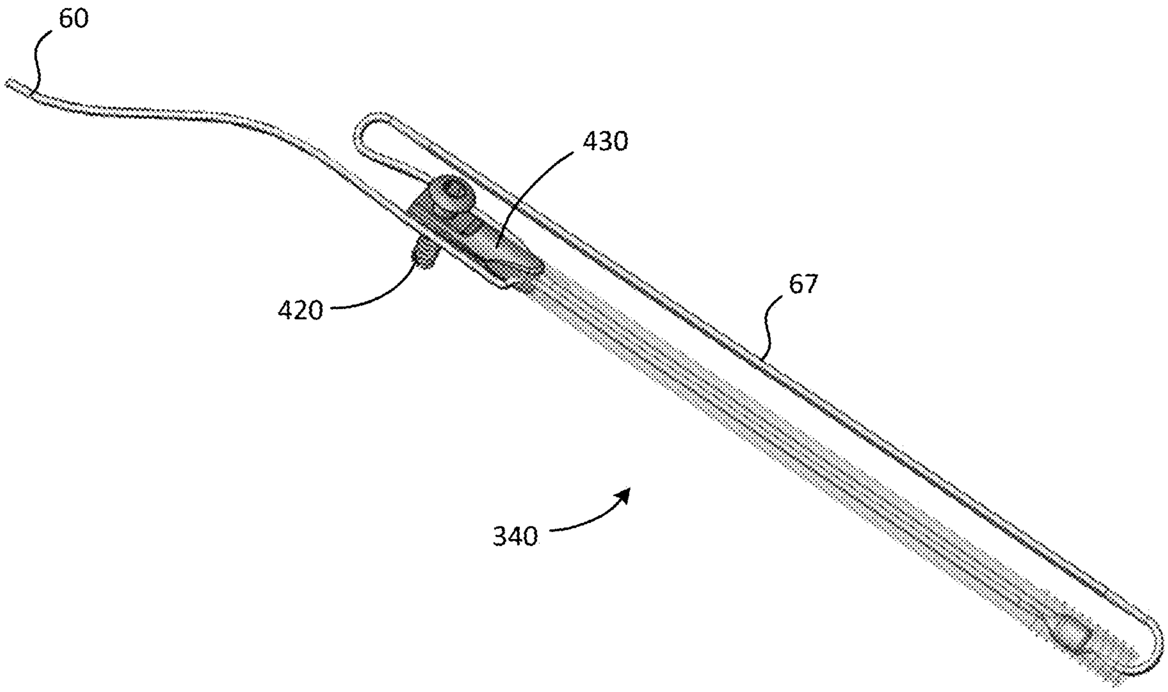
Figure 52:
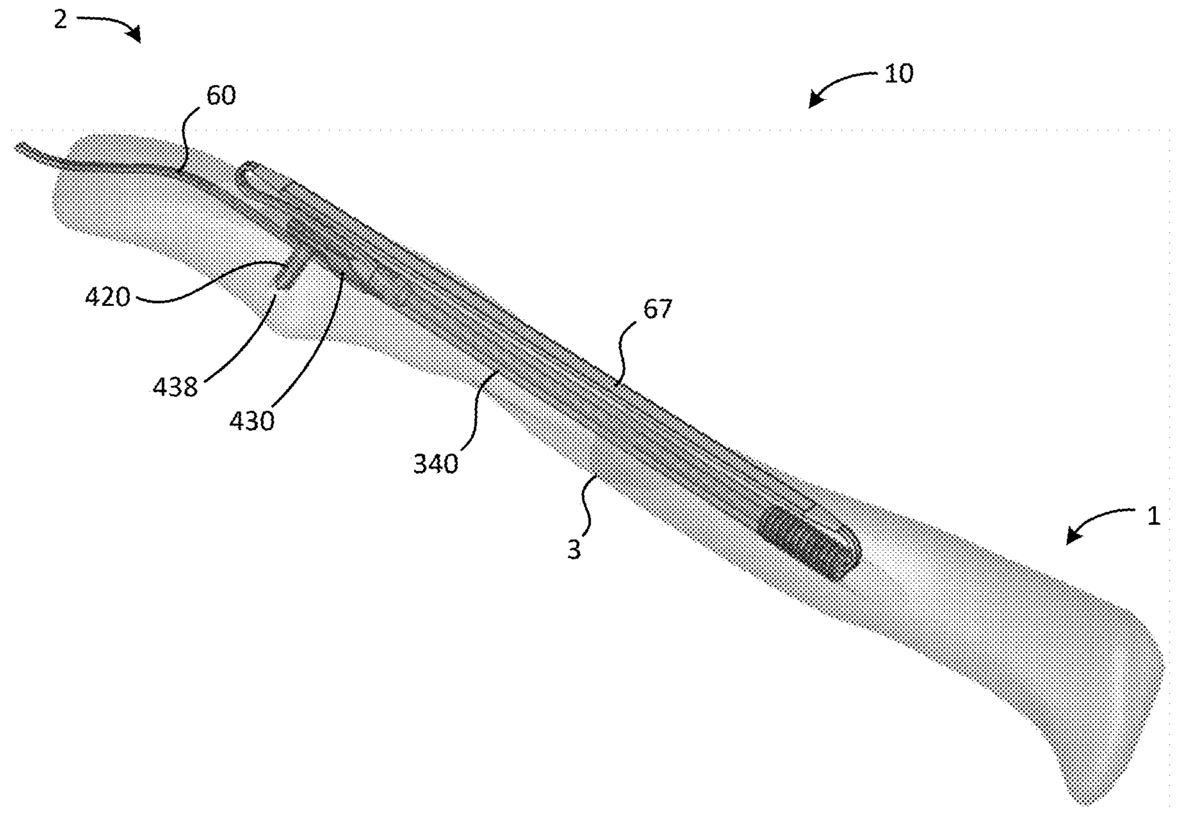
Figure 53:
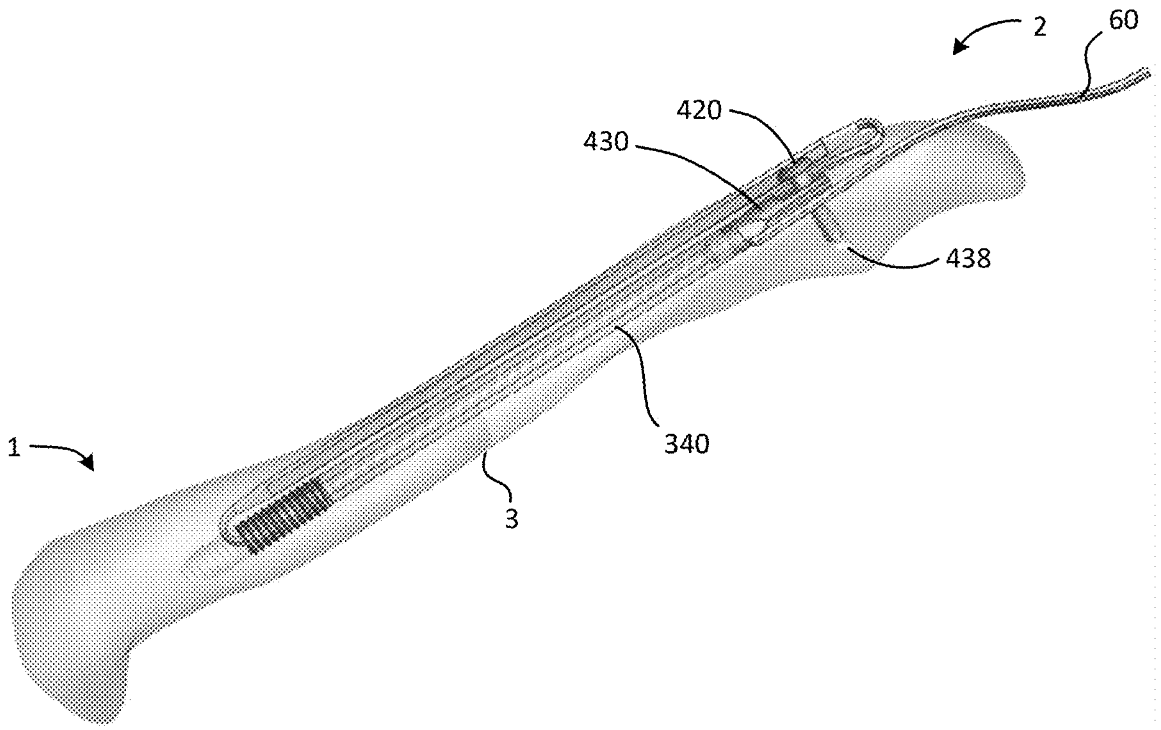
Figure 54:
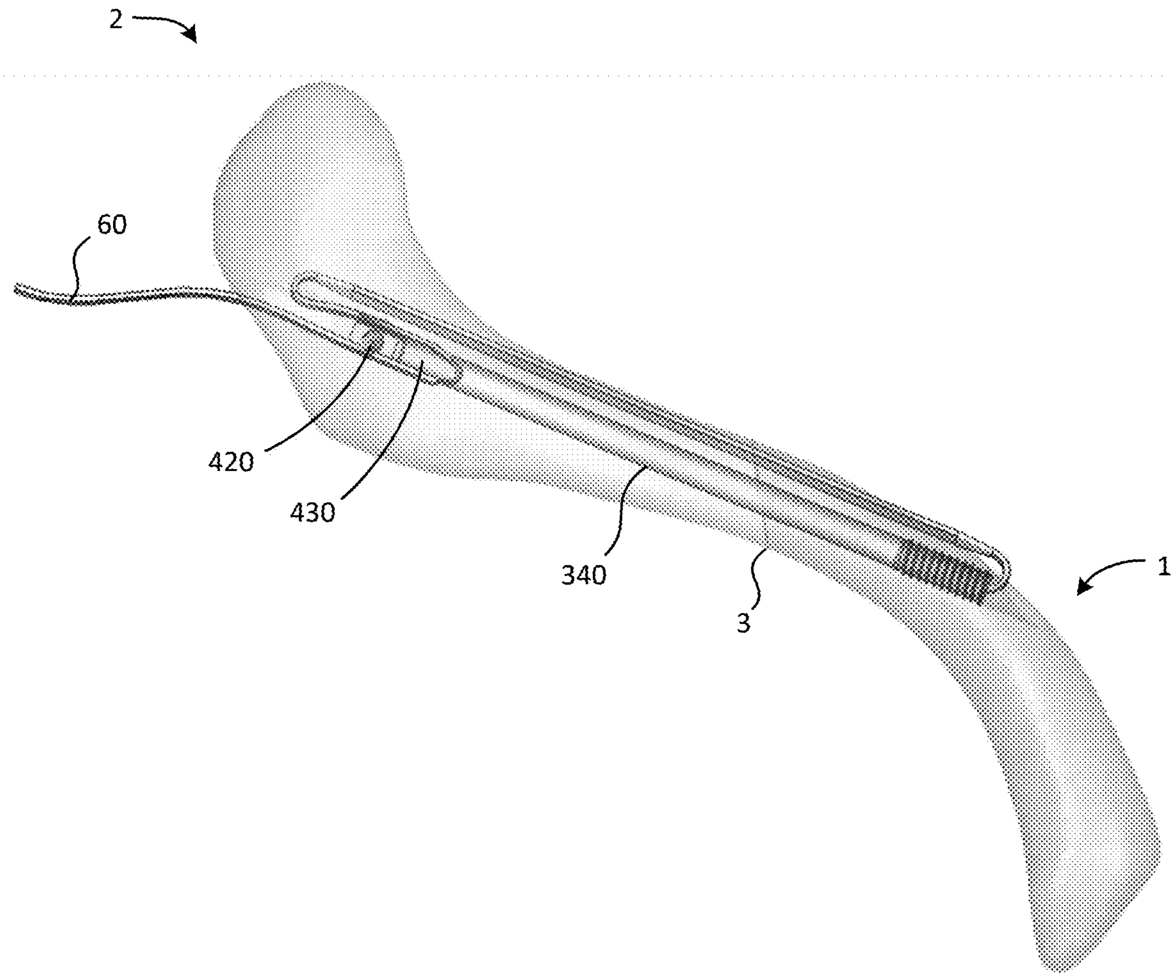
Figure 55:
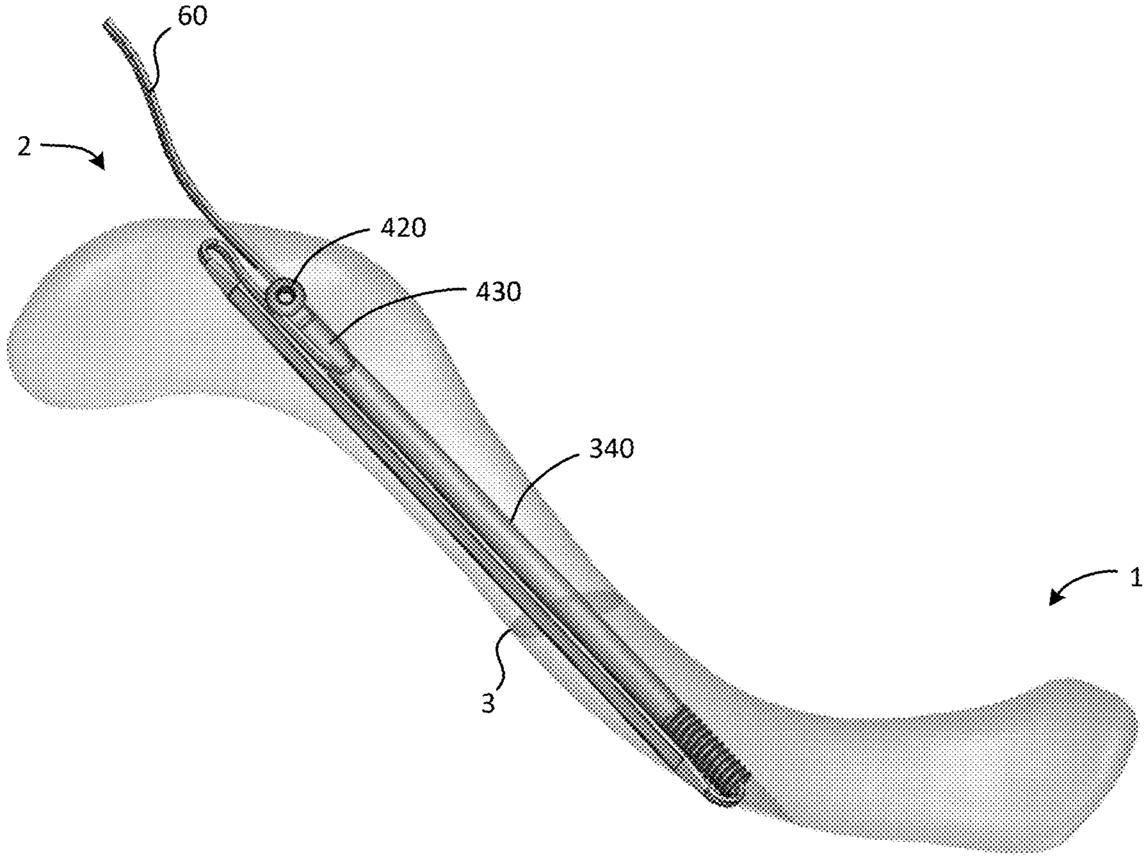
Figure 56:
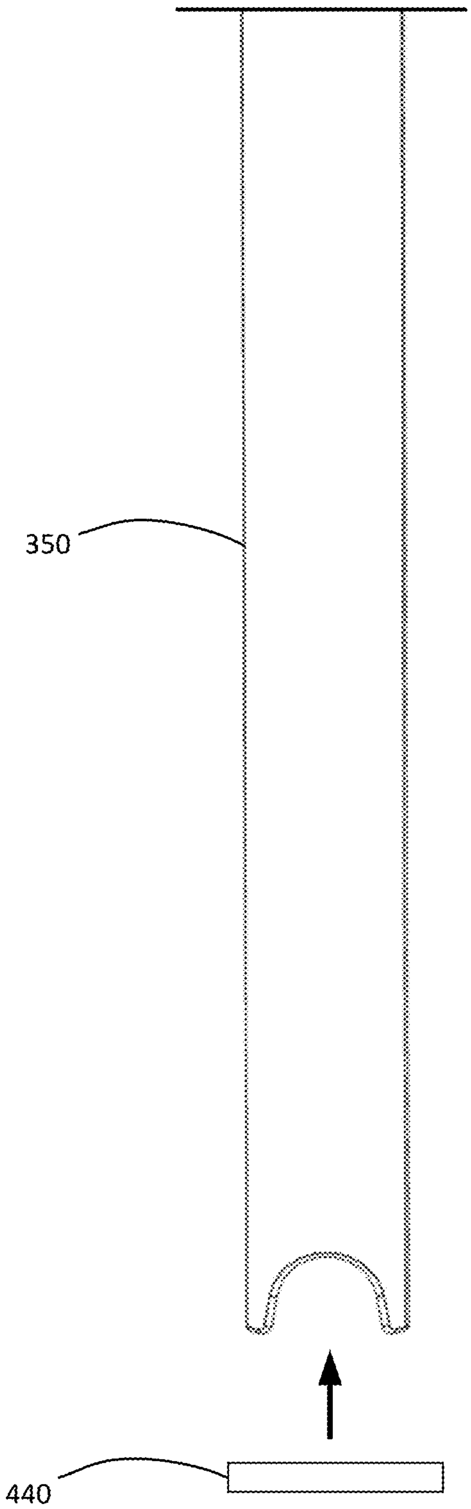
Figure 57:
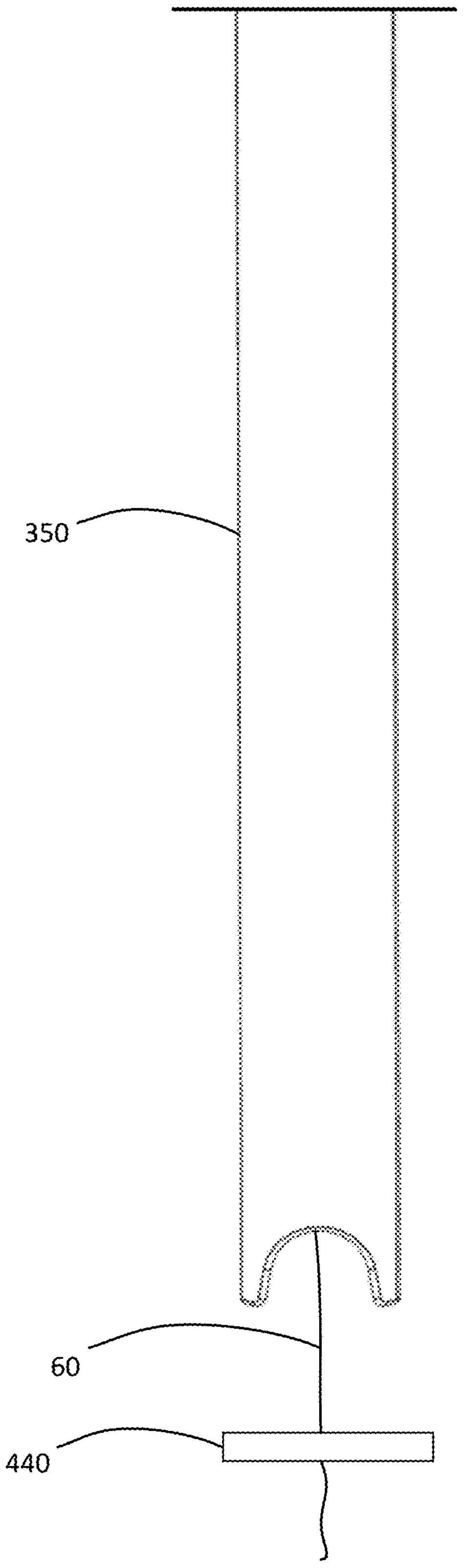
Figure 58:
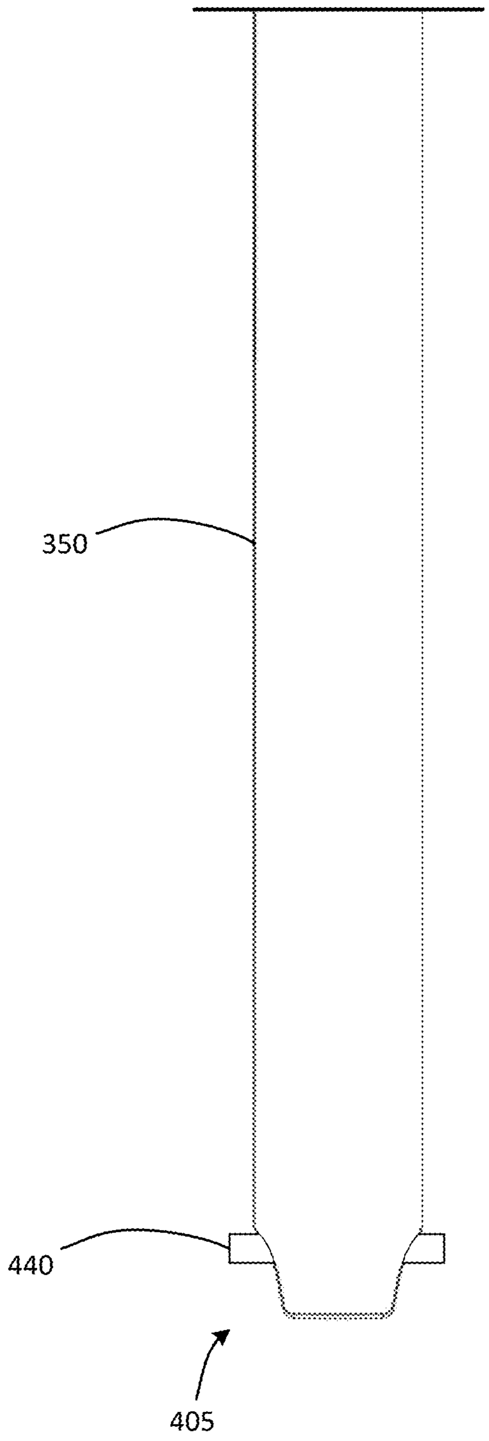
Figure 59A:
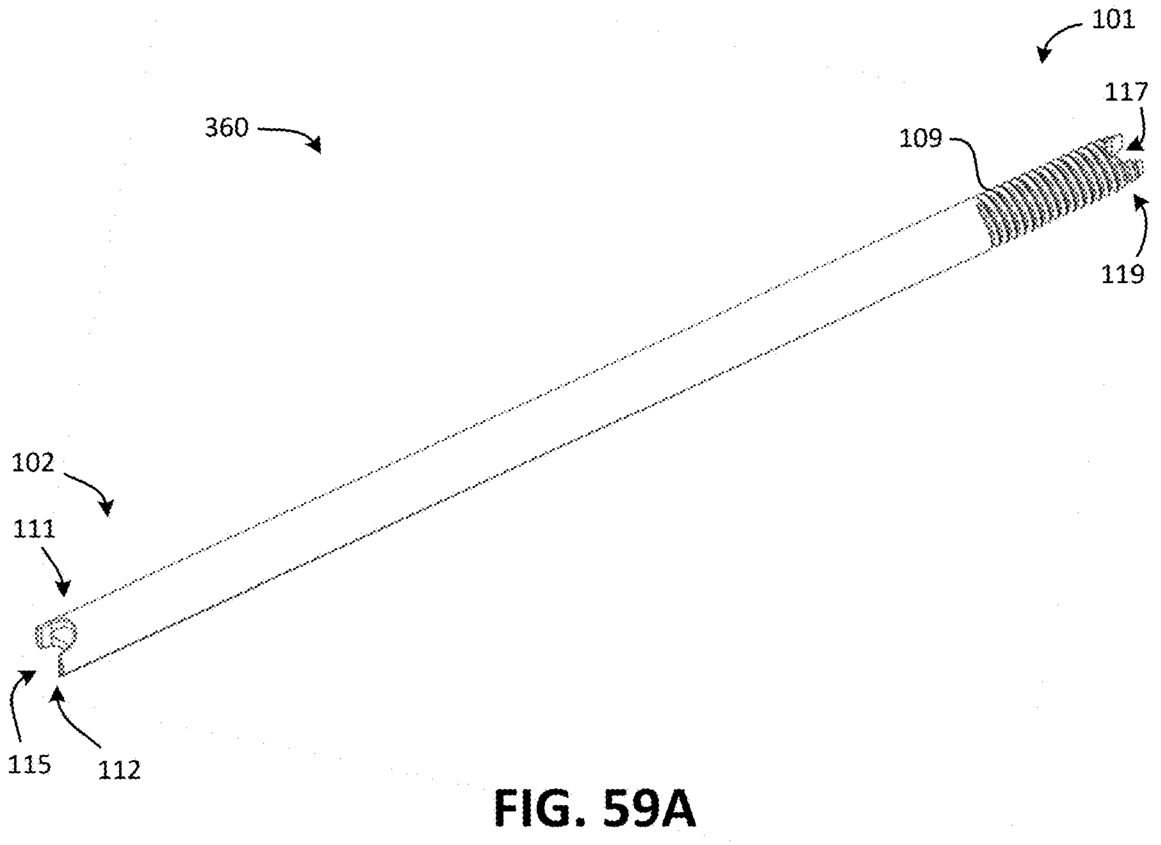
Figure 59B:
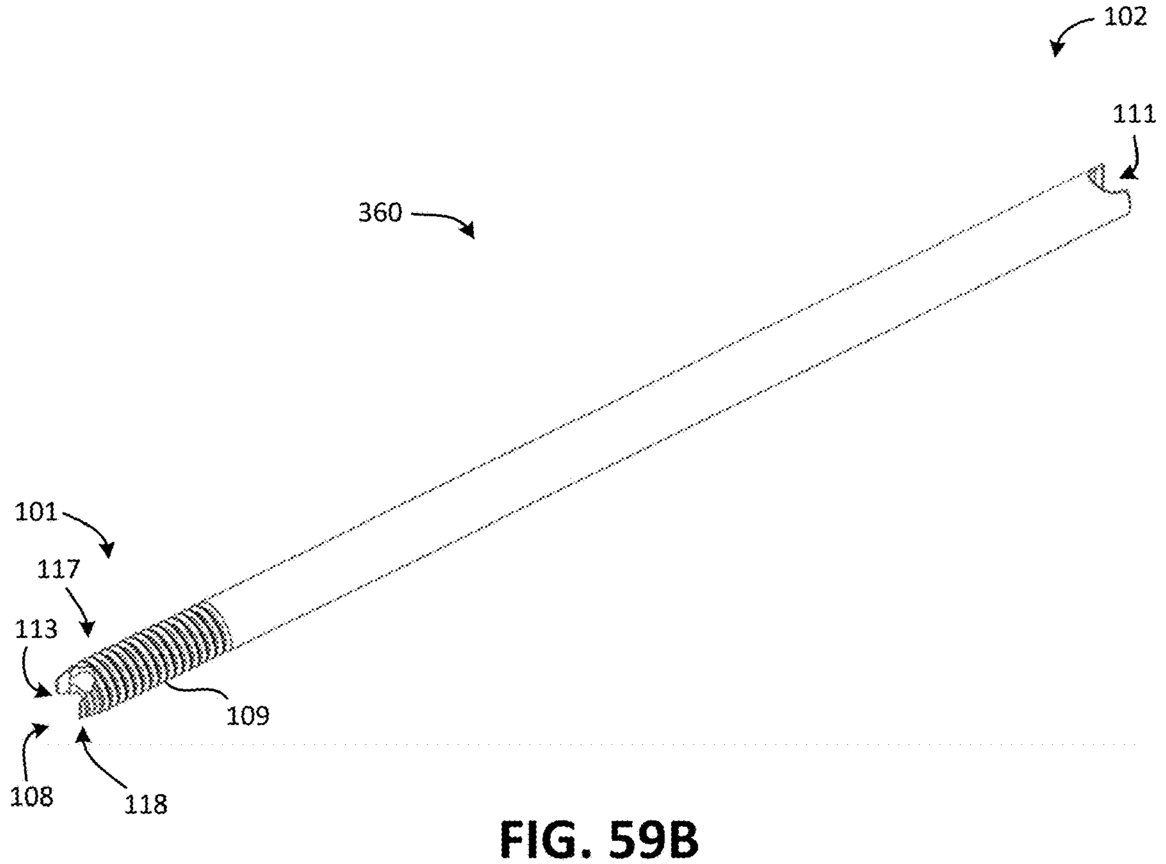
Figure 59C:
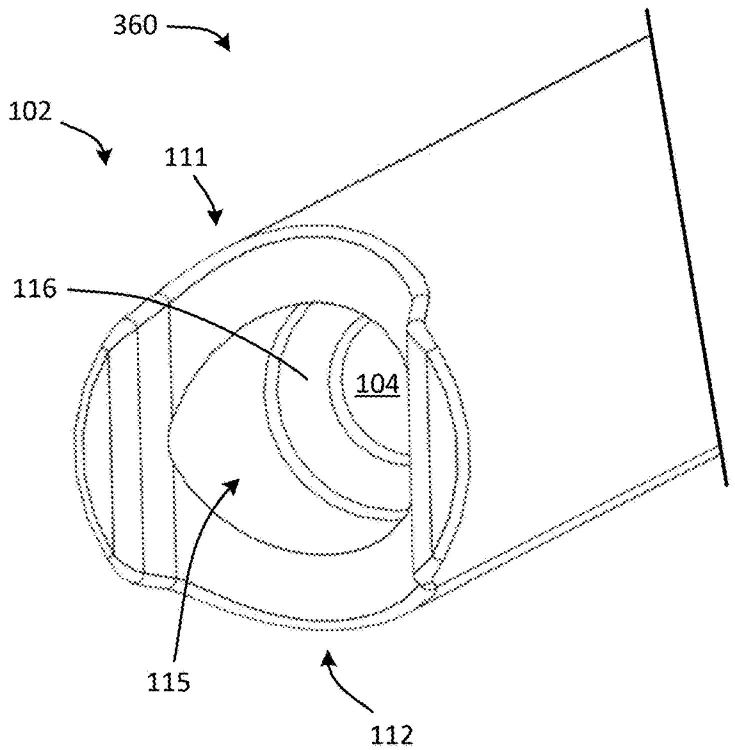
Figure 59D:
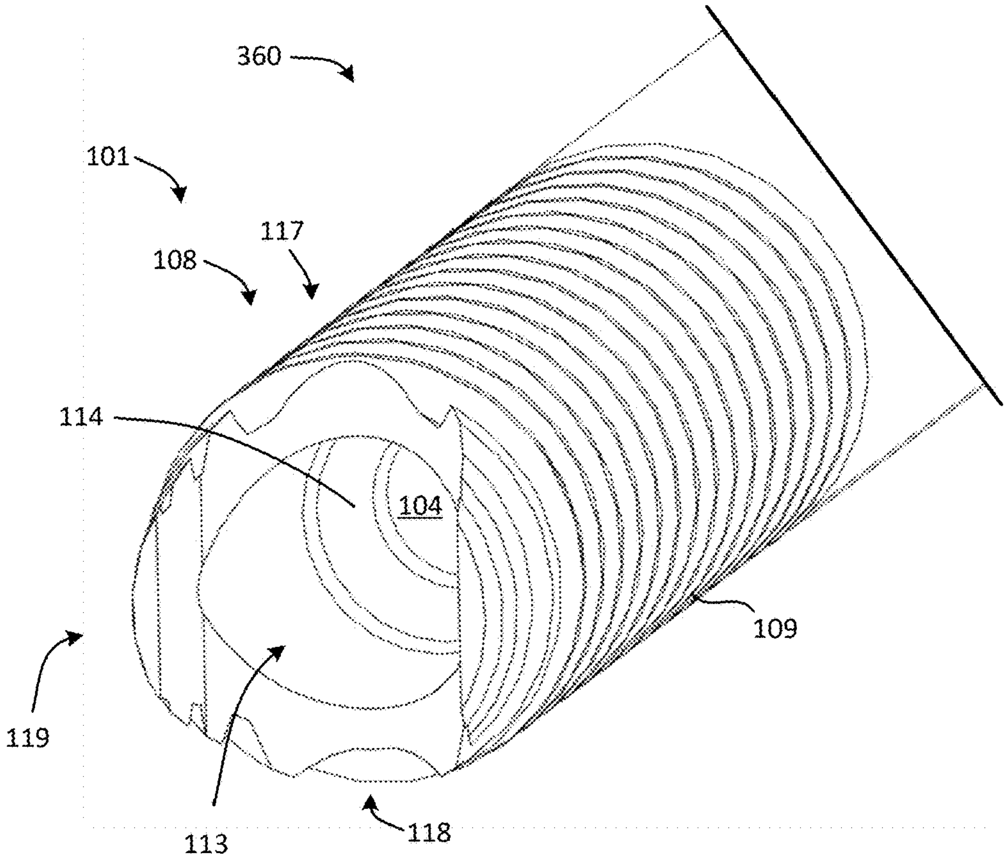
Figure 60A:
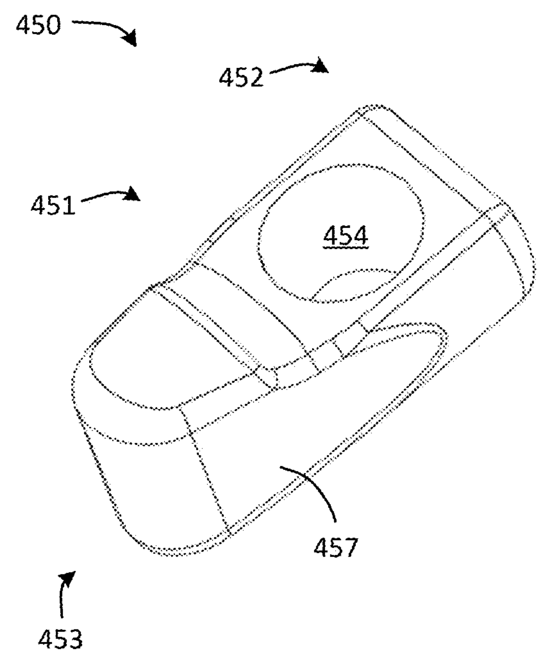
Figure 60B:
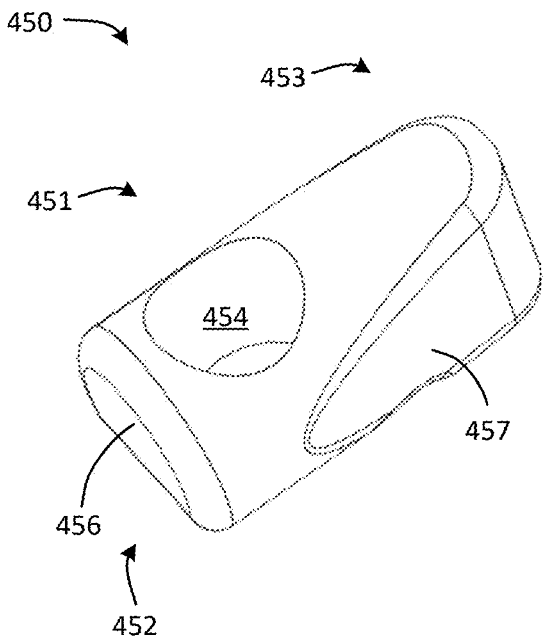
Figure 60C:
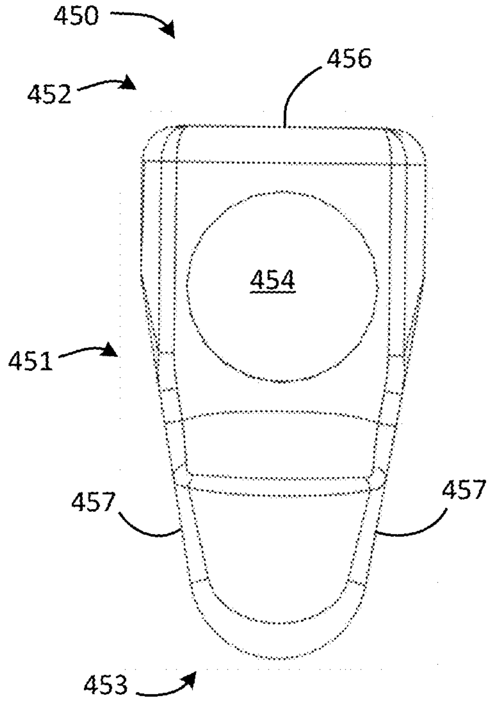
Figure 60D:
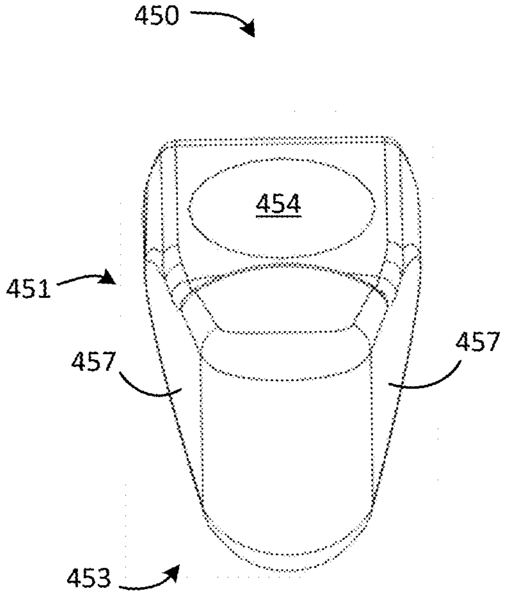
Figure 61:
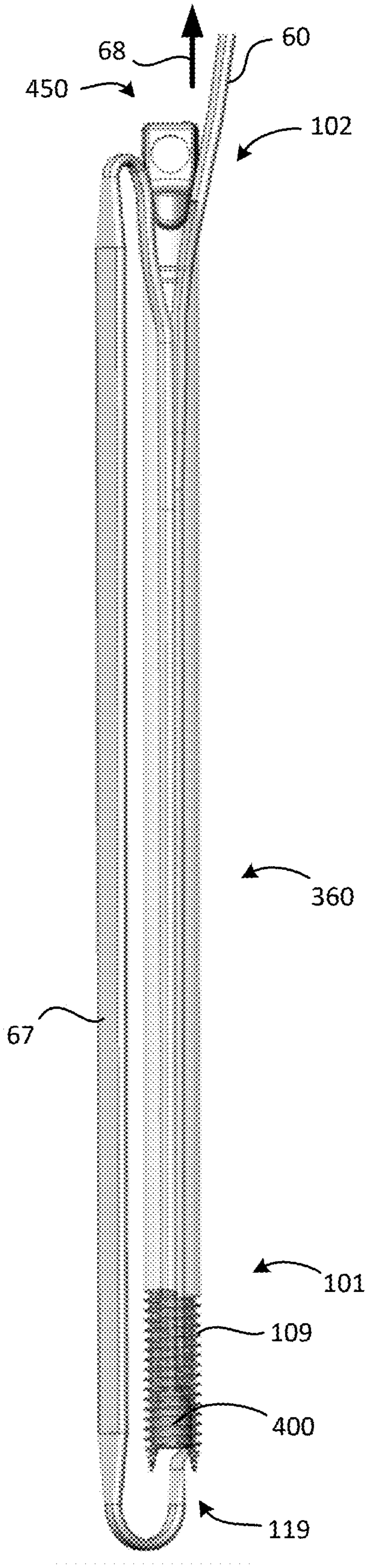
Figure 62:
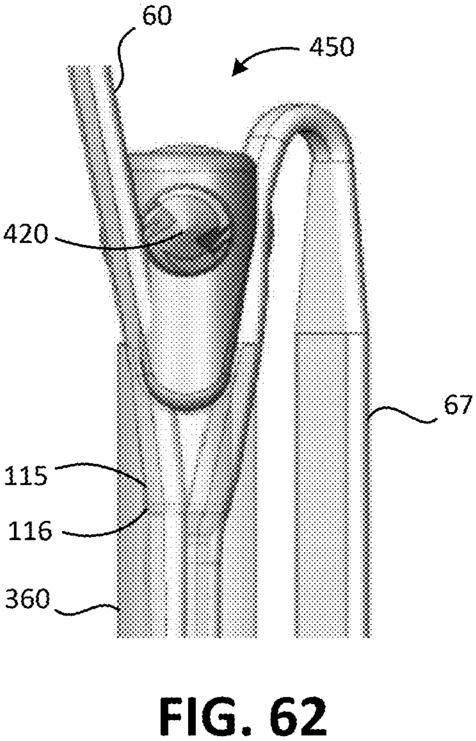
Figure 63:
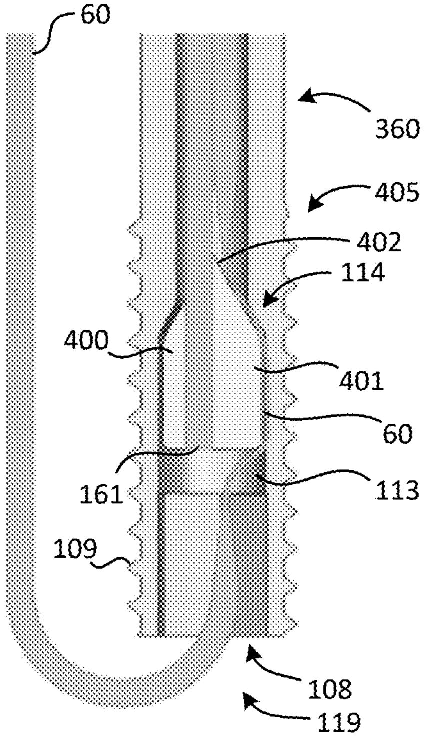
Figure 64:
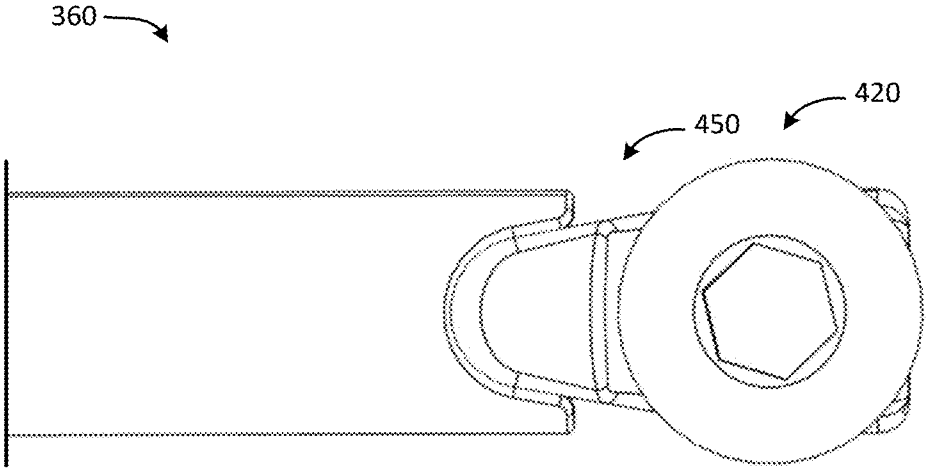
Figure 65:
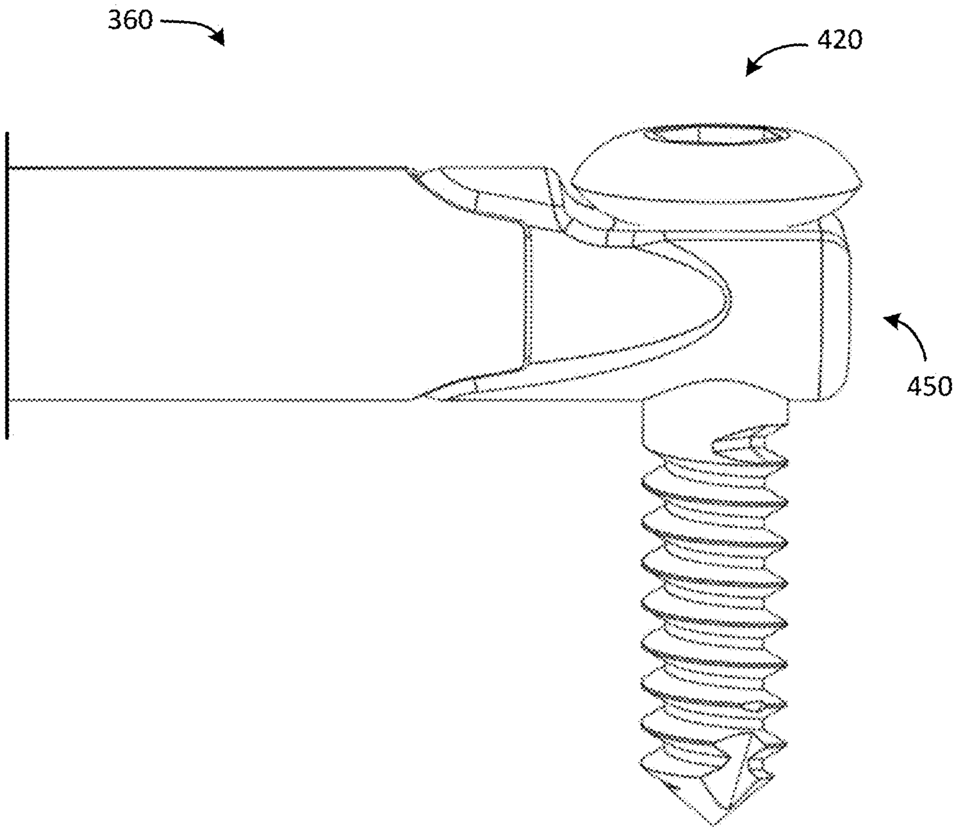
Figure 66:
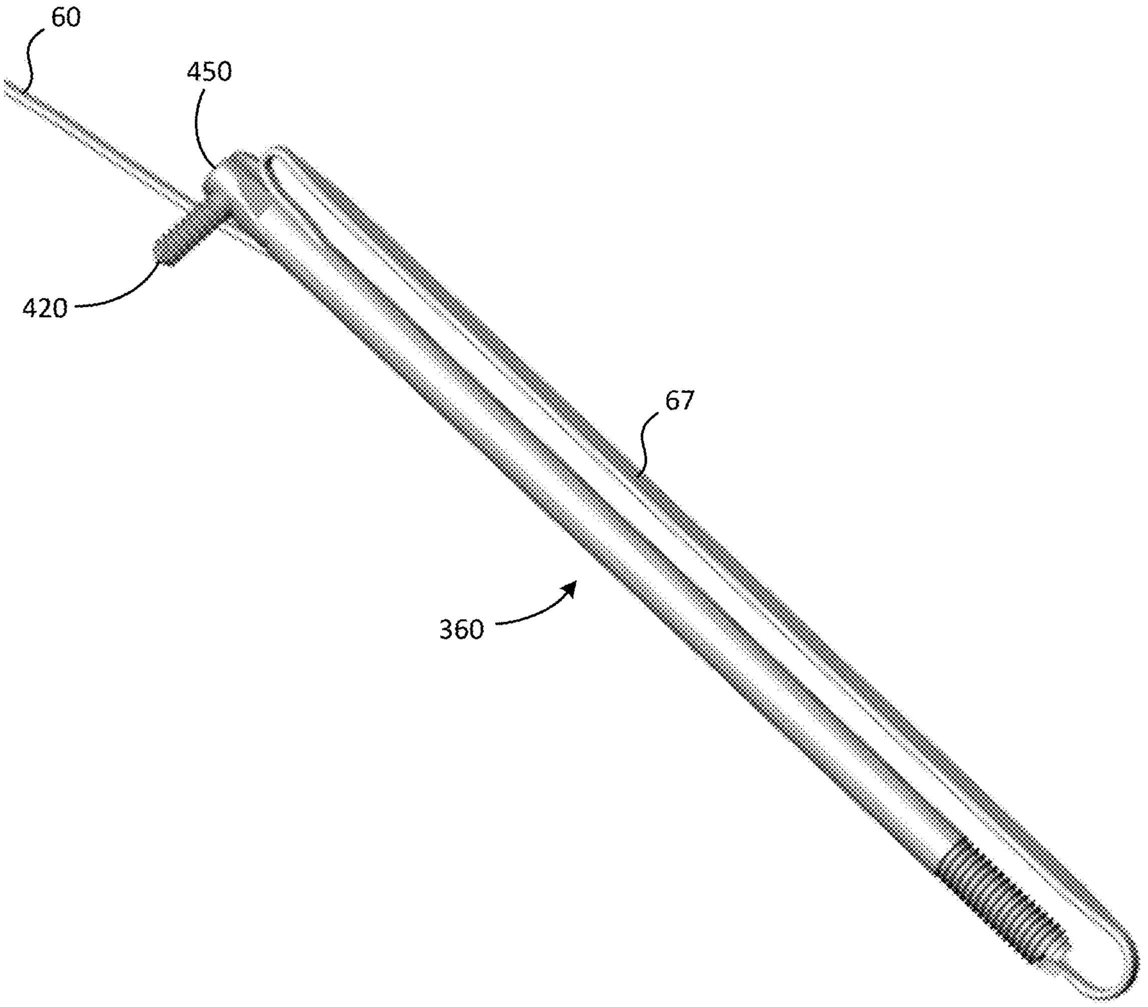
Figure 67:
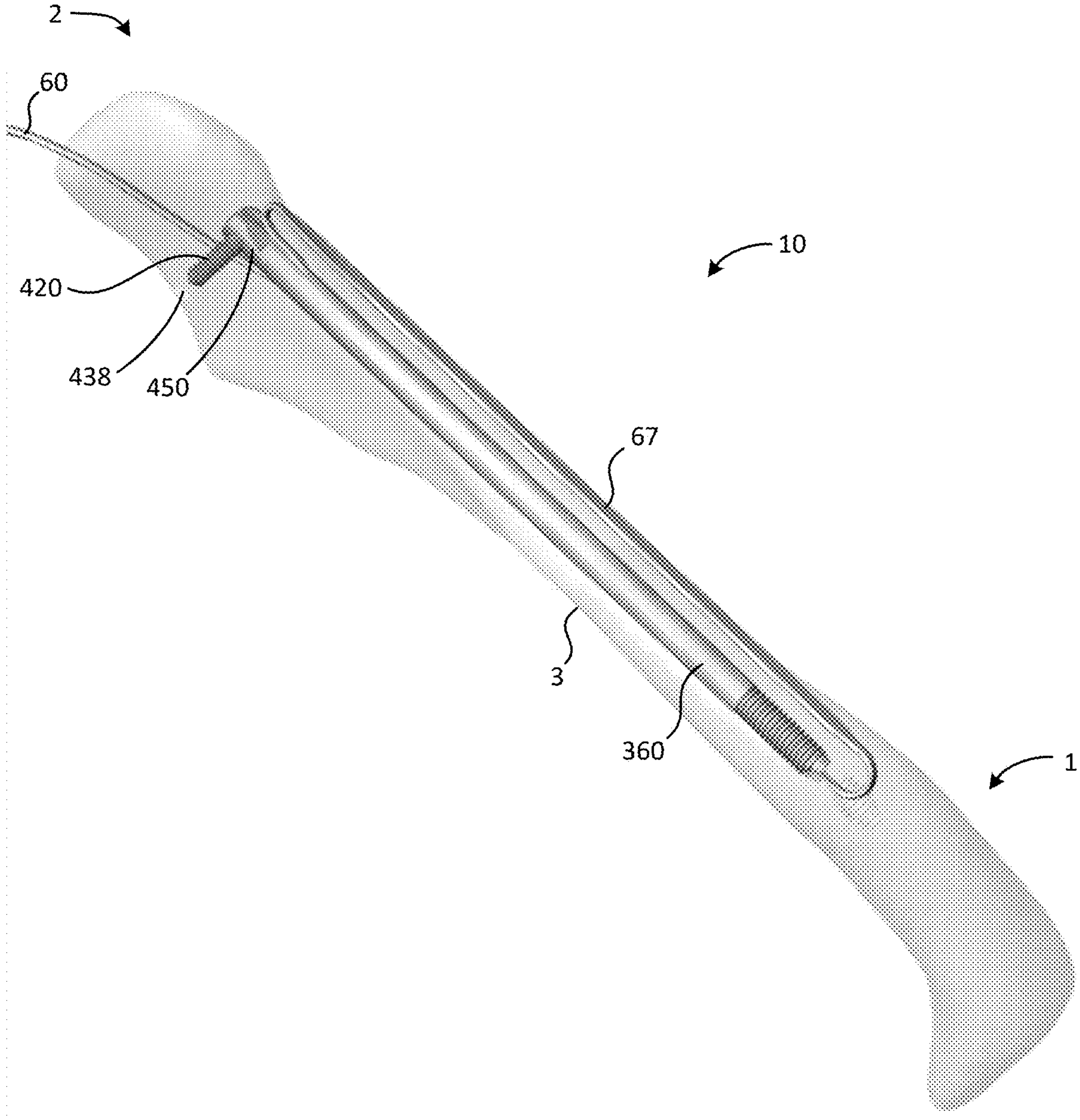
Figure 68:
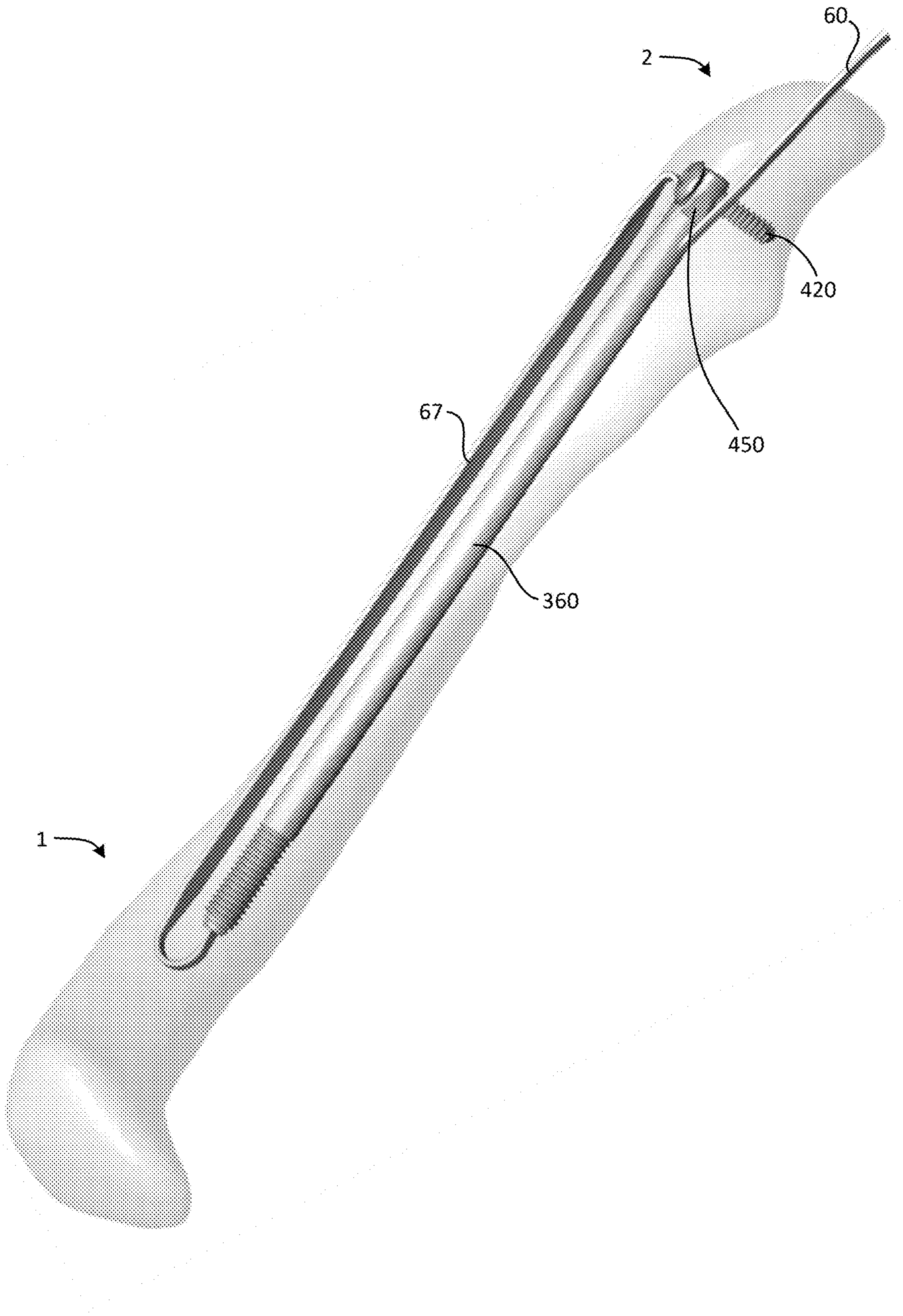
Figure 69:
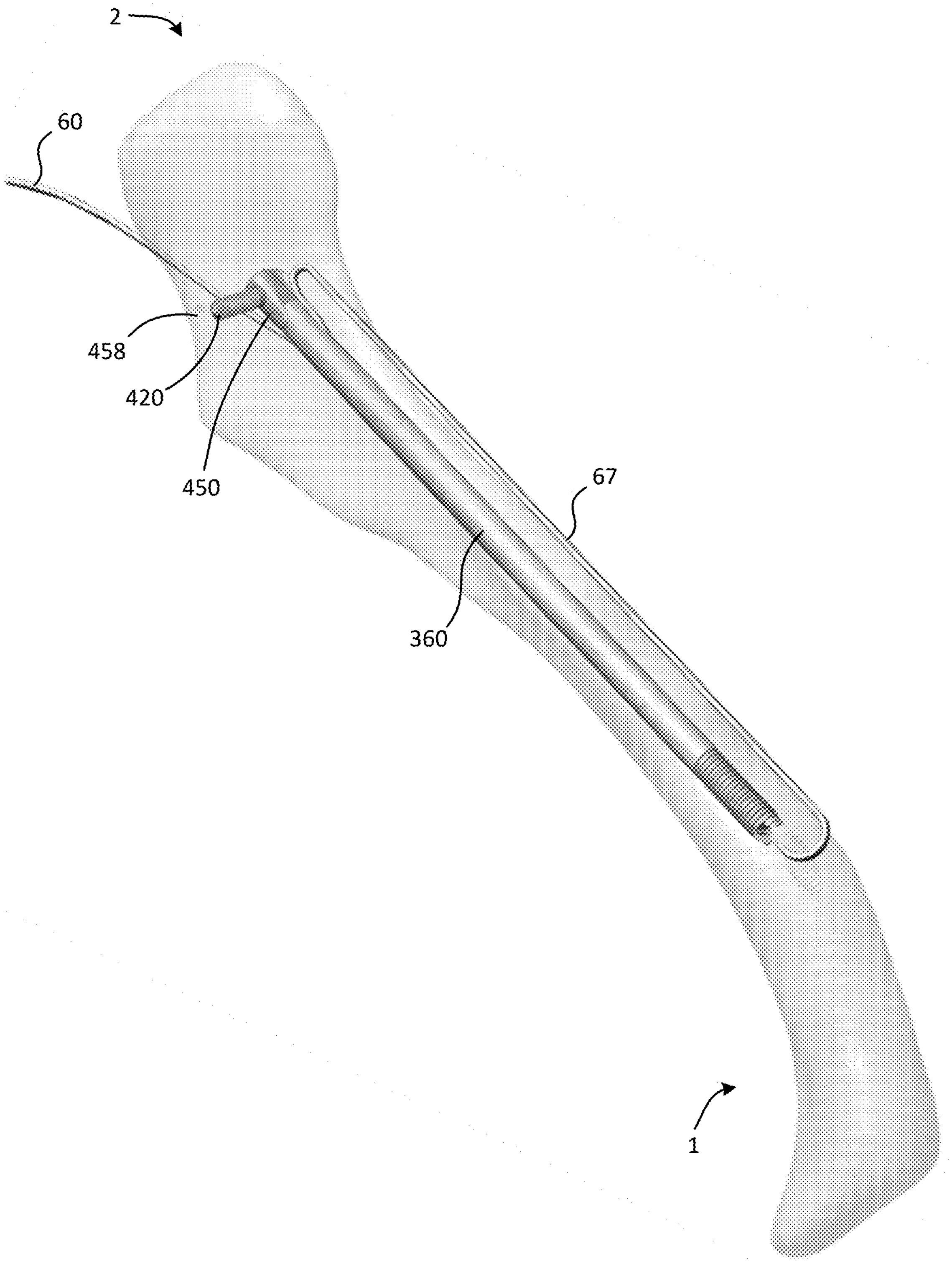
Figure 70:
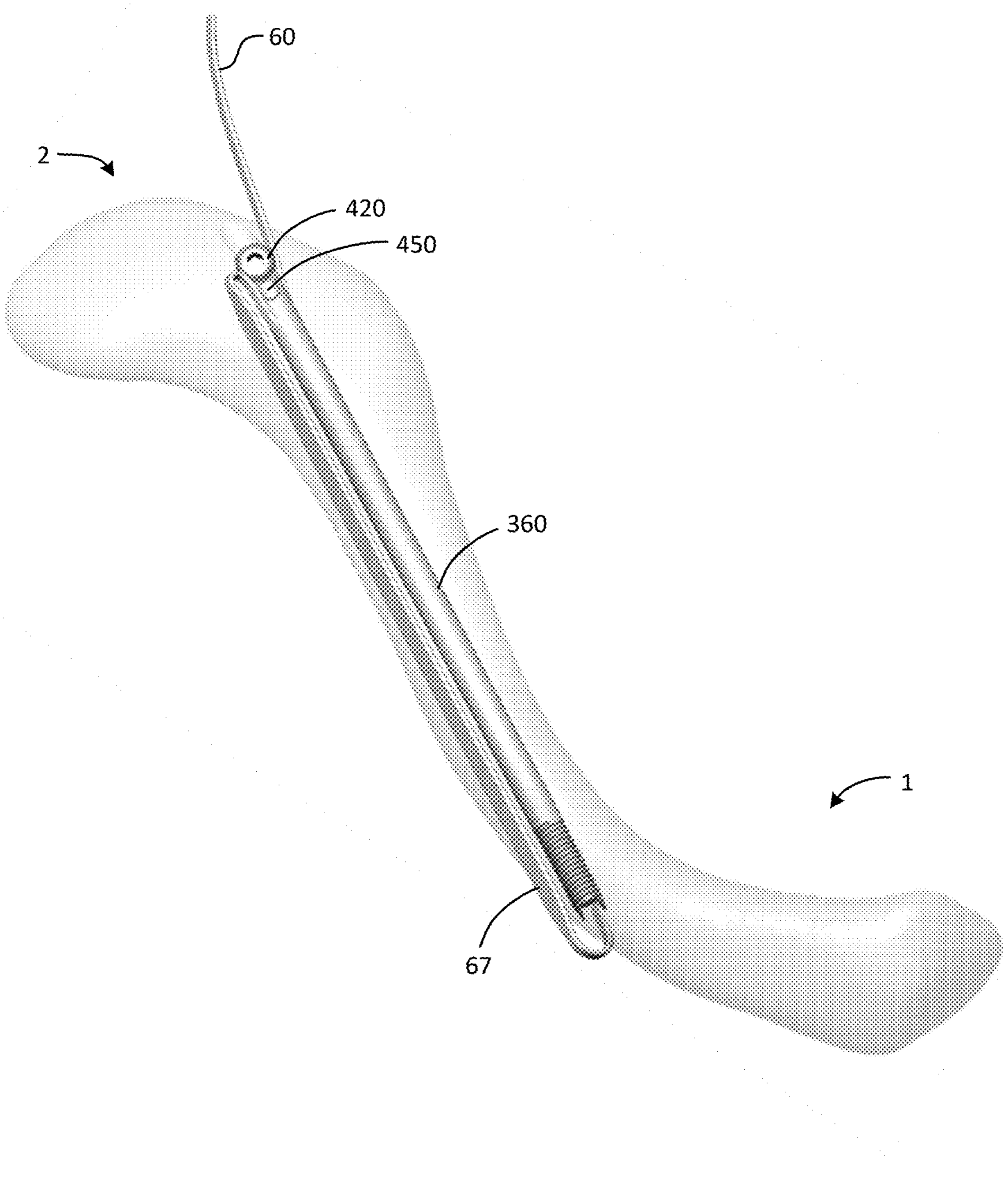
Figure 71A:
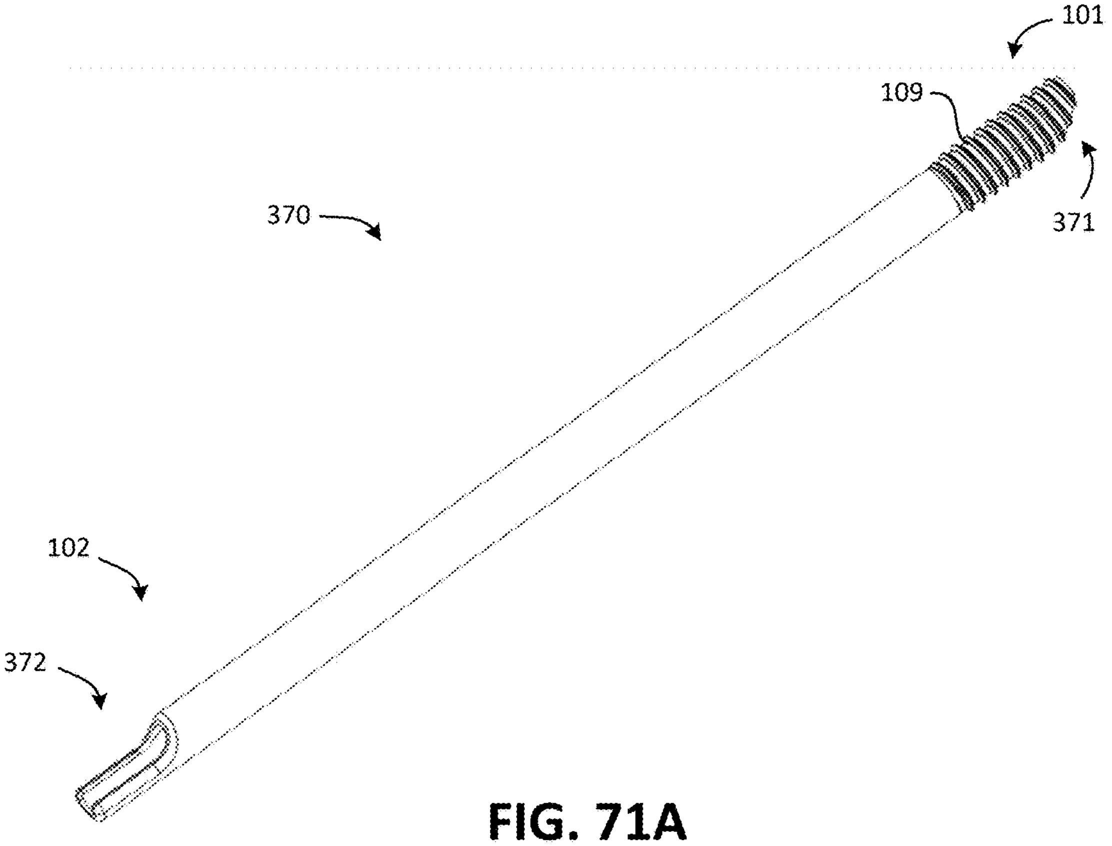
Figure 71B:
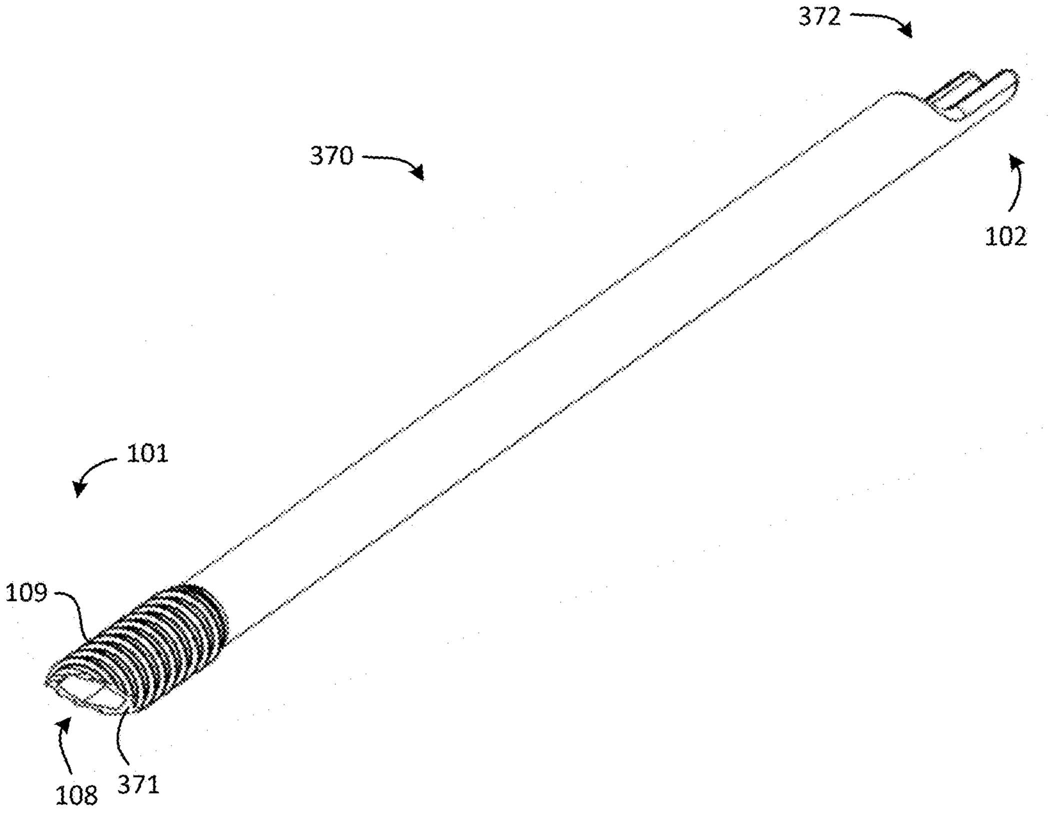
Figure 71C:
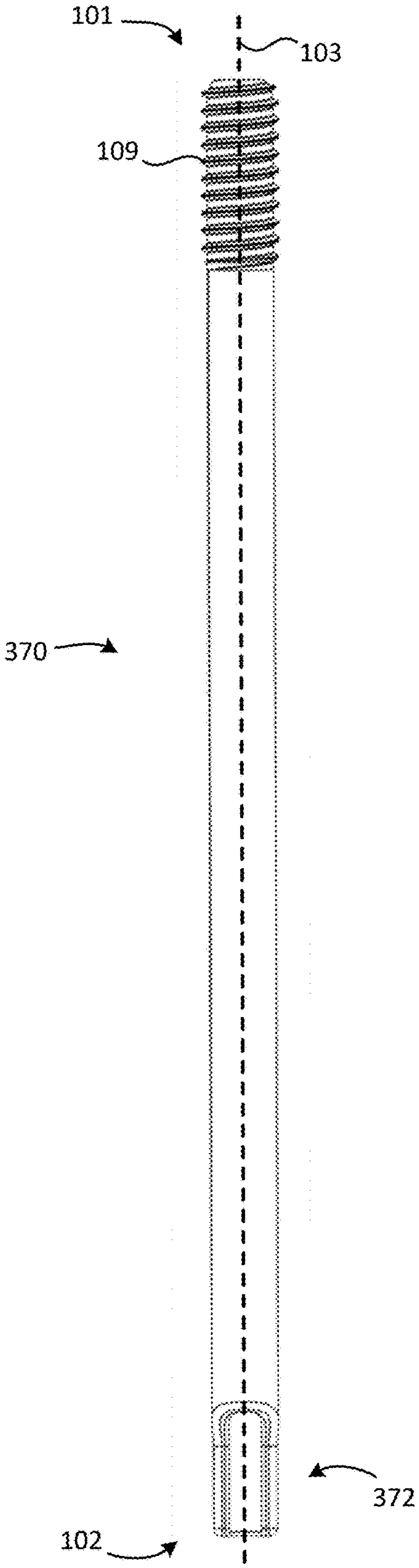
Figure 71D:
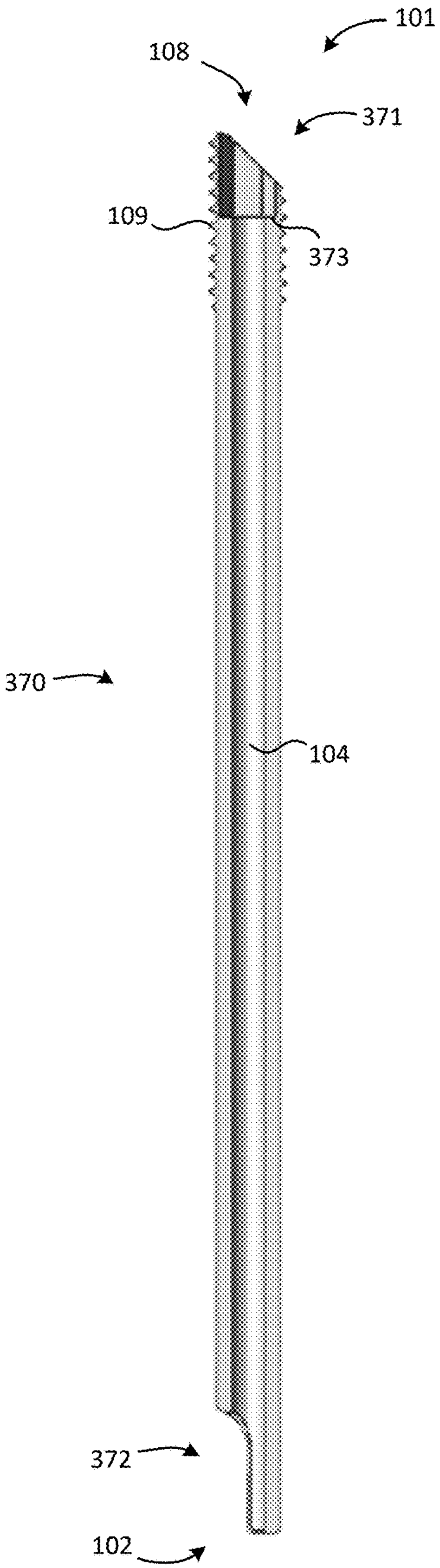
Figure 72A:
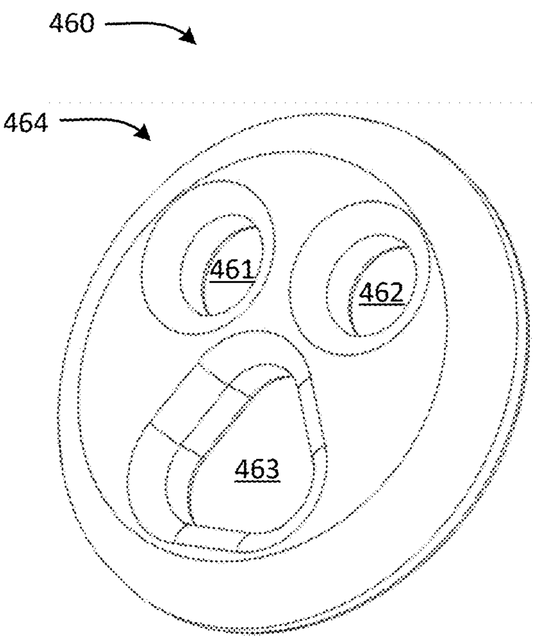
Figure 72B:
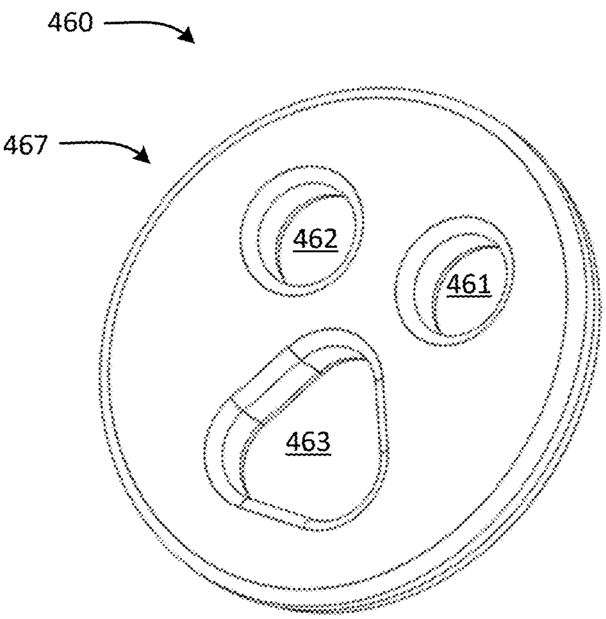
Figure 72C:
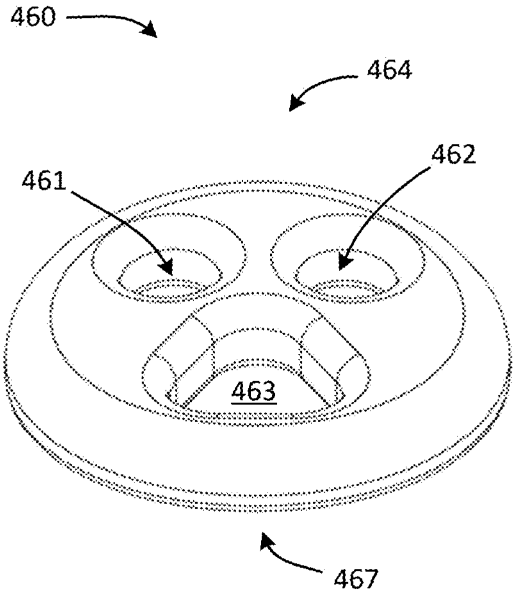
Figure 72D:
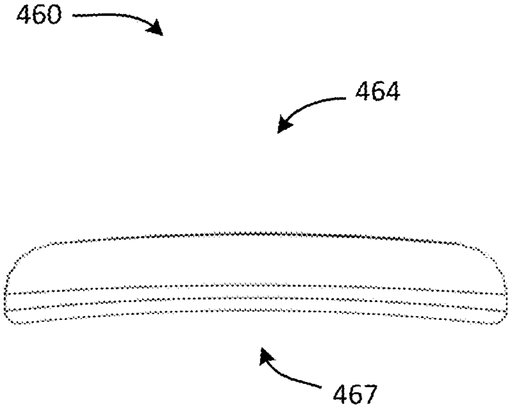
Figure 73A:
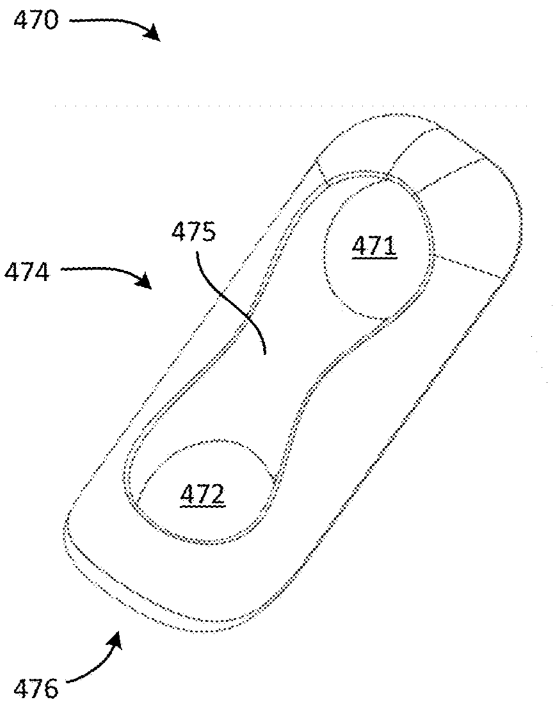
Figure 73B:
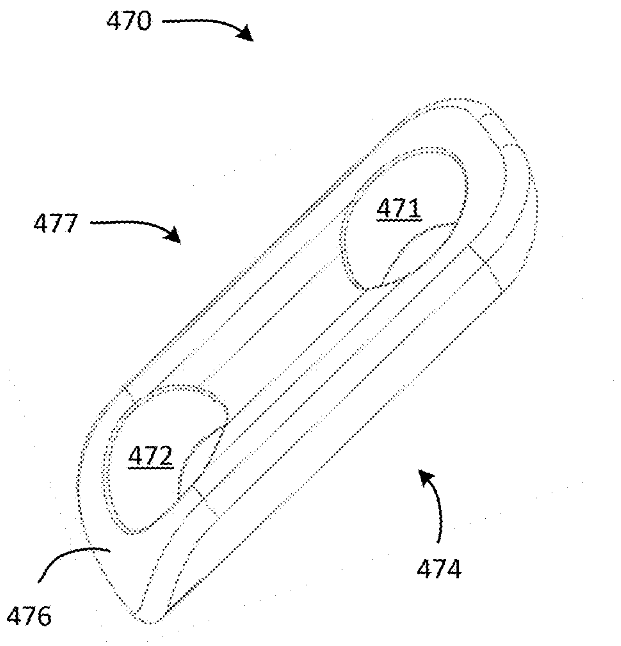
Figure 73C:
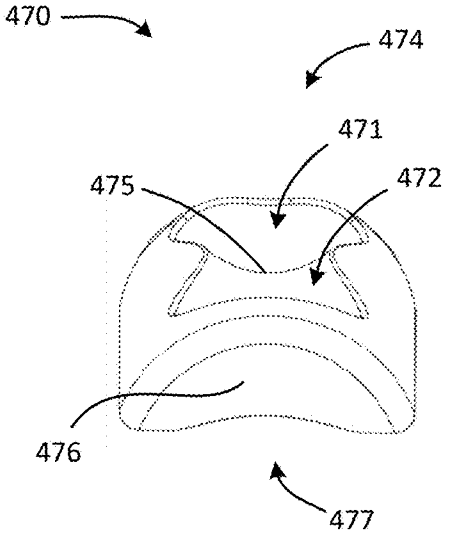
Figure 73D:
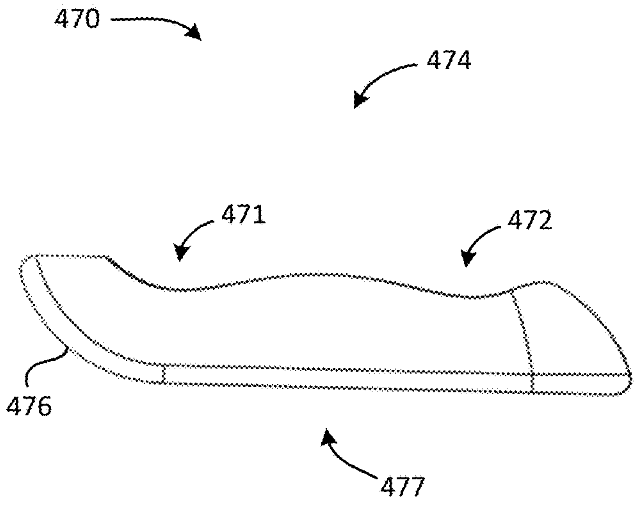
Figure 74:
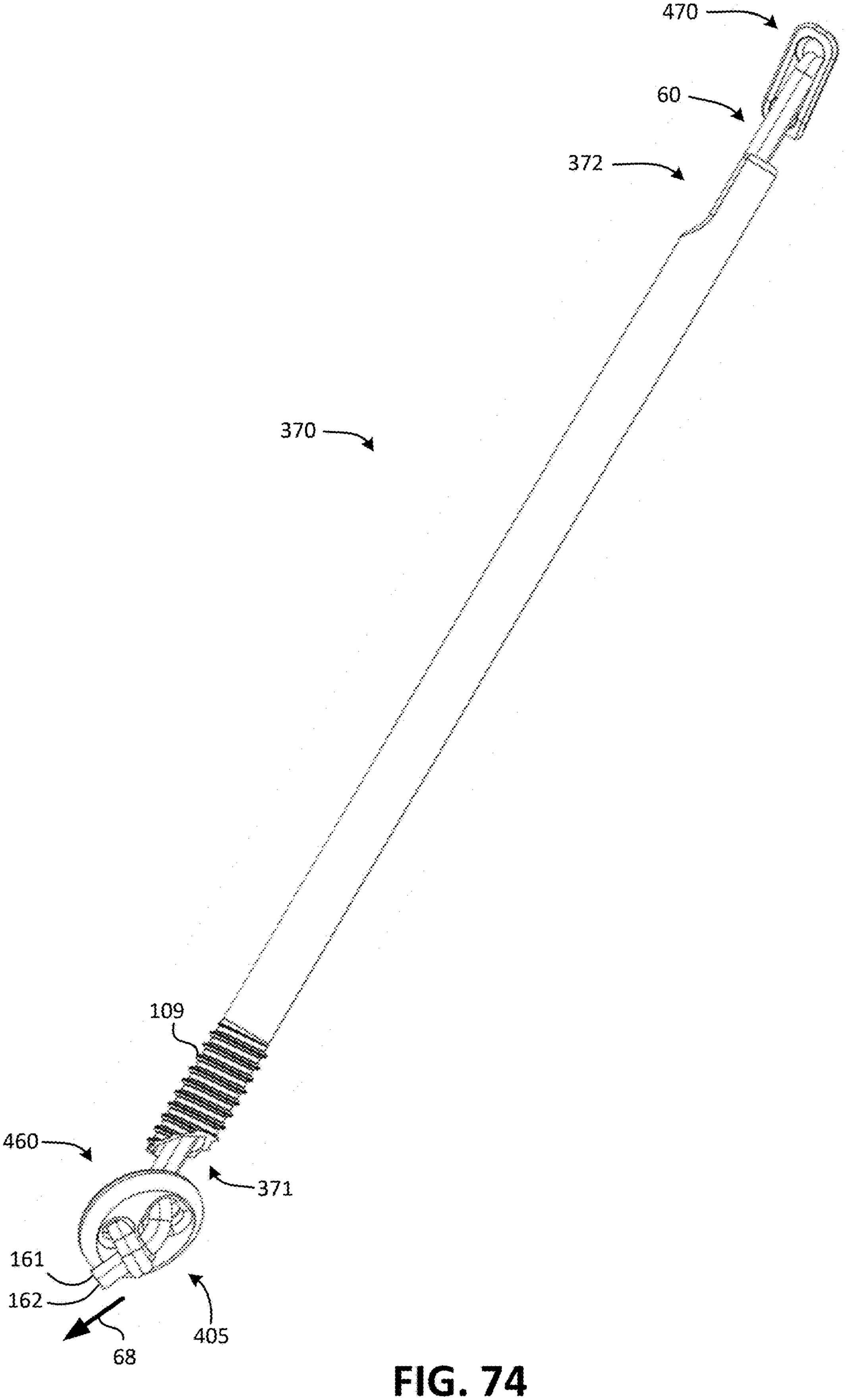
Figure 75:
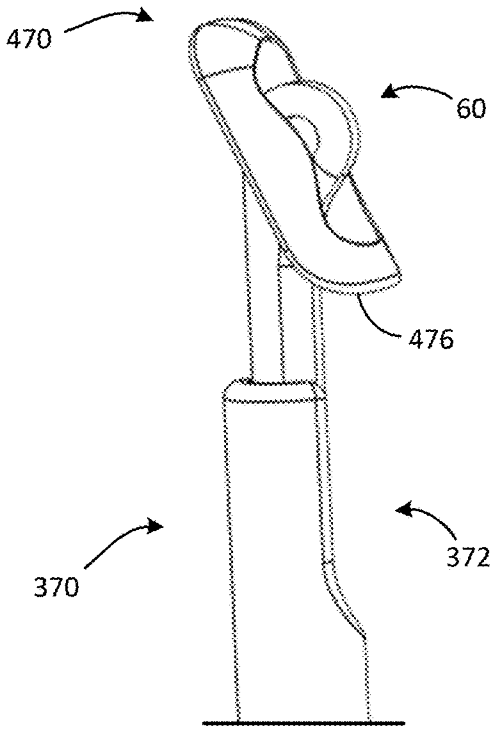
Figure 76:
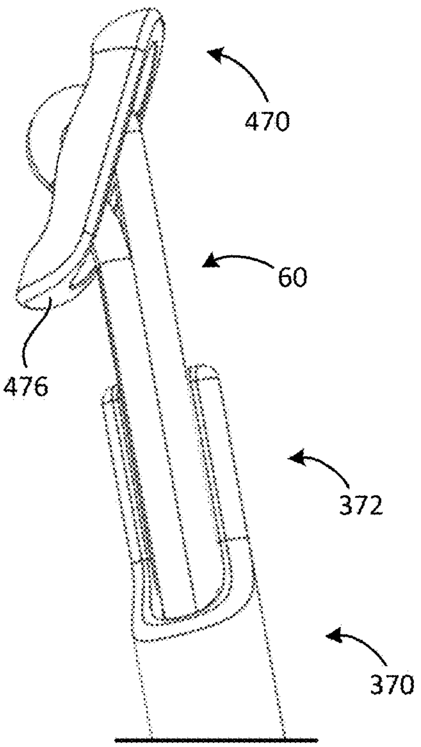
Figure 77:
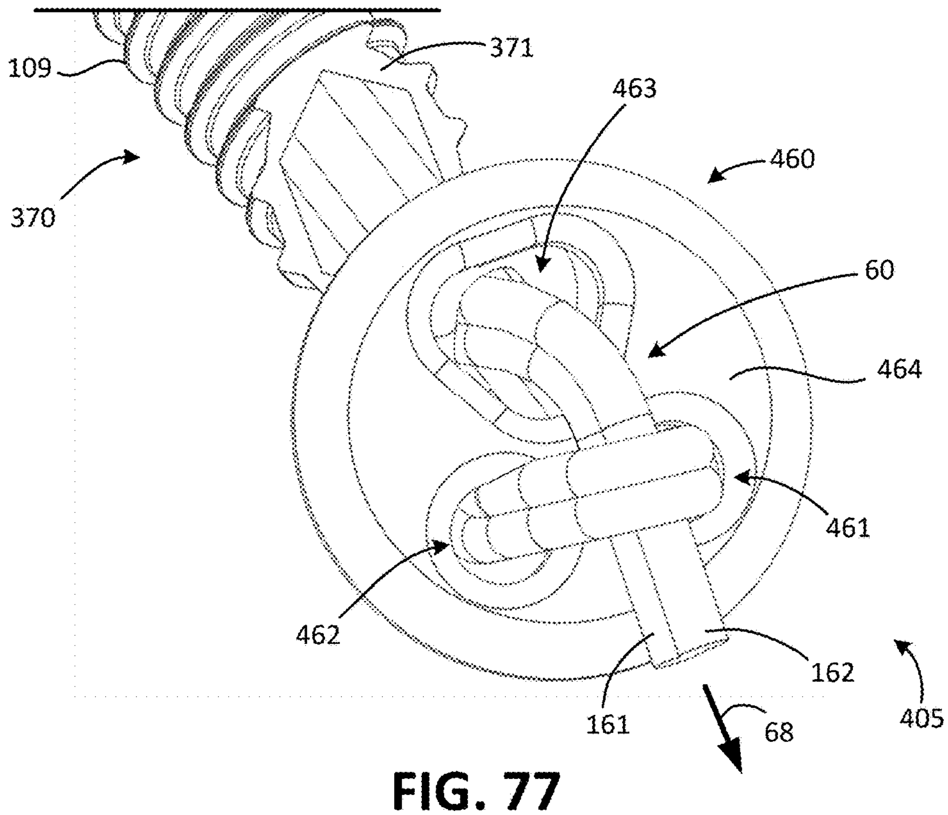
Figure 78:
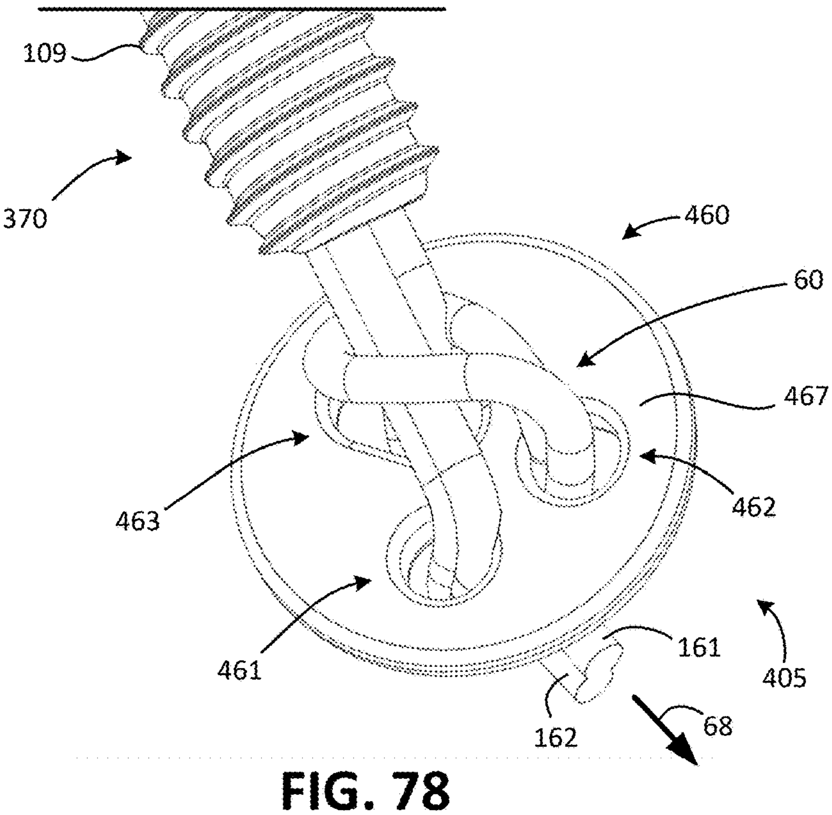
Figure 79:
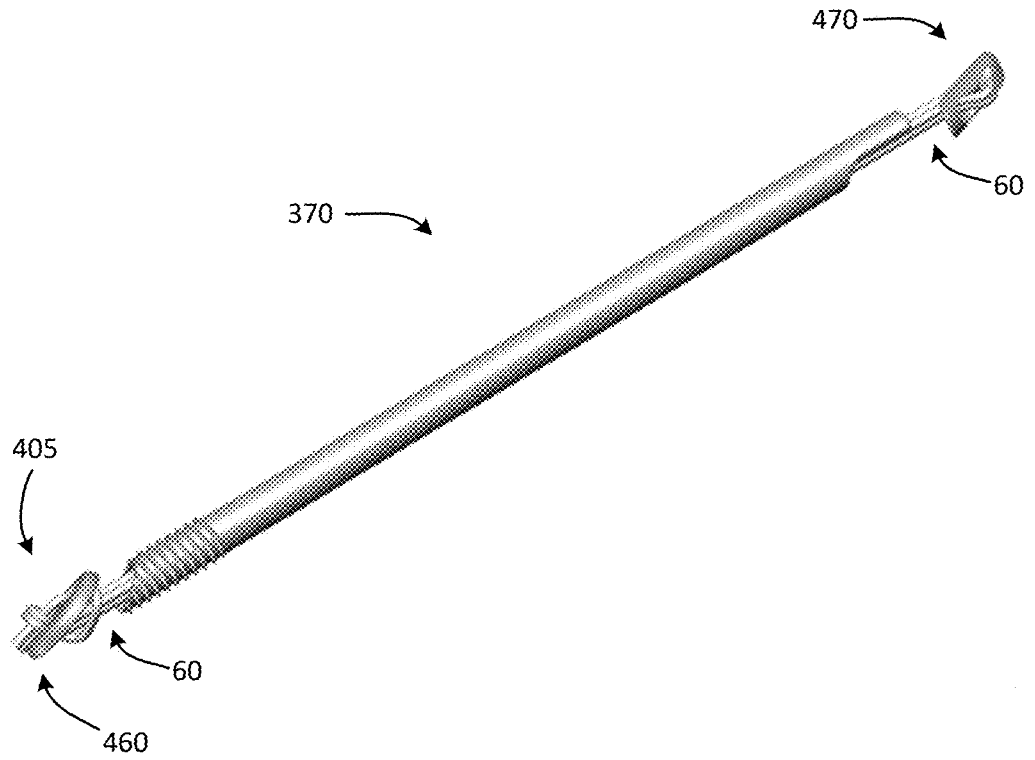
Figure 80:
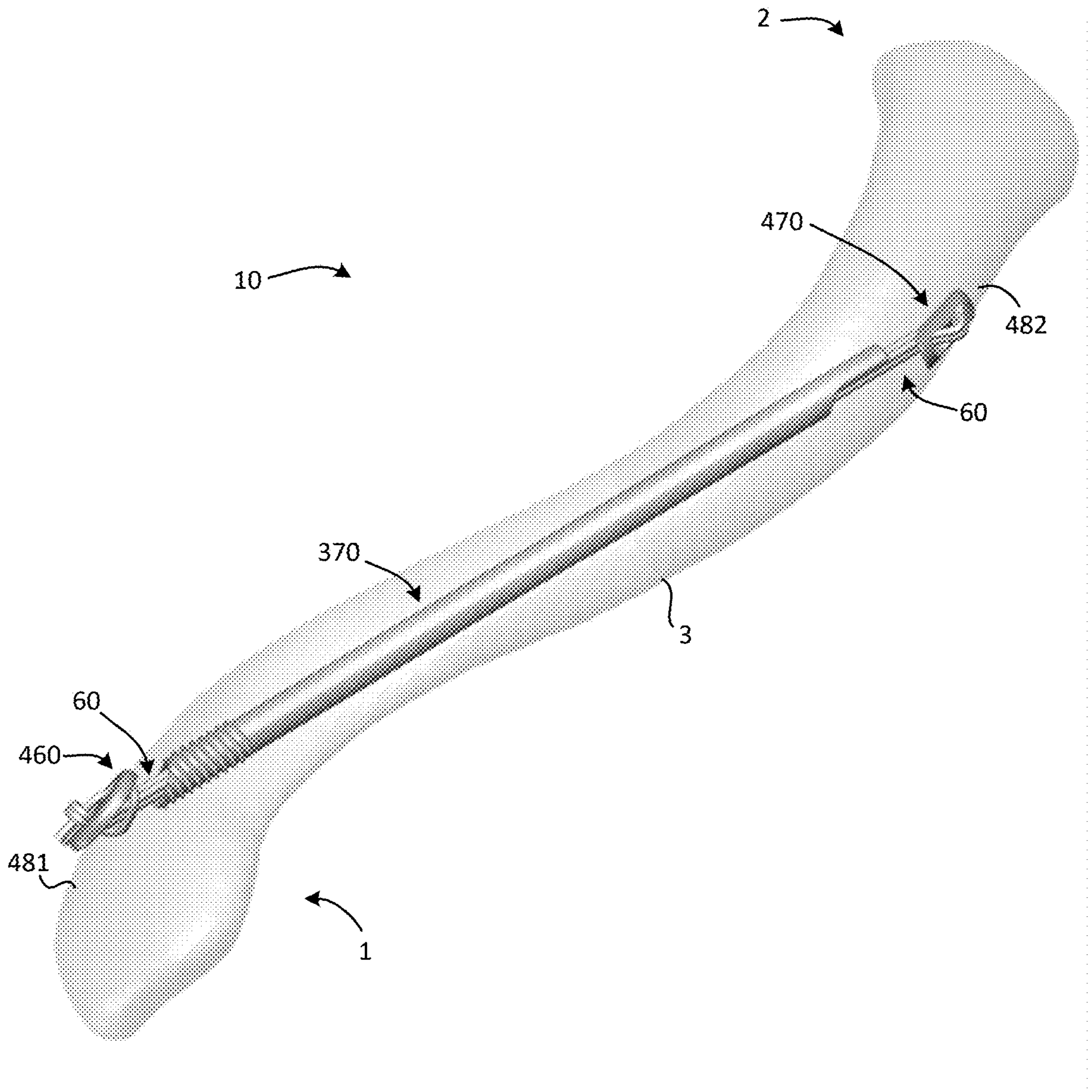
Figure 81:
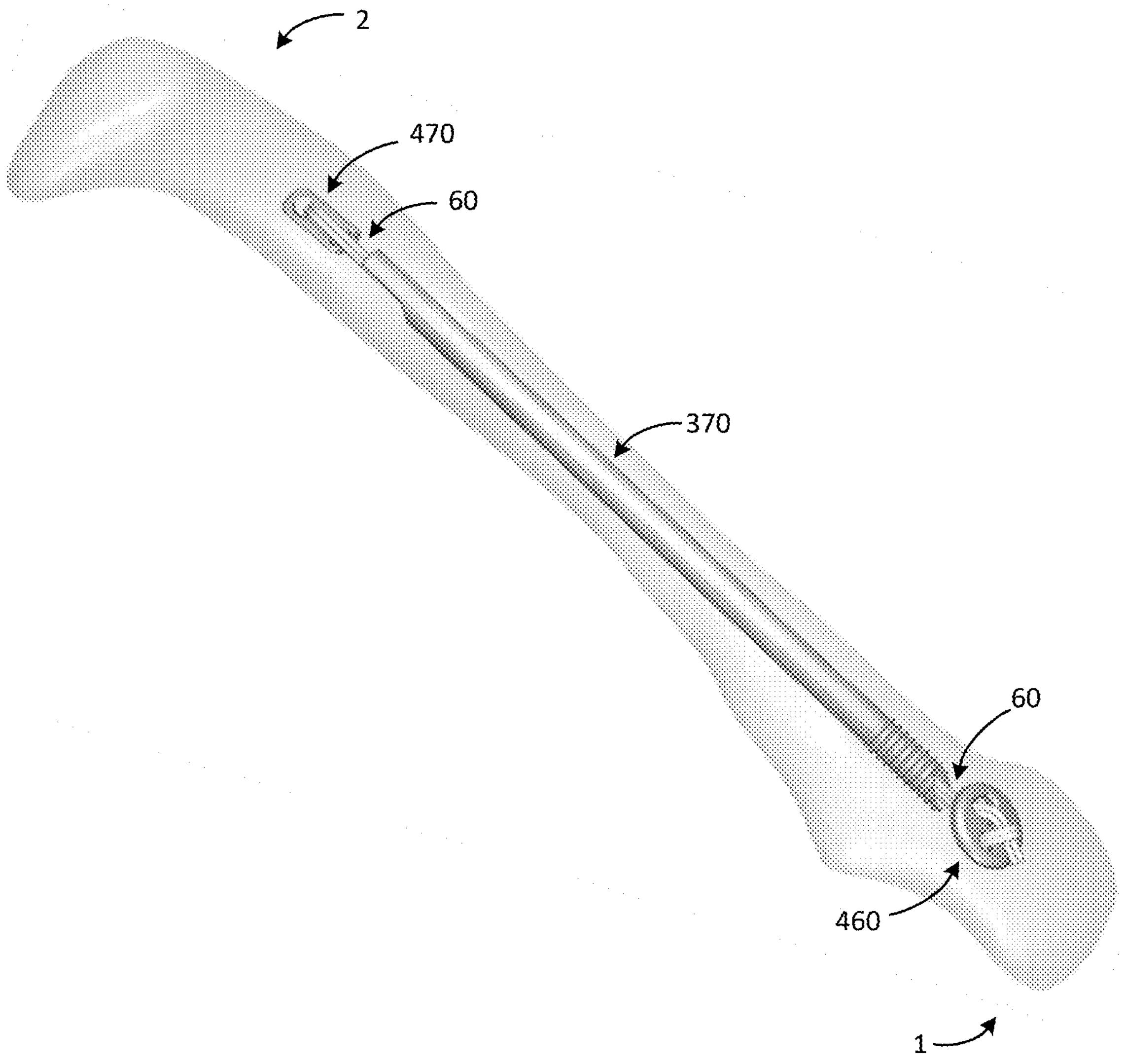
Figure 82:
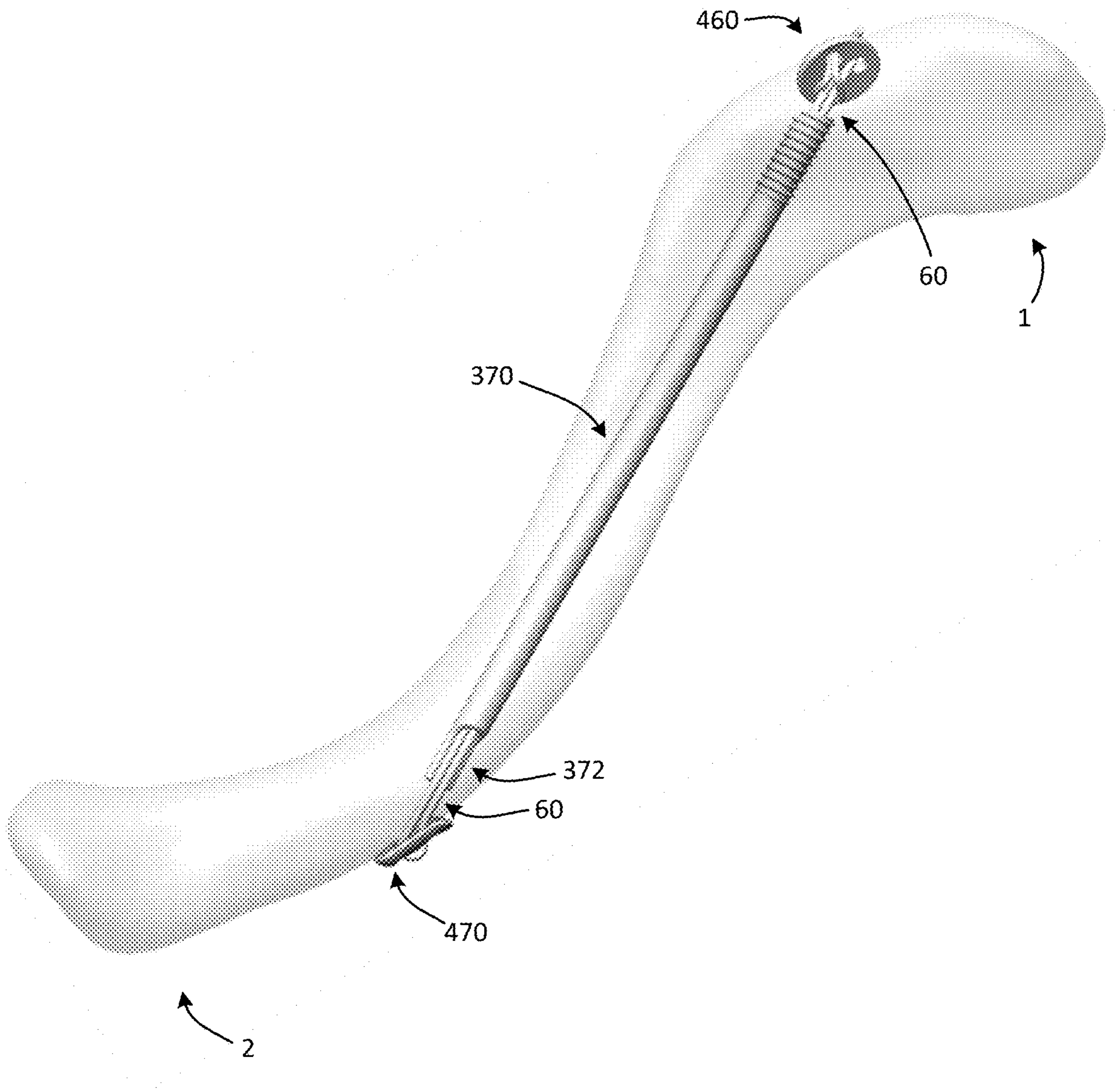
Figure 83:
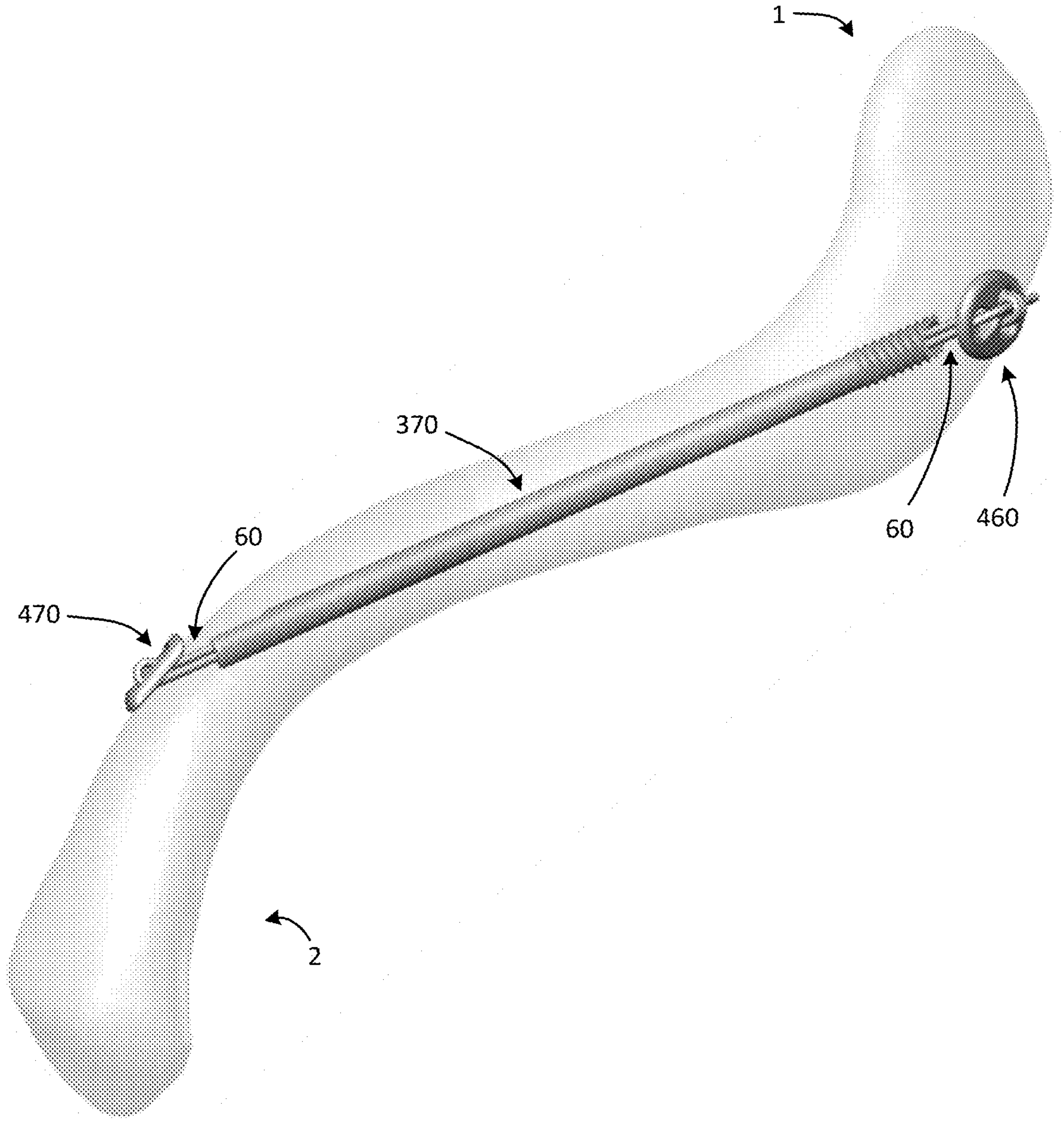
Figure 84A:
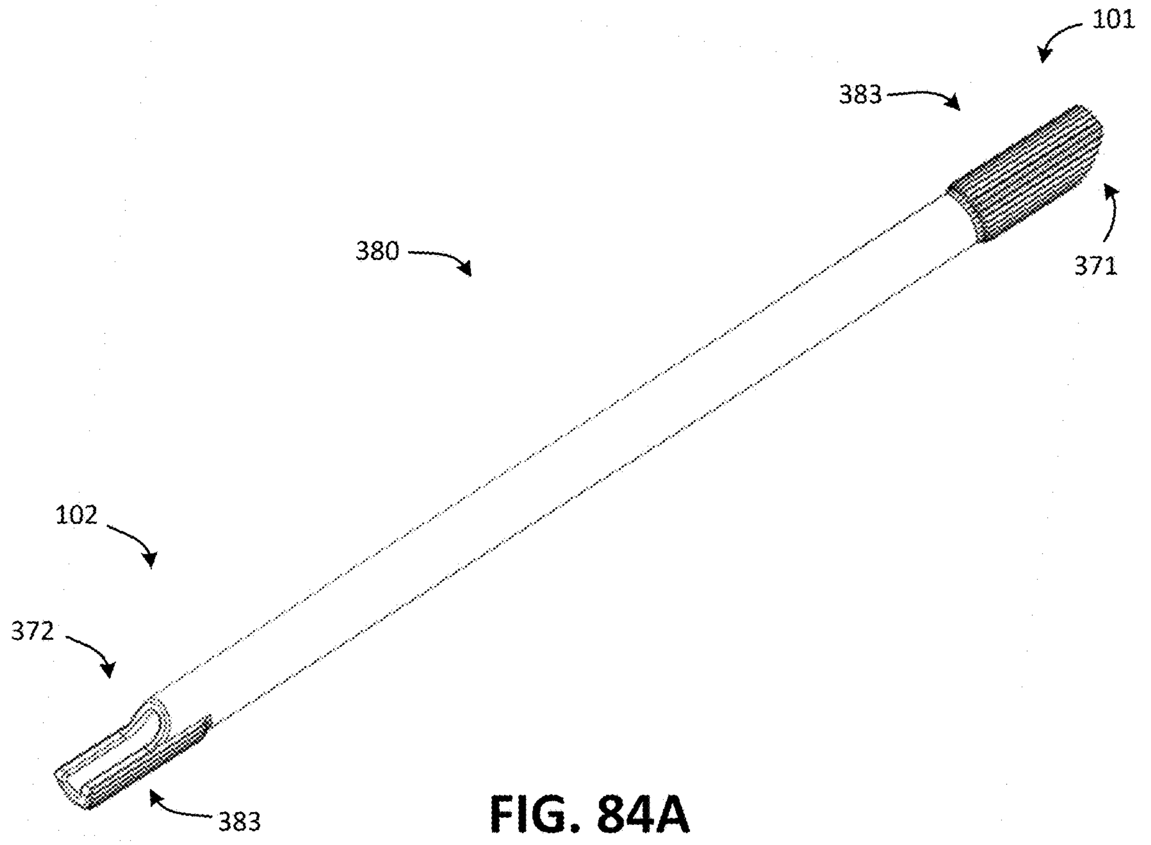
Figure 84B:
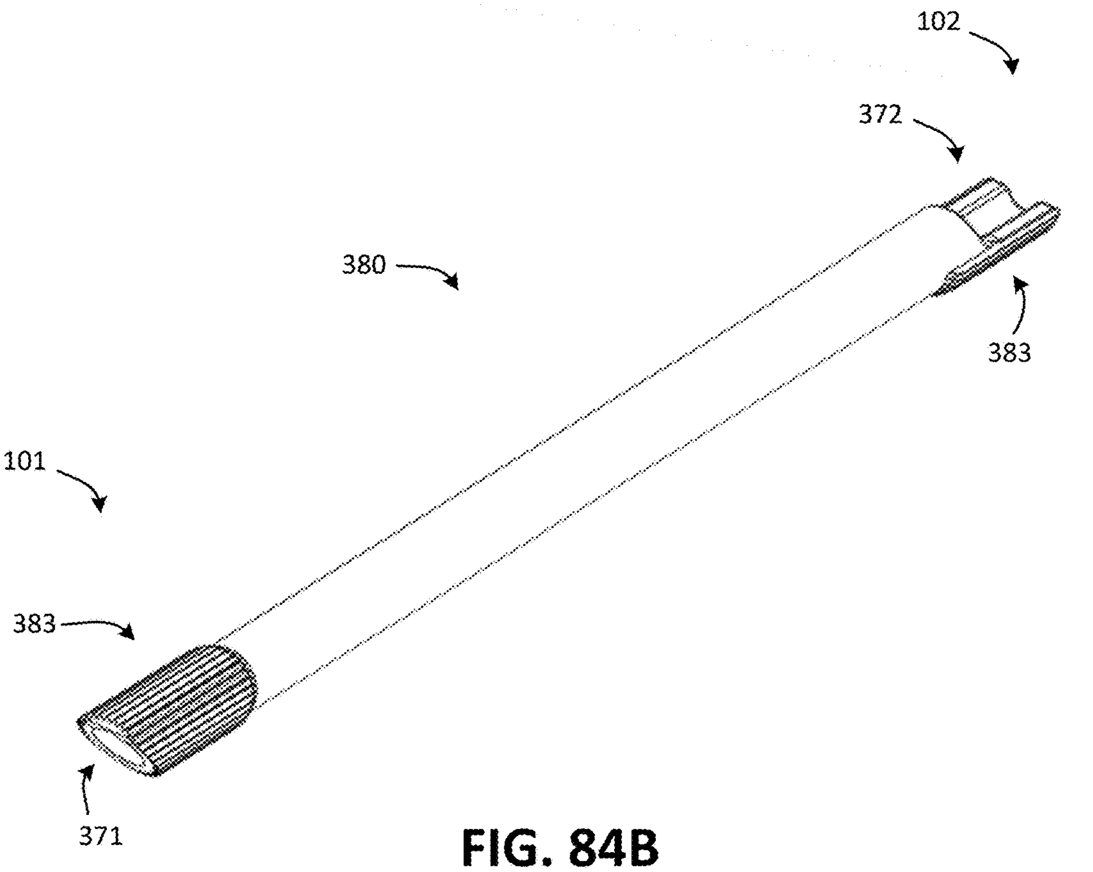
Figure 84C:
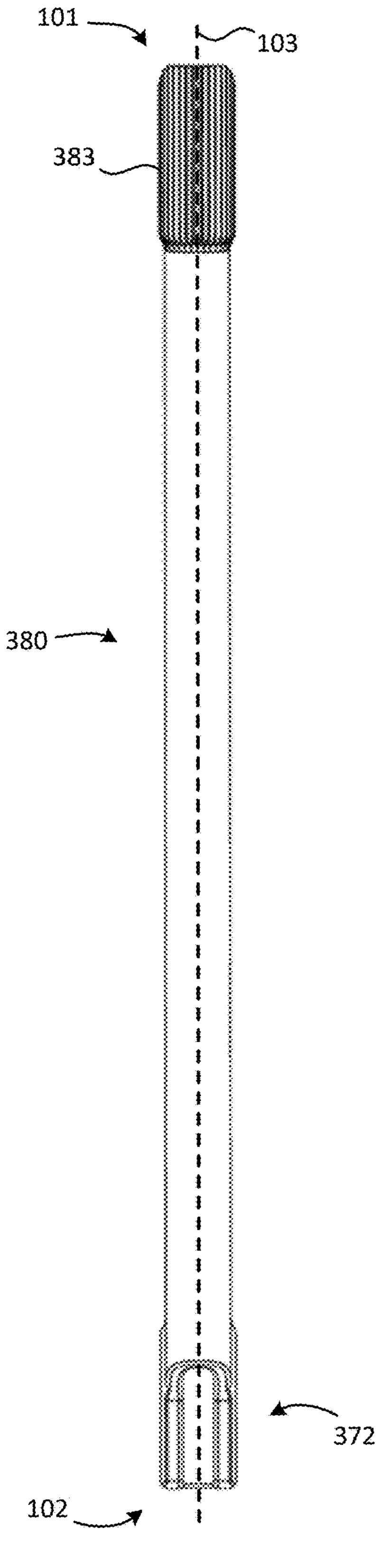
Figure 84D:
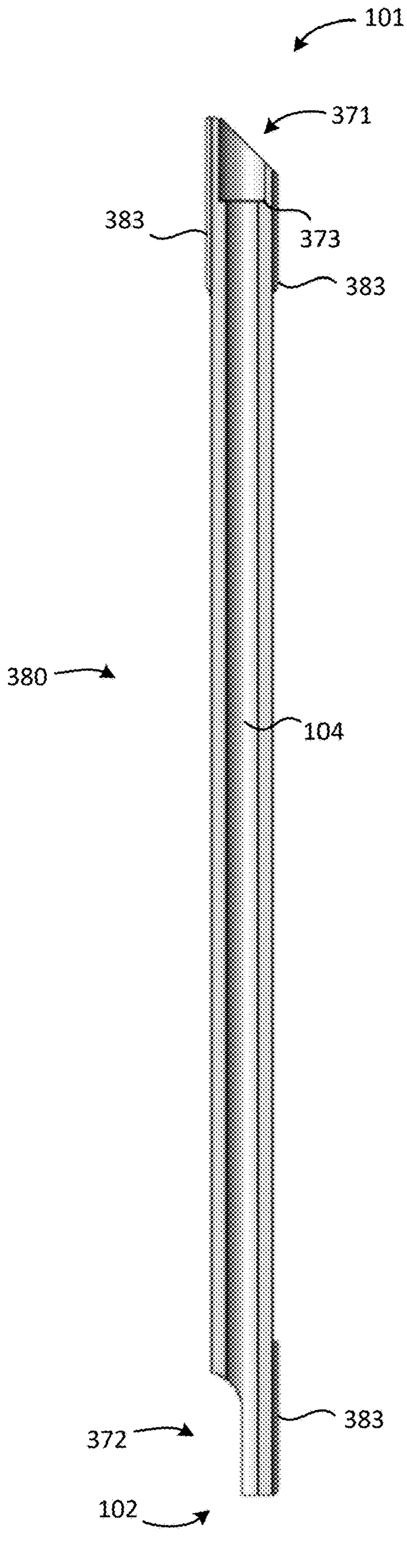
Figure 84E:
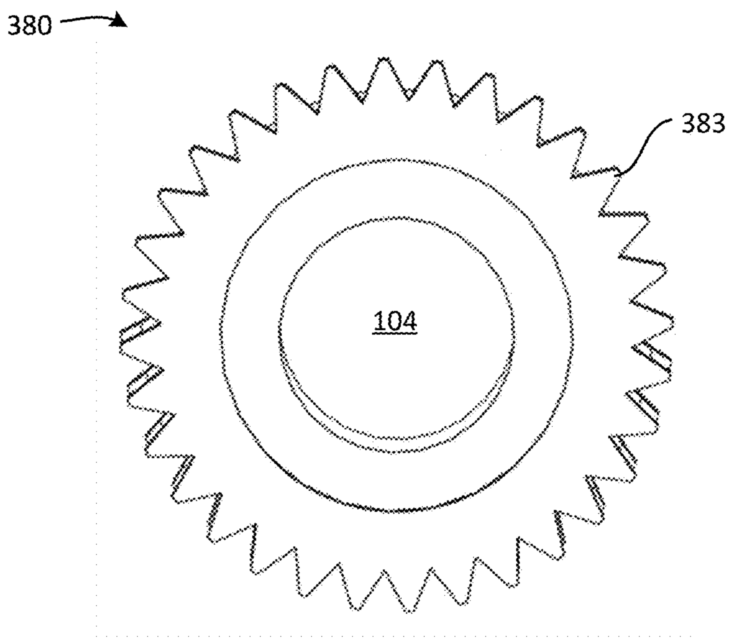
Figure 84F:
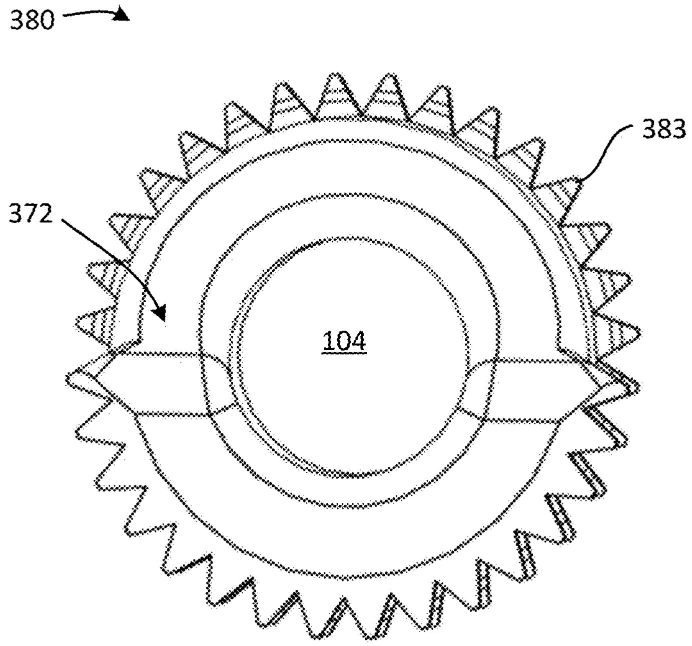
Figure 85:
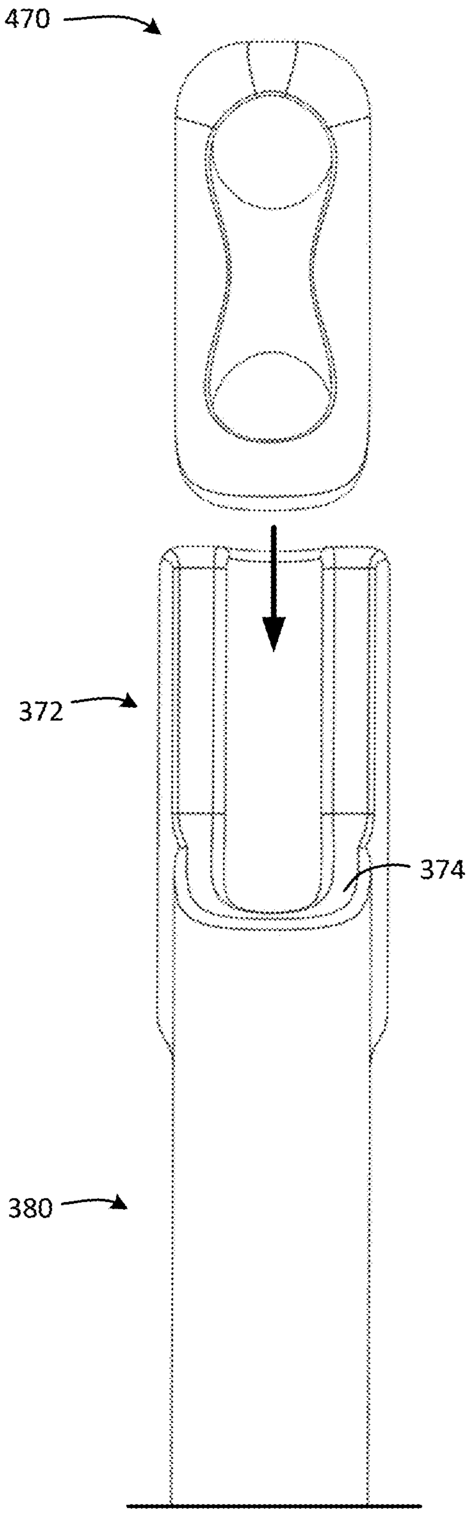
Figure 86:
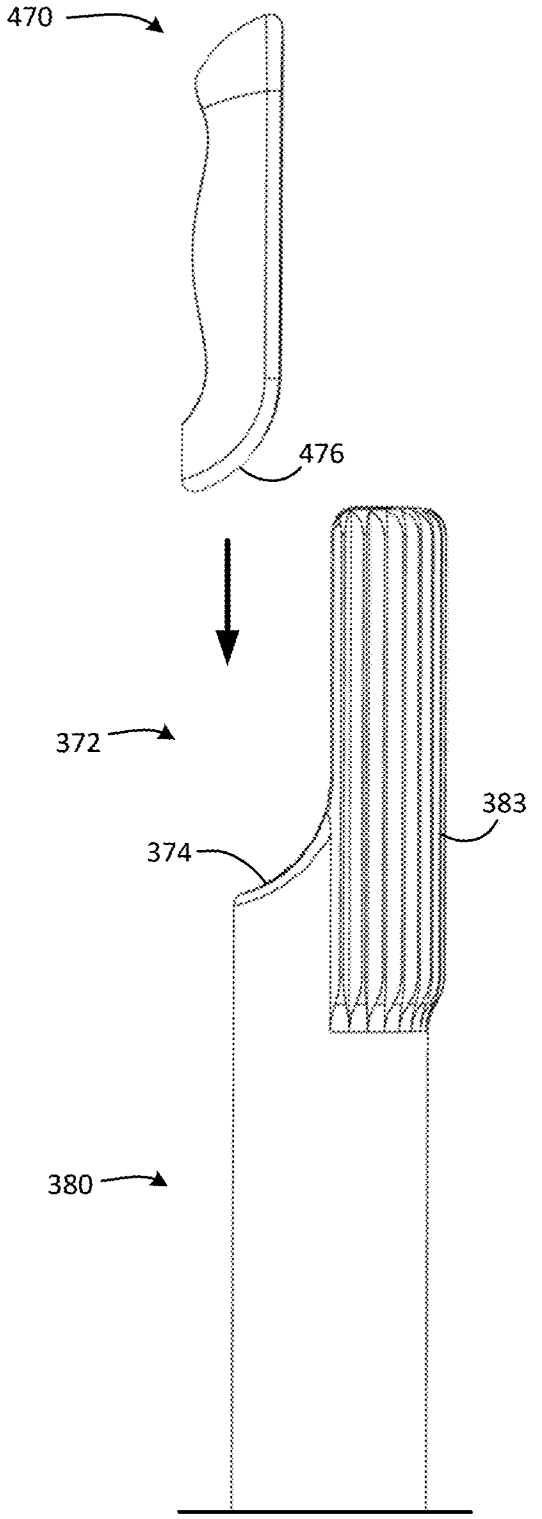
Figure 87:
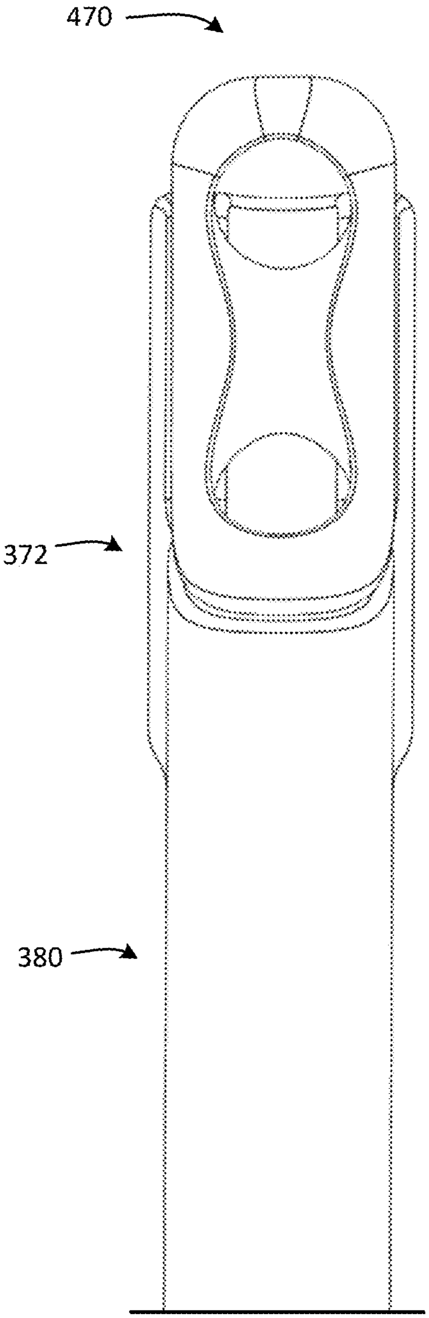
Figure 88:
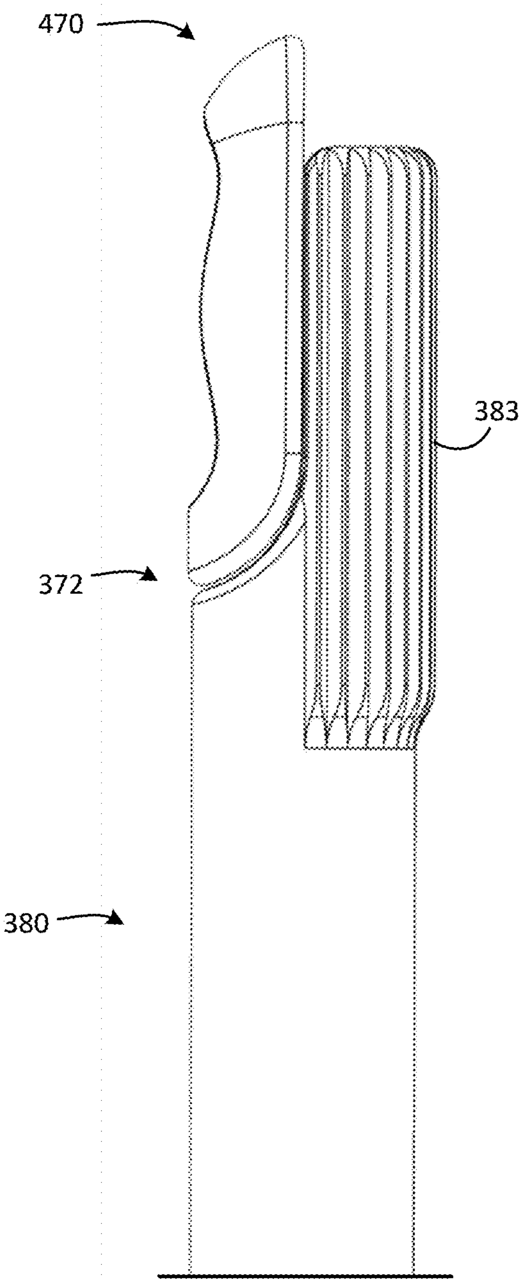
Figure 89:
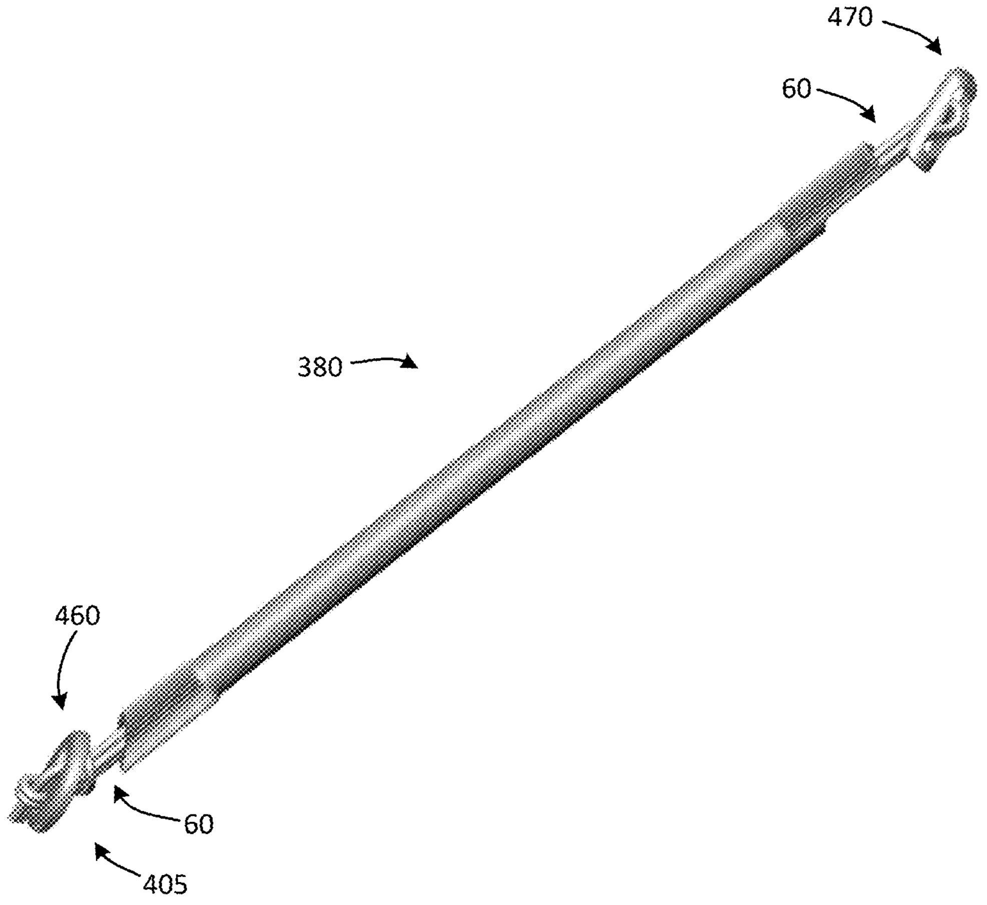
Figure 90:
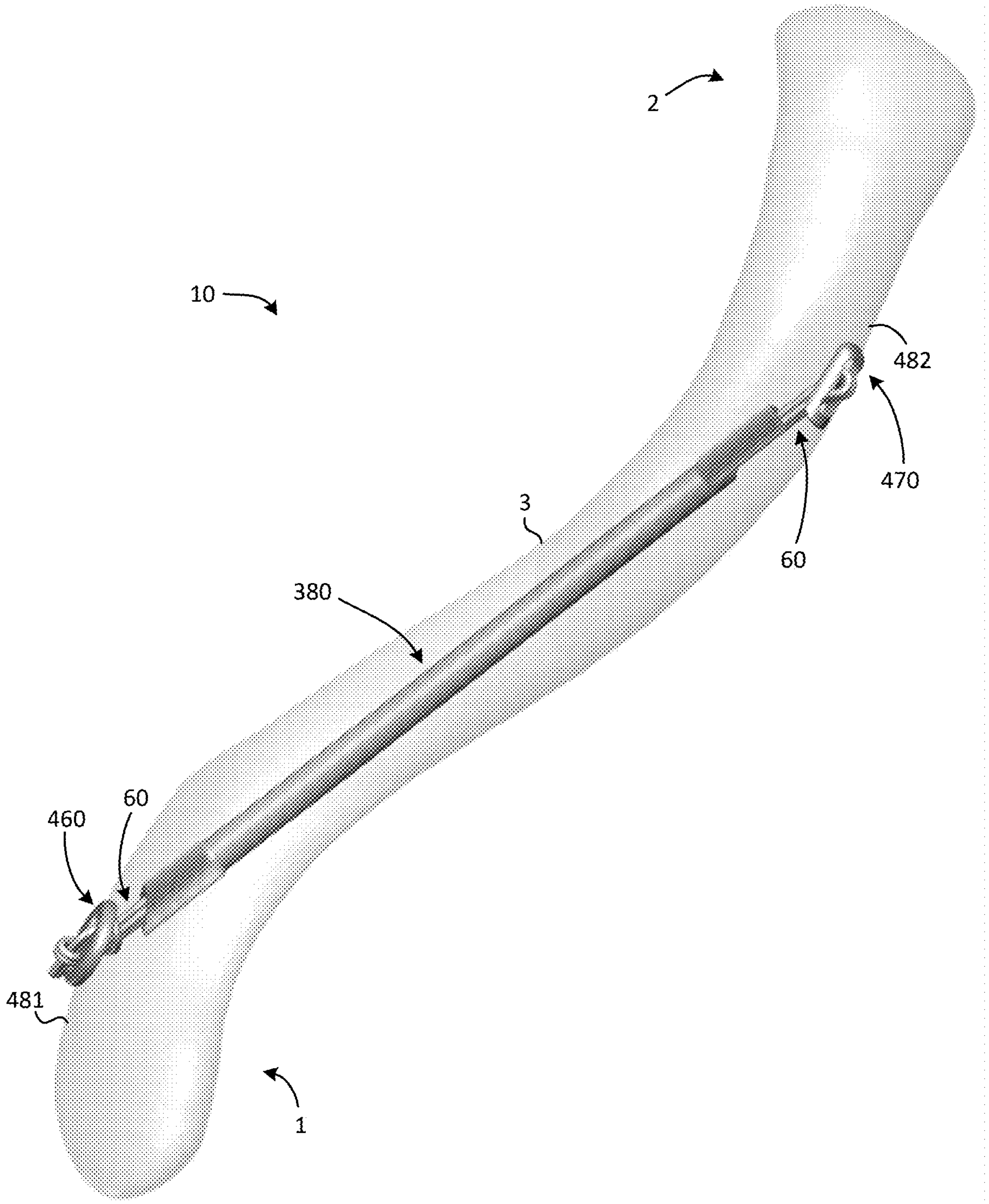
Figure 91:
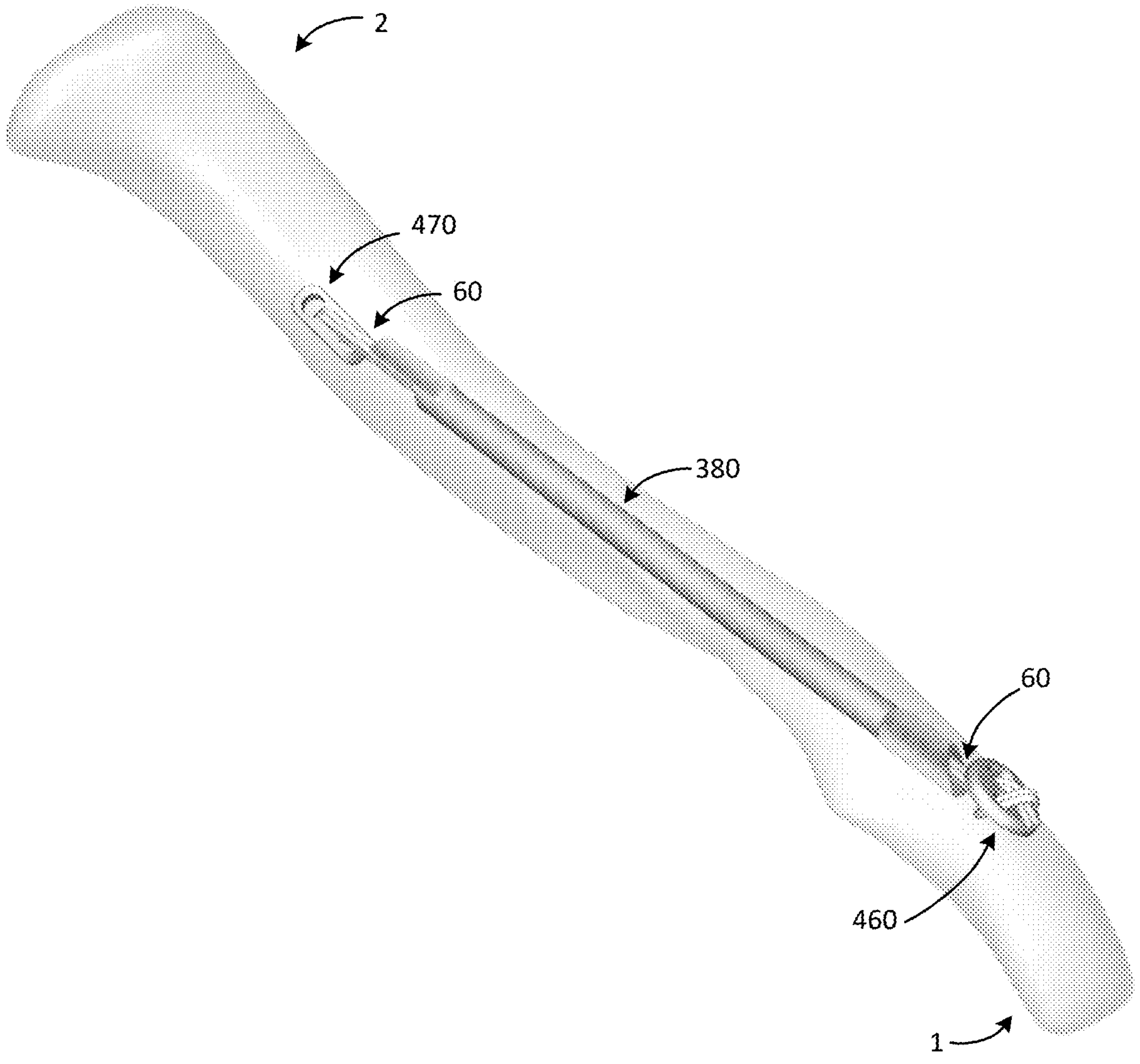
Figure 92:
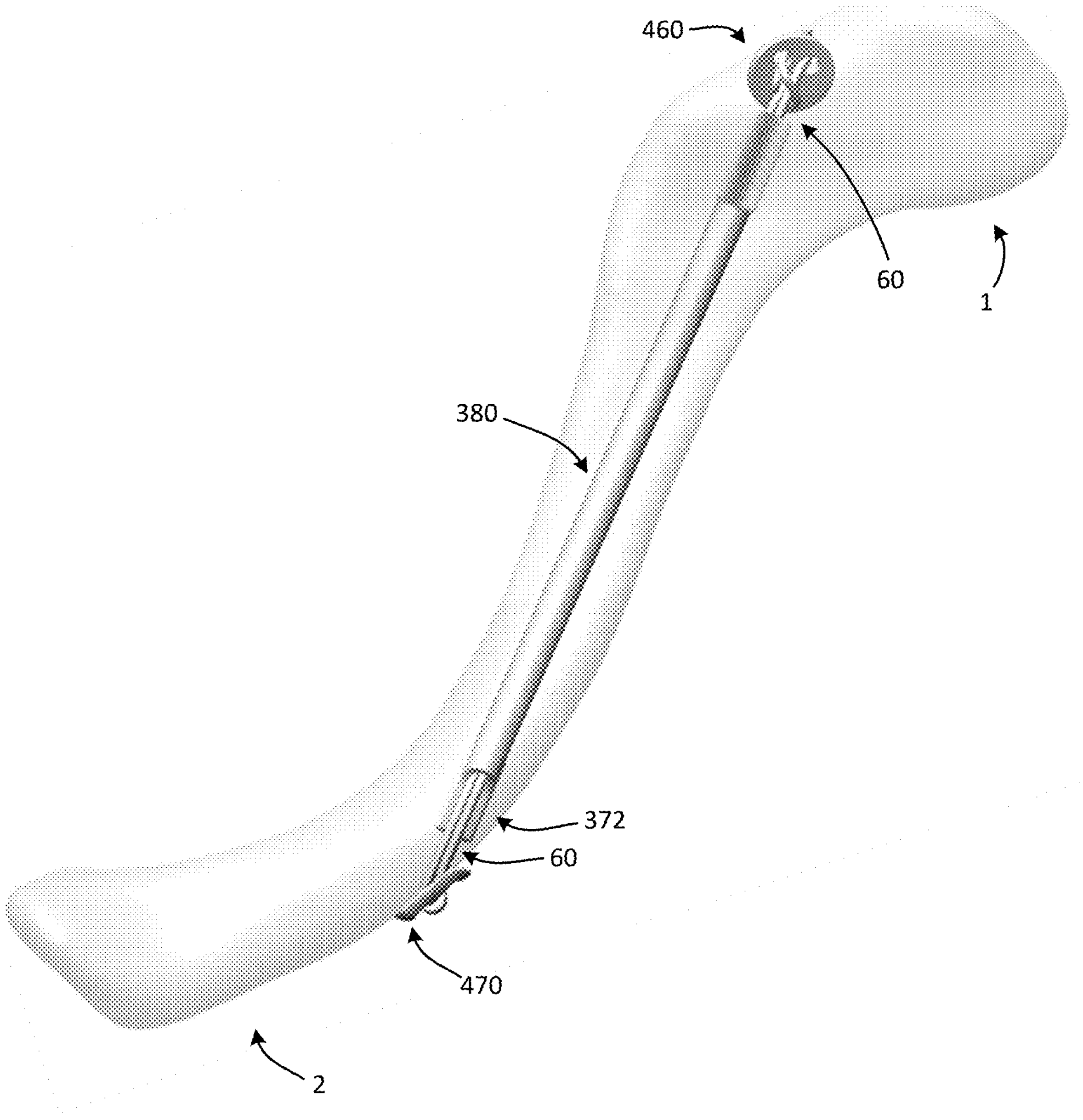
Figure 93:
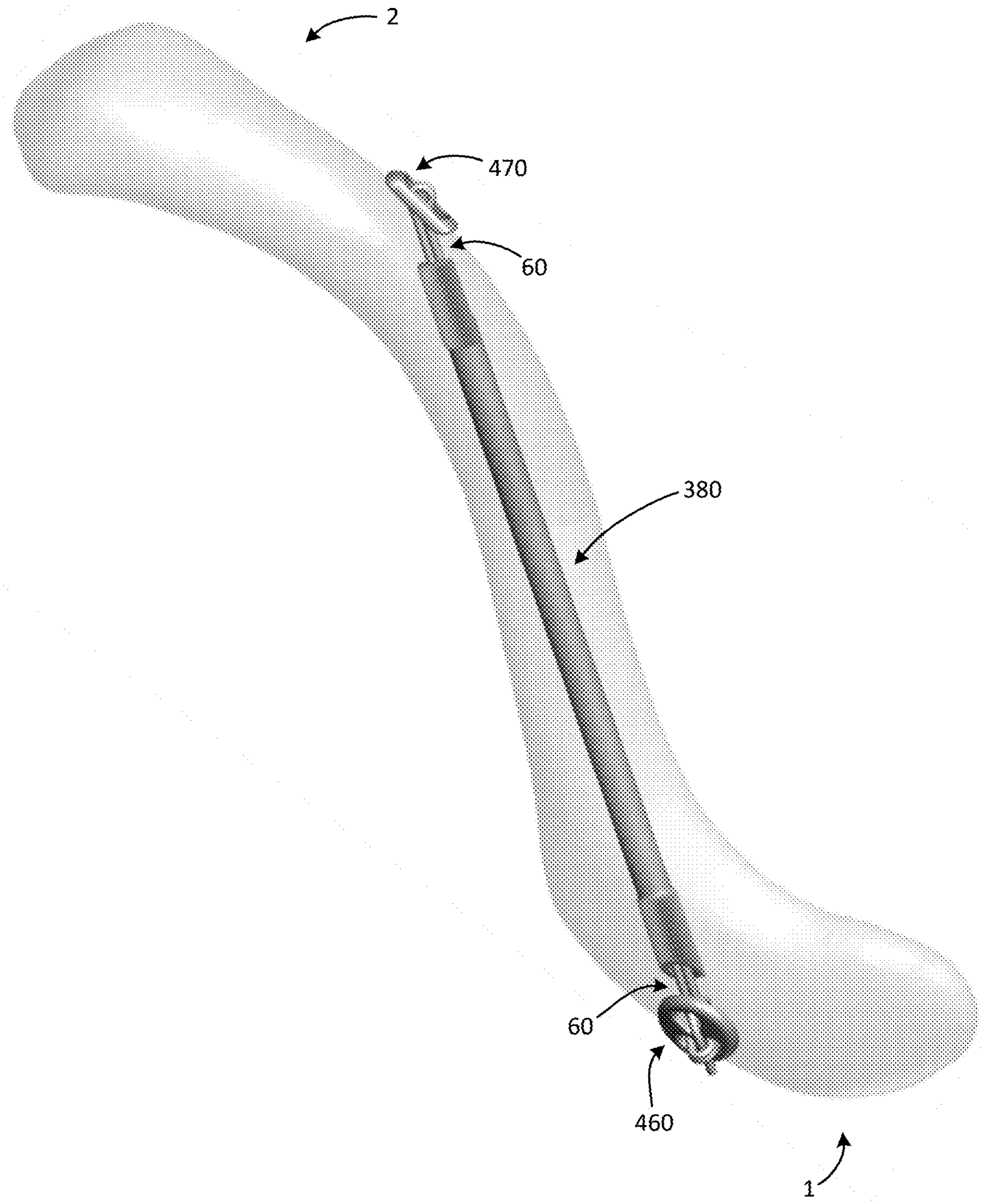

FIG. 48 illustrates a transparent proximal perspective view of the bone fixation assembly of FIG. 41 implanted in the bone;

FIG. 49 illustrates a close up top view of a distal end of the elongate fixation member of FIG. 39C with the anti-rotation bone anchor of FIG. 40C placed therein, and a transverse bone screw placed through the anti-rotation bone anchor;

FIG. 50 illustrates a side view of the assembly shown in FIG. 49;

FIG. 51 illustrates a perspective view of the bone fixation assembly of FIG. 44, with a transverse bone screw placed through the anti-rotation bone anchor;

FIG. 52 illustrates a transparent anterior perspective view of the bone fixation assembly of FIG. 44 implanted in a bone, with the transverse bone screw placed through the anti-rotation bone anchor;

FIG. 53 illustrates a transparent posterior perspective view of the bone fixation assembly shown in FIG. 52;

FIG. 54 illustrates a transparent distal perspective view of the bone fixation assembly shown in FIG. 52;

FIG. 55 illustrates a transparent proximal perspective view of the bone fixation assembly shown in FIG. 52;

FIG. 56 illustrates a ratcheting bone fixation assembly, according to another embodiment of the present disclosure;

FIG. 57 illustrates the ratcheting bone fixation assembly of FIG. 56, including a suture coupling with a rotating ratchet member of the ratcheting bone fixation assembly;

FIG. 58 illustrates the ratcheting bone fixation assembly of FIG. 57 with the suture wrapped around the rotating ratchet member;

FIG. 59A illustrates a distal perspective view of an elongate fixation member, according to another embodiment of the present disclosure;

FIG. 59B illustrates a proximal perspective view of the elongate fixation member of FIG. 59A;

FIG. 59C illustrates a close up perspective view of the distal end of the elongate fixation member shown in FIG. 59A;

FIG. 59D illustrates a close up perspective view of the proximal end of the elongate fixation member shown in FIG. 59B;

FIG. 60A illustrates a distal perspective view of an anti-rotation bone anchor, according to another embodiment of the present disclosure;

FIG. 60B illustrates a proximal perspective view of the anti-rotation bone anchor of FIG. 60A;

FIG. 60C illustrates a side view of the anti-rotation bone anchor of FIG. 60A;

FIG. 60D illustrates a proximal end view of the anti-rotation bone anchor of FIG. 60A;

FIG. 61 illustrates a partially transparent side view of a bone fixation assembly, according to another embodiment of the present disclosure;

FIG. 62 illustrates a close up view of a distal end of the bone fixation assembly of FIG. 61;

FIG. 63 illustrates a close up view of a proximal end of the bone fixation assembly of FIG. 61;

FIG. 64 illustrates a close up top view of a distal end of the elongate fixation member of FIG. 59A with the anti-rotation bone anchor of FIG. 60C placed therein, and a transverse bone screw placed through the anti-rotation bone anchor;

FIG. 65 illustrates a side view of the assembly shown in FIG. 64;

FIG. 66 illustrates a perspective view of the bone fixation assembly of FIG. 61, with a transverse bone screw placed through the anti-rotation bone anchor;

FIG. 67 illustrates a transparent anterior perspective view of the bone fixation assembly of FIG. 66 implanted in a bone;

FIG. 68 illustrates a transparent posterior perspective view of the bone fixation assembly shown in FIG. 67;

FIG. 69 illustrates a transparent distal perspective view of the bone fixation assembly shown in FIG. 67;

FIG. 70 illustrates a transparent proximal perspective view of the bone fixation assembly shown in FIG. 67;

FIG. 71A illustrates a distal perspective view of an elongate fixation member, according to another embodiment of the present disclosure;

FIG. 71B illustrates a proximal perspective view of the elongate fixation member of FIG. 71A;

FIG. 71C illustrates a side view of the elongate fixation member of FIG. 71A;

FIG. 71D illustrates a cross-sectional view of the elongate fixation member of FIG. 71C;

FIG. 72A illustrates a top perspective view of a cortical fixation element, according to an embodiment of the present disclosure;

FIG. 72B illustrates a bottom perspective view of the cortical fixation element of FIG. 72A;

FIG. 72C illustrates a front perspective view of the cortical fixation element of FIG. 72A;

FIG. 72D illustrates a side view of the cortical fixation element of FIG. 72A;

FIG. 73A illustrates a top perspective view of a cortical fixation element, according to another embodiment of the present disclosure;

FIG. 73B illustrates a bottom perspective view of the cortical fixation element of FIG. 73A;

FIG. 73C illustrates a front perspective view of the cortical fixation element of FIG. 73A;

FIG. 73D illustrates a side view of the cortical fixation element of FIG. 73A;

FIG. 74 illustrates a perspective view a bone fixation assembly, according to another embodiment of the present disclosure;

FIG. 75 illustrates a close up perspective view of a distal end of the bone fixation assembly of FIG. 74;

FIG. 76 illustrates another close up perspective view of the distal end of the bone fixation assembly of FIG. 74;

FIG. 77 illustrates a close up perspective view of a proximal end of the bone fixation assembly of FIG. 74;

FIG. 78 illustrates another close up perspective view of the proximal end of the bone fixation assembly of FIG. 74;

FIG. 79 illustrates another perspective view the bone fixation assembly of FIG. 74;

FIG. 80 illustrates an anterior perspective view of the bone fixation assembly of FIG. 79 implanted in a bone;

FIG. 81 illustrates a posterior perspective view of the bone fixation assembly shown in FIG. 80;

FIG. 82 illustrates a distal perspective view of the bone fixation assembly shown in FIG. 80;

FIG. 83 illustrates a proximal perspective view of the bone fixation assembly shown in FIG. 80;

FIG. 84A illustrates a distal perspective view of an elongate fixation member, according to another embodiment of the present disclosure;

FIG. 84B illustrates a proximal perspective view of the elongate fixation member of FIG. 84A;

FIG. 84C illustrates a side view of the elongate fixation member of FIG. 84A;

FIG. 84D illustrates a cross-sectional view of the elongate fixation member of FIG. 84C;

FIG. 84E illustrates a proximal end view of the elongate fixation member of FIG. 84A;

FIG. 84F illustrates a distal end view of the elongate fixation member of FIG. 84A;

FIG. 85 illustrates a front view of the cortical fixation element of FIG. 73A being placed on a docking surface of the elongate fixation member of FIG. 84C;

FIG. 86 illustrates a side view of the assembly of FIG. 85;

FIG. 87 illustrates a front view of the cortical fixation element of FIG. 73A placed on the docking surface of the elongate fixation member of FIG. 84C;

FIG. 88 illustrates a side view of the assembly of FIG. 87;

FIG. 89 illustrates a perspective view of a bone fixation assembly, according to another embodiment of the present disclosure;

FIG. 90 illustrates an anterior perspective view of the bone fixation assembly of FIG. 89 implanted in a bone;

FIG. 91 illustrates a posterior perspective view of the bone fixation assembly shown in FIG. 90;

FIG. 92 illustrates a distal perspective view of the bone fixation assembly shown in FIG. 90; and FIG. 93 illustrates a proximal perspective view of the bone fixation assembly shown in FIG. 90.

It is to be understood that the drawings are for purposes of illustrating the concepts of the disclosure and may not be drawn to scale. Furthermore, the drawings illustrate exemplary embodiments and do not represent limitations to the scope of the present disclosure.

DETAILED DESCRIPTION

Exemplary embodiments of the present disclosure will be best understood by reference to the drawings, wherein like parts are designated by like numerals throughout. It will be readily understood that the components of the present disclosure, as generally described and illustrated in the drawings, could be arranged and designed in a wide variety of different configurations. Thus, the following more detailed description of the embodiments of the devices, systems, and methods, as represented in the drawings, is not intended to limit the scope of the present disclosure but is merely representative of exemplary embodiments of the present disclosure.

The word "exemplary" is used herein to mean "serving as an example, instance, or illustration." Any embodiment described herein as "exemplary" is not necessarily to be construed as preferred or advantageous over other embodiments. While the various aspects of the embodiments are presented in the drawings, the drawings are not necessarily drawn to scale unless specifically indicated.

The terms "coupled" and "couplable" can include components that are coupled to each other, or that are capable of being coupled to each other, via integral formation, as well as components that are removably and/or non-removably coupled/couplable with each other. Two components may be functionally coupled to each other even though they are not in direct contact with each other. The term "abutting" refers to components that may be in direct physical contact with each other, although the components may not necessarily be attached together.

Standard medical planes of reference and descriptive terminology are employed in this specification. While these terms are commonly used to refer to the human body, certain terms may also be applicable to physical objects in general.

A standard system of three mutually perpendicular reference planes is employed. A sagittal plane divides a body into right and left portions. A coronal plane divides a body into anterior and posterior portions. A transverse plane divides a body into superior and inferior portions. A mid-sagittal, mid-coronal, or mid-transverse plane divides a body into equal portions, which may be bilaterally symmetric. The intersection of the sagittal and coronal planes defines a superior-inferior or cephalad-caudal axis. The intersection of the sagittal and transverse planes defines an anterior-posterior axis. The intersection of the coronal and transverse planes defines a medial-lateral axis. The superior-inferior or cephalad-caudal axis, the anterior-posterior axis, and the medial-lateral axis are mutually perpendicular.

Anterior means toward the front of a body. Posterior means toward the back of a body. Superior or cephalad means toward the head. Inferior or caudal means toward the feet or tail. Medial means toward the midline of a body, particularly toward a plane of bilateral symmetry of the body. Lateral means away from the midline of a body or away from a plane of bilateral symmetry of the body. Axial means toward a central axis of a body. Abaxial means away from a central axis of a body. Ipsilateral means on the same side of the body. Contralateral means on the opposite side of the body. Proximal means toward the trunk of the body. Proximal may also mean toward a user or operator. Distal means away from the trunk. Distal may also mean away from a user or operator. Dorsal means toward the top of the foot. Plantar means toward the sole of the foot. Varus means deviation of the distal part of the leg below the knee inward, resulting in a bowlegged appearance. Valgus means deviation of the distal part of the leg below the knee outward, resulting in a knock-kneed appearance.

As defined herein, the terms "flexible tensioning element" and "tension band" can comprise any tensioning element that may be utilized to preload a bone fracture in compression to resist tensile or distraction forces imparted across the bone fracture and maintain fixation/reduction of the bone fracture. Any flexible tensioning element or tension band described herein may include, but is not limited to a wire, a suture, a suture tape, a fabric, a strap, a strip, etc. Moreover, any flexible tensioning element or tension band described herein can comprise any flexible, semi-flexible, semi-rigid, or rigid material, or any combination thereof suitable for preloading a bone fracture in compression. Additionally, any flexible tensioning element or tension band described herein may include, but is not limited to a metal, an alloy, a plastic, a fiber (or group of fibers braided/woven together such as Dacron, etc.), a polymer, an elastomeric material, a flexible laminate, a resin, a film, an adhesive, etc.

Any of the devices, features, instruments, method steps, etc., that are described herein with respect to any particular bone fixation assembly or procedure may be utilized in conjunction with (or omitted from) any other bone fixation assembly that is described or contemplated herein to form any number of different combinations of devices, features, instruments, or method steps. Moreover, any of the devices, features, or instruments described or contemplated herein may be combined in any manner to produce any number of different surgical kits.

FIGS. 1A-1L illustrate example devices, instruments, and method steps for a bone fixation assembly and procedure, according to an embodiment of the present disclosure.

FIG. 1 illustrates a bone 10 comprising a first bone fragment 1 and a second bone fragment 2 separated by a bone fracture 3. In some embodiments, the bone 10 may comprise a clavicle bone. However, it will be understood that the various devices, instruments, and method steps described herein can be utilized in any combination with each other and for any type of bone fracture including, but not limited to olecranon fractures, fibula fractures, patellar fractures, malleolar fractures, etc.

Figure 1A:
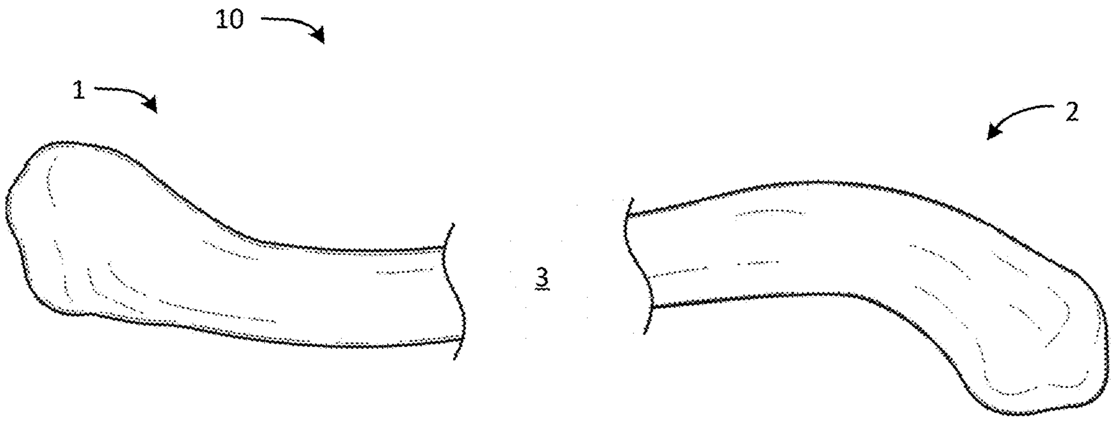
FIG. 1A illustrates a perspective side view of a fractured bone with first and second bone fragments, according to an example of the present disclosure.
Figure 1B:
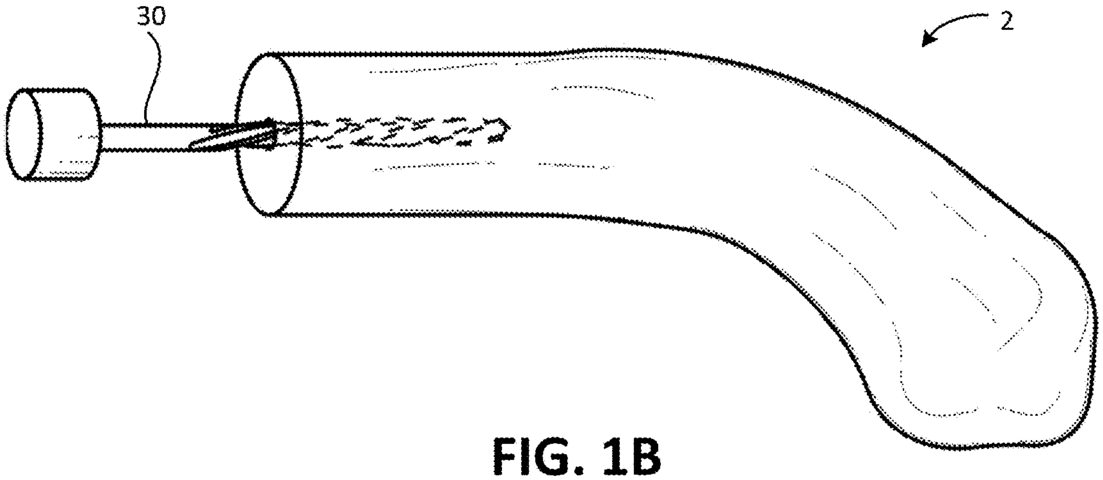
FIG. 1B illustrates a perspective side view of a reamer that may be utilized to prepare the intramedullary canals of the bone fragments of FIG. 1A.

FIG. 1B illustrates a first step of some embodiments of the procedure, in which the intramedullary canals of the first and second bone fragments 1, 2 may be prepared with a drill bit or reamer 30. The intramedullary canals of the first and second bone fragments 1, 2 may be drilled and/or reamed with any diameter drill bit or reamer to any desired depth within the intramedullary canal in order to form a prepared intramedullary canal. FIG. 1D illustrates the first and second bone fragments 1, 2 with prepared intramedullary canals including a first longitudinal bone tunnel or first intramedullary canal 11, and a second longitudinal bone tunnel or second intramedullary canal 12.

In some non-limiting embodiments of the procedure, a 4.2 mm diameter drill bit may be utilized and each intramedullary canal of the first and second bone fragments 1, 2 may be drilled and/or reamed to a depth of about 3 cm. However, it will be understood that in other embodiments any diameter size and/or any depth may be utilized, as desired.

Moreover, it will also be understood that in some embodiments of the procedure the intramedullary canals of the bone fragments may not require preparation, such as drilling, reaming, etc. For example, in some embodiments a suitable intramedullary rod may be press-fit and/or tamped into an unprepared intramedullary canal of a bone fragment.

Figure 1C:
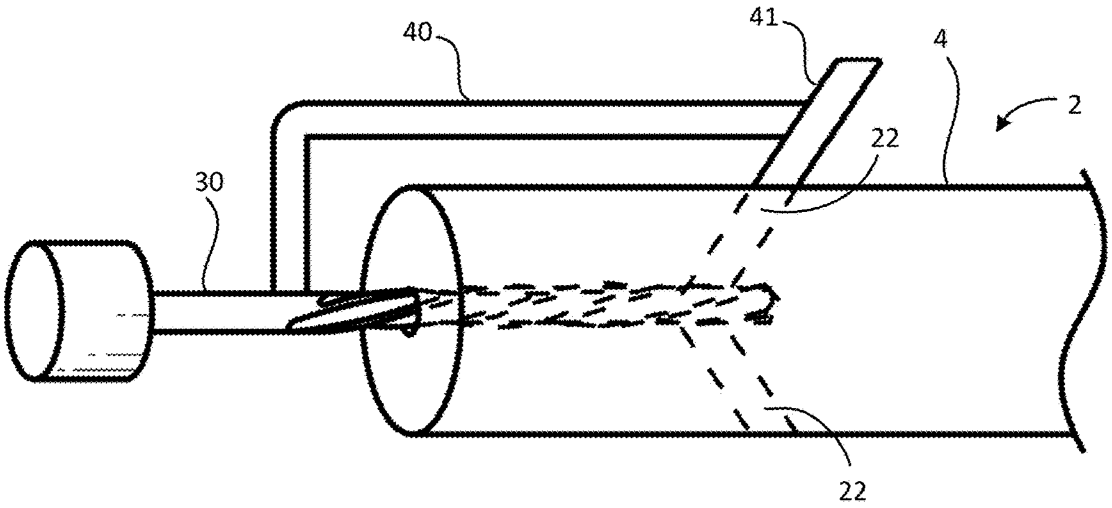
FIG. 1C illustrates a perspective side view of a drill guide that may be utilized to prepare one or more transverse bone tunnels in the bone fragments of FIG. 1A.
Figure 1D:
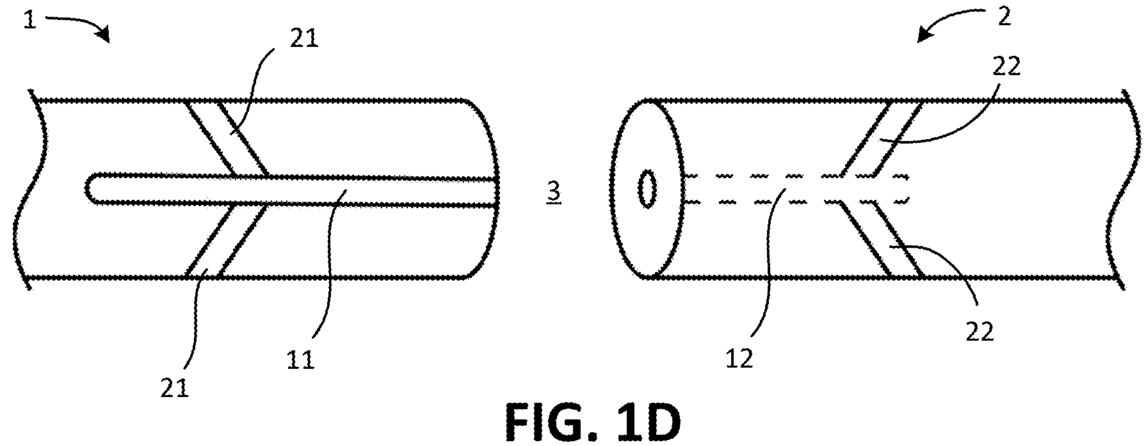
FIG. 1D illustrates a perspective side view of the bone fragments of FIG. 1A with prepared intramedullary canals and transverse bone tunnels.

FIG. 1C illustrates a second step of some embodiments of the procedure, in which a drill guide 40 may be utilized to place one or more transverse bone tunnels through a cortical surface 4 of the bone 10 and down into the prepared intramedullary canals of the bone fragments with a suitable drill bit (not shown).

In some embodiments, the drill guide 40 may be configured to utilize the reamer 30 as a reference to place a drill guide barrel 41 at a correct location along the cortical surface 4 of the bone 10, as shown in FIG. 1C. In this manner, the drill guide 40 may utilize the morphology and/or depth of the prepared intramedullary canals to guide the placement of the one or more transverse bone tunnels via the drill guide barrel 41. FIG. 1D illustrates the first and second bone fragments 1, 2 with prepared transverse bone tunnels including one or more first transverse bone tunnels 21 and one or more second transverse bone tunnels 22.

Figure 1E:
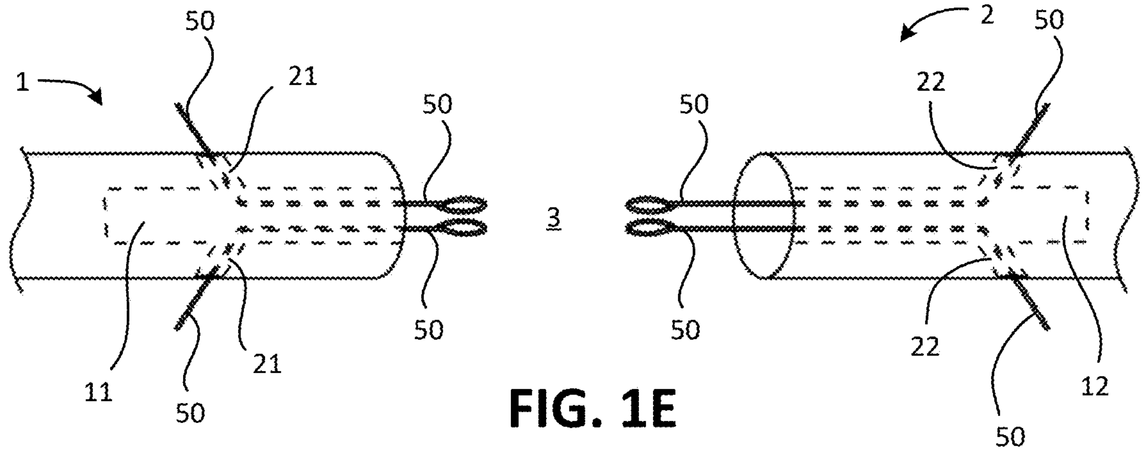
FIG. 1E illustrates a perspective side view of the bone fragments of FIG. 1A with retrieval wires inserted through the intramedullary canals and transverse bone tunnels.

FIG. 1E illustrates a third step of some embodiments of the procedure, in which one or more retrieval wires 50 may be placed through the first and second transverse bone tunnels 21, 22 and out the first and second intramedullary canals 11, 12. This step (and/or other similar steps described herein) may be facilitated with any suitable tool. In some embodiments, a magnetic wire retriever (not shown) with one or more magnets located on a tip of the magnetic wire retriever may be utilized. The magnetic wire retriever may be inserted into a bone tunnel to magnetically capture a wire and retrieve the wire from the bone tunnel. However, it will be understood that any other tool (or not tool at all) may be utilized to help facilitate the step of threading a flexible tensioning element through a bone tunnel.

Figure 1F:
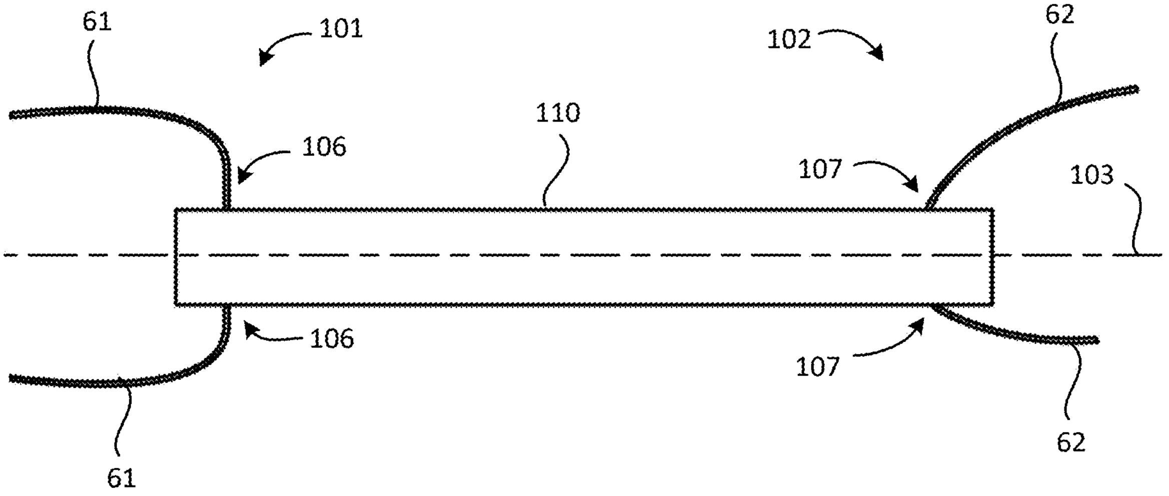
FIG. 1F illustrates a side view of an elongate fixation member with flexible tensioning elements passing through transverse passageways of the elongate fixation member, according to another embodiment of the present disclosure.

FIG. 1F illustrates an elongate fixation member 110, according to an embodiment of the present disclosure. The elongate fixation member 110 may generally include a proximal portion or first portion 101, a distal portion or second portion 102, and a central longitudinal axis 103.

In some embodiments, the elongate fixation member 110 may be configured to couple with at least one flexible tensioning element to secure the elongate fixation member to the bone 10.

In some embodiments, a first end of the flexible tensioning element may be couplable with a second end of the flexible tensioning element to secure the elongate fixation member 110 to the bone 10.

In some embodiments, the flexible tensioning element may comprise a first tension band or a first flexible tensioning element 61, as well as a second tension band or a second flexible tensioning element 62 in order to secure the elongate fixation member 110 to the bone 10.

In some embodiments, the elongate fixation member 110 may include a first transverse passageway 106 configured to receive the first flexible tensioning element 61 therethrough from a first direction transverse to the central longitudinal axis 103 of the elongate fixation member 110. The elongate fixation member 110 may also include a second transverse passageway 107 configured to receive the second flexible tensioning element 62 therethrough from a second direction transverse to the central longitudinal axis 103 of the elongate fixation member 110.

In some embodiments, the first direction and the second direction may be similar to each other.

In some embodiments, the first direction and the second direction may be opposite from each other.

In some embodiments, the first and second flexible tensioning elements 61, 62 may be couplable to each other in order to secure the elongate fixation member 110 to the bone 10.

Figure 1G:
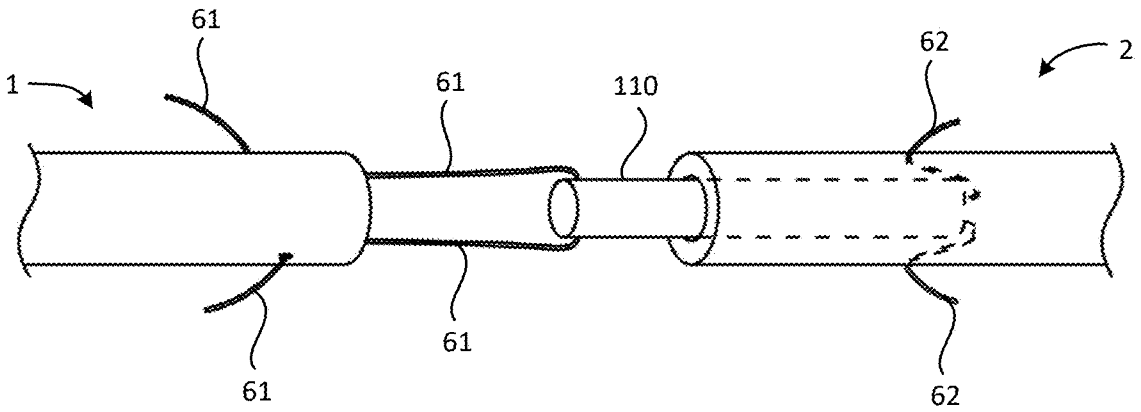
FIG. 1G illustrates a perspective side view of the elongate fixation member of FIG. 1F inserted into one of the prepared bone fragments of FIG. 1D with the flexible tensioning elements passing through the transverse bone tunnels.
Figure 1H:
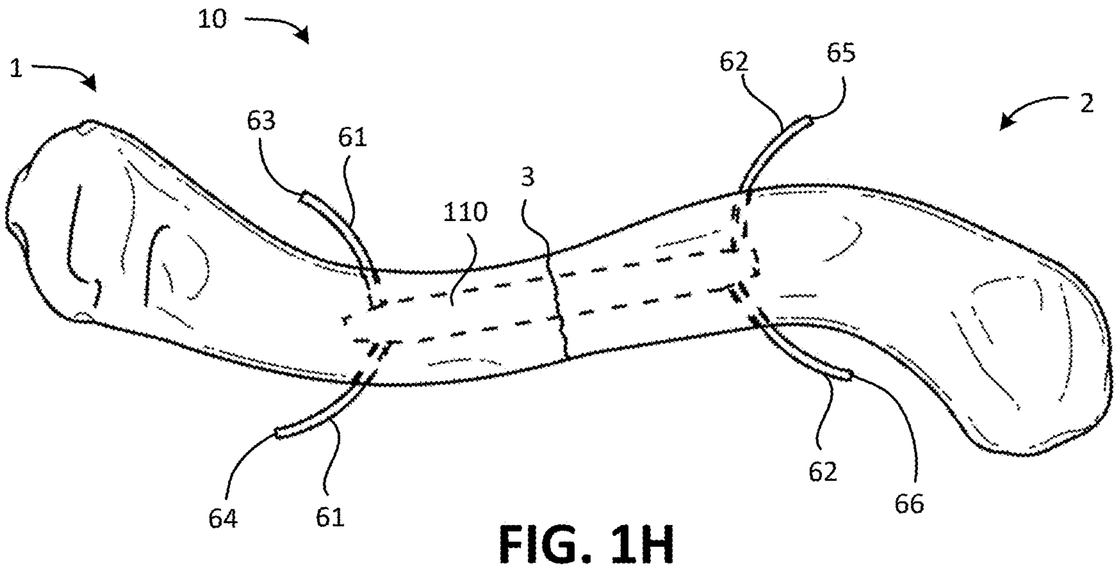
FIG. 1H illustrates a perspective side view of FIG. 1G with the elongate fixation member inserted into both bone fragments and the bone fracture reduced.
Figure 1I:
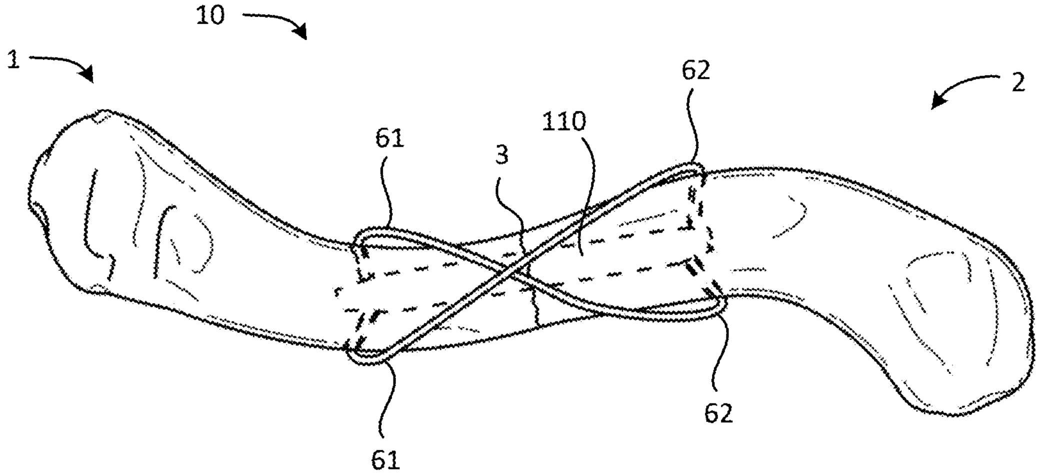
FIG. 1I illustrates a perspective side view of FIG. 1H with the flexible tensioning elements coupled to each other.

With reference to FIGS. 1H and 1I, in some embodiments a first end 63 of the first flexible tensioning element 61 may be couplable with a second end 66 of the second flexible tensioning element 62, and a second end 64 of the first flexible tensioning element 61 may be couplable with a first end 65 of the second flexible tensioning element 62 to form a crisscross pattern that spans the bone fracture 3 and secures the elongate fixation member 110 to the bone 10.

In some embodiments, the flexible tensioning elements may be configured to span the bone fracture 3 intermediate the first bone fragment 1 and the second bone fragment 2 to preload the bone fracture 3 in compression to resist tensile force imparted across the bone fracture 3, thereby maintaining fixation of the first bone fragment 1 relative to the second bone fragment 2.

In some embodiments, the elongate fixation member 110 may comprise an intramedullary rod.

In some embodiments, the elongate fixation member 110 may include a generally cylindrical shape.

In some embodiments, the elongate fixation member 110 may be solid or substantially solid. However, it will also be understood that in some embodiments the elongate fixation member 110 may comprise an at least partially hollow interior.

In some embodiments, the elongate fixation member 110 may comprise a rigid material to provide rigid fixation of the first and second bone fragments 1, 2 relative to each other.

FIG. 1G illustrates a fourth step of some embodiments of the procedure, in which the one or more retrieval wires 50 shown in FIG. 1E may be utilized to couple with and retrieve the first and second flexible tensioning elements 61, 62 in order to pull the first and second flexible tensioning elements 61, 62 through the intramedullary canals and back through the transverse bone tunnels formed in the bone fragments.

FIGS. 1G and 1H illustrate a fifth and sixth step of some embodiments of the procedure, in which the elongate fixation member 110 may be inserted into the prepared intramedullary canals of the first and second bone fragments 1, 2. Specifically, FIG. 1G illustrates the elongate fixation member 110 inserted into the second bone fragment 2 in a fifth step, and FIG. 1H illustrates the elongate fixation member 110 inserted into both the first and second bone fragments 1, 2 in a sixth step with the bone fracture 3 reduced.

Thus, in some embodiments the first portion 101 of the elongate fixation member 110 may be couplable within the first intramedullary canal 11 of the first bone fragment 1 of the bone 10, and the second portion 102 of the elongate fixation member 110 may be couplable within the second intramedullary canal 12 of the second bone fragment 2 of the bone 10 to provide fixation of the second bone fragment 2 relative to the first bone fragment 1.

In some embodiments, steps four through six discussed above can be performed together in a partial stepwise manner in order to ensure the flexible tensioning elements remain threaded through the transverse bone tunnels during the procedure. In this manner, initial reduction and/or initial fixation of the bone fracture 3 may be achieved through either or both of: (1) inserting the elongate fixation member 110 into the intramedullary canals of the bone fragments via a press fit; and/or (2) tensioning the flexible tensioning elements in order to draw the bone fragments together to achieve initial reduction and/or initial fixation of the bone fracture 3.

FIG. 1I illustrates a seventh step of some embodiments of the procedure, in which the first and second flexible tensioning elements 61, 62 may be woven around the bone fracture 3 and secured together. The first and second flexible tensioning elements 61, 62 may be configured to span the bone fracture 3 and preload the bone fracture 3 in compression to resist tensile and/or distraction forces imparted across the bone fracture 3, thereby maintaining fixation of the first bone fragment 1 relative to the second bone fragment 2. In this manner, the bone fracture 3 may receive improved fixation and reduction strength by combining the elongate fixation member 110 with the first and second flexible tensioning elements 61, 62.

In some embodiments, the first and second flexible tensioning elements 61, 62 may be woven around the bone fracture 3 such that they form a crisscross pattern that spans the bone fracture 3 on a side of the bone 10.

In some embodiments, the first and second flexible tensioning elements 61, 62 may be woven around the bone fracture 3 such that they form a crisscross pattern that spans the bone fracture 3 on a superior side of the bone 10. However, it will also be understood that in other embodiments the flexible tensioning elements may be woven around the bone fracture 3 to form any suitable pattern and on any side of the bone 10 to achieve a desired resistance to tensile and/or distraction force that may be imparted across the bone fracture 3.

Figure 1J:
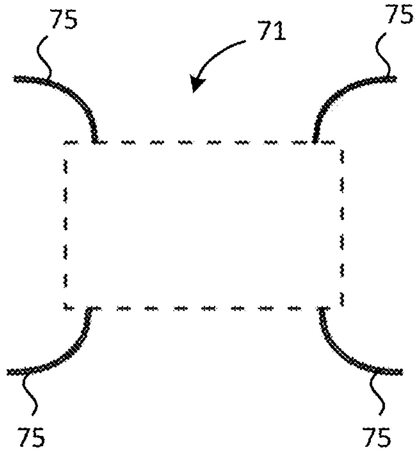
FIG. 1J illustrates a top view of a securing element, according to an embodiment of the present disclosure.
Figure 1K:
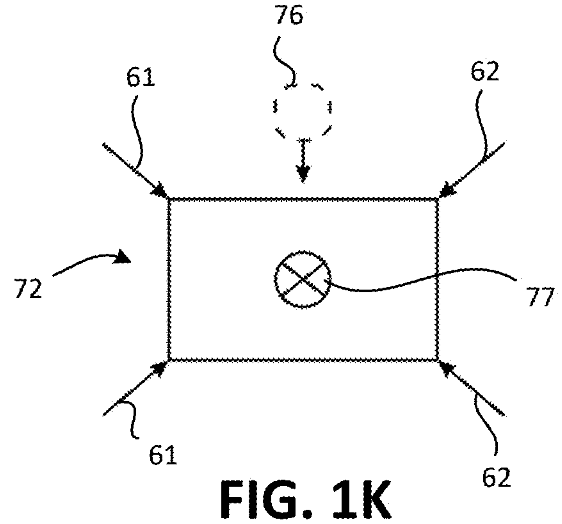
FIG. 1K illustrates a top view of a securing element, according to another embodiment of the present disclosure.
Figure 1L:
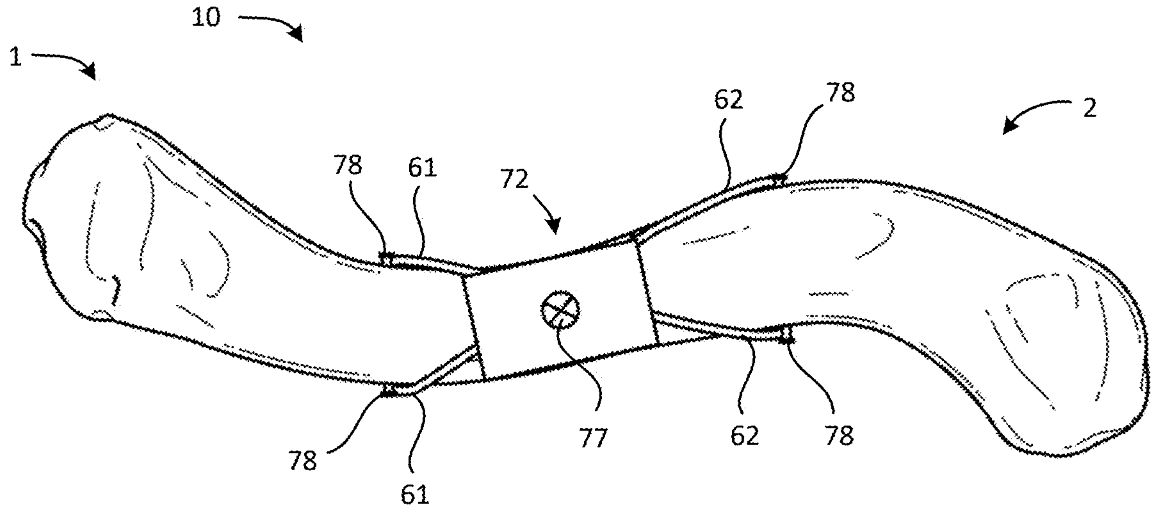
FIG. 1L illustrates a perspective side view of the securing element of FIG. 1K coupled to the flexible tensioning elements of FIG. 1J.

FIGS. 1J-1L illustrate an eighth step of some embodiments of the procedure, in which a clamp or securing element may be applied to the flexible tensioning elements to secure flexible tensioning elements in place and prevent the flexible tensioning elements from loosening over time.

FIG. 1J illustrates a top view of a first securing element 71, as one non-limiting example of the present disclosure, that may be utilized to secure the first and second flexible tensioning elements 61, 62 in place and prevent the first and second flexible tensioning elements 61, 62 from loosening over time. The first securing element 71 may include one or more attachment features 75 that may be configured to couple with the bone 10 and/or the first and second flexible tensioning elements 61, 62 to prevent loosening of the first and second flexible tensioning elements 61, 62 over time.

FIG. 1K illustrates a top view of a second securing element 72, as another non-limiting example of the present disclosure, that may be utilized to secure the first and second flexible tensioning elements 61, 62 in place and prevent the first and second flexible tensioning elements 61, 62 from loosening over time. FIG. IL illustrates the second securing element 72 of FIG. 1K coupled to the first and second flexible tensioning elements 61, 62 of the bone fixation assembly from FIG. 1I.

In some embodiments, the second securing element 72 may be configured to receive and/or couple with the crisscross pattern formed by the first and second flexible tensioning elements 61, 62 to prevent the first and second flexible tensioning elements 61, 62 from loosening over time.

In some embodiments, the second securing element 72 may include one or more holes or channels (not shown) configured to receive the first and second flexible tensioning elements 61, 62 therein.

In some embodiments, the first and second flexible tensioning elements 61, 62 may be threaded into/through the second securing element 72 via the holes/channels in order to secure the flexible tensioning elements in place and prevent the flexible tensioning elements from loosening over time.

In some embodiments, the second securing element 72 may include a fastener 76 (e.g., such as a set screw, a screw cap, etc.) and a fastener aperture 77 configured to receive the fastener 76 therein. In these embodiments, the fastener 76 may removably couple with the second securing element 72 (e.g., via threading or by some other means) and may be configured to apply a compression force to the first and second flexible tensioning elements 61, 62 to prevent the first and second flexible tensioning elements 61, 62 from loosening over time.

In some embodiments, the fastener 76 may also be configured to apply a tension force to the first and second flexible tensioning elements 61, 62 in order to preload the bone fracture in compression to further resist tensile/distraction forces that may be imparted across the bone fracture 3 and provide additional fixation of the first bone fragment 1 relative to the second bone fragment 2. For example, the fastener 76 may include one or more prongs (not shown) that may engage with the first and second flexible tensioning elements 61, 62 as the fastener 76 rotates into the fastener aperture 77 via threading or by some other means. In this manner, the one or more prongs may also engage with and rotate the first and second flexible tensioning elements 61, 62 to tighten them up and impart a tension force to the first and second flexible tensioning elements 61, 62 to preload the bone fracture 3 in compression.

In some embodiments, the flexible tensioning elements may cross each other on top of the second securing element 72. However, it will also be understood that in other embodiments the flexible tensioning elements may cross each other within the second securing element 72 and/or under the second securing element 72.

In some embodiments, one or more bone fasteners 78 may also be utilized to provide additional tension and/or fixation to the first and second flexible tensioning elements 61, 62 in order to preload the bone fracture 3 in compression and/or to prevent the first and second flexible tensioning elements 61, 62 from loosening over time, as shown in FIG. 1L. In these embodiments, the one or more bone fasteners 78 may be configured to hold the ends of the first and second flexible tensioning elements 61, 62 in place with respect to the first and second bone fragments 1, 2.

In some embodiments, the one or more bone fasteners 78 may comprise bone screws configured to couple with the bone 10. The bone screws may include bone screw heads configured to capture and/or hold the first and second flexible tensioning elements 61, 62 in order to preload the bone fracture 3 in compression and/or to prevent the first and second flexible tensioning elements 61, 62 from loosening over time.

FIGS. 2A-2F illustrate example devices, instruments, and method steps for a bone fixation assembly and procedure, according to another embodiment of the present disclosure.

In some embodiments the bone 10 may comprise a distal or proximal end of a bone, such as a fractured olecranon process of the ulna, as one non-limiting example. However, it will be understood that the various devices, instruments, and method steps described herein can be utilized in any combination with each other and for any type of bone fracture including, but not limited to clavicle fractures, fibula fractures, patellar fractures, malleolar fractures, olecranon process fractures, etc.

Figure 2A:
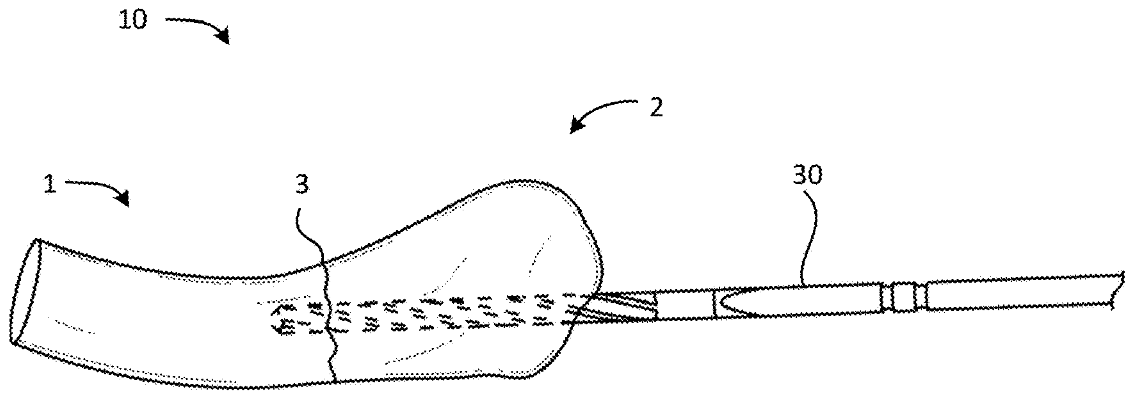
FIG. 2A illustrates a perspective side view of a fractured bone and reamer, according to another example of the present disclosure.
Figure 2B:
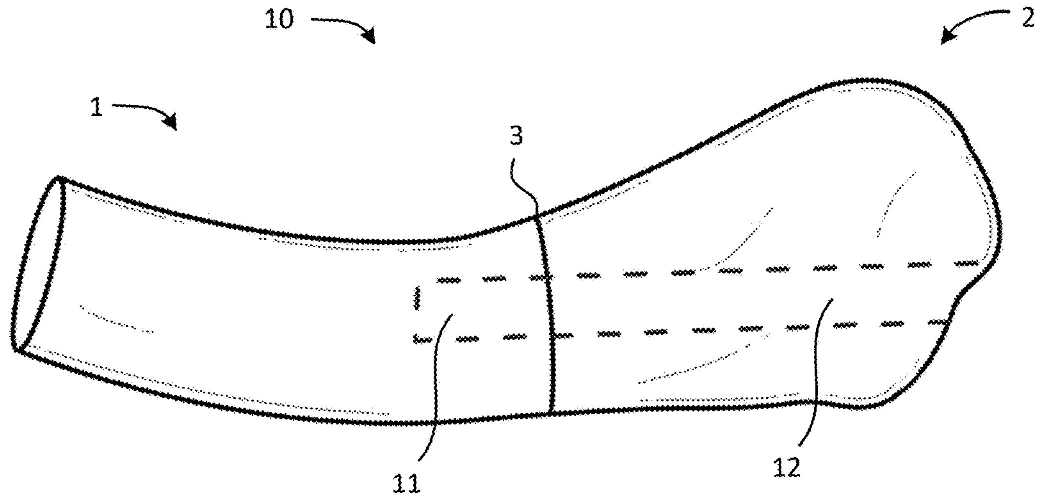
FIG. 2B illustrates a perspective side view of the bone of FIG. 2A with prepared intramedullary canals.

FIG. 2A illustrates a first step of some embodiments of the procedure, in which the intramedullary canals of the first and second bone fragments 1, 2 may be prepared with the reamer 30. The intramedullary canals of the first and second bone fragments 1, 2 may be drilled and/or reamed with any diameter drill bit or reamer to any desired depth within the intramedullary canals. FIG. 2B illustrates the first and second bone fragments 1, 2 with prepared first and second intramedullary canals 11, 12.

Figure 2C:
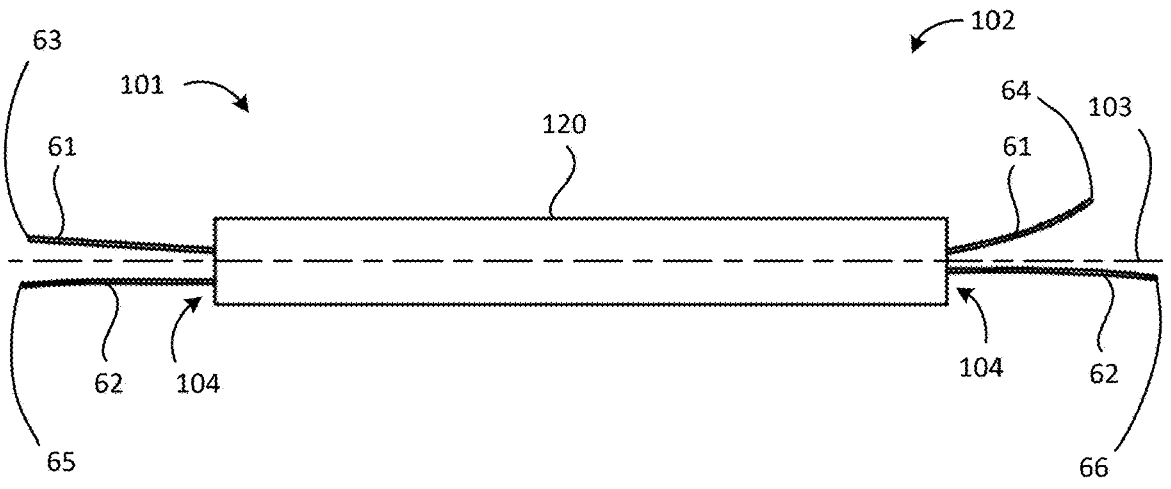
FIG. 2C illustrates a side view of an elongate fixation member with flexible tensioning elements passing through a longitudinal passageway of the elongate fixation member, according to an embodiment of the present disclosure.

FIG. 2C illustrates a side view of an elongate fixation member 120, according to another embodiment of the present disclosure. The elongate fixation member 120 may generally include the proximal or first portion 101, the distal or second portion 102, and the central longitudinal axis 103.

In some embodiments, the elongate fixation member 120 may be configured to couple with at least one flexible tensioning element to secure the elongate fixation member 120 to the bone 10.

In some embodiments, the elongate fixation member 120 may comprise a longitudinal passageway 104 formed through the elongate fixation member 120 and configured to receive the at least one flexible tensioning element therethrough.

In some embodiments, a first end of the at least one flexible tensioning element may be couplable with a second end of the at least one flexible tensioning element to secure the elongate fixation member 110 to the bone 10.

In some embodiments, the at least one flexible tensioning element may comprise the first flexible tensioning element 61 and the second flexible tensioning element 62 to secure the elongate fixation member 110 to the bone 10.

In some embodiments, the first and second flexible tensioning elements 61, 62 may be couplable to each other in order to secure the elongate fixation member 110 to the bone 10.

Figure 2D:
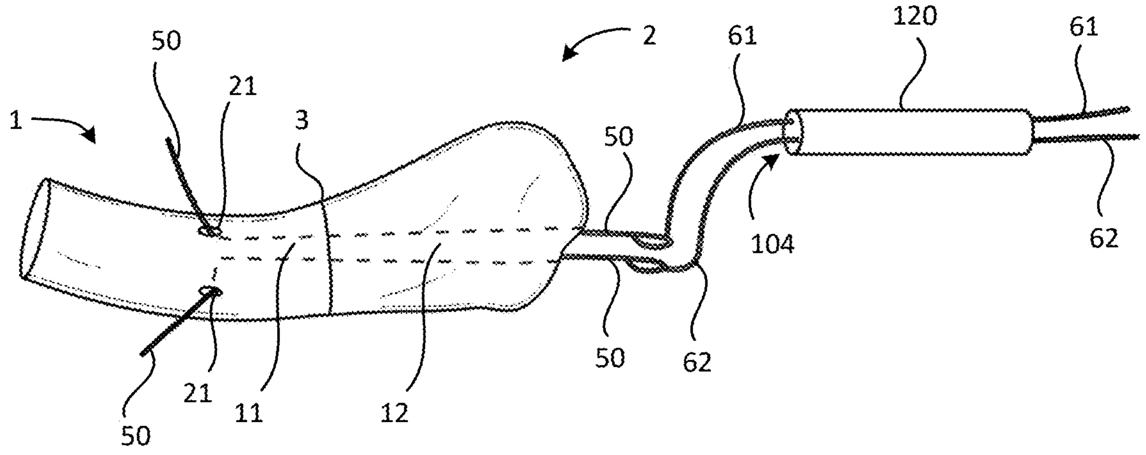
FIG. 2D illustrates a perspective side view of the bone of FIG. 2B with retrieval wires passing through transverse bone tunnels and the prepared intramedullary canals to retrieve flexible tensioning elements passing through the elongate fixation member of FIG. 2C.
Figure 2E:
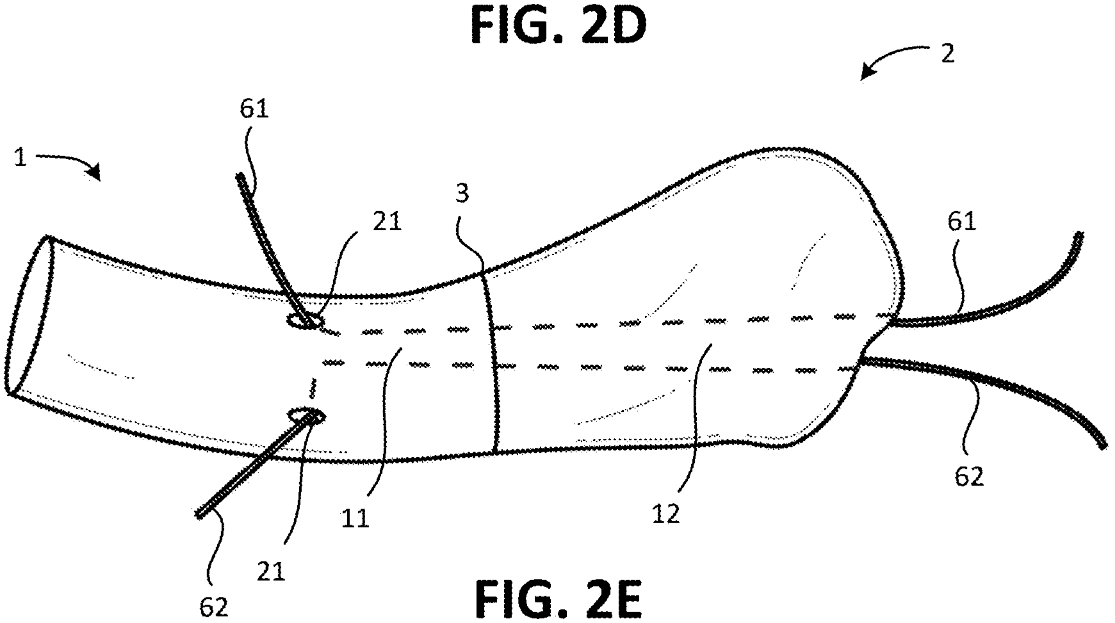
FIG. 2E illustrates a perspective side view of the bone of FIG. 2D with the flexible tensioning elements pulled through the transverse bone tunnels.
Figure 2F:
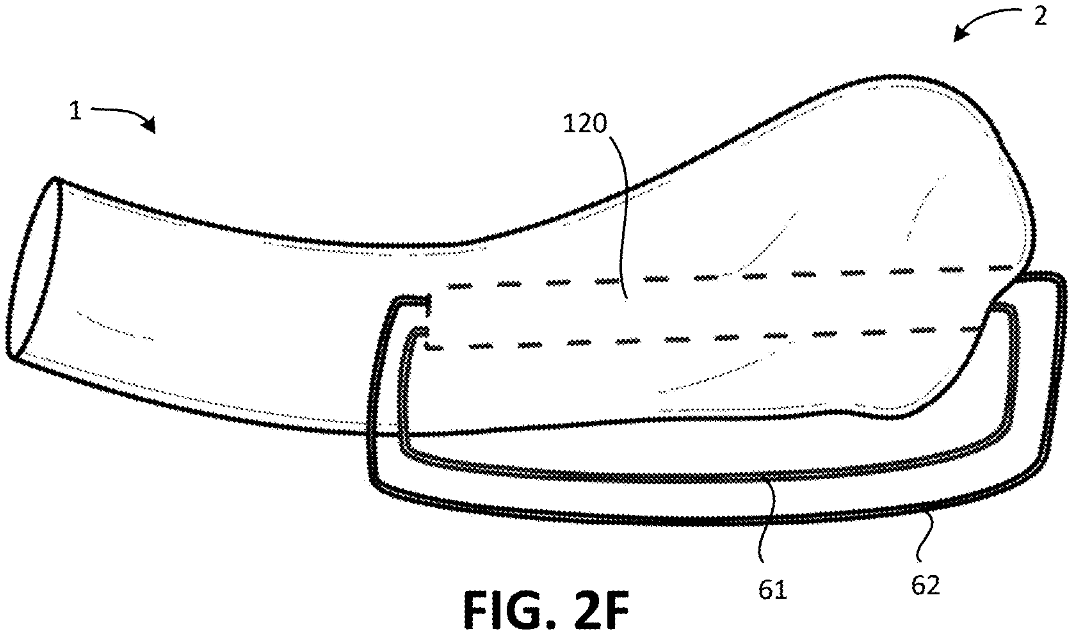
FIG. 2F illustrates a perspective side view of the bone of FIG. 2E with the elongate fixation member inserted into the prepared intramedullary canal and the flexible tensioning elements coupled to each other.

In some embodiments, the first end 63 of the first flexible tensioning element 61 may be couplable with the second end 64 of the first flexible tensioning element 61, and the first end 65 of the second flexible tensioning element 62 may be couplable with the second end 66 of the second flexible tensioning element 62 such that the first and second flexible tensioning elements 61, 62 span the bone fracture 3 and secure the elongate fixation member 120 to the bone 10, as shown in FIG. 2F.

In a second step of some embodiments of the procedure, one or more first transverse bone tunnels 21 may be formed in the first bone fragment 1, as can be seen in FIG. 2D. The one or more first transverse bone tunnels 21 may intersect the first intramedullary canal 11, as previously described herein. In some embodiments, one or more second transverse bone tunnels (not shown) may also be formed in the second bone fragment 2 that may intersect the second intramedullary canal 12. The one or more second transverse bone tunnels may be slightly spread apart from each other in the tip of the fractured olecranon process on either side of the second intramedullary canal 12. This will create more distance between the first and second flexible tensioning elements 61, 62 which can provide more rotational control of the fracture and/or allow the first and second flexible tensioning elements 61, 62 to be buried underneath soft tissues with a lower profile to avoid prominent and/or painful protrusion of the first and second flexible tensioning elements 61, 62 (e.g., under the skin, muscles, soft tissues, etc.).

FIG. 2D illustrates a third step of some embodiments of the procedure, in which one or more retrieval wires 50 may be placed through the first transverse bone tunnels 21 and the first and second intramedullary canals 11, 12 to retrieve the first and second flexible tensioning elements 61, 62, as previously described herein. FIG. 2E shows the first and second flexible tensioning elements 61, 62 pulled through the first transverse bone tunnels 21.

FIG. 2F illustrates a fourth step of some embodiments of the procedure, in which the elongate fixation member 120 may be inserted into the prepared first and second intramedullary canals 11, 12 of the first and second bone fragments 1, 2.

FIG. 2F also illustrates a fifth step of some embodiments of the procedure, in which the first and second flexible tensioning elements 61, 62 may be coupled to each other, woven around the bone fracture 3, and secured together.

In some embodiments, the first and second flexible tensioning elements 61, 62 may be additionally secured in place and/or tensioned via any of the securing element and/or tensioning element designs described or contemplated herein.

Thus, the first and second flexible tensioning elements 61, 62 may be configured to span the bone fracture 3 and preload the bone fracture in compression to resist tensile and/or distraction forces imparted across the bone fracture 3, thereby maintaining fixation of the first bone fragment 1 relative to the second bone fragment 2. In this manner, the bone fracture 3 may receive improved fixation and reduction strength by combining the elongate fixation member 120 with the first and second flexible tensioning elements 61, 62.

As previously discussed, the devices and procedures described herein can be utilized for bone fractures in other various locations throughout the body. For example, the procedure for an olecranon process fracture could be slightly modified for a different type of bone fracture, such as a fractured fibula. In this example, the technique would be similar to the olecranon process, except the surgeon would drill up initially from the tip of the fibula along the lateral ankle, then drill holes past the fracture into the fibulae shaft proximal to the fracture. Then, the surgeon would pull the device from the tip of the lateral malleolus, through the fracture site, and then secure the flexible tensioning element as previously discussed.

Figure 3A:
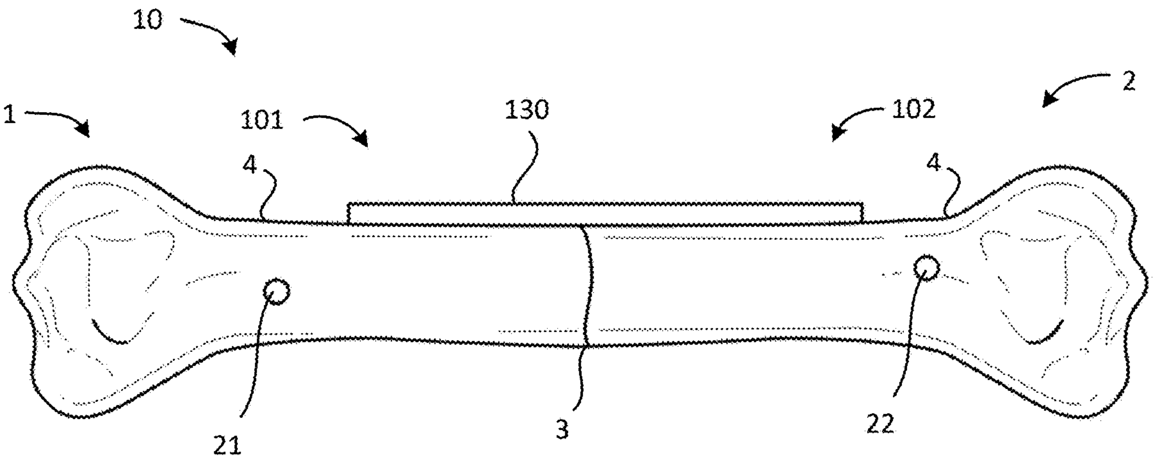
FIG. 3A illustrates a side view of a fractured bone coupled to a bone plate, according to another example of the present disclosure.
Figure 3B:
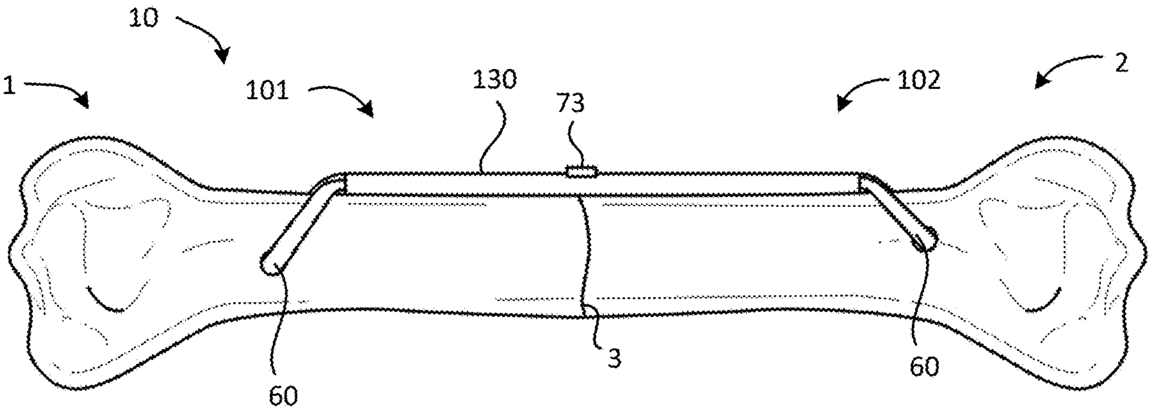
FIG. 3B illustrates a side view of the fractured bone of FIG. 3A including a flexible tensioning element coupled to the bone plate.
Figure 3C:
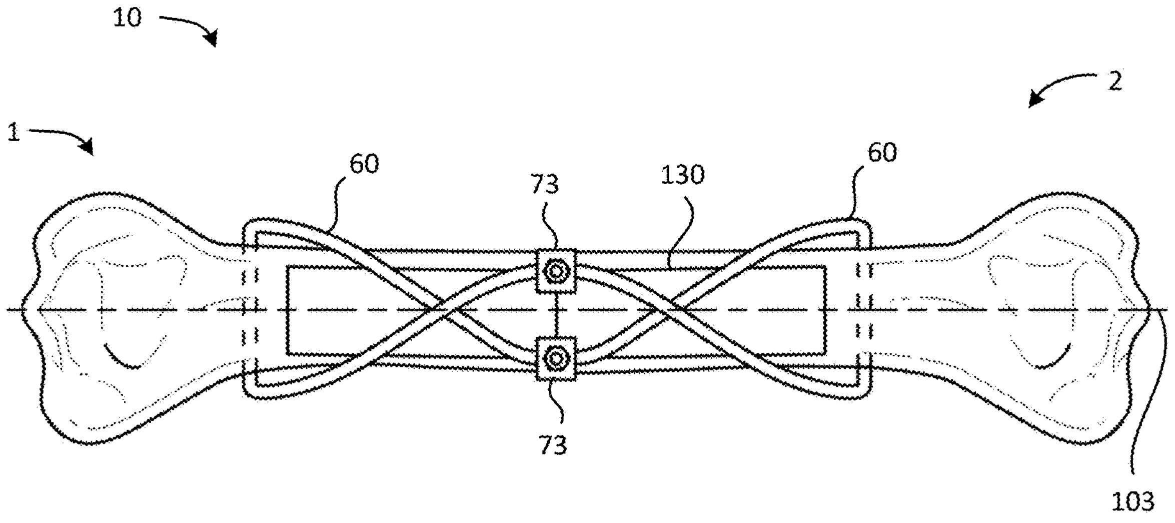
FIG. 3C illustrates a top view of fractured bone of FIG. 3B.

FIGS. 3A-3C illustrate an example bone fixation assembly and procedure that utilizes an elongate fixation member 130 comprising a bone plate in combination with a flexible tensioning element 60, according to another embodiment of the present disclosure.

In some embodiments, the bone fracture 3 may be provisionally reduced and the elongate fixation member 130 may be secured to cortical surfaces 4 of the first and second bone fragments 1, 2 (e.g., via bone screws, not shown) in order to provide initial fixation for the bone fracture 3. In some embodiments, the elongate fixation member 130 may be located superiorly on the bone 10. However, in other embodiments the elongate fixation member 130 may be placed along any side of the bone 10, and/or multiple bone plates may be utilized to stabilize the bone fracture 3 on any side of the bone 10.

In some embodiments, first and second transverse bone tunnels 21, 22 may be drilled through the first and second bone fragments 1, 2. In some embodiments, the first and second transverse bone tunnels 21, 22 may be drilled through the first and second bone fragments 1, 2 in an anterior to posterior direction (e.g., for a clavicle bone). In some embodiments, the first and second transverse bone tunnels 21, 22 may be drilled through the first and second bone fragments 1, 2 at locations that are past the proximal and distal portions 101, 102 of the elongate fixation member 130. However, it will be understood that in other embodiments the first and second transverse bone tunnels 21, 22 may not be drilled through the first and second bone fragments 1, 2 in any particular direction, or at any location past the proximal and distal portions 101, 102 of the elongate fixation member 130.

In some embodiments, the flexible tensioning element 60 may be threaded through the first and second transverse bone tunnels 21, 22 and woven around or cinched over the bone fracture 3 such that the flexible tensioning element 60 forms one or more crisscross patterns on top of, within, and/or below the elongate fixation member 130. However, it will also be understood that in other embodiments the flexible tensioning element 60 may be woven around the bone fracture 3 to form any suitable pattern on any side of the bone 10 and/or any side of the elongate fixation member 130 to preload the bone fracture 3 in compression and resist tensile/distraction forces imparted across the bone fracture 3.

In some embodiments, the flexible tensioning element 60 may comprise a single flexible tensioning element.

In some embodiments, the flexible tensioning element 60 may comprise one or more flexible tensioning elements that may be couplable to each other, such as the first and second flexible tensioning elements 61, 62 previously described herein.

In some embodiments, the elongate fixation member 130 may comprise one or more grooves (not shown) located on top of, within, or on the bottom of the elongate fixation member 130 that may be configured to receive the flexible tensioning element 60 therein to achieve a lower overall profile and reduce the risk of prominence and/or complications due to soft tissue disturbances.

In some embodiments, the flexible tensioning element 60 may be threaded through one or more sleeves (not shown) to prevent the flexible tensioning element 60 from cutting through the bone 10 over time. The one or more sleeves may be made of any biocompatible material including, but not limited to metals, plastics, PEEK, rubber, silicone, etc.

In some embodiments, the flexible tensioning element 60 may also be secured in place and/or tensioned via one or more third securing elements 73 (see FIG. 3C), which may include any of the securing element designs and/or tensioning element designs described or contemplated herein.

Figure 4A:
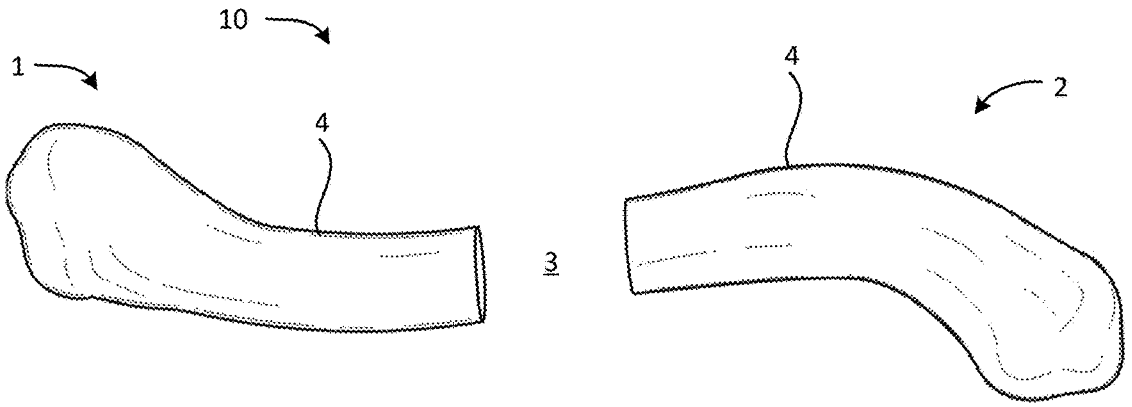
FIG. 4A illustrates a perspective side view of a fractured bone with first and second bone fragments, according to an example of the present disclosure.
Figure 4B:
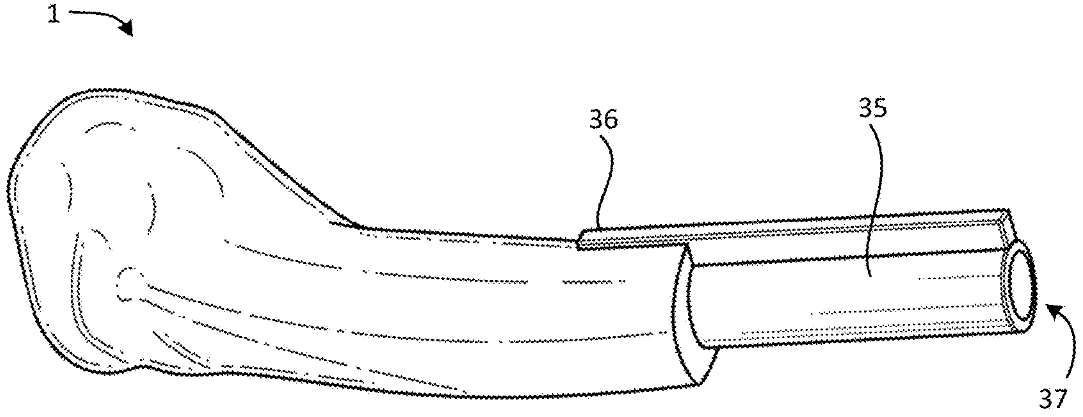
FIG. 4B illustrates a perspective side view of a reamer guide that may be utilized with the bone fragments of FIG. 4A.
Figure 4C:
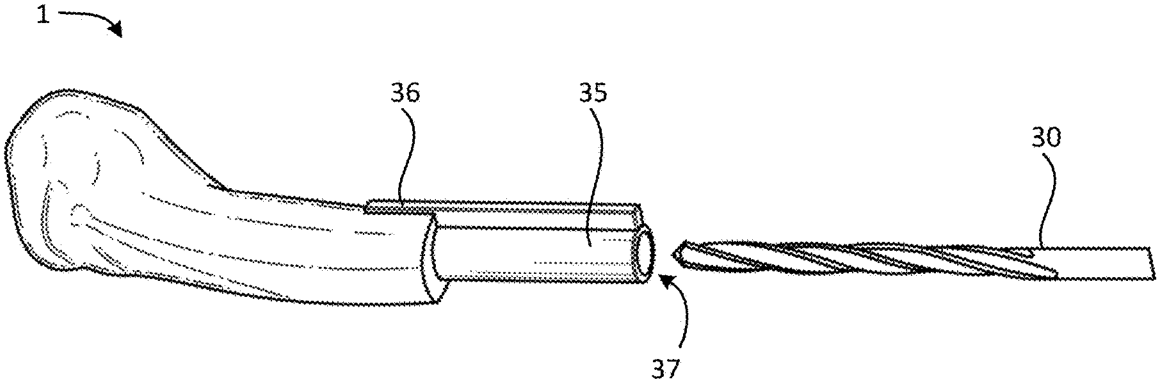
FIG. 4C illustrates a perspective side view of a reamer that may be utilized to prepare the intramedullary canals of the bone fragments of FIG. 4A.
Figure 4D:
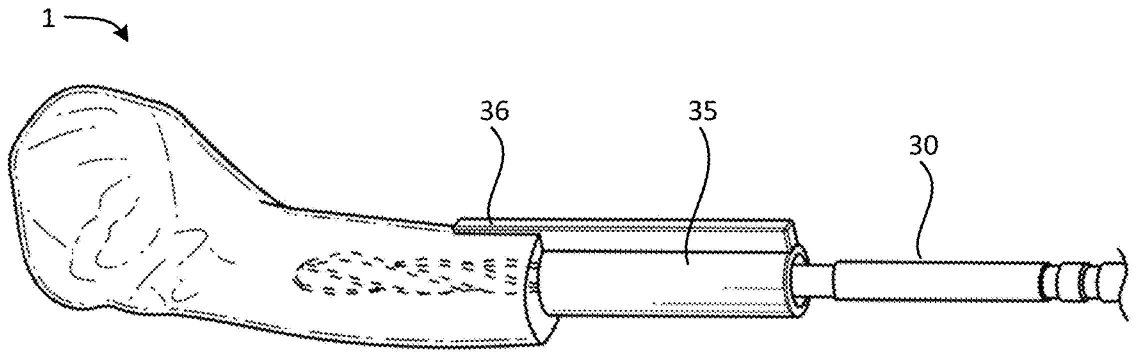
FIG. 4D illustrates a perspective side view of the reamer and reamer guide preparing the intramedullary canal of the first bone fragment of FIG. 4A.
Figure 4E:
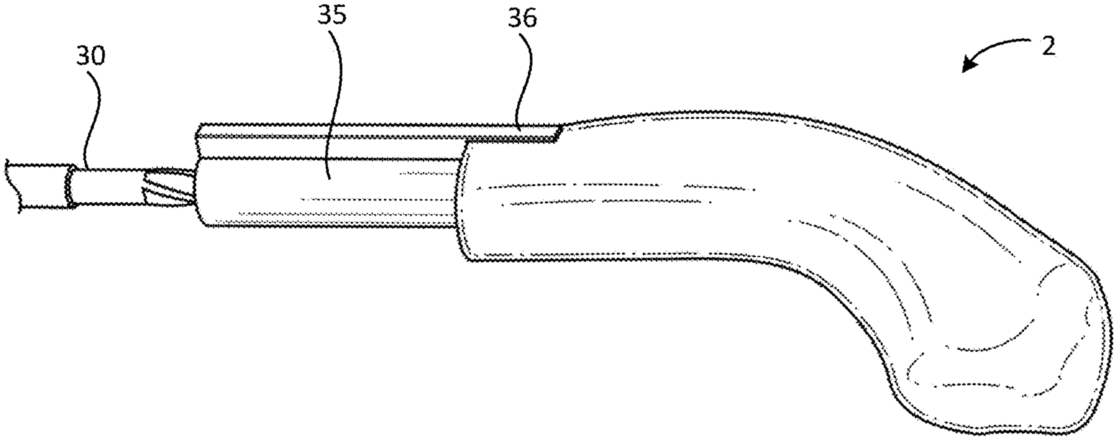
FIG. 4E illustrates a perspective side view of the reamer and reamer guide preparing the intramedullary canal of the second bone fragment of FIG. 4A.
Figure 4F:
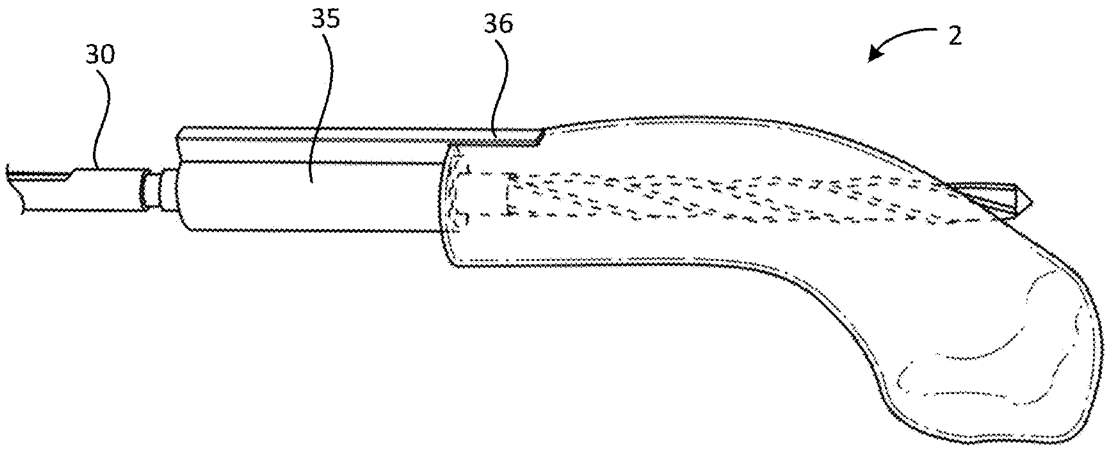
FIG. 4F illustrates another perspective side view of the reamer and reamer guide preparing the intramedullary canal of the second bone fragment of FIG. 4A.
Figure 4G:
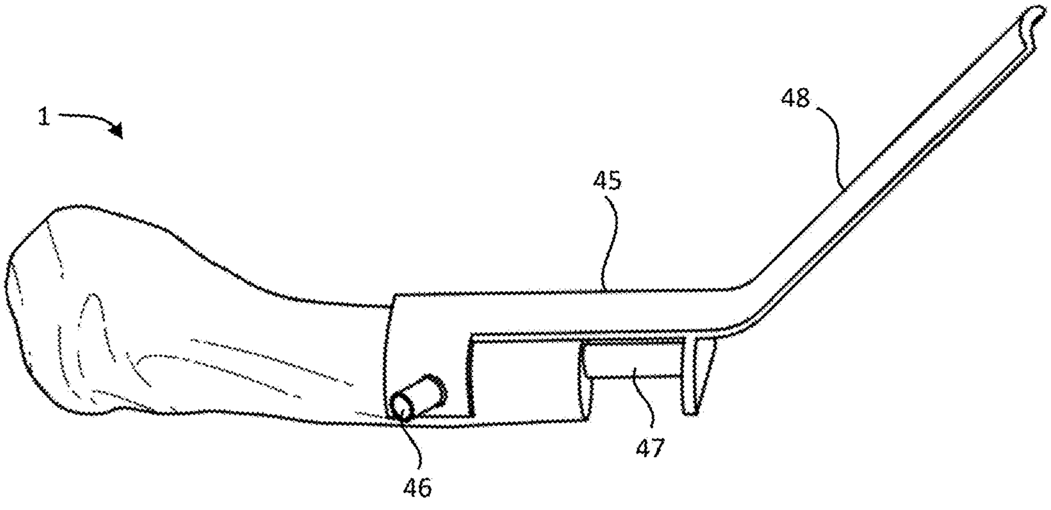
FIG. 4G illustrates a perspective side view of a drill guide that may be utilized to prepare transverse bone tunnels through the bone fragments of FIG. 4A.
Figure 4H:
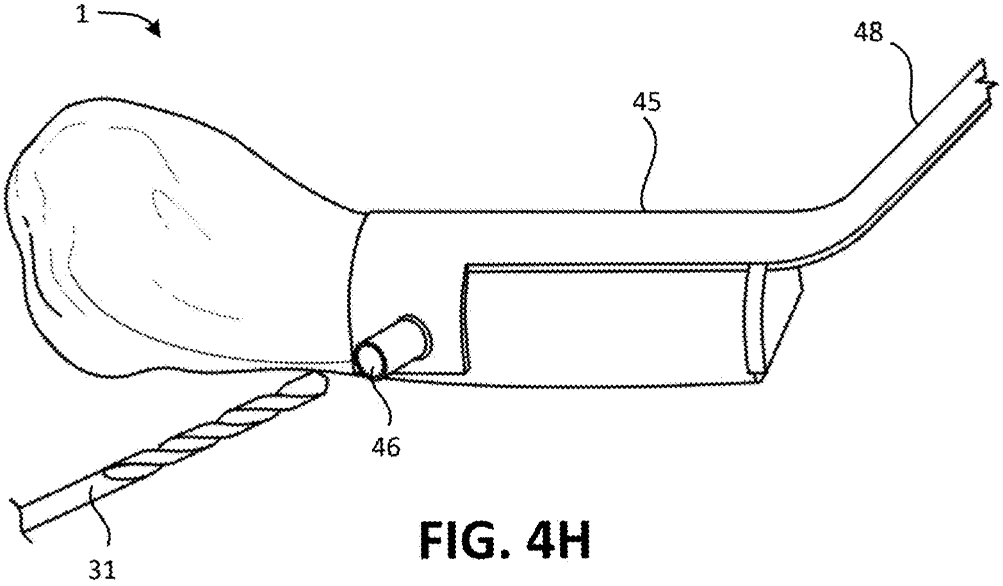
FIG. 4H illustrates a perspective side view of a drill bit that may be utilized to prepare the transverse bone tunnels through the bone fragments of FIG. 4A.
Figure 4I:
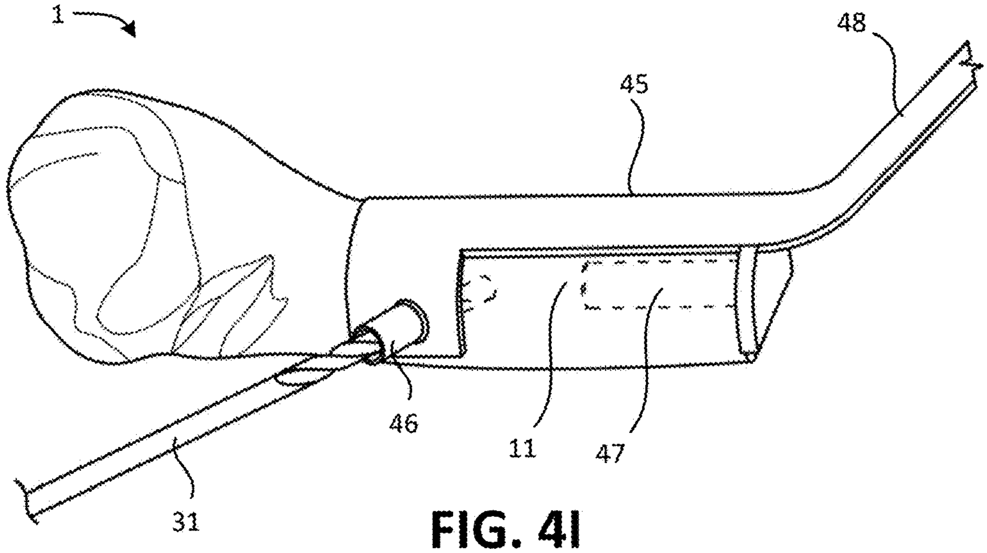
FIG. 4I illustrates a perspective side view of the drill guide and the drill bit preparing the transverse bone tunnels through the bone fragments of FIG. 4A.
Figure 4J:
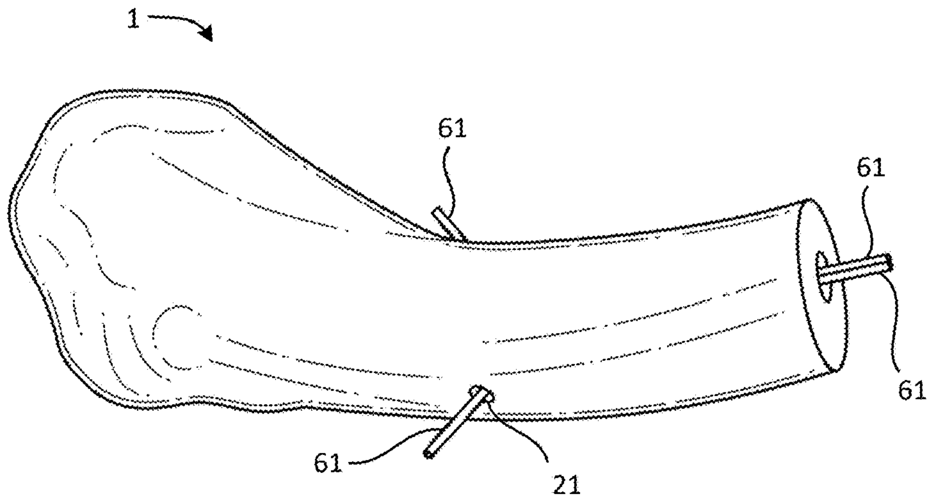
FIG. 4J illustrates a perspective side view of a prepared first bone fragment with flexible tensioning elements passing therethrough.
Figure 4K:
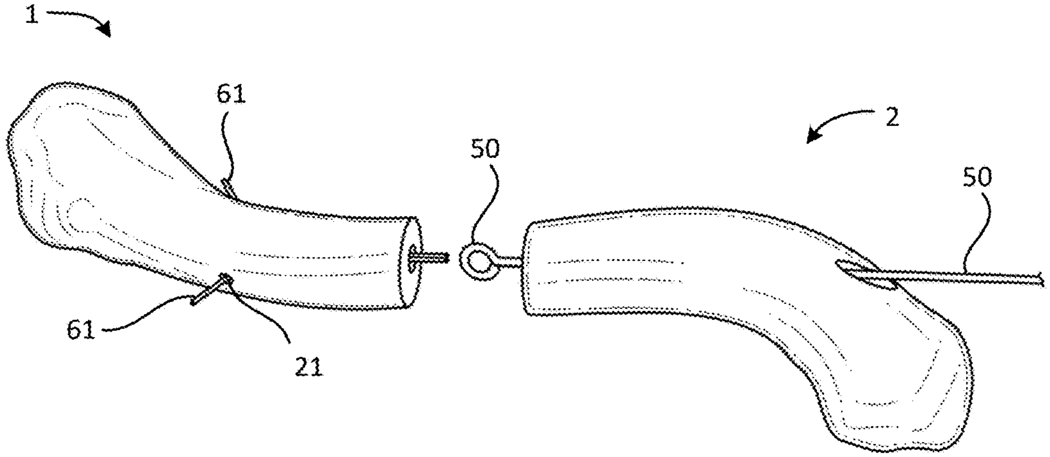
FIG. 4K illustrates a perspective side view of the prepared first bone fragment shown in FIG. 4J and a prepared second bone fragment with a retrieval wire passing therethrough.
Figure 4L:
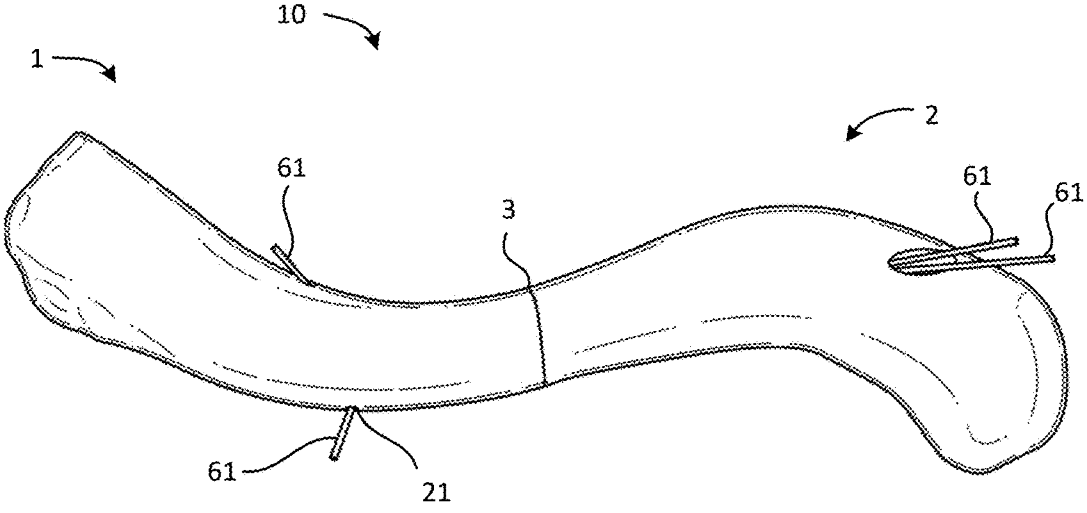
FIG. 4L illustrates a perspective side view of the bone fragments of FIG. 4K with flexible tensioning elements passing therethrough.
Figure 4M:
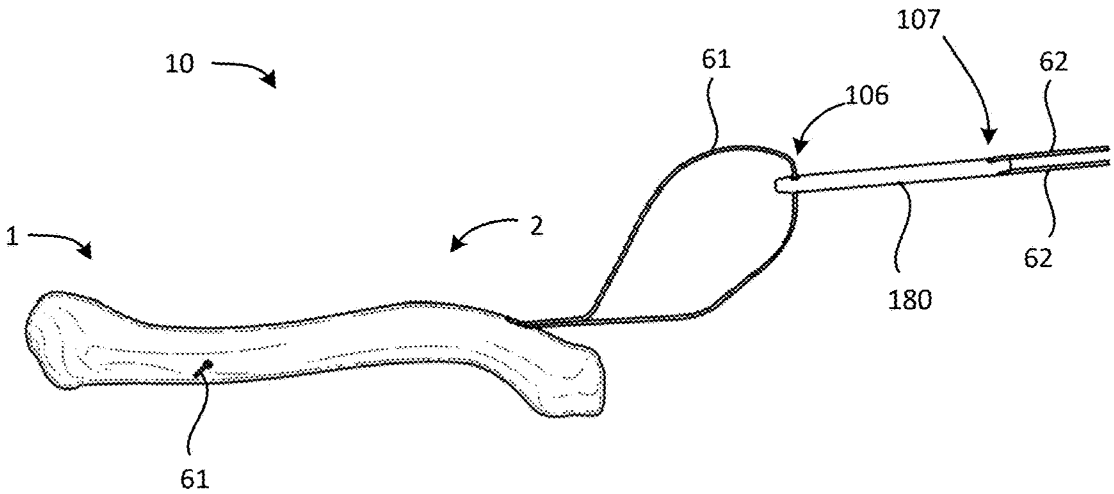
FIG. 4M illustrates a perspective side view of FIG. 4L with the flexible tensioning elements coupled to an elongate fixation member, similar to that shown in FIG. 8E.
Figure 4N:
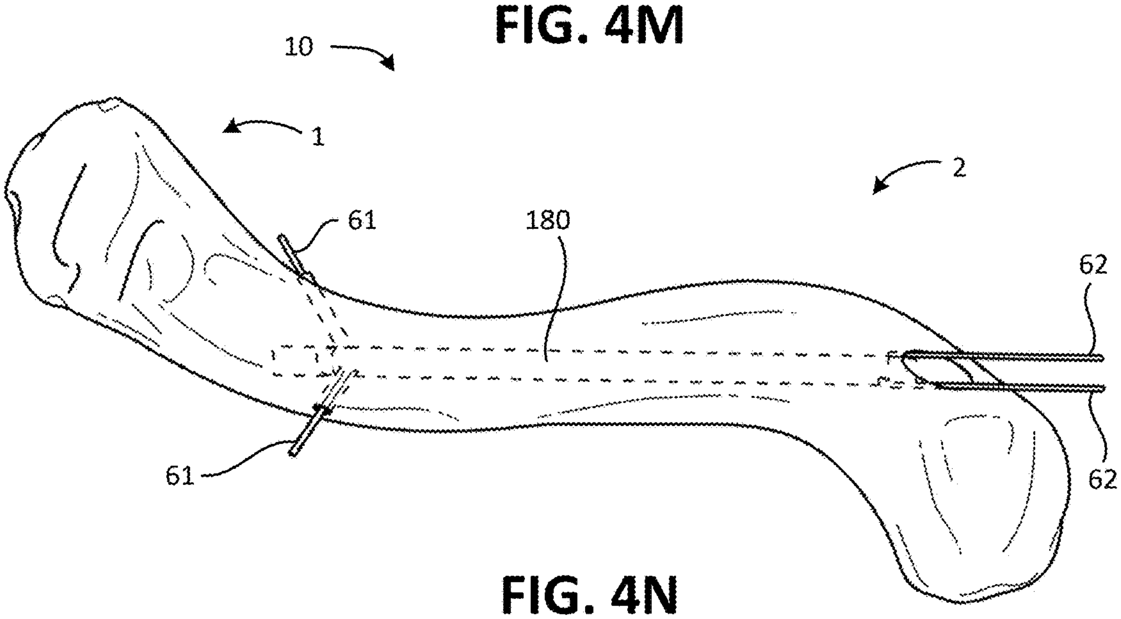
FIG. 4N illustrates a perspective side view of FIG. 4M with the elongate fixation member inserted into the intramedullary canals of the bone fragments.
Figure 4O:
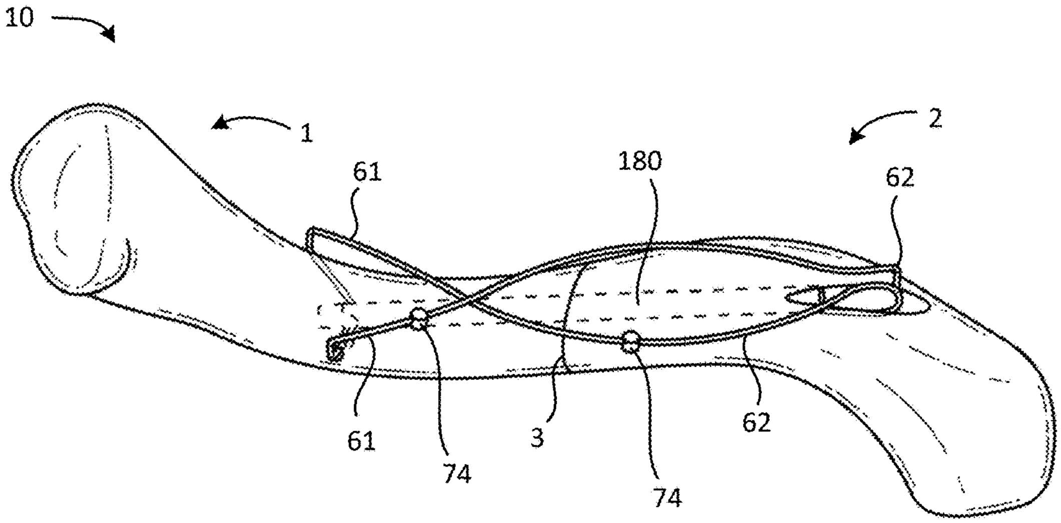
FIG. 4O illustrates a perspective side view of FIG. 4N with the flexible tensioning elements coupled to each other.

FIGS. 4A-4O illustrate example devices, instruments, and method steps for a bone fixation assembly and surgical procedure that may be performed from a lateral approach, according to another embodiment of the present disclosure.

In some embodiments, the bone 10 illustrated in FIG. 4A may comprise a clavicle bone. However, it will be understood that the various devices, instruments, and method steps described herein may be utilized in any combination with each other and for any type of bone fracture including, but not limited to olecranon fractures, fibula fractures, patellar fractures, malleolar fractures, etc.

FIG. 4B-4F illustrate a first step of some embodiments of the procedure, in which the first and second intramedullary canals 11, 12 of the first and second bone fragments 1, 2 may be prepared with a drill bit or reamer 30.

In some embodiments, the reamer 30 may be guided through a reamer passageway 37 that is formed through a reamer guide 35.

In some embodiments, the reamer guide 35 may also include a reference member 36 projecting from the reamer guide 35.

In some embodiments, the reference member 36 may be configured to abut a cortical surface 4 of the first and/or second bone fragments 1, 2 to orient the reamer passageway 37 with respect to the cortical surfaces 4 of the first and/or second bone fragments 1, 2.

As previously discussed, the first and second intramedullary canals 11, 12 of the first and second bone fragments 1, 2 may be drilled and/or reamed with any diameter drill bit or reamer to any desired depth within the intramedullary canal in order to form prepared intramedullary canals. Moreover, it will also be understood that in some embodiments of the procedure the intramedullary canals of the bone fragments may not require preparation, such as drilling, reaming, etc. For example, in some embodiments a suitable elongate fixation member may be press-fit and/or tamped into an unprepared intramedullary canal of a bone fragment.

FIGS. 4G-4I illustrate a second step of some embodiments of the procedure, in which a drill guide 45 and drill bit 31 may be utilized to place one or more first transverse bone tunnels 21 through the cortical surface 4 of the first bone fragment 1 down into the prepared first intramedullary canal 11.

In some embodiments, the drill guide 45 may include one or more drill guide barrels 46, an insert member 47, and a handle 48.

In some embodiments, the insert member 47 may be inserted into the prepared first intramedullary canal 11 to orient the one or more drill guide barrels 46 with respect to the prepared first intramedullary canal 11 of the first bone fragment 1.

FIGS. 4J-4L illustrate a third step of some embodiments of the procedure, in which a retrieval wire 50 may be placed through the second intramedullary canal 12 of the second bone fragment 2 in order to capture and pull the first flexible tensioning elements 61 through the second intramedullary canal 12 of the second bone fragment 2, as shown in FIG. 4L.

FIG. 4M illustrates a fourth step of some embodiments of the procedure, in which one of the first flexible tensioning elements 61 may be passed through the first transverse passageway 106 of the elongate fixation member 180 and then coupled to the other one of the first flexible tensioning elements 61, as can be seen in FIG. 4M. The elongate fixation member 180 will be discussed in more detail below with respect to FIG. 8E.

FIG. 4N illustrates a fifth step of some embodiments of the procedure, in which the elongate fixation member 180 may be inserted into the prepared first and second intramedullary canals 11, 12 of the first and second bone fragments 1, 2 from a lateral approach. This may be accomplished by pulling the first flexible tensioning elements 61 through the first transverse bone tunnels 21, and/or by impacting the distal end of the elongate fixation member 180 with an impact driver (not shown).

FIG. 4O illustrates a sixth step of some embodiments of the procedure, in which the first and second flexible tensioning elements 61, 62 may be woven around the bone fracture 3 and secured together, as previously described herein. The first and second flexible tensioning elements 61, 62 may be configured to span the bone fracture 3 and preload the bone fracture 3 in compression to resist tensile and/or distraction forces imparted across the bone fracture 3, thereby maintaining fixation of the first bone fragment 1 relative to the second bone fragment 2. In this manner, the bone fracture 3 may receive improved fixation and reduction strength by combining the elongate fixation member 180 with the first and second flexible tensioning elements 61, 62.

In some embodiments, the first and second flexible tensioning elements 61, 62 may also be secured in place and/or tensioned via one or more fourth securing elements 74 (see FIG. 4O), which may include any of the securing element designs and/or tensioning element designs described or contemplated herein.

FIGS. 5A-5H illustrate example devices, instruments, and method steps for a bone fixation assembly and surgical procedure that may be performed from a lateral approach, according to another embodiment of the present disclosure.

In some embodiments, the first and second bone fragments 1, 2 may be prepared in a similar manner to the first bone fragment 1 shown in FIGS. 4A-4I in a first step and a second step. However, the first and second intramedullary canals 11, 12 of the first and second bone fragments 1, 2 may also be tapped with a tap tool 80 in a third step to form internal bone threads 81 within the first and second intramedullary canals 11, 12 (e.g., see FIG. 5A).

Figure 5A:
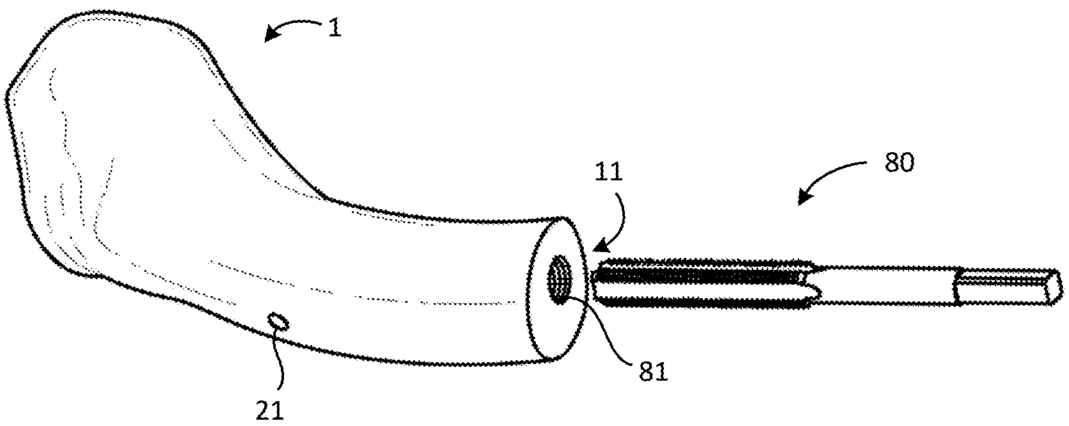
FIG. 5A illustrates a perspective side view of a tap that may be utilized to prepare a threaded intramedullary canal within the bone fragments of FIG. 4A, according to another example of the present disclosure.
Figure 5B:
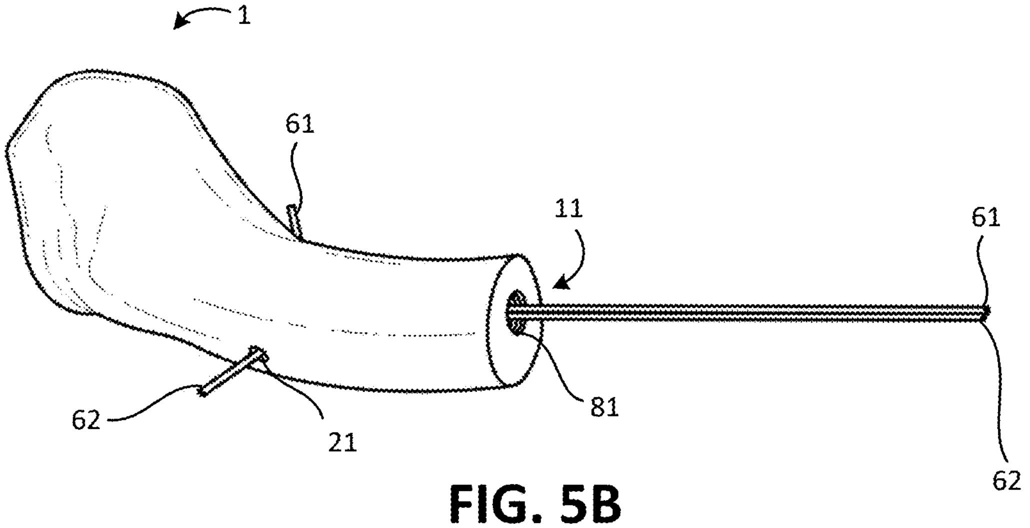
FIG. 5B illustrates a perspective side view of the prepared first bone fragment shown in FIG. 5A with flexible tensioning elements passing therethrough.
Figure 5C:
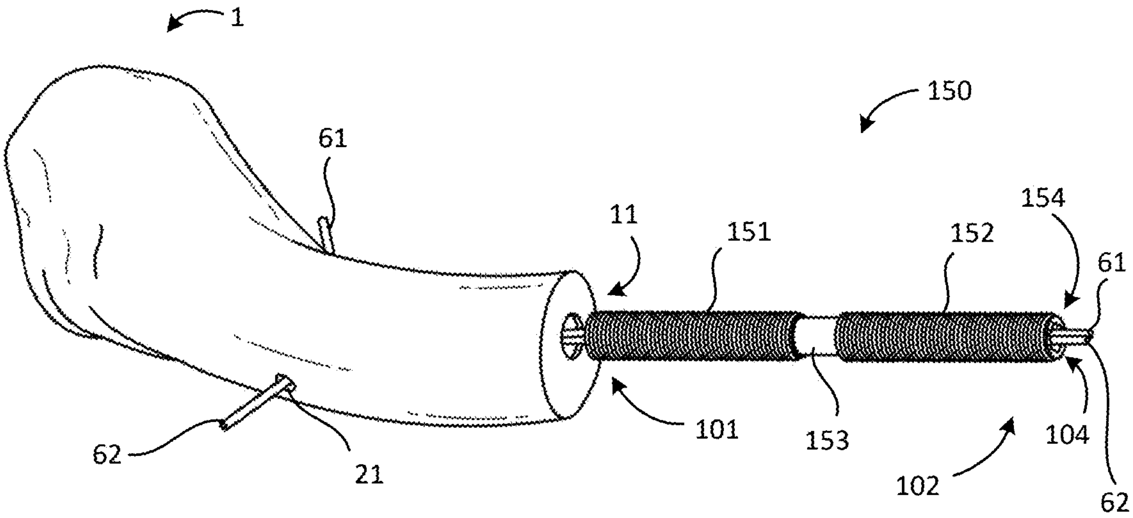
FIG. 5C illustrates a perspective side view of FIG. 5B with an elongate fixation member, according to another embodiment of the present disclosure.
Figure 5D:
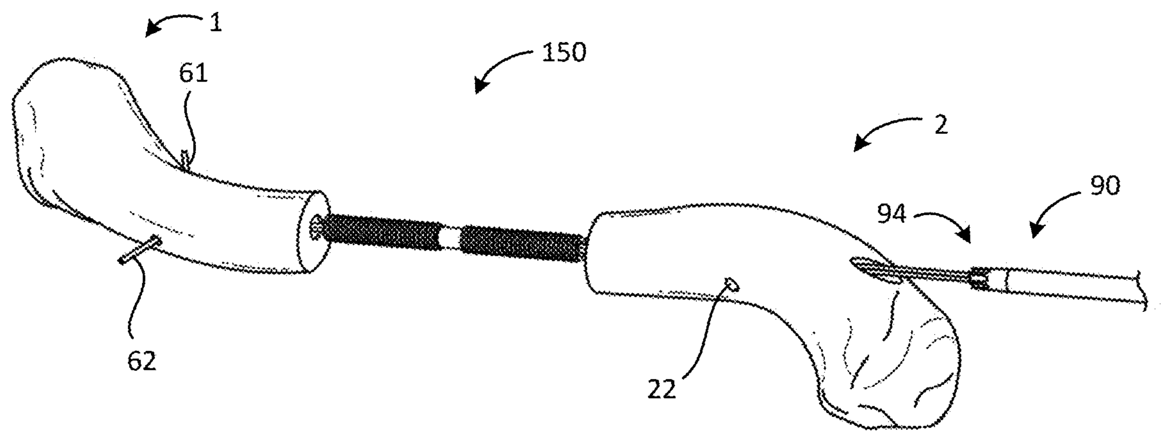
FIG. 5D illustrates a perspective side view of FIG. 5C with a prepared second bone fragment and a driver that may be utilized to couple the elongate fixation member to the bone fragments from a lateral approach.

FIGS. 5B-5D illustrate a fourth step of some embodiments of the procedure, in which the first and second flexible tensioning elements 61, 62 may be pulled through the bone tunnels of the first bone fragment 1, the longitudinal passageway 104 of the elongate fixation member 150, and the second intramedullary canal 12 of the second bone fragment 2 via a retrieval wire (not shown) in FIGS. 5B-5D.

The elongate fixation member 150 may generally include a proximal or first portion 101, a distal or second portion 102, a central longitudinal axis 103, a longitudinal passageway 104, a first thread 151, a second thread 152, an intermediate portion 153, and a torque reception feature 154.

In some embodiments, the elongate fixation member 150 may comprise a compression screw design.

In some embodiments, the first thread 151 may comprise a first pitch, and the second thread 152 may comprise a second pitch that is different from the first pitch of the first thread 151. In these embodiments, the first and second bone fragments 1, 2 may be drawn toward each other in compression as the elongate fixation member 150 is inserted into the first and second intramedullary canals 11, 12, due to the differential thread pitches between the first and second threads 151, 152.

In some embodiments, the elongate fixation member 150 (and/or any other elongate fixation member described or contemplated herein) may comprise a resorbable material (such as PEEK, hydroxyapatite, etc.), and/or any other biocompatible material such as titanium, stainless steel, polymer, etc.

Figure 5E:
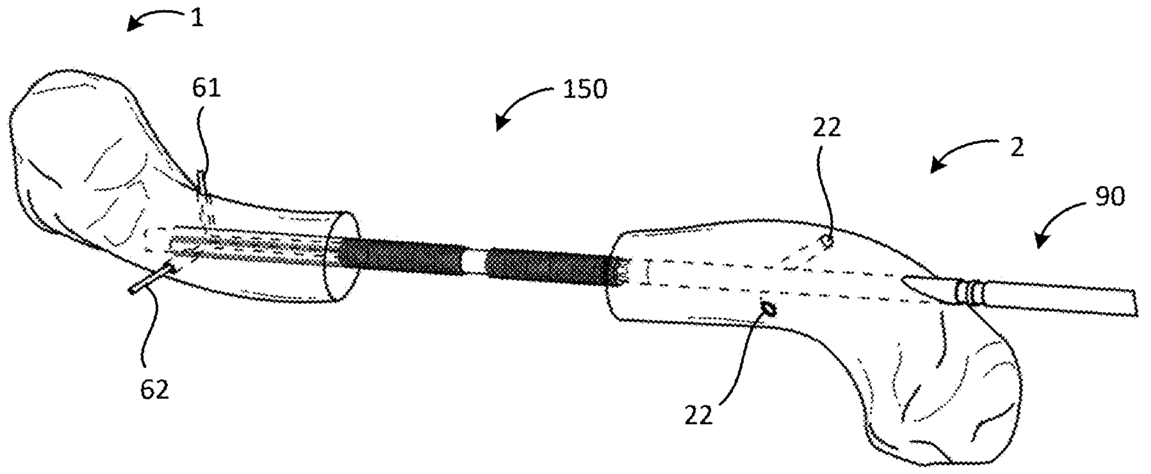
FIG. 5E illustrates a perspective side view of FIG. 5D with the driver coupled to the elongate fixation member.
Figure 5F:
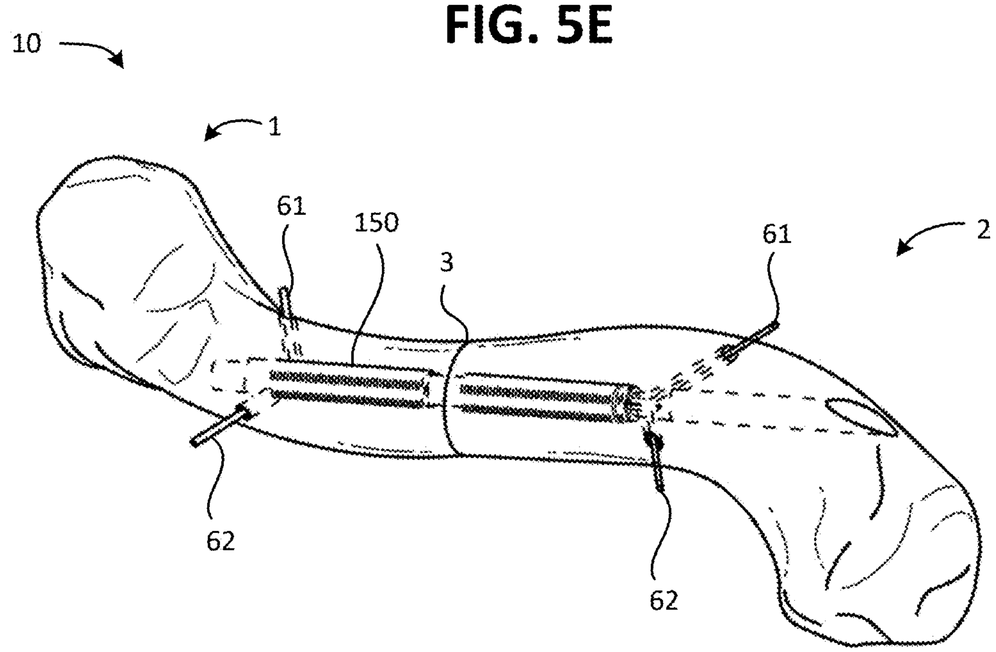
FIG. 5F illustrates a perspective side view of FIG. 5E with the elongate fixation member inserted within the intramedullary canals of the bone fragments and the flexible tensioning elements passing through the transverse bone tunnels.

FIGS. 5D-5F illustrate a fifth step of some embodiments of the procedure, in which the elongate fixation member 150 may be inserted into the first and second intramedullary canals 11, 12 of the first and second bone fragments 1, 2 from a lateral approach.

FIGS. 5D and 5E illustrate a driver 90 that may be utilized to couple the elongate fixation member 150 to the first and second bone fragments 1, 2. In some embodiments, the driver 90 may include a torque transmission feature 94 that may be configured to mate with a complementary shaped torque reception feature formed within the longitudinal passageway 104 of the elongate fixation member 150 to drive the elongate fixation member 150 into the first and second intramedullary canals 11, 12 of the first and second bone fragments 1, 2. FIG. 5F shows the elongate fixation member 150 after it has been fully inserted into the first and second intramedullary canals 11, 12 and the bone fracture 3 has been reduced in compression by the compression screw design of the elongate fixation member 150.

FIG. 5F also illustrates a sixth step of some embodiments of the procedure, in which the first and second flexible tensioning elements 61, 62 may be pulled through the second transverse bone tunnels 22 of the second bone fragment 2 after the driver 90 is removed. This may be accomplished with one or more retrieval wires, as previously discussed.

Figure 5G:
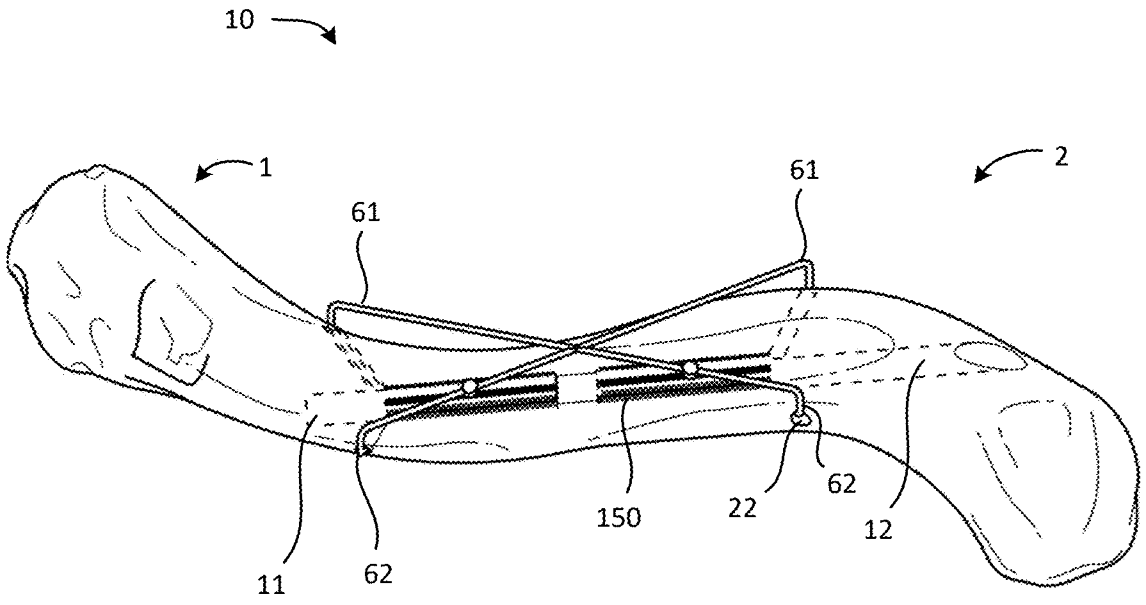
FIG. 5G illustrates a perspective side view of FIG. 5F with the flexible tensioning elements coupled to each other.
Figure 5H:
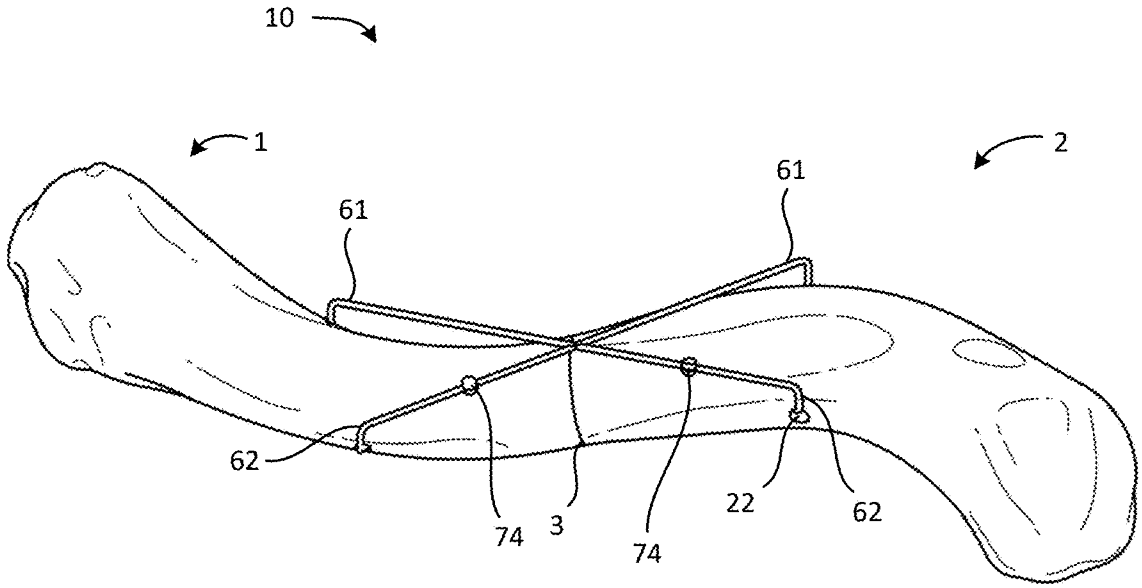
FIG. 5H illustrates another perspective side view of FIG. 5G.

FIGS. 5G and 5H illustrate a seventh step of some embodiments of the procedure, in which the first and second flexible tensioning elements 61, 62 may be coupled to each other and woven around the bone fracture 3 to further preload the bone fracture 3 in compression to resist tensile/distraction forces that may be imparted across the bone fracture 3, as previously described. Thus, combining the elongate fixation member 150 with the first and second flexible tensioning elements 61, 62 provides additional fixation, stabilization, and reduction of the bone fracture 3 over an elongate fixation member or flexible tensioning element alone.

In some embodiments, the first and second flexible tensioning elements 61, 62 may also be secured in place and/or tensioned via one or more fourth securing elements 74, which may include any of the securing element designs and/or tensioning element designs described or contemplated herein.

FIGS. 6A-6F illustrate example devices, instruments, and method steps for a bone fixation assembly and surgical procedure that may be performed from both a medial and lateral approach, according to another embodiment of the present disclosure.

In some embodiments, the first and second bone fragments 1, 2 may be prepared in a similar manner to the first bone fragment 1 shown in FIGS. 4A-4I in a first step and a second step. However, the first and second intramedullary canals 11, 12 of the first and second bone fragments 1, 2 may also be tapped with the tap tool 80 shown in FIG. 5A in a third step to form internal bone threads 81 within the first and second intramedullary canals 11, 12.

Figure 6A:
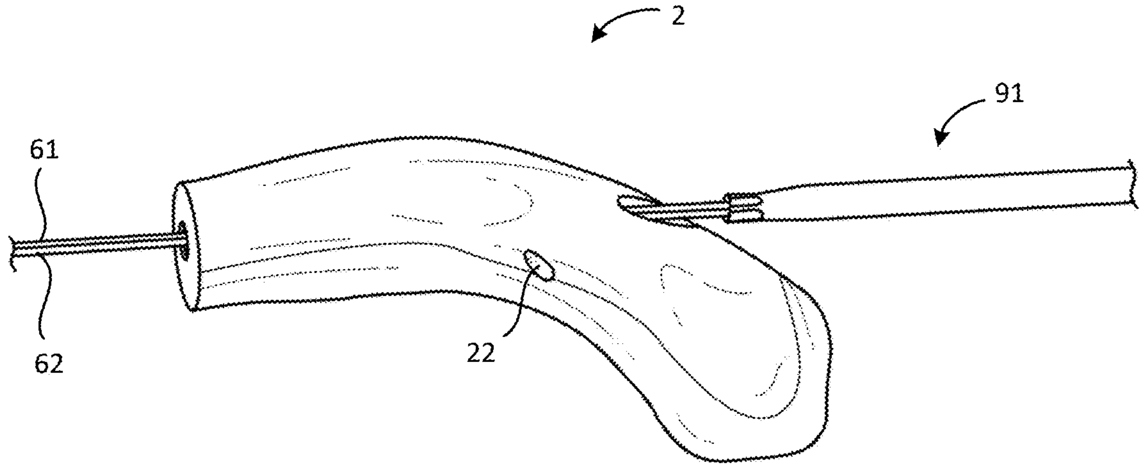
FIG. 6A illustrates a perspective side view of the prepared second bone fragment of FIG. 5D.
Figure 6B:
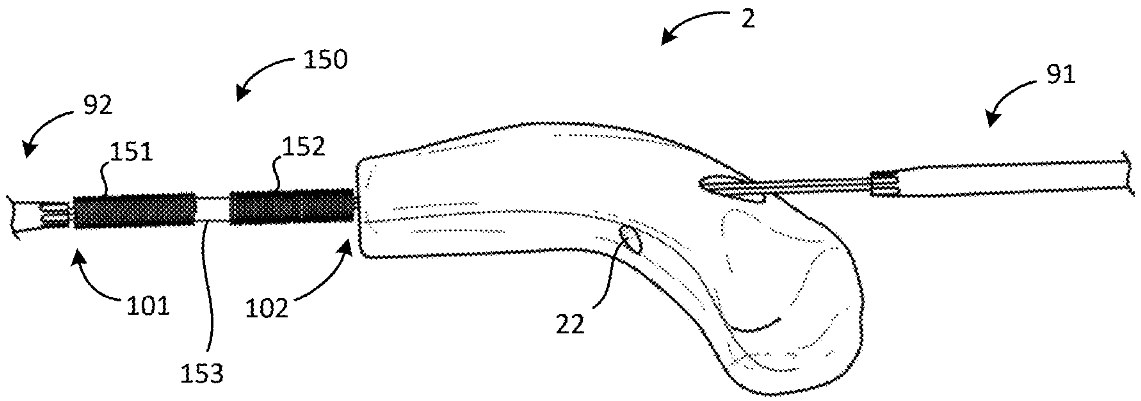
FIG. 6B illustrates a perspective side view of FIG. 6A with an elongate fixation member and first and second drivers that may be utilized to couple the elongate fixation member to the bone fragments from both a medial and a lateral direction, according to another embodiment of the present disclosure.

FIGS. 6A and 6B illustrate a fourth step of some embodiments of the procedure, in which the first and second flexible tensioning elements 61, 62 may be pulled through a first driver 91, the second intramedullary canal 12 of the second bone fragment 2, the elongate fixation member 150, and a second driver 92. This may be accomplished with one or more retrieval wires, as previously discussed.

Figure 6C:
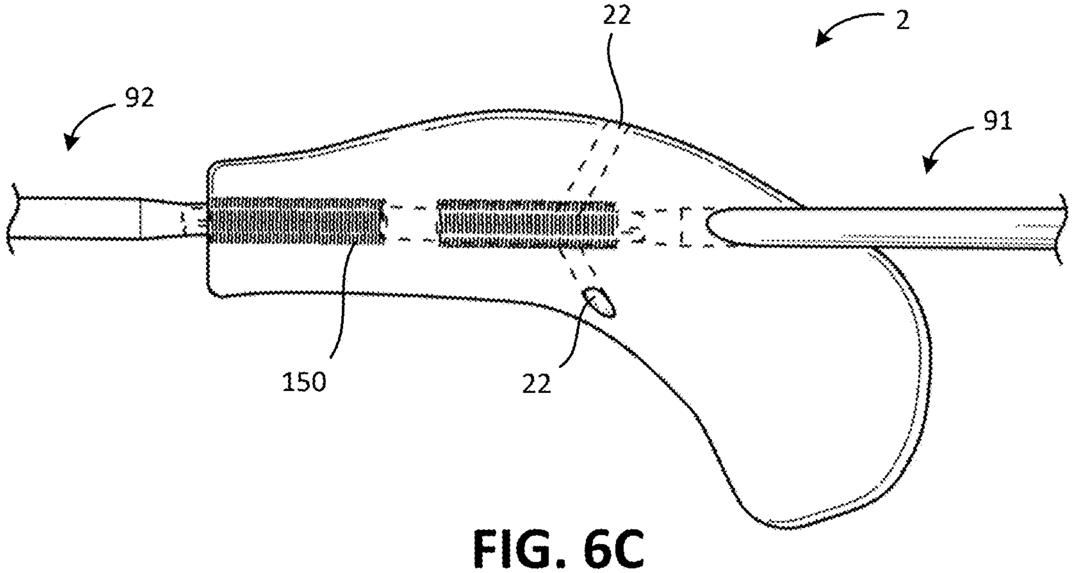
FIG. 6C illustrates a perspective side view of FIG. 6B with the second driver inserting the elongate fixation member into the intramedullary canal of the second bone fragment.

FIG. 6C illustrates a fifth step of some embodiments of the procedure, in which the second driver 92 may be utilized to drive the elongate fixation member 150 into the second intramedullary canal 12 of the second bone fragment 2 from a medial direction.

Figure 6D:
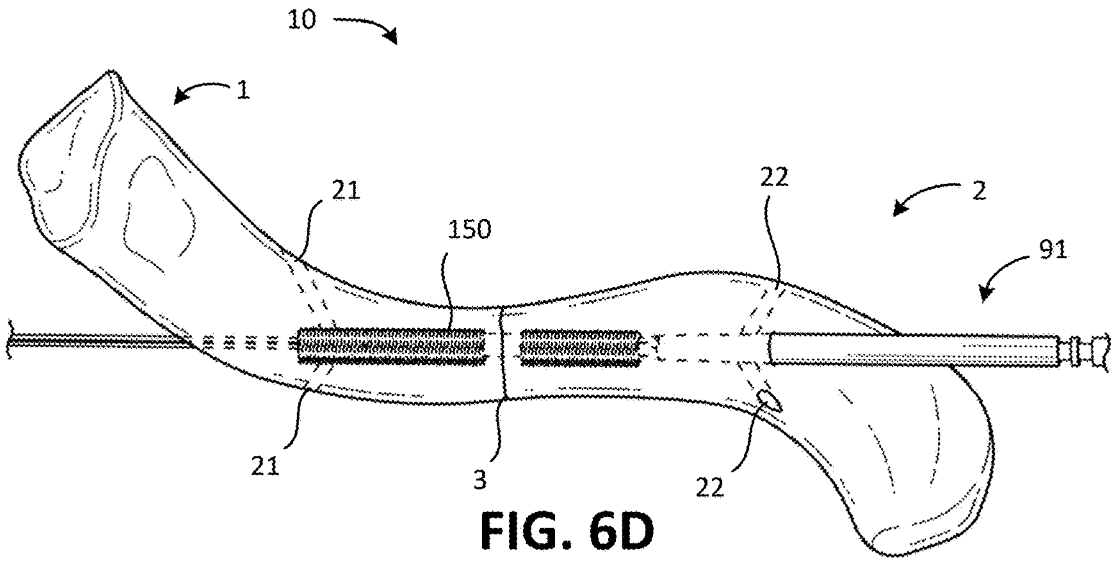
FIG. 6D illustrates a perspective side view of FIG. 6C with the first driver inserting the elongate fixation member into the intramedullary canal of the first bone fragment.

FIG. 6D illustrates a sixth step of some embodiments of the procedure, in which the first bone fragment 1 may be positioned adjacent the second bone fragment 2 and the first driver 91 may be utilized to drive the elongate fixation member 150 into the first intramedullary canal 11 of the first bone fragment 1 from a lateral direction in order to couple the elongate fixation member 150 to the first and second bone fragments 1, 2.

Figure 6E:
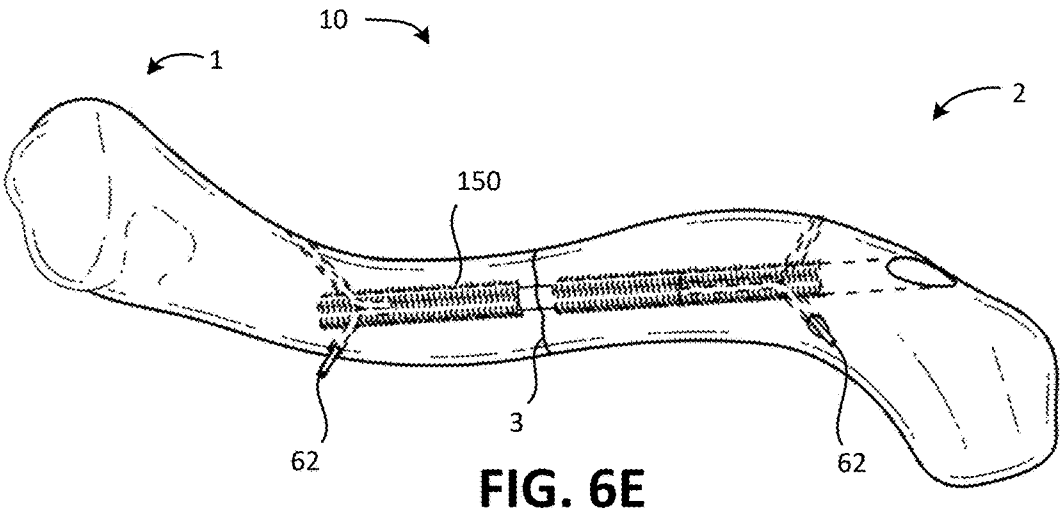
FIG. 6E illustrates a perspective side view of FIG. 6D with the elongate fixation member inserted into the intramedullary canals of the bone fragments and the flexible tensioning elements passing through the transverse bone tunnels.

FIG. 6E illustrates a seventh step of some embodiments of the procedure, in which the first and second flexible tensioning elements 61, 62 may be pulled through the first and second transverse bone tunnels 21, 22 of the bone fragments after the first and second drivers 91, 92 have been removed. This may be accomplished with one or more retrieval wires, as previously discussed.

Figure 6F:
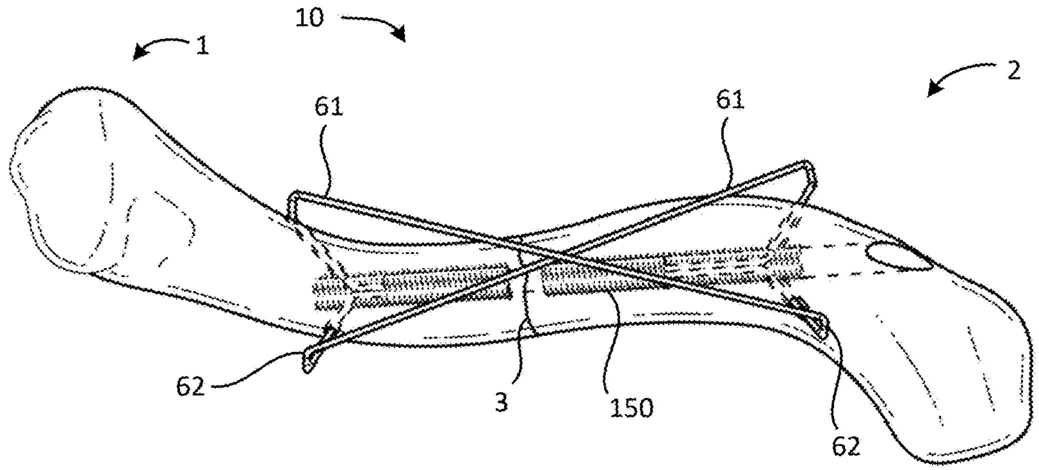
FIG. 6F illustrates a perspective side view of FIG. 6E with the flexible tensioning elements coupled to each other.

FIG. 6F illustrates an eighth step of some embodiments of the procedure, in which the first and second flexible tensioning elements 61, 62 may be coupled to each other and woven around the bone fracture 3 to preload the bone fracture 3 in compression to further resist tensile/distraction forces that may be imparted across the bone fracture 3, as previously described. Thus, combining the elongate fixation member 150 with the first and second flexible tensioning elements 61, 62 provides additional fixation, stabilization, and reduction of the bone fracture 3 over an elongate fixation member or flexible tensioning element alone.

In some embodiments, the first and second flexible tensioning elements 61, 62 may also be secured in place and/or tensioned via one or more securing elements (not shown), which may include any of the securing element designs and/or tensioning element designs described or contemplated herein.

FIGS. 7A-7D illustrate example devices, instruments, and method steps for a bone fixation assembly and surgical procedure, according to another embodiment of the present disclosure.

In some embodiments, the first and second bone fragments 1, 2 may be prepared in a similar manner to the first and second bone fragments 1, 2 shown in FIGS. 1B-1D in a first step and a second step.

Figure 7A:
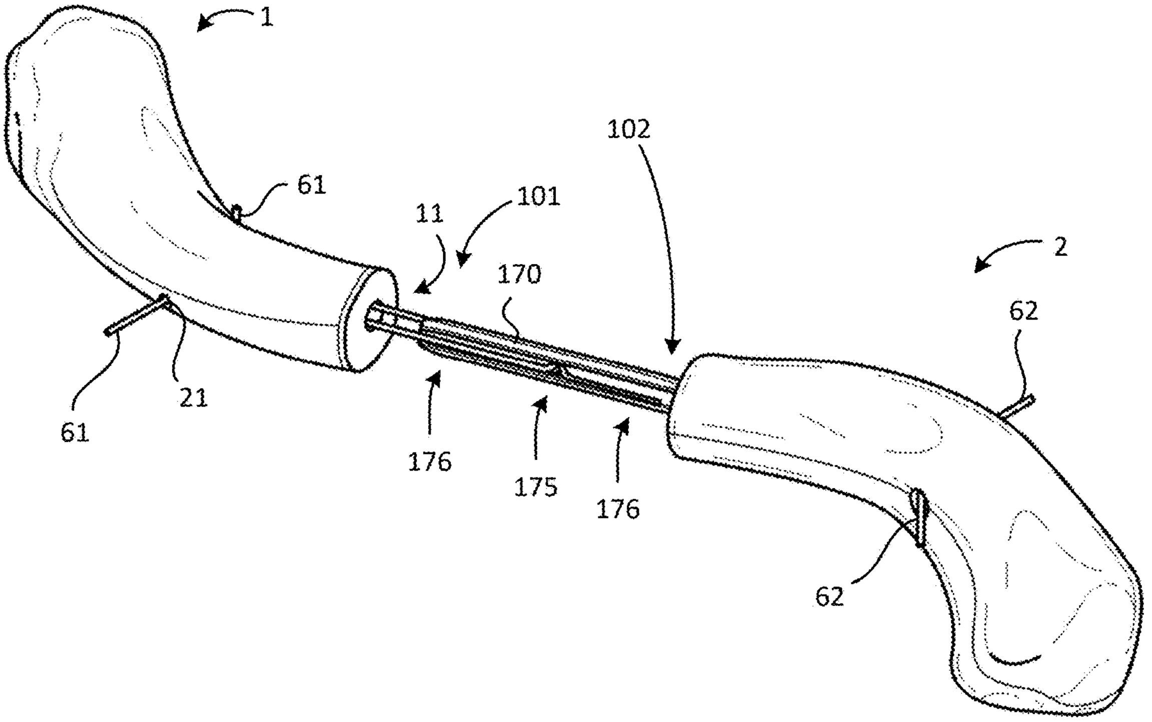
FIG. 7A illustrates a perspective side view of prepared bone fragments and an elongate fixation member, according to another embodiment of the present disclosure.

FIG. 7A illustrates a third step of some embodiments of the procedure, in which the first and second flexible tensioning elements 61, 62 may be passed through a centrally located transverse passageway 175 of an elongate fixation member 170, through the first and second intramedullary canals 11, 12, and out of the first and second transverse bone tunnels 21, 22. This may be accomplished with one or more retrieval wires, as previously discussed.

In some embodiments, the elongate fixation member 170 may include one or more grooves 176 formed in opposing sides of the elongate fixation member 170. The one or more grooves 176 may be configured to receive the first and second flexible tensioning elements 61, 62 therein to facilitate insertion of the elongate fixation member 170 into the first and second intramedullary canals 11, 12 by preventing frictional binding of the first and second flexible tensioning elements 61, 62 against the walls of the first and second intramedullary canals 11, 12.

Figure 7B:
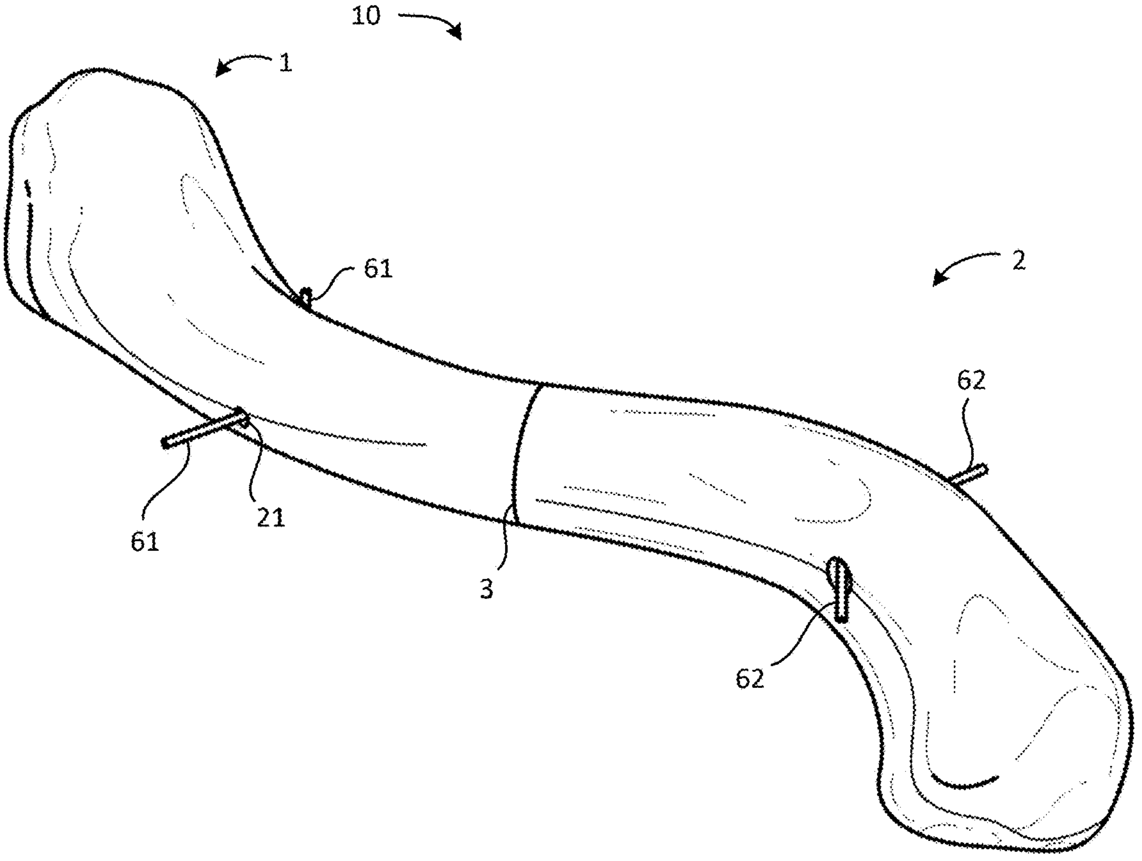
FIG. 7B illustrates a perspective side view of FIG. 7A with the elongate fixation member inserted into the bone fragments and flexible tensioning elements passing through transverse bone tunnels.
Figure 7C:
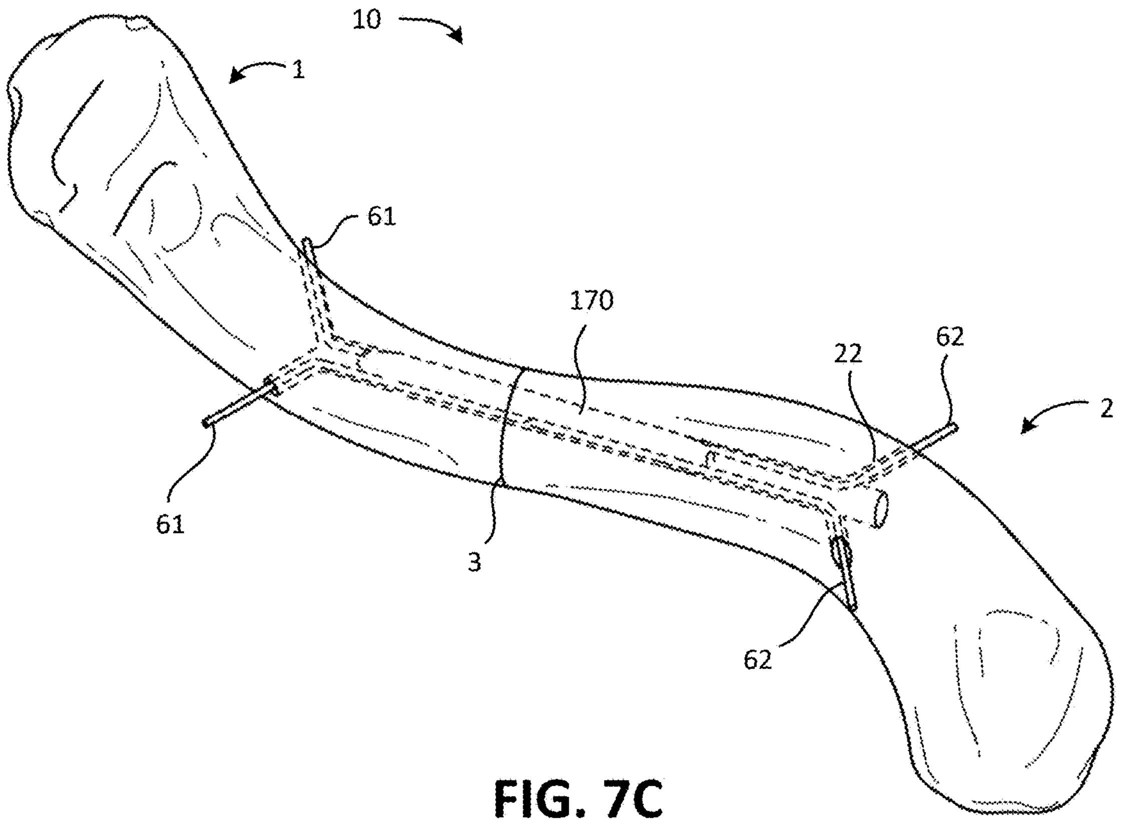
FIG. 7C illustrates another perspective side view of FIG. 7B.

FIGS. 7B and 7C illustrate a fourth step of some embodiments of the procedure, in which the elongate fixation member 170 may be inserted into the first and second intramedullary canals 11, 12 of the first and second bone fragments 1, 2 reducing the bone fracture 3.

Figure 7D:
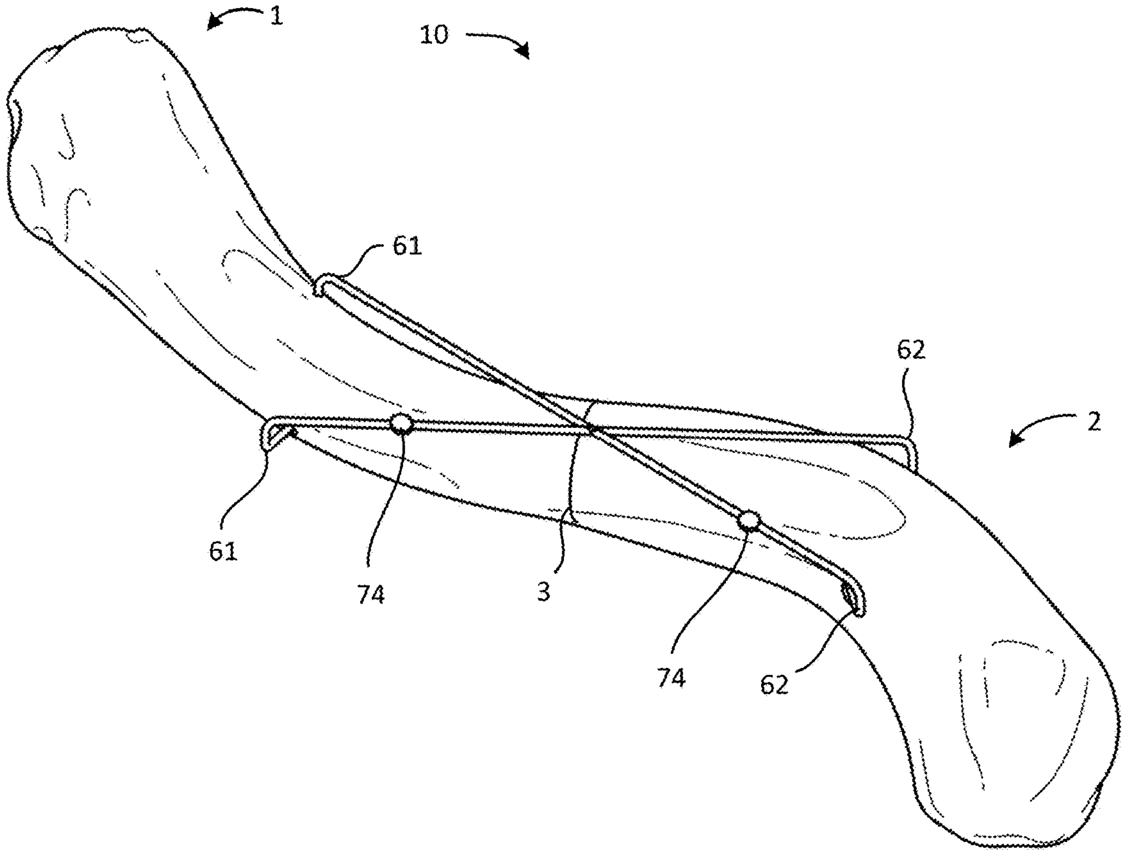
FIG. 7D illustrates a perspective side view of FIG. 7C with the flexible tensioning elements coupled to each other.

FIG. 7D illustrates a fifth step of some embodiments of the procedure, in which the first and second flexible tensioning elements 61, 62 may be coupled to each other and woven around the bone fracture 3 to preload the bone fracture 3 in compression to further resist tensile/distraction forces that may be imparted across the bone fracture 3, as previously described. Thus, combining the elongate fixation member 170 with the first and second flexible tensioning elements 61, 62 provides additional fixation, stabilization, and reduction of the bone fracture 3 over an elongate fixation member or flexible tensioning element alone.

In some embodiments, the first and second flexible tensioning elements 61, 62 may also be secured in place and/or tensioned via one or more fourth securing elements 74, which may include any of the securing element designs and/or tensioning element designs described or contemplated herein.

Figure 8A:
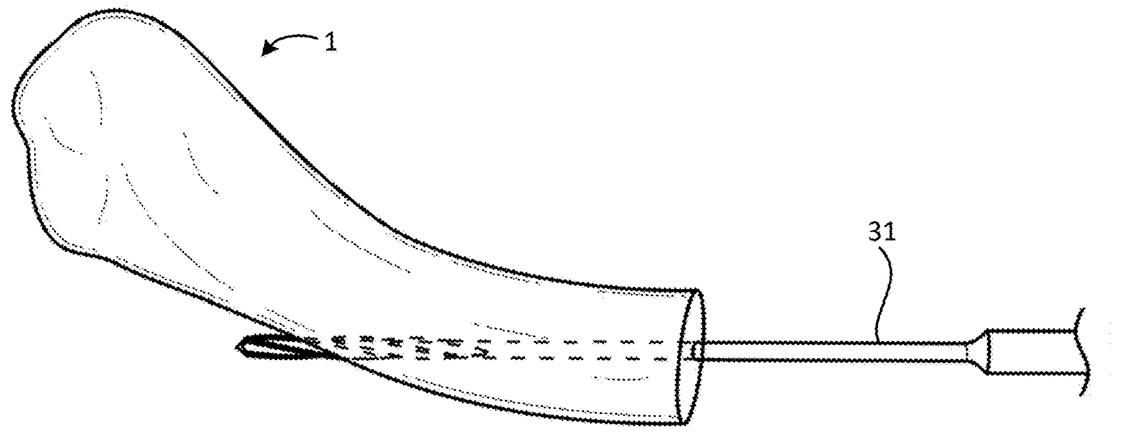
FIG. 8A illustrates a perspective side view of a drill bit preparing a pilot hole in a first bone fragment.

FIGS. 8A-80 illustrate example devices, instruments, and method steps for a bone fixation assembly and one or more simplified surgical procedures, according to embodiments of the present disclosure.

Figure 8B:
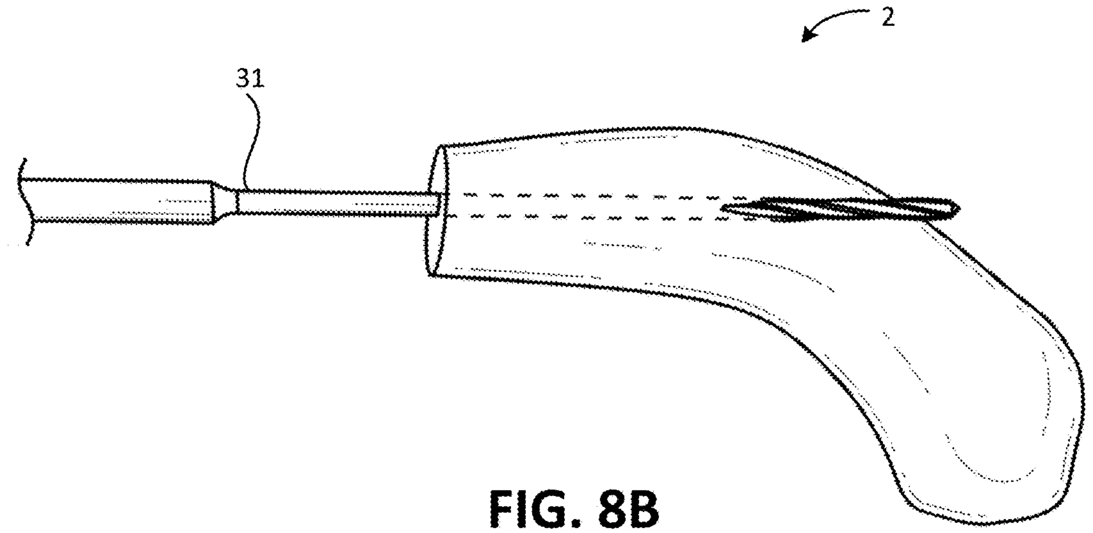
FIG. 8B illustrates a perspective side view of a drill bit preparing a pilot hole in a second bone fragment.

FIGS. 8A and 8B illustrate a first step of some embodiments of a simplified procedure, in which a drill bit 31 may be utilized to create pilot holes through the first and second intramedullary canals 11, 12 of the first and second bone fragments 1, 2.

Figure 8C:
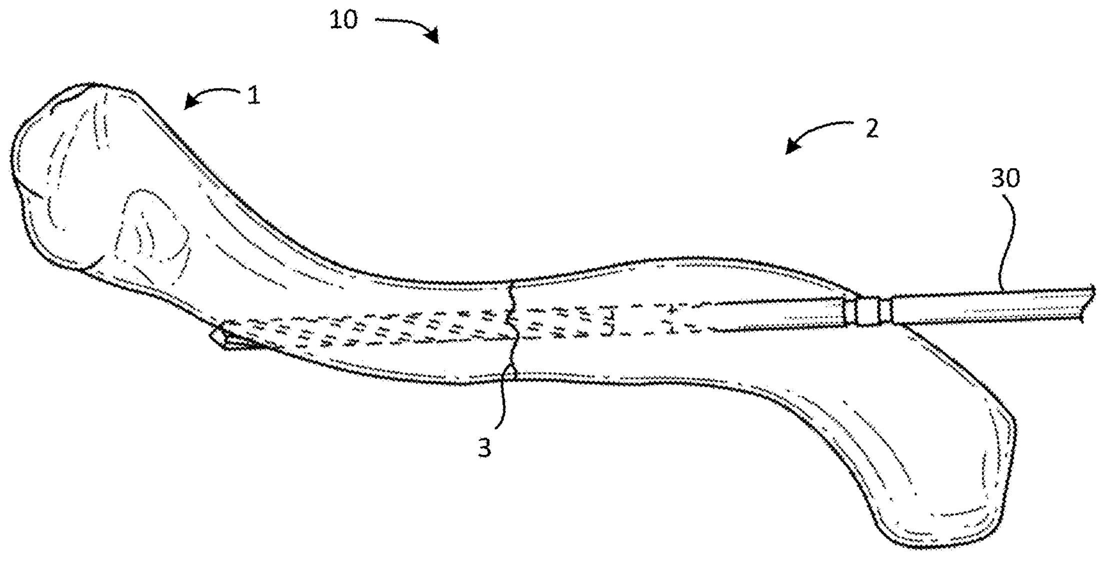
FIG. 8C illustrates a perspective side view of a reamer preparing the intramedullary canals of the bone fragments of FIGS. 8A and 8B from a lateral approach.
Figure 8D:
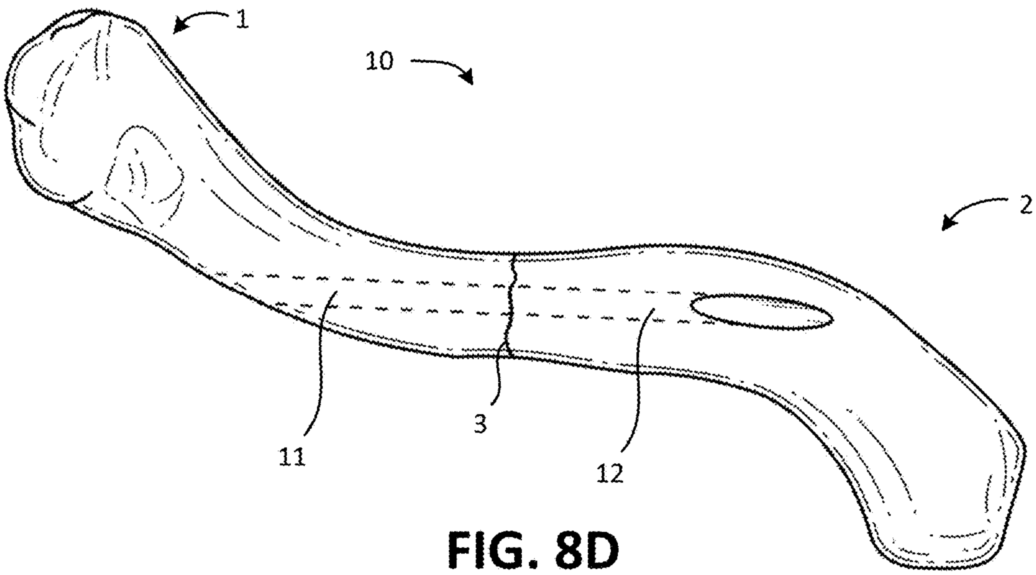
FIG. 8D illustrates a perspective side view of FIG. 8C showing the prepared intramedullary canals.

FIGS. 8C and 8D illustrate a second step of some embodiments of the simplified procedure, in which the first and second bone fragments 1, 2 may be aligned with each other to reduce the bone fracture 3 and a reamer 30 may then be utilized to enlarge or ream out the pilot holes of FIGS. 8A and 8B in order to create prepared first and second intramedullary canals 11, 12 that are aligned with each other. In some embodiments, the reamer 30 may be utilized from a lateral direction. However, it will be understood that in other embodiments the reamer 30 may be utilized from a medial direction.

Figure 8E:
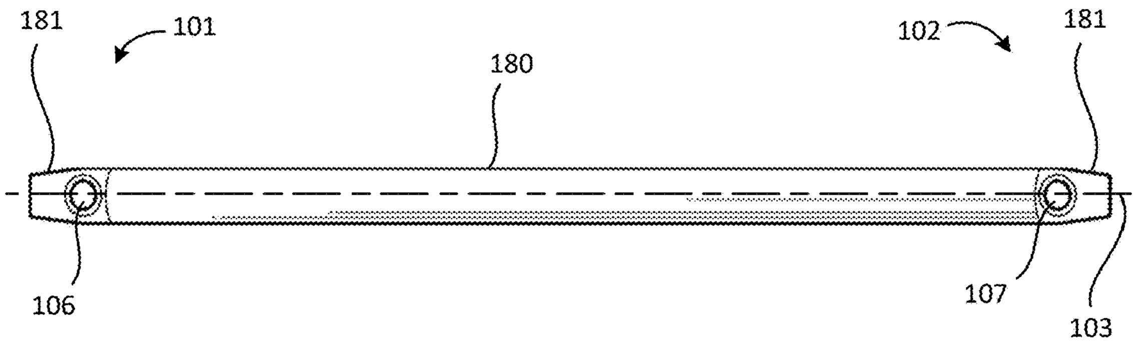
FIG. 8E illustrates a side view of an elongate fixation member, according to another embodiment of the present disclosure.

FIG. 8E illustrates an elongate fixation member 180, according to another embodiment of the present disclosure. The elongate fixation member 180 may generally include a proximal portion or first portion 101, a distal portion or second portion 102, and a central longitudinal axis 103.

In some embodiments, the proximal and/or distal portions 101, 102 may comprise tapered ends 181 to facilitate insertion of the elongate fixation member 180 into bone.

In some embodiments, the elongate fixation member 180 may include a first transverse passageway 106 configured to receive a first flexible tensioning element 61 therethrough from a first direction that may be transverse to the central longitudinal axis 103 of the elongate fixation member 180. The elongate fixation member 180 may also include a second transverse passageway 107 configured to receive a second flexible tensioning element 62 therethrough from a second direction that may be transverse to the central longitudinal axis 103 of the elongate fixation member 180.

In some embodiments, the first direction and the second direction may be the same, or similar to each other.

In some embodiments, the first direction and the second direction may be opposite from each other.

In some embodiments, the elongate fixation member 180 may comprise an intramedullary rod.

In some embodiments, the elongate fixation member 180 may include a generally cylindrical shape.

In some embodiments, the elongate fixation member 180 may be solid or substantially solid. However, it will also be understood that in some embodiments the elongate fixation member 180 may comprise an at least partially hollow interior.

In some embodiments, the elongate fixation member 180 may comprise a rigid material to provide rigid fixation of the first and second bone fragments 1, 2 relative to each other.

Figure 8F:
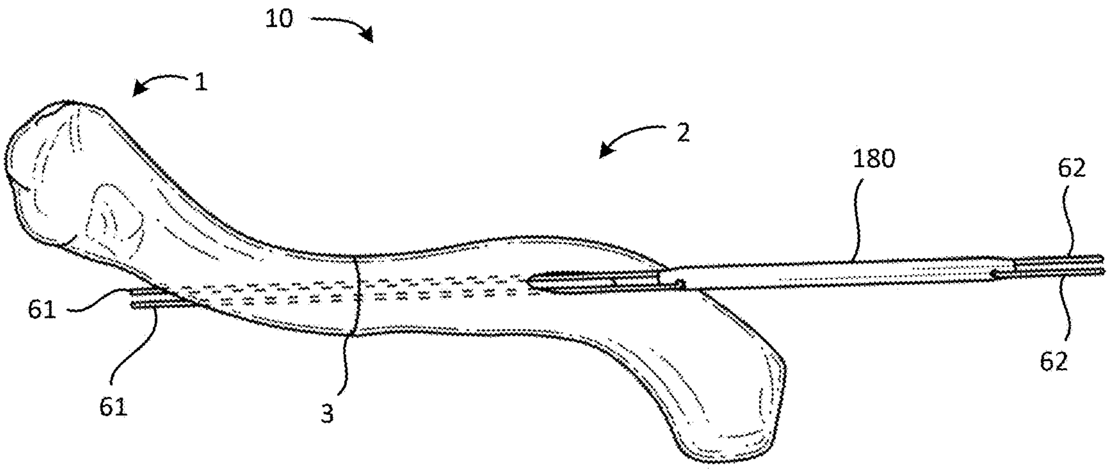
FIG. 8F illustrates a perspective side view of FIG. 8D with the elongate fixation member of FIG. 8E being inserted into the bone fragments from a lateral approach.
Figure 8G:
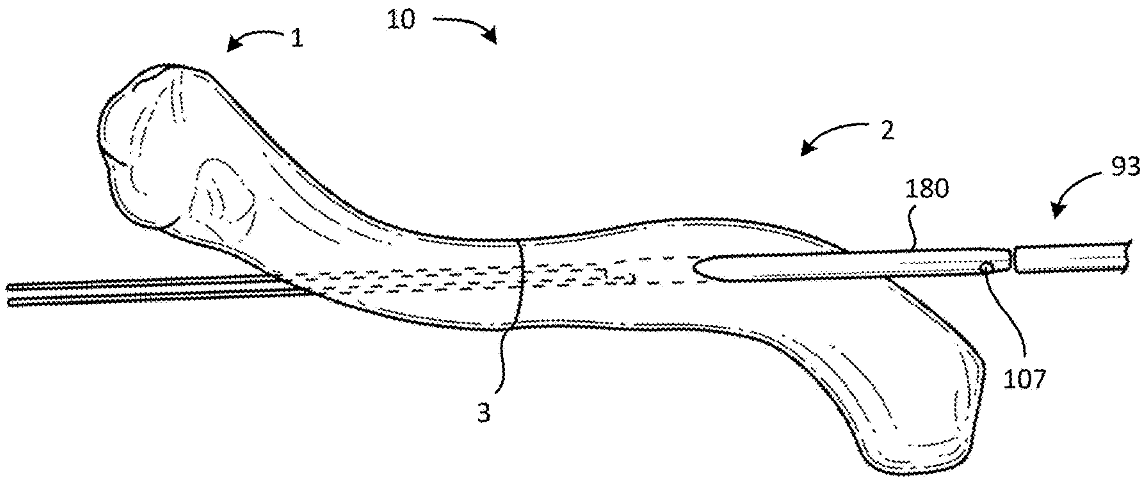
FIG. 8G illustrates a perspective side view of FIG. 8F with an impact tool driving the elongate fixation member into the bone fragments.
Figure 8H:
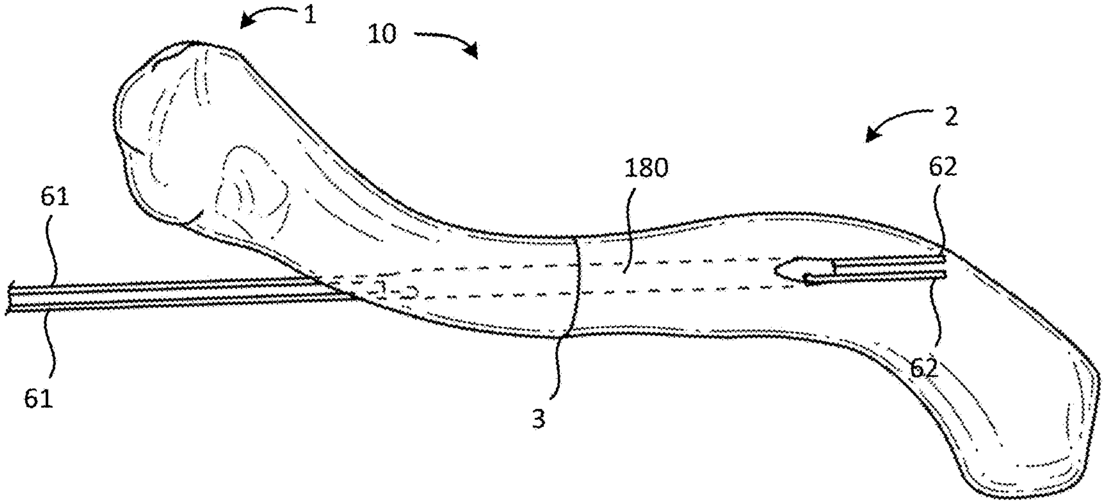
FIG. 8H illustrates a perspective side view of FIG. 8G with the elongate fixation member inserted into the bone fragments and flexible tensioning elements coupled to the elongate fixation member.

FIGS. 8F-8H illustrate a third step of some embodiments of the simplified procedure, in which the elongate fixation member 180 may be inserted into the first and second intramedullary canals 11, 12 of the first and second bone fragments 1, 2. FIG. 8F shows the first flexible tensioning element 61 passing through the first and second intramedullary canals 11, 12. This may be accomplished with one or more retrieval wires, as previously discussed. FIG. 8G shows the elongate fixation member 180 being forced into the first and second intramedullary canals 11, 12 with an impact driver tool 93, and FIG. 8H shows the elongate fixation member 180 placed within the first and second intramedullary canals 11, 12.

Figure 8I:
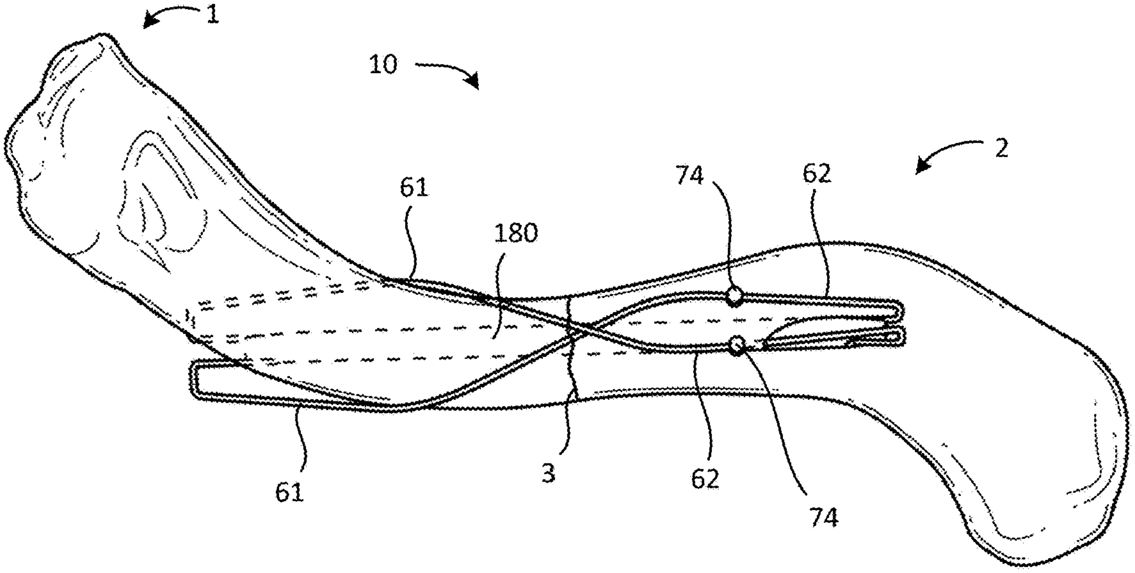
FIG. 8I illustrates a perspective side view of FIG. 8H with the flexible tensioning elements coupled to each other.

FIG. 8I illustrates a fourth step of some embodiments of the simplified procedure, in which the first and second flexible tensioning elements 61, 62 may be woven around the bone fracture 3 and secured together. The first and second flexible tensioning elements 61, 62 may be configured to span the bone fracture 3 and preload the bone fracture 3 in compression to resist tensile and/or distraction forces imparted across the bone fracture 3, thereby maintaining fixation of the first bone fragment 1 relative to the second bone fragment 2. In this manner, the bone fracture 3 may receive improved fixation and reduction strength by combining the elongate fixation member 180 with the first and second flexible tensioning elements 61, 62.

In some embodiments, the first and second flexible tensioning elements 61, 62 may also be secured in place and/or tensioned via one or more fourth securing elements 74, which may include any of the securing element designs and/or tensioning element designs described or contemplated herein.

FIGS. 8J-8O illustrate example devices, instruments, and method steps for a bone fixation assembly and an alternative simplified surgical procedure, according to another embodiment of the present disclosure.

In some embodiments, the first and second bone fragments 1, 2 may be prepared in a similar manner to the first and second bone fragments 1, 2 shown in FIGS. 8A-8D in a first step and a second step.

Figure 8J:
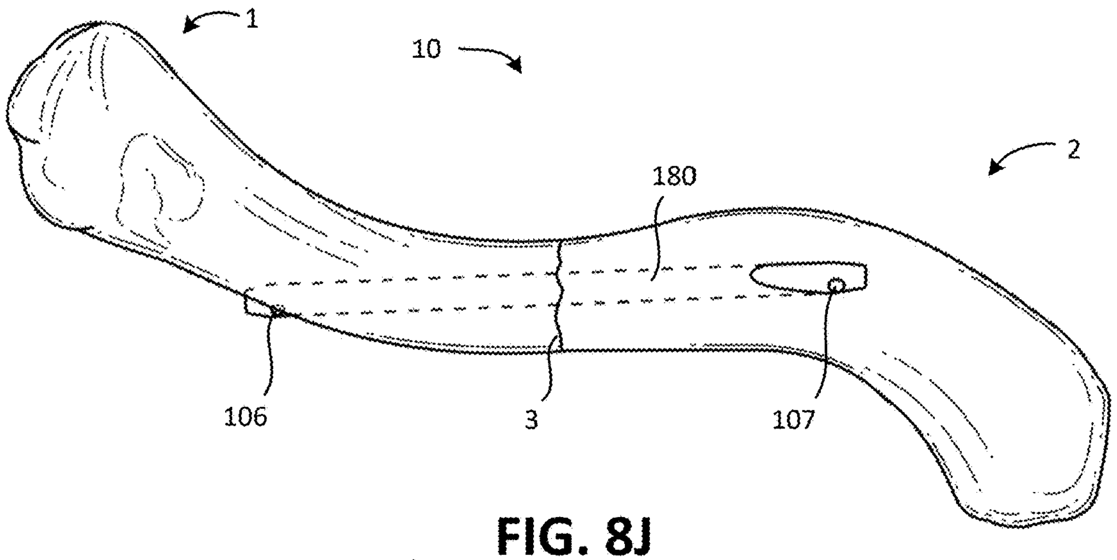
FIG. 8J illustrates a perspective side view of FIG. 8J without flexible tensioning elements.

FIG. 8J illustrates a third step of some embodiments of the alternative simplified procedure, in which the elongate fixation member 180 may be inserted into the first and second intramedullary canals 11, 12 of the first and second bone fragments 1, 2 without the first and second flexible tensioning elements 61, 62 being coupled to the elongate fixation member 180.

Figure 8K:
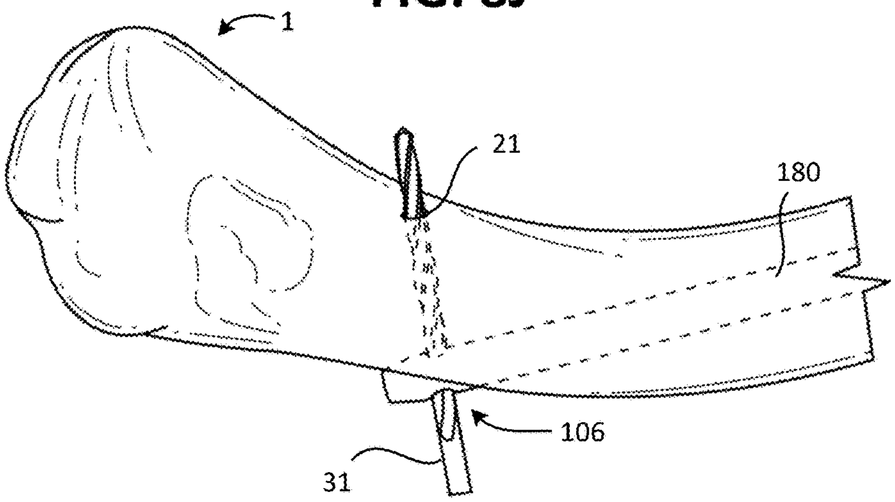
FIG. 8K illustrates a perspective side view of FIG. 8J with a drill bit forming a transverse bone tunnel through the first bone fragment.
Figure 8L:
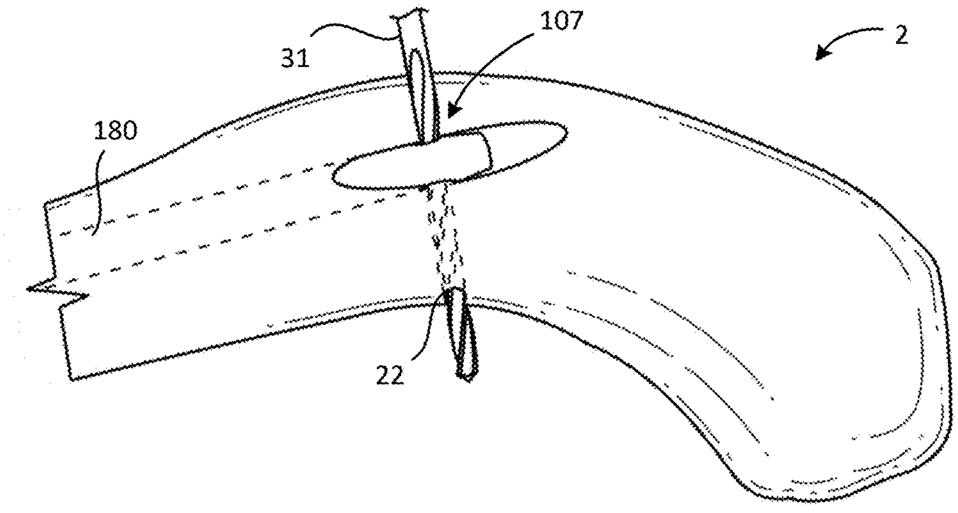
FIG. 8L illustrates a perspective side view of FIG. 8J with a drill bit forming a transverse bone tunnel through the second bone fragment.
Figure 8M:
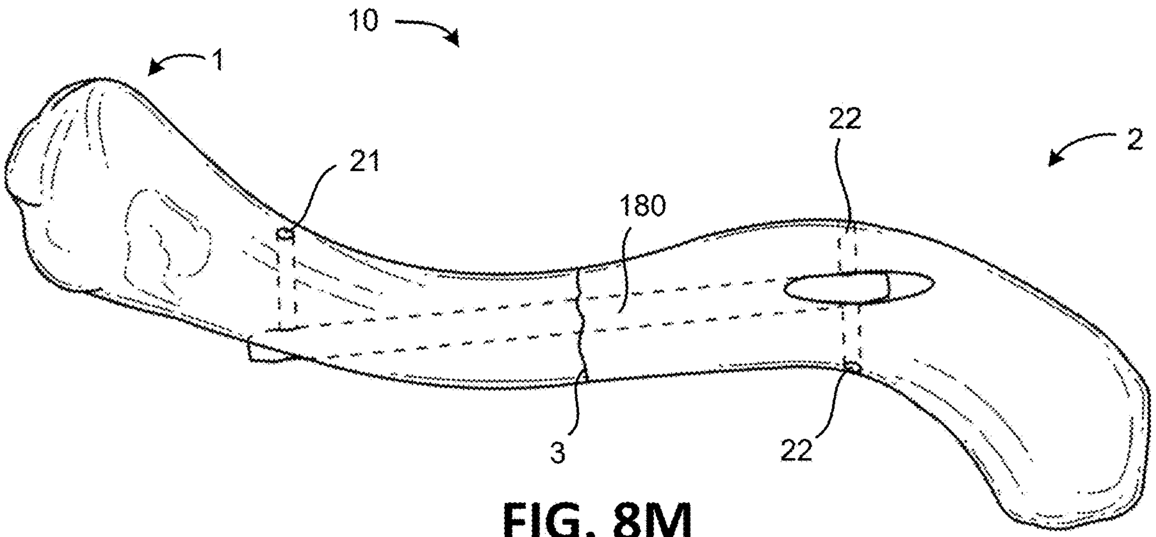
FIG. 8M illustrates another perspective side view of the first and second bone fragments of FIGS. 8K and 8L.

FIGS. 8K-8M illustrate a fourth step of some embodiments of the alternative simplified procedure, in which the first and second transverse bone tunnels 21, 22 may be formed through the first and second bone fragments 1, 2 with a drill bit 31.

In some embodiments, the first and second transverse passageways 106, 107 of the elongate fixation member 180 may be utilized to guide the drill bit 31 through the first and second bone fragments 1, 2 to quickly form the first and second transverse bone tunnels 21, 22 therethrough.

Figure 8N:
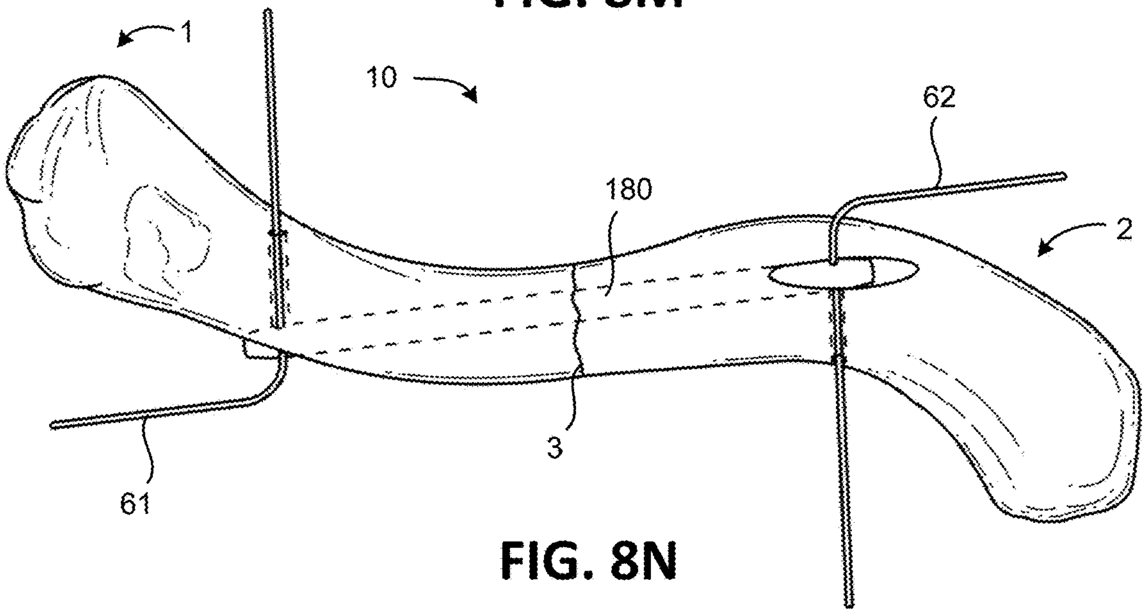
FIG. 8N illustrates a perspective side view of FIG. 8M with flexible tensioning elements passing through the transverse bone tunnels.

FIG. 8N illustrates a fifth step of some embodiments of the alternative simplified procedure, in which the first and second flexible tensioning elements 61, 62 may be inserted through the first and second transverse bone tunnels 21, 22 and through the first and second transverse passageways 106, 107 of the elongate fixation member 180.

Figure 8O:
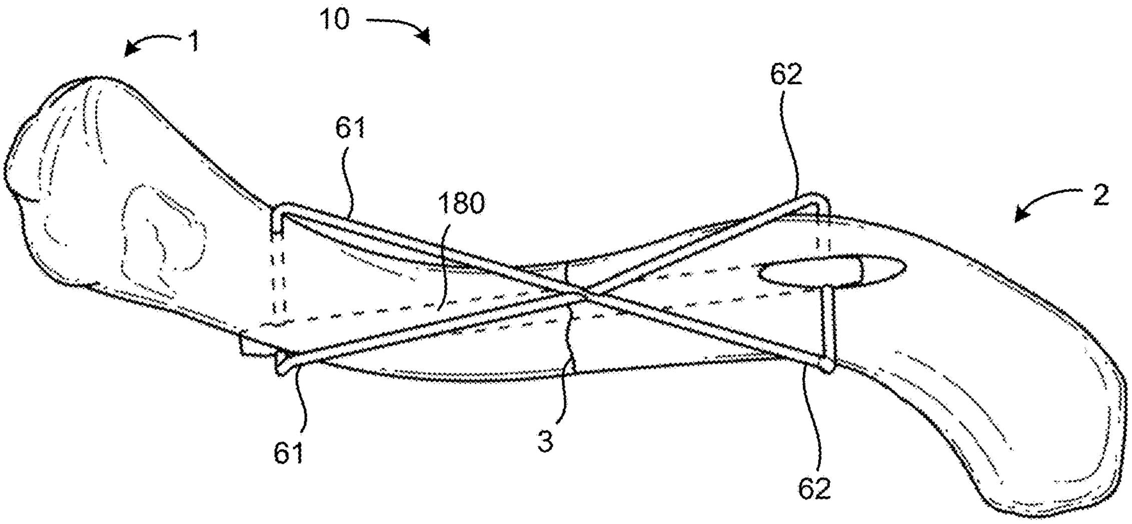
FIG. 8O illustrates a perspective side view of FIG. 8N with the flexible tensioning elements coupled to each other.

FIG. 8O illustrates a sixth step of some embodiments of the alternative simplified procedure, in which the first and second flexible tensioning elements 61, 62 may be woven around the bone fracture 3 and secured together. The first and second flexible tensioning elements 61, 62 may be configured to span the bone fracture 3 and preload the bone fracture 3 in compression to resist tensile and/or distraction forces imparted across the bone fracture 3, thereby maintaining fixation of the first bone fragment 1 relative to the second bone fragment 2. In this manner, the bone fracture 3 may receive improved fixation and reduction strength by combining the elongate fixation member 180 with the first and second flexible tensioning elements 61, 62.

In some embodiments, the first and second flexible tensioning elements 61, 62 may also be secured in place and/or tensioned via one or more securing elements (not shown), which may include any of the securing element designs and/or tensioning element designs described or contemplated herein.

FIGS. 9A-9E illustrate example devices, instruments, and method steps for a bone fixation assembly and procedure, according to another embodiment of the present disclosure.

Figure 9A:
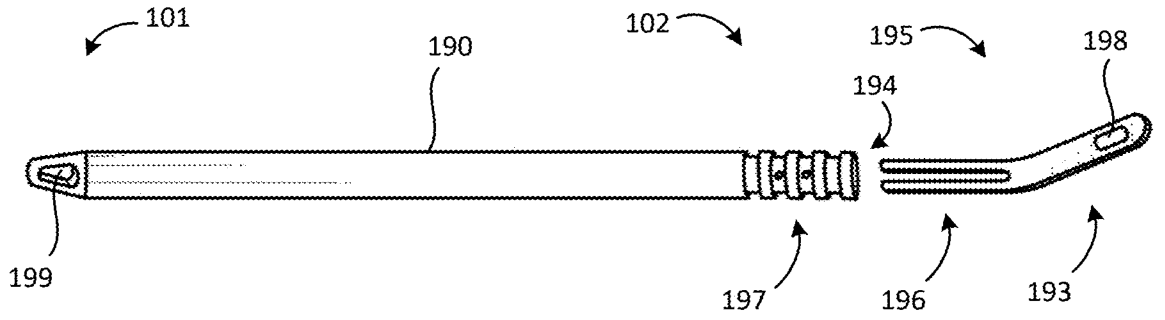
FIG. 9A illustrates a perspective side view of an elongate fixation member including a tensioner element, according to another embodiment of the present disclosure.

FIG. 9A illustrates an elongate fixation member 190 couplable with a tensioner element 195, according to an embodiment of the present disclosure.

The elongate fixation member 190 may include a proximal or first portion 101, a distal or second portion 102, an eyelet 199 at the distal portion, one or more attachment features 197, and a recess 194 formed in the proximal portion of the elongate fixation member 190.

The tensioner element 195 may include an attachment member 196, a resilient member 193, and an opening 198 formed in the resilient member 193.

In some embodiments, the resilient member 193 may be slightly angled with respect to the attachment member 196 in a free state.

Figure 9B:
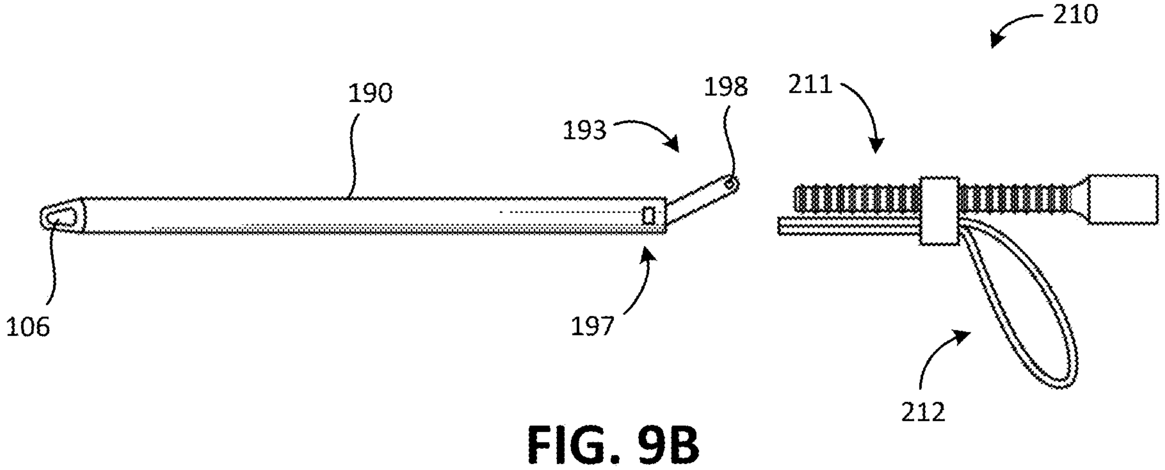
FIG. 9B illustrates a side view of the elongate fixation member of FIG. 9A and a bending tool, according to an embodiment of the present disclosure.
Figure 9C:
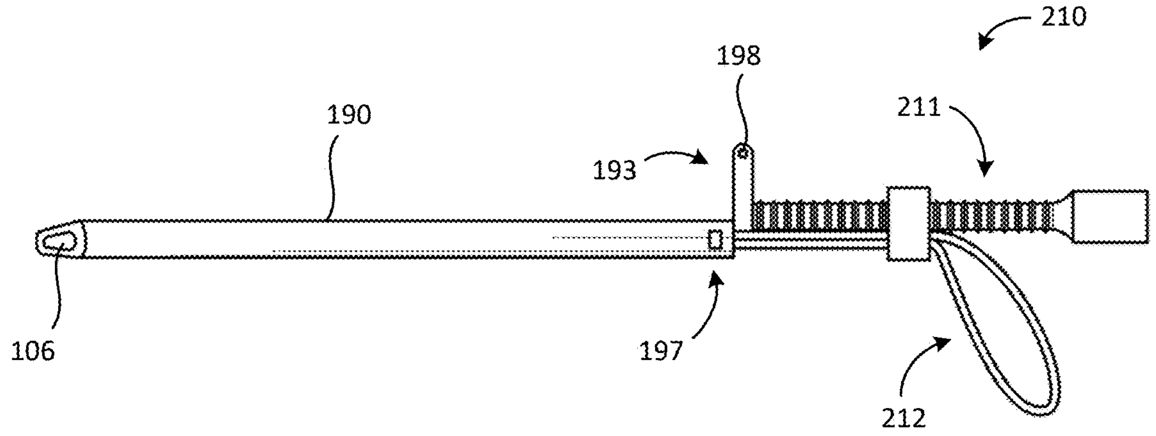
FIG. 9C illustrates a side view of FIG. 9B with the bending tool coupled to the elongate fixation member and engaging the tensioner element.
Figure 9D:
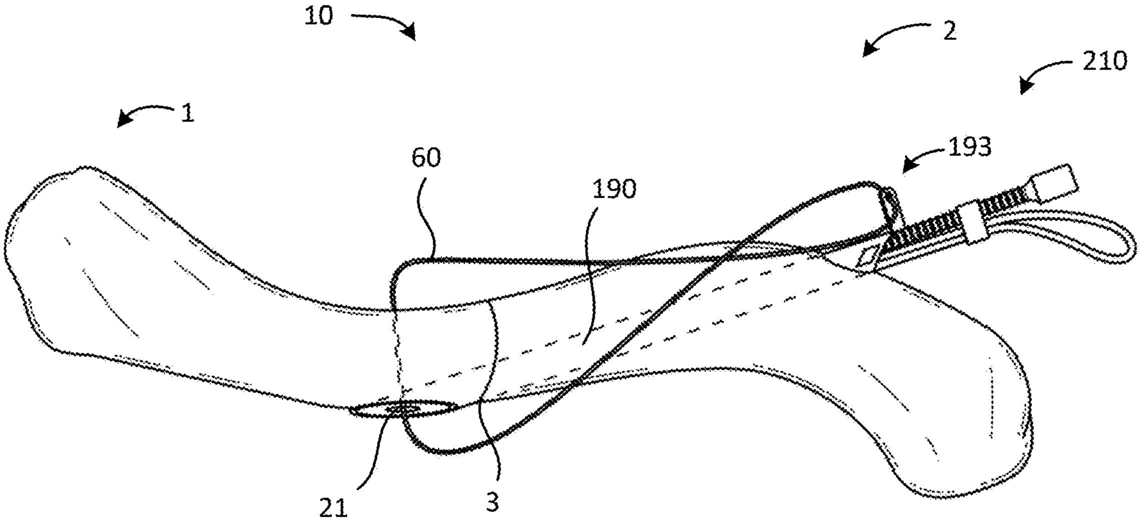
FIG. 9D illustrates a perspective side view FIG. 9C with the elongate fixation member inserted into a fractured bone and a flexible tensioning element passing through the tensioner element.
Figure 9E:
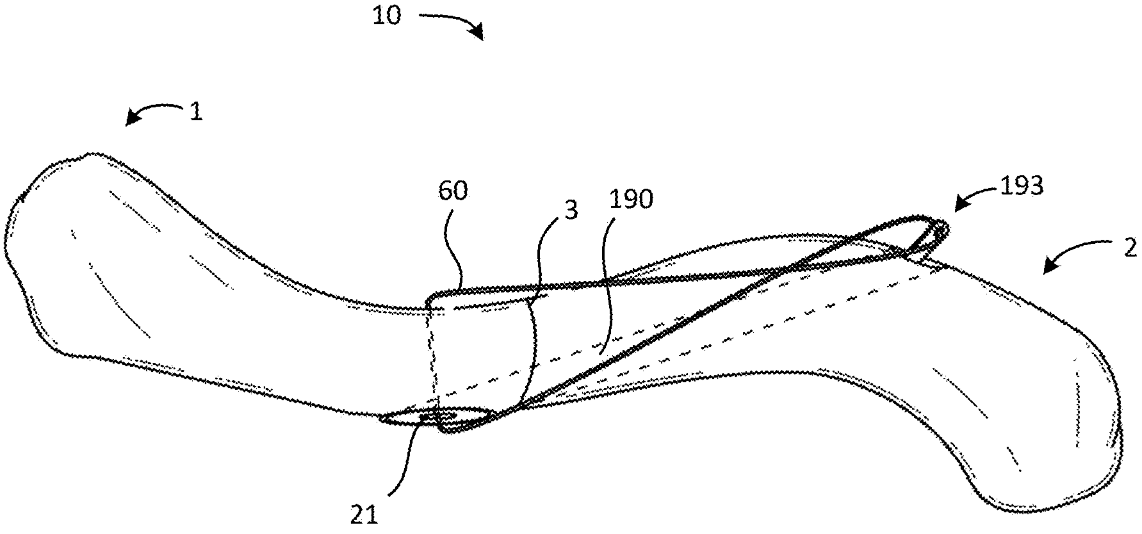
FIG. 9E illustrates a perspective side view of FIG. 9D with the bending tool removed from the elongate fixation member.

In some embodiments, the tensioner element 195 may comprise a super elastic material (e.g., such as nitinol, etc.)

that may be configured to provide a tensioning force to the flexible tensioning element 60, as shown in FIGS. 9D and 9E.

In some embodiments, the attachment member 196 may be received within the recess 194 formed in the proximal portion of the elongate fixation member 190 to removably couple the tensioner element 195 with the elongate fixation member 190.

In some embodiments, the tensioner element 195 may be integrally formed with, or otherwise permanently attached to, the elongate fixation member 190.

In some embodiments, the elongate fixation member 190 may comprise a resorbable material (such as PEEK, hydroxyapatite, etc.) and/or any other biocompatible material such as titanium, stainless steel, polymer, etc.

FIGS. 9B and 9C illustrate the elongate fixation member 190 of FIG. 9A in conjunction with an actuation tool 210, according to an embodiment of the present disclosure.

In some embodiments, the actuation tool 210 may include an actuator 211 coupled with a handle 212.

In some embodiments, the actuation tool 210 may also include one or more attachment features (not shown) which may be configured to engage with the one or more attachment features 197 of the elongate fixation member 190 to removably couple the actuation tool 210 with the elongate fixation member 190, as shown in FIGS. 9C and 9D.

In some embodiments, the actuator 211 may comprise a threaded thumb screw which may be advanced toward the resilient member 193 via rotation in a first direction to bend the resilient member 193 forward, as shown in FIGS. 9C and 9D.

In some embodiments, the resilient member 193 of the tensioner element 195 may be bent to about 90 degrees when fully loaded by the actuator 211.

In some embodiments, the actuator 211 may be retracted from the resilient member 193 via rotation in a second direction to release the resilient member 193 and/or remove the actuation tool 210 from the elongate fixation member 190, as shown in FIGS. 9B and 9E.

FIG. 9D illustrates the elongate fixation member 190 inserted into a bone 10 and a flexible tensioning element 60 passing through the opening 198 in the resilient member 193 with the actuation tool 210 attached to the elongate fixation member 190 and applying a bending force to the resilient member 193. In this manner, the surgeon can couple the flexible tensioning element 60 to the resilient member 193 as tight as possible while the resilient member 193 is bent forward by the actuator 211.

FIG. 9E illustrates the bone fixation assembly of FIG. 9D with the actuation tool 210 removed from the elongate fixation member 190, thus allowing the resilient member 193 to pull the flexible tensioning element 60 even tighter and further preload the bone fracture 3 in compression to resist tensile/distraction forces that may be imparted across the bone fracture 3, as previously described.

FIGS. 10A-11B illustrate various alternative devices and methods for tensioning a flexible tensioning element, according to embodiments of the present disclosure.

Figure 10A:
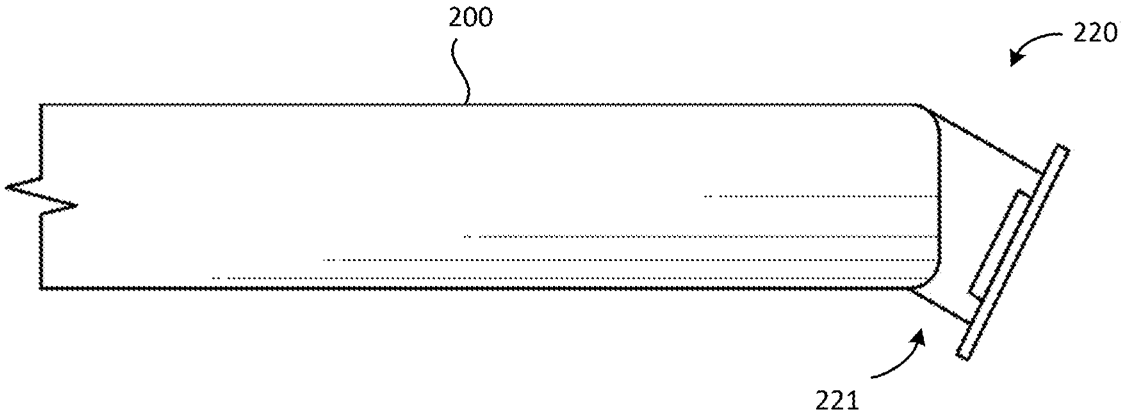
FIG. 10A illustrates a side view of an elongate fixation member with an angled cap attached thereto, according to an embodiment of the present disclosure.

FIG. 10A illustrates an elongate fixation member 200 with an angled cap 220 attached thereto at an angle with respect to the elongate fixation member 200. In this embodiment, a bottom surface 221 of the angled cap 220 may act to press downward on a flexible tensioning element (not shown) that may be coupled to the bottom surface 221 of the angled cap 220. This may further tension the flexible tensioning element and preload a bone fracture in compression to resist tensile/distraction forces that may be imparted across the bone fracture, as previously described herein.

Figure 10B:
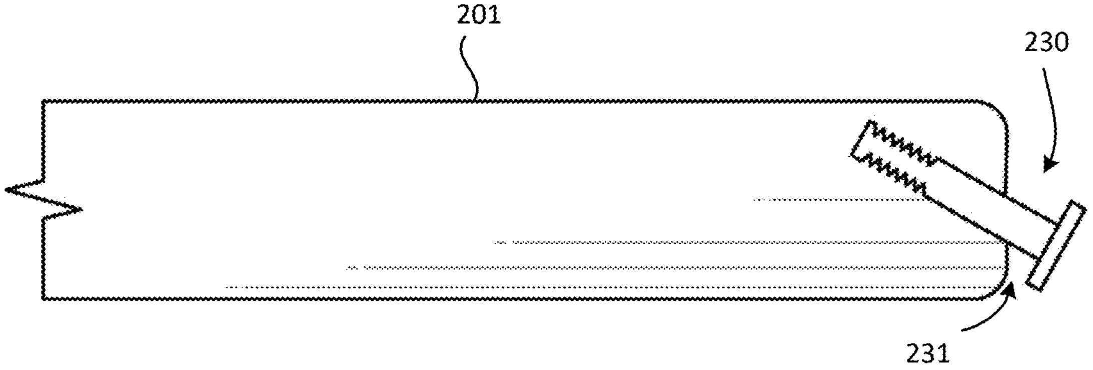
FIG. 10B illustrates a side view of an elongate fixation member with an angled fastener attached thereto, according to an embodiment of the present disclosure.
Figure 10C:
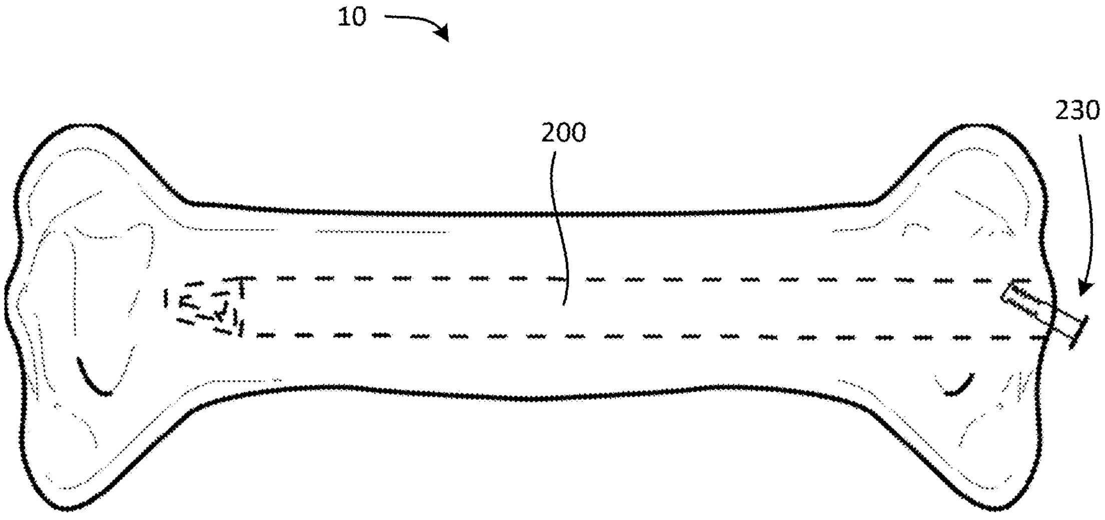
FIG. 10C illustrates a side view of the elongate fixation member of FIG. 10B inserted into a bone.

FIG. 10B illustrates an elongate fixation member 201 with an angled fastener 230 attached thereto at an angle with respect to the elongate fixation member 201. In this embodiment, a bottom surface 231 of the angled fastener 230 may likewise act to press downward on a flexible tensioning element (not shown) that may be coupled to the bottom surface 231 of the angled fastener 230. This may further tension the flexible tensioning element and preload a bone fracture in compression to resist tensile/distraction forces that may be imparted across the bone fracture, as previously described herein. FIG. 10C illustrates the elongate fixation member 201 and the angled fastener 230 inserted into a bone 10.

Figure 11A:
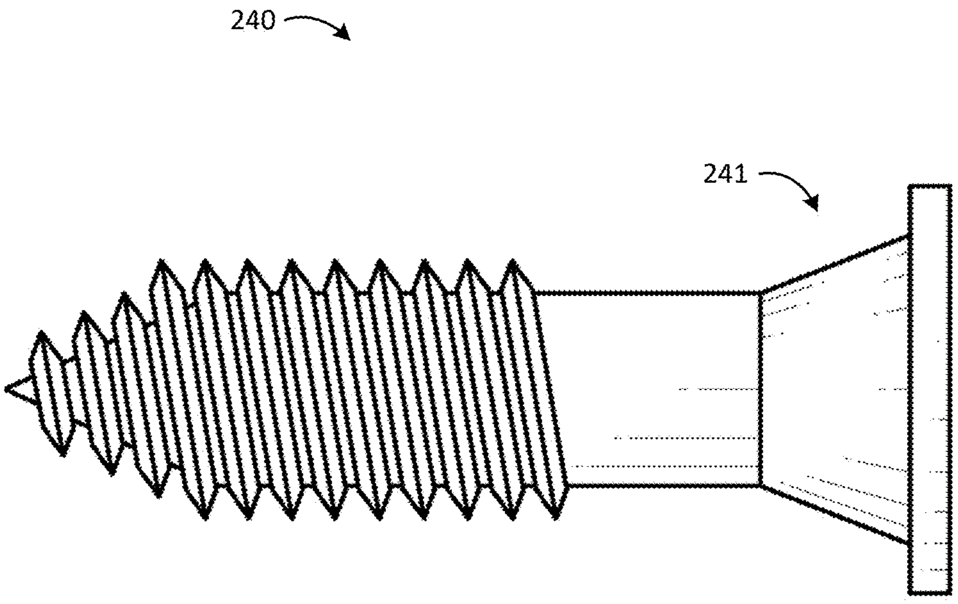
FIG. 11A illustrates a side view of flared fastener, according to an embodiment of the present disclosure.

FIG. 11A illustrates a flared fastener 240 comprising a flared portion 241 near the head of the flared fastener 240. In this manner, the flared fastener 240 may be coupled with an elongate fixation member (not shown) without the need of angling the flared fastener 240 with respect to the elongate fixation member, due to the inherent angle already created by the flared portion 241. In this embodiment, the flared portion 241 may act to press on a flexible tensioning element (not shown) as the flared fastener 240 couples with an elongate fixation member. This may further tension the flexible tensioning element and preload a bone fracture in compression to resist tensile/distraction forces that may be imparted across the bone fracture, as previously described herein.

Figure 11B:
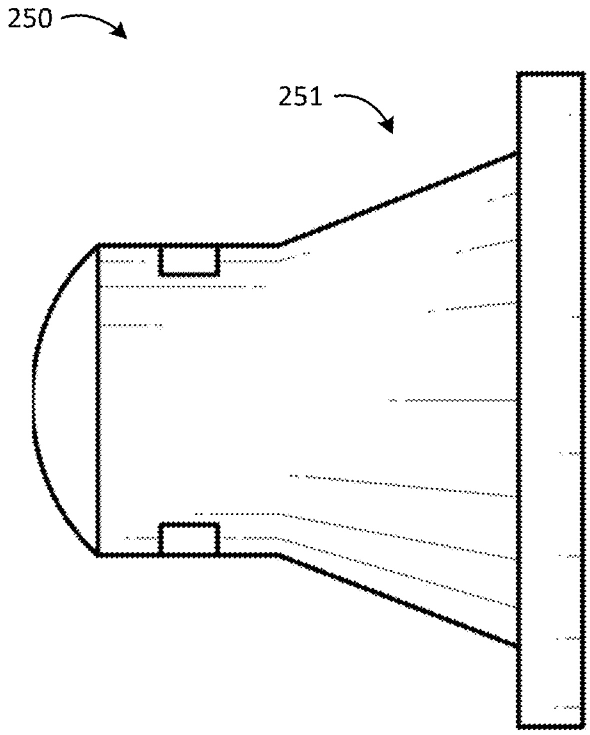
FIG. 11B illustrates a side view of flared cap, according to an embodiment of the present disclosure.
Figure 12A:
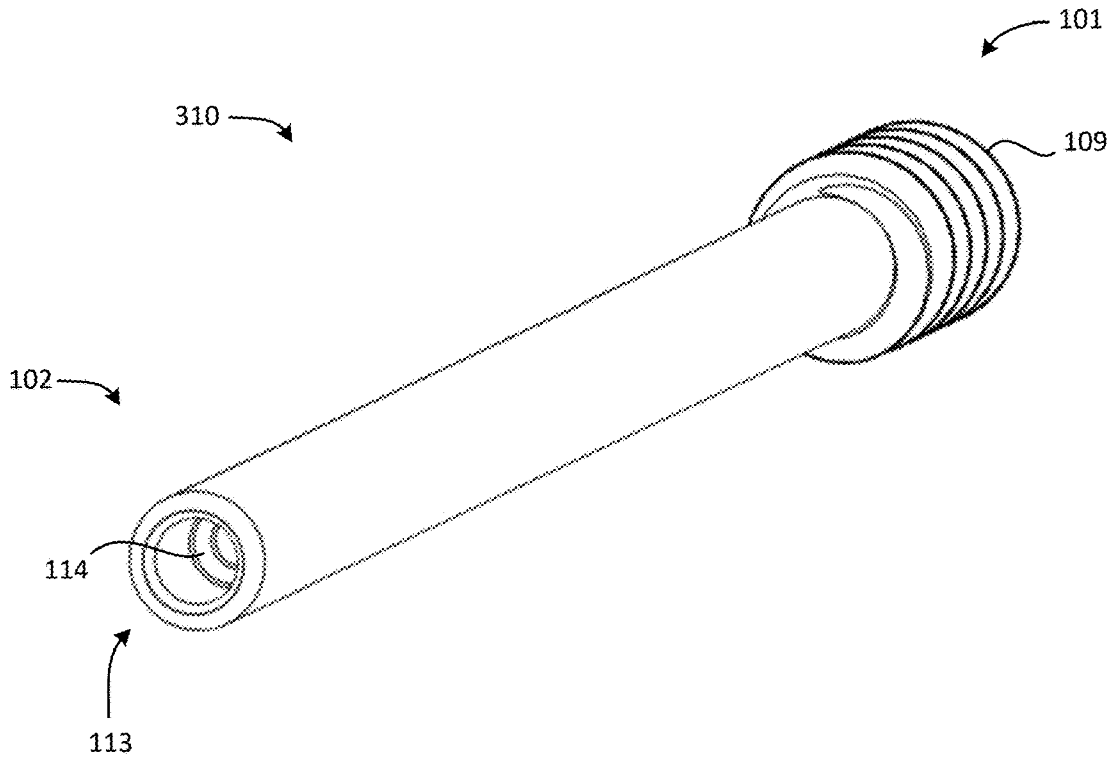
FIG. 12A illustrates a distal perspective view of an elongate fixation member, according to another embodiment of the present disclosure.
Figure 12B:
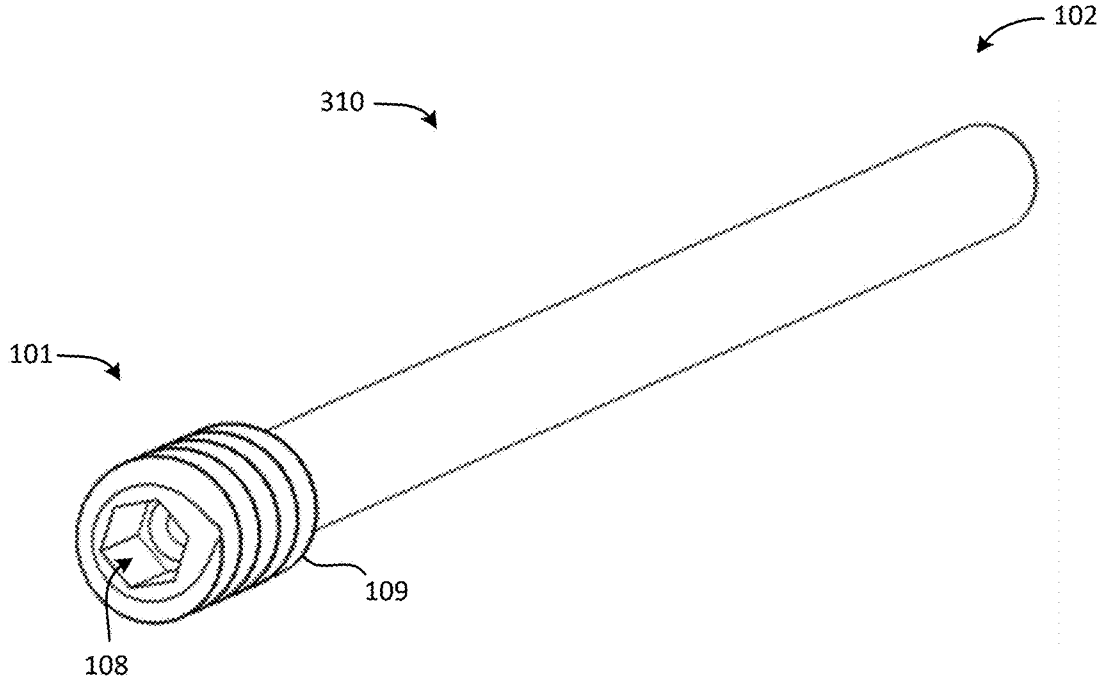
FIG. 12B illustrates a proximal perspective view of the elongate fixation member of FIG. 12A.
Figure 12C:
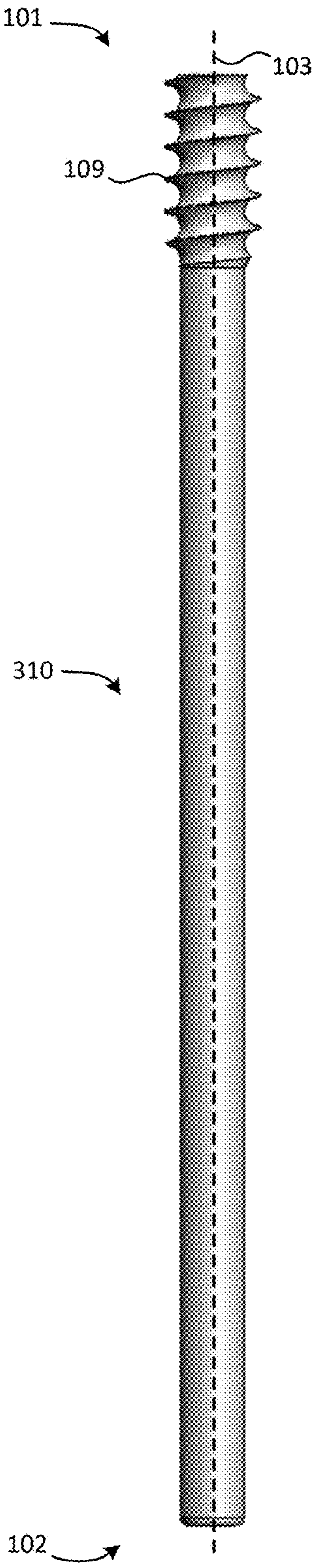
FIG. 12C illustrates a side view of the elongate fixation member of FIG. 12A.
Figure 12D:
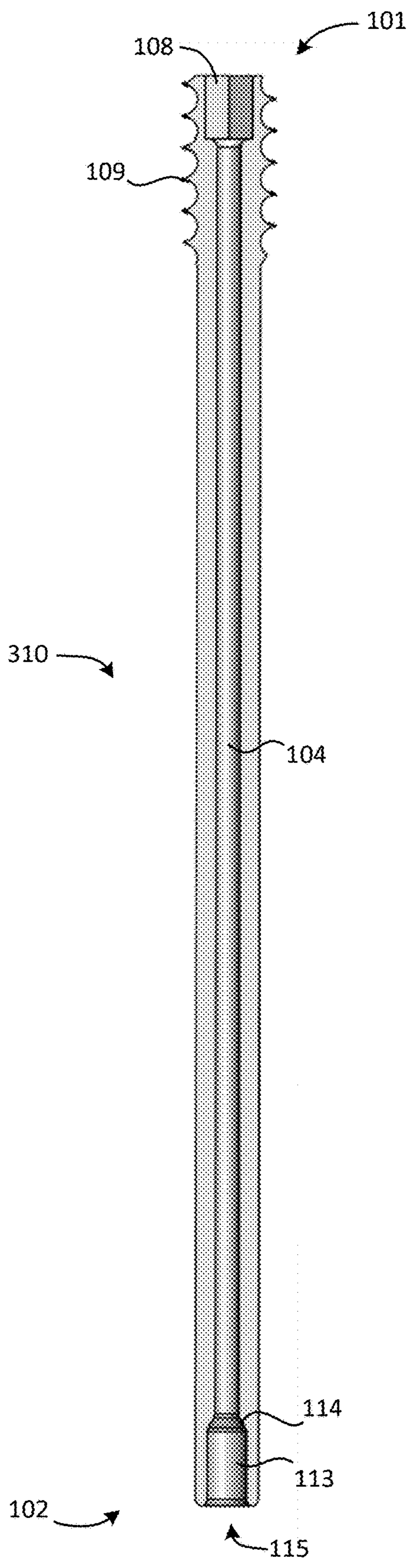
FIG. 12D illustrates a cross-sectional view of the elongate fixation member of FIG. 12C.

FIG. 11B illustrates a flared cap 250 comprising a flared portion 251 near the head of the flared cap 250. In this manner, the flared cap 250 may likewise be coupled with an elongate fixation member (not shown) without the need of angling the flared cap 250 with respect to the elongate fixation member, due to the inherent angle already created by the flared portion 251. In this embodiment, the flared portion 251 may likewise act to press on a flexible tensioning element (not shown) as the flared cap 250 couples with an elongate fixation member. This may further tension the flexible tensioning element and preload a bone fracture in compression to resist tensile/distraction forces that may be imparted across the bone fracture, as previously described herein.

Figure 13:
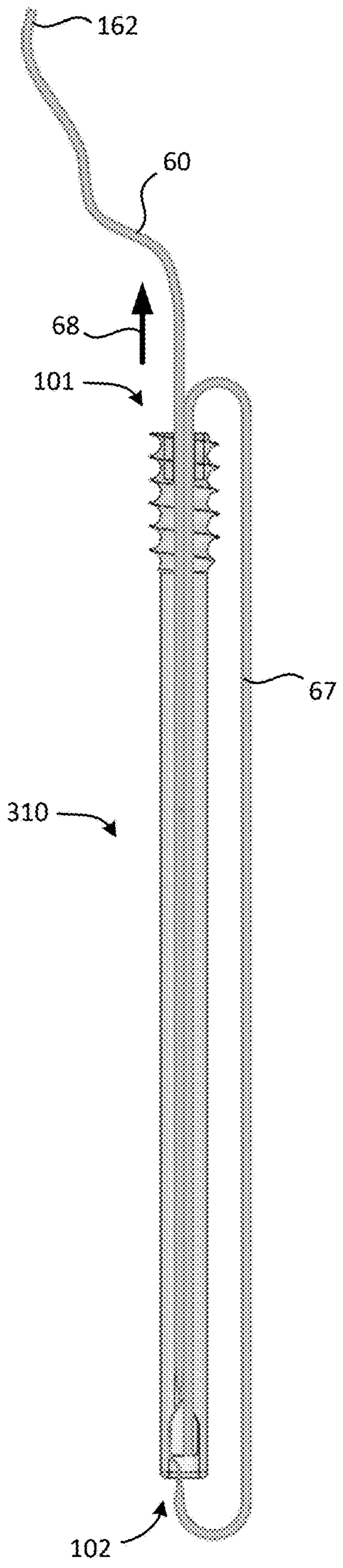
FIG. 13 illustrates a partially transparent side view of a bone fixation assembly, according to an embodiment of the present disclosure.
Figure 14:
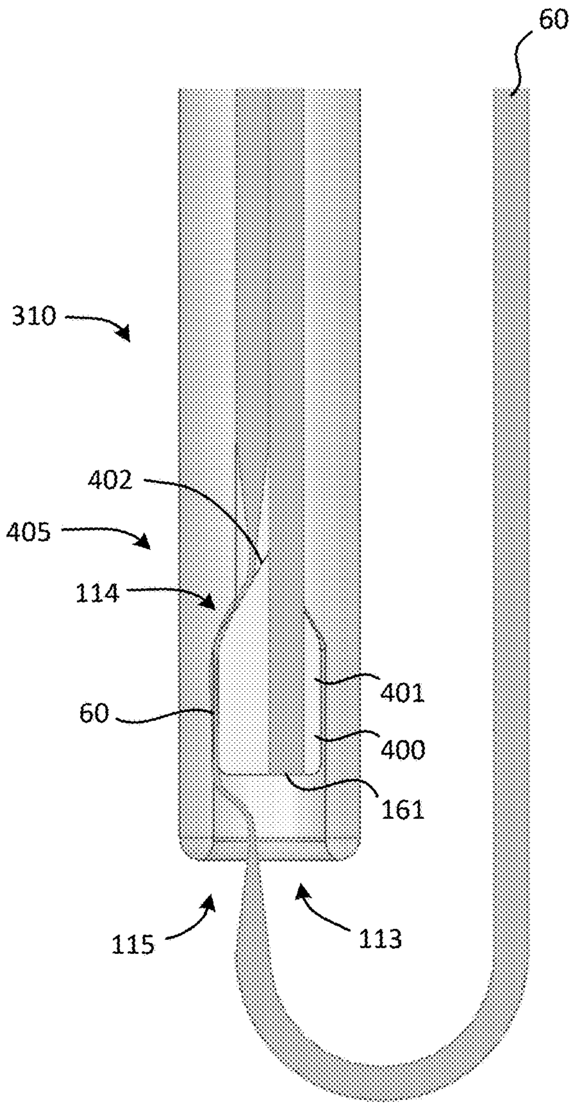
FIG. 14 illustrates a close up view of a distal end of the bone fixation assembly of FIG. 13.
Figure 15:
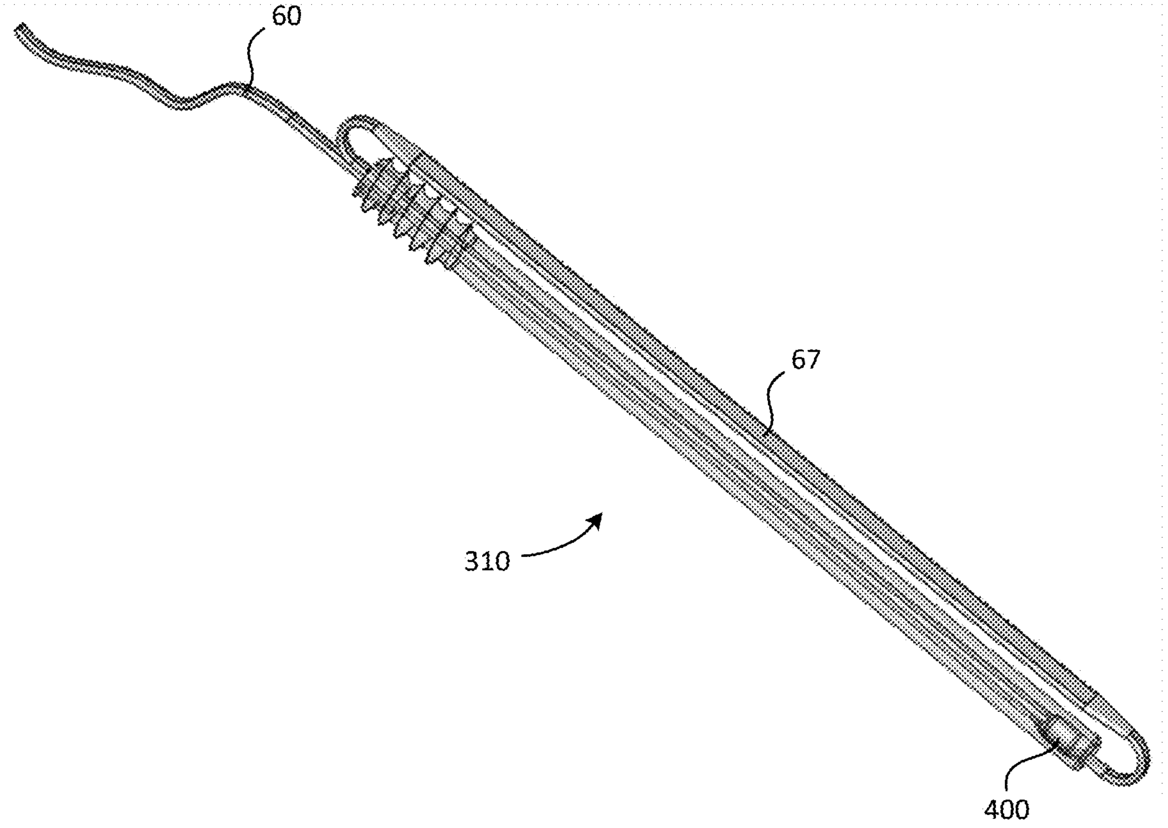
FIG. 15 illustrates a perspective view of the bone fixation assembly of FIG. 13.
Figure 16:
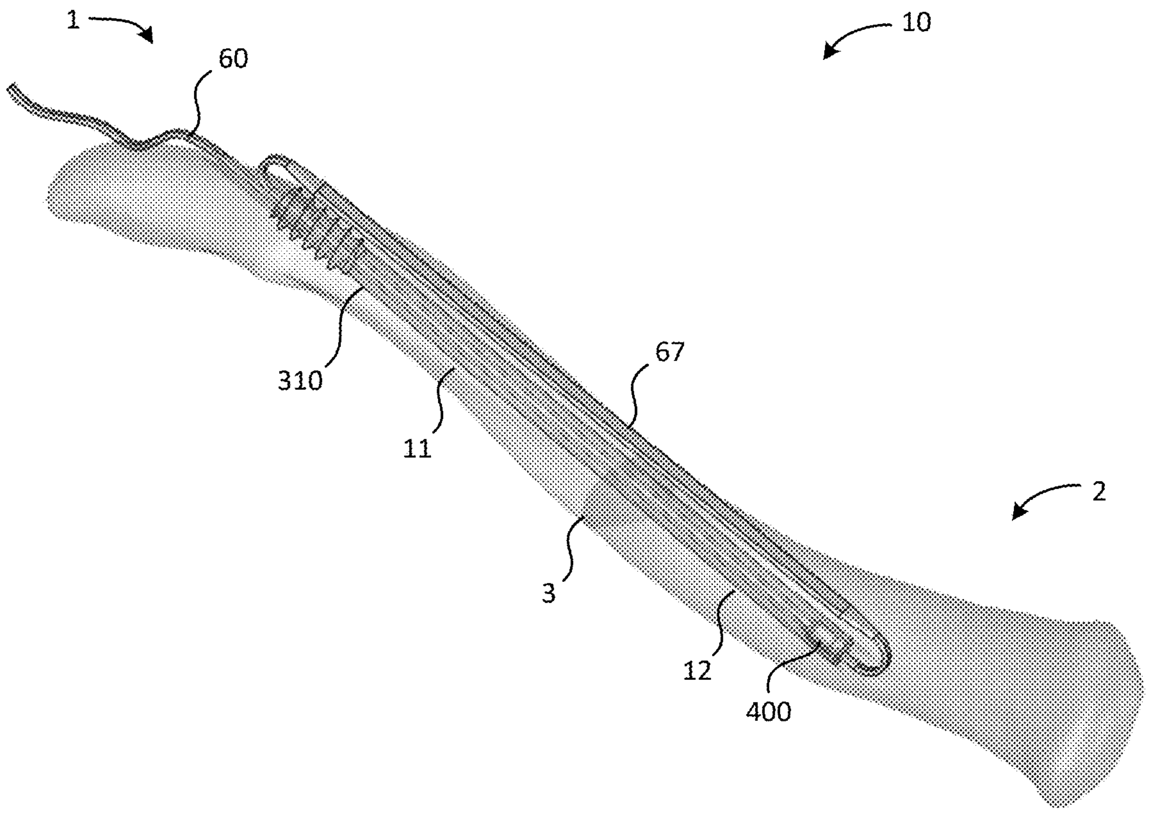
FIG. 16 illustrates a transparent perspective view of the bone fixation assembly of FIG. 13 implanted in a bone.
Figure 17:
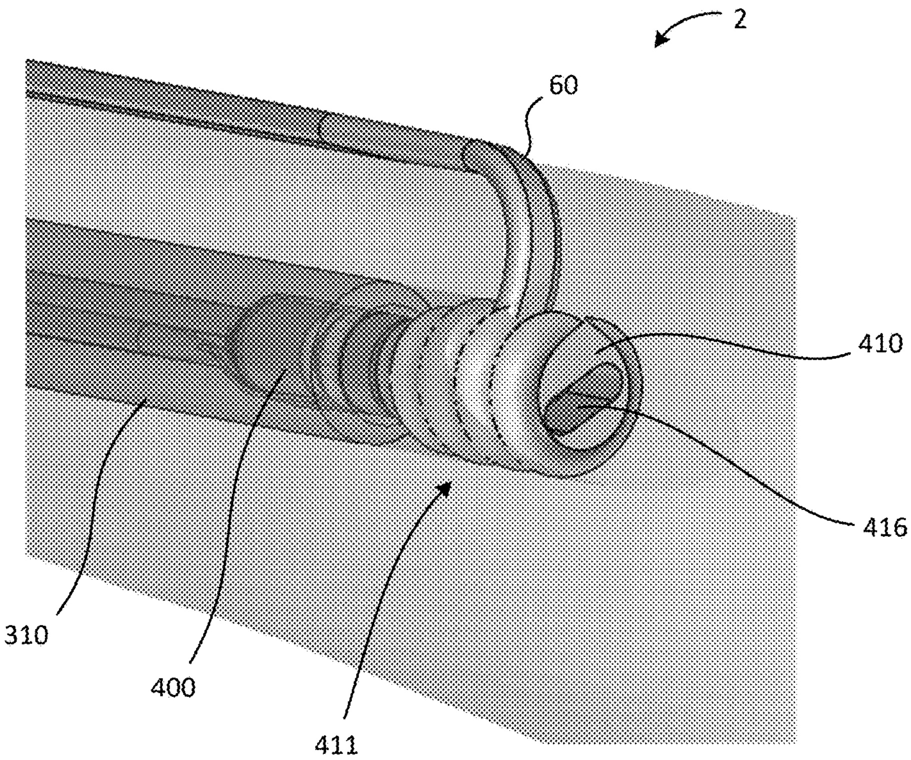
FIG. 17 illustrates a close up perspective view of a distal end of the bone fixation assembly of FIG. 16 with a threaded suture anchor placed therein.
Figure 18:
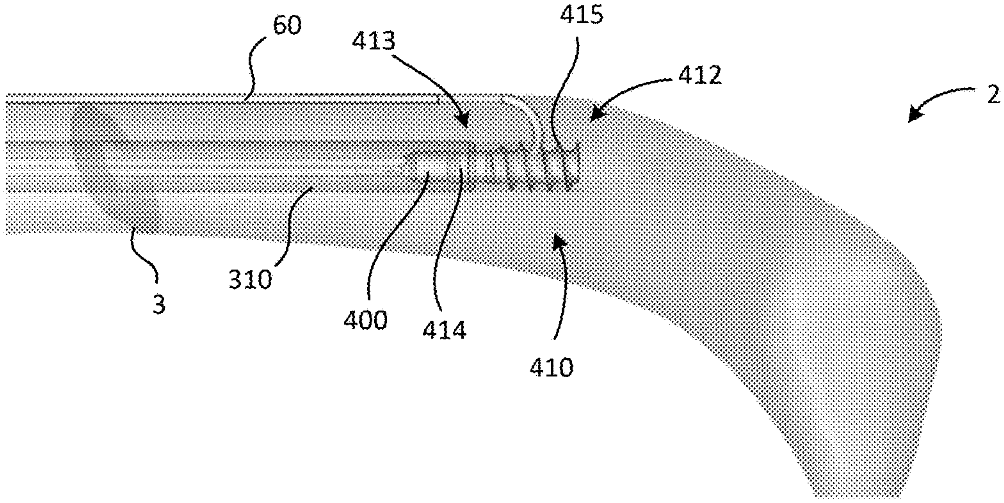
FIG. 18 illustrates a close up side view of the distal end of the bone fixation assembly of FIG. 17.
Figure 19A:
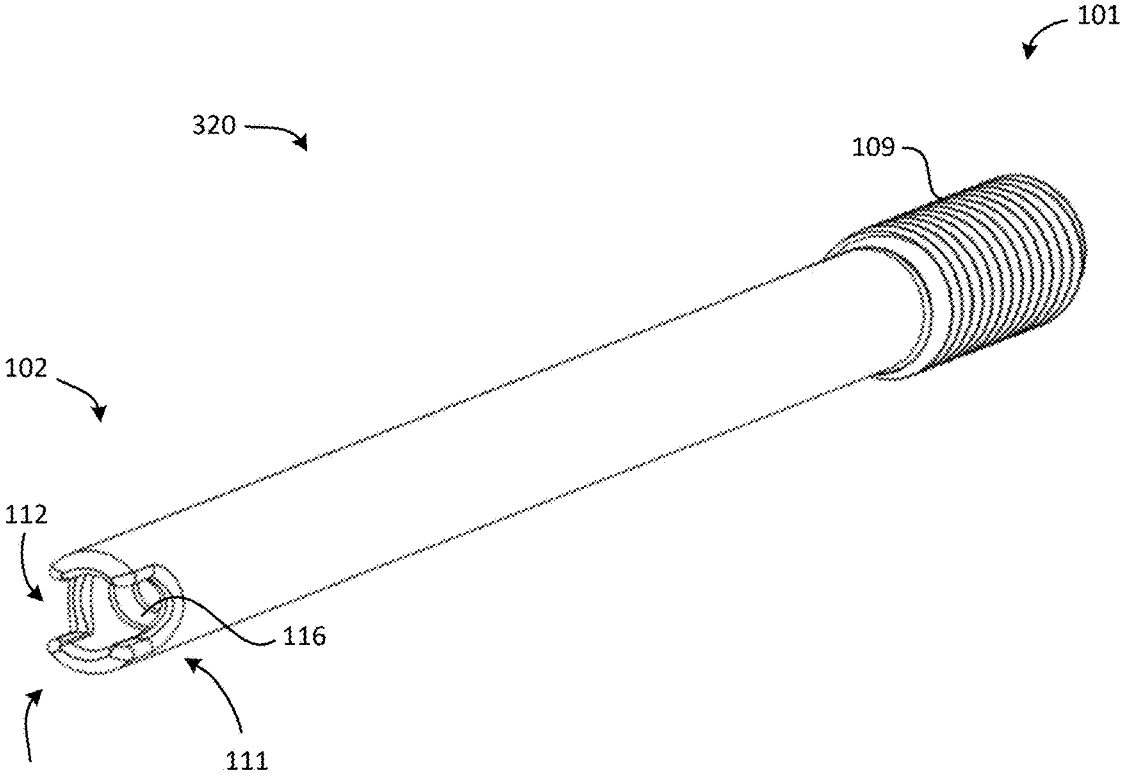
FIG. 19A illustrates a distal perspective view of an elongate fixation member, according to another embodiment of the present disclosure.
Figure 19B:
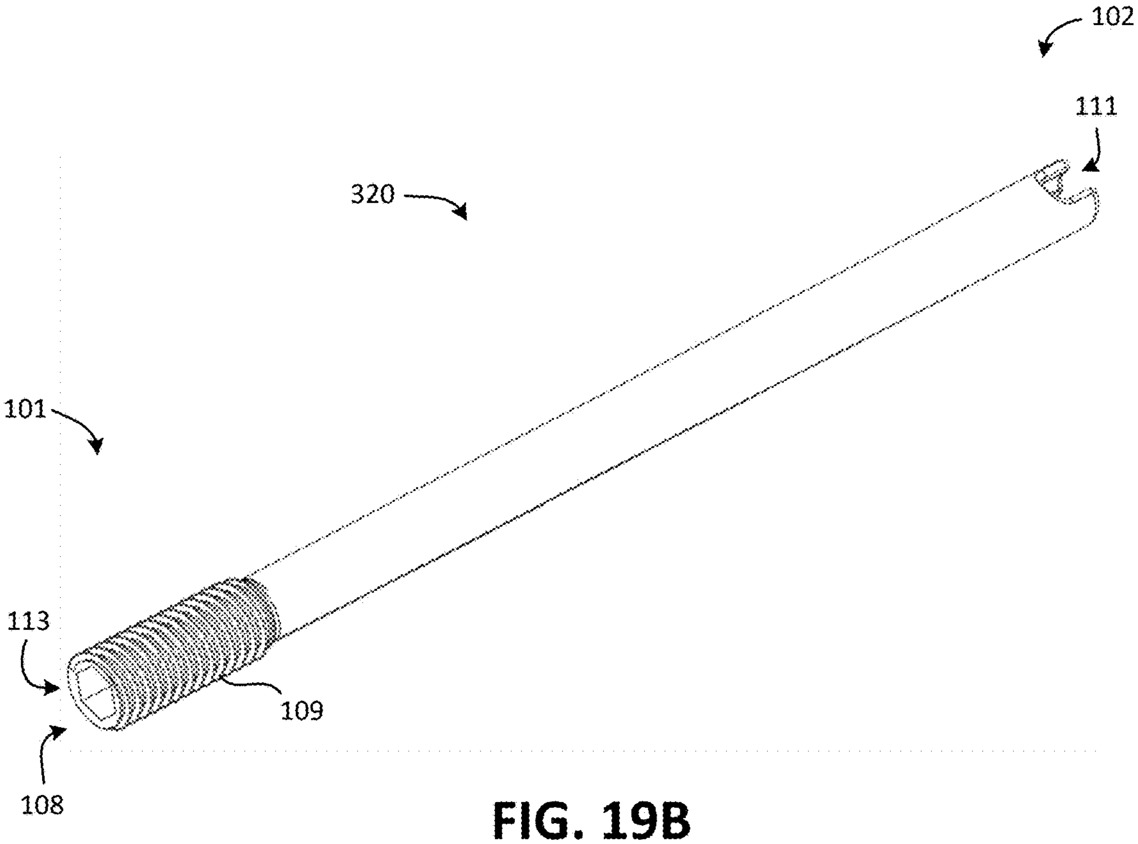
FIG. 19B illustrates a proximal perspective view of the elongate fixation member of FIG. 19A.
Figure 19C:
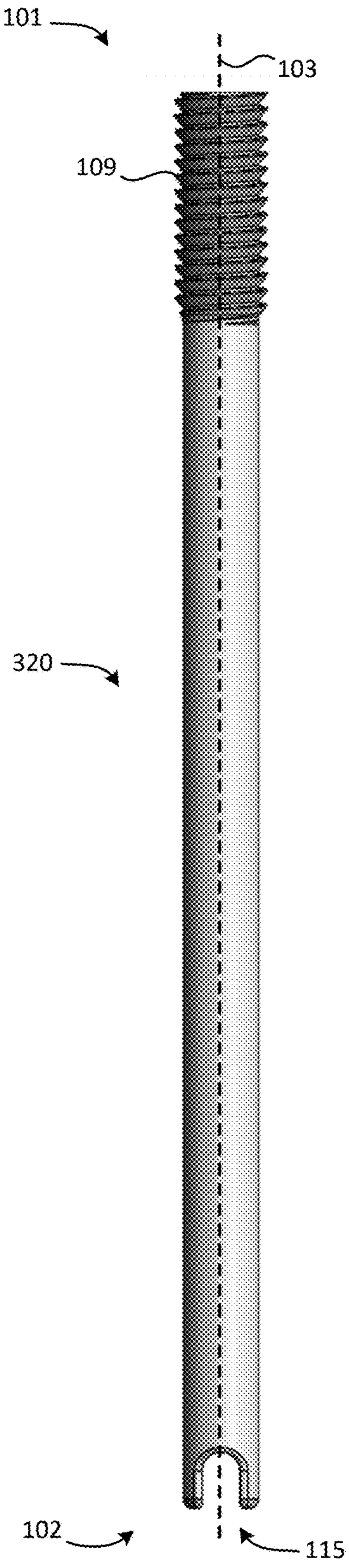
FIG. 19C illustrates a side view of the elongate fixation member of FIG. 19A.
Figure 19D:
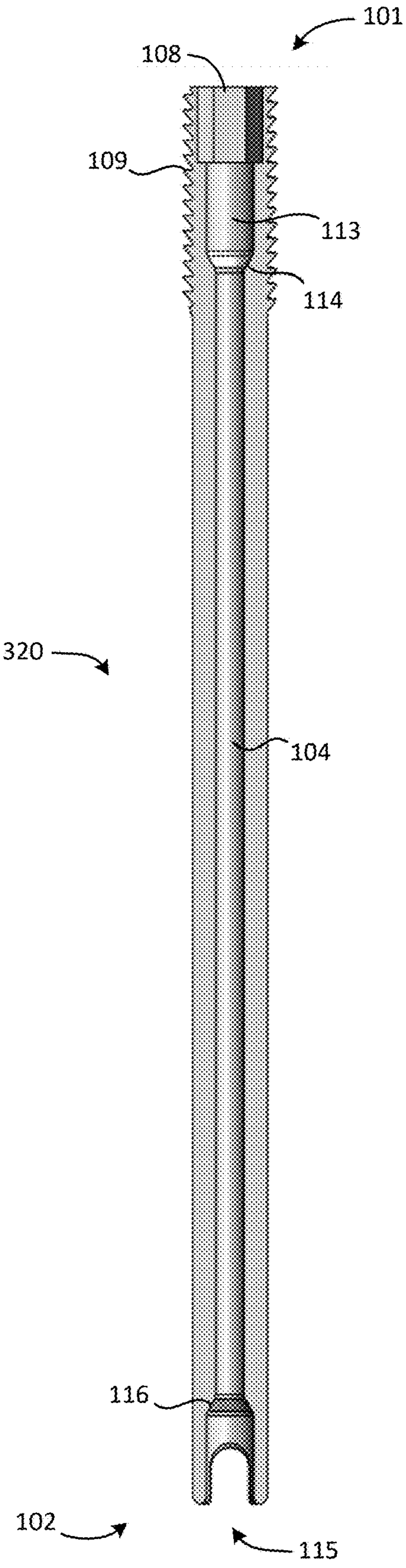
FIG. 19D illustrates a cross-sectional view of the elongate fixation member of FIG. 19C.
Figure 20:
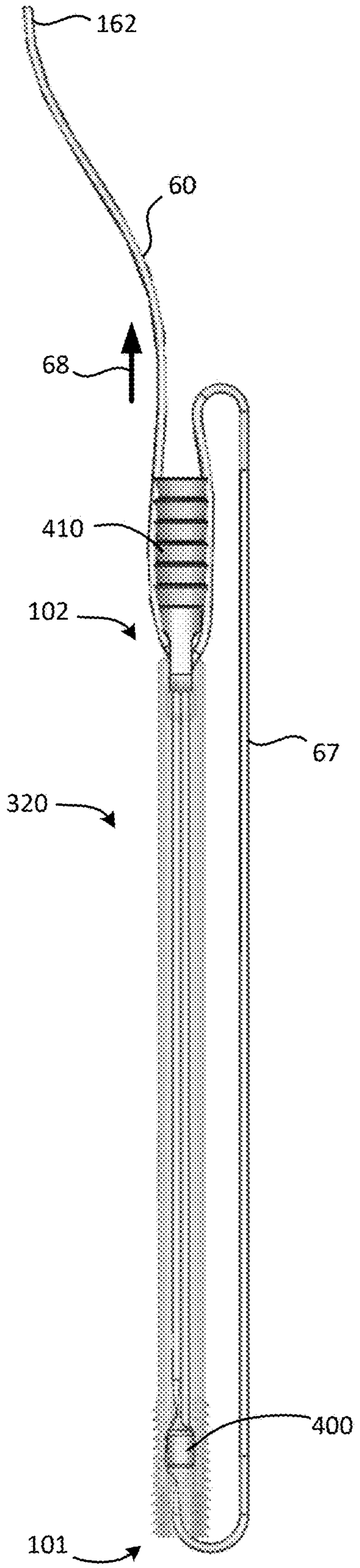
FIG. 20 illustrates a partially transparent side view of a bone fixation assembly, according to an embodiment of the present disclosure.

FIGS. 12A-18 illustrate example devices and systems for a bone fixation assembly, according to another embodiment of the present disclosure. Specifically, FIGS. 12A-12D show various views of an elongate fixation member 310, according to another embodiment of the present disclosure, FIGS. 13-15 show various views of a bone fixation assembly utilizing the elongate fixation member 310, and FIGS. 16-18 show various views of the bone fixation assembly implanted in a bone 10.

In some embodiments, the elongate fixation member 310 may include a proximal end, first end, or first portion 101, a distal end, second end, or second portion 102, a central longitudinal axis 103, a longitudinal passageway 104, a torque connection feature 108, a proximal helical thread 109 (or a plurality of anti-back out fins or splines), an anchor reception chamber 115, and at least a portion of a tension locking mechanism 405.

In some embodiments, the tension locking mechanism 405 may comprise a one-way tensioning mechanism, such as a slip-buckle tensioning mechanism, a taper bullet tensioning mechanism, a Chinese finger trap suture tensioning mechanism, or any other suitable one-way tensioning mechanism, as will be described in more detail below.

In some embodiments, the first portion 101 of the elongate fixation member 310 may be couplable to a first bone fragment 1 of a bone 10, and the second portion 102 of the elongate fixation member 310 may be couplable to a second bone fragment 2 of the bone 10 to provide fixation of the second bone fragment 2 relative to the first bone fragment 1, as can be seen in FIGS. 16-18.

In some embodiments, the flexible tensioning element 60 may be configured to pass through the longitudinal passageway 104 that is formed through the elongate fixation member 310 and may also form a loop 67 that spans the first and second bone fragments to secure the elongate fixation member 310 to the bone 10 (e.g., see FIGS. 13 and 16).

In some embodiments, the loop 67 spanning the first and second bone fragments may also span a bone fracture 3 intermediate the first and second bone fragments.

In some embodiments, a selected tension force 68 applied to the flexible tensioning element 60 may be locked and maintained by the tension locking mechanism 405 to preload the bone fracture 3 in compression to resist tensile force imparted across the bone fracture 3, thereby maintaining fixation of the first bone fragment 1 relative to the second bone fragment 2. In this manner, the flexible tensioning element 60 may provide additional fixation strength vs. the elongate fixation member 310 alone, as previously described herein.

In some embodiments, a bone fixation assembly may include the elongate fixation member 310, the flexible tensioning element 60 (e.g., a suture, suture tape, etc., as previously described herein), the tension locking mechanism 405 configured to lock and maintain a selected tension force 68 applied to the flexible tensioning element 60 (e.g., see FIGS. 13 and 14), and a bone anchor 410 to provide a secondary lock to the flexible tensioning element 60 (e.g., see FIGS. 17 and 18).

In some embodiments, the tension locking mechanism 405 may include a taper bullet 400 placed inside a tension chamber 113 that is formed within the elongate fixation member 310, as well as a chamfered edge or tension chamber locking surface 114 positioned at one end of the tension chamber 113.

In some embodiments, the tension chamber may be formed within any of the proximal or first portion 101 of the elongate fixation member, the distal or second portion 102, or any intermediate portion of the elongate fixation member therebetween.

In some embodiments, the taper bullet 400 may include a taper bullet body 401 and a taper bullet locking surface 402.

In some embodiments, the taper bullet body 401 may comprise a generally cylindrical shape, and the taper bullet locking surface 402 may comprise an at least partially conical shape.

As shown in FIGS. 13 and 16, in at least some embodiments, a first end 161 of the flexible tensioning element 60 may be configured to couple with the taper bullet 400, and a second end 162 of the flexible tensioning element 60 may be configured to: (1) exit the longitudinal passageway 104 at the first end 101 of the elongate fixation member 310; (2) wrap back around the first and second bone fragments to form the loop 67 spanning the first and second bone fragments; (3) enter back into the longitudinal passageway 104 at the second end 102 of the elongate fixation member 310; (4) pass through the tension chamber 113 that is formed within the elongate fixation member 310 such that the flexible tensioning element 60 becomes trapped between the tension chamber locking surface 114 and the taper bullet locking surface 402; and exit back out of the longitudinal passageway at the first end 101 of the elongate fixation member.

In this manner, the second end 162 of the flexible tensioning element 60 exiting the longitudinal passageway 104 may be configured to receive the selected tension force 68 to tension the entire flexible tensioning element and pull the first end 161 of the flexible tensioning element (with the taper bullet 400 coupled thereto) toward the first end 101 of the elongate fixation member 310 within the tension chamber 113. This will cause the taper bullet 400 to compress the flexible tensioning element 60 that is trapped between the taper bullet locking surface 402 and the tension chamber locking surface 114 to lock and maintain the selected tension force 68 that is applied to the flexible tensioning element 60, forming a one-way tension locking mechanism.

In some embodiments, the tension chamber 113 may be formed within the distal or second portion 102 of the elongate fixation member 310.

In some embodiments, the tension chamber 113 may be formed within the proximal or first portion 101 of the elongate fixation member 310.

In some embodiments, the tension chamber 113 may be formed within an intermediate portion of the elongate fixation member 310.

In some embodiments, the bone fixation assembly of FIGS. 12A-18 may be generally implanted within the bone 10 by performing one or more of the following steps: (1) drilling/reaming at least a portion of the intramedullary canals of the first bone fragment 1 and the second bone fragment 2; (2) inserting the elongate fixation member 310 into the prepared intramedullary canals to provisionally fix the first bone fragment 1 relative to the second bone fragment 2 along the rigid elongate fixation member; (3) rotating the elongate fixation member 310 to thread the proximal helical thread 109 into one of the prepared intramedullary canals (e.g., the elongate fixation member 310 may be placed into the first and second bone fragments from either a medial or lateral direction); (4) coupling the first end 161 of the flexible tensioning element 60 to the taper bullet 400 (or it may be pre-coupled); (5) threading the second end 162 of the flexible tensioning element 60 through the longitudinal passageway 104 (from the second end 102 to the first end 101), until the taper bullet 400 enters the tension chamber 113 (e.g., utilizing one or more retrieval wires 50); (6) wrapping the second end 162 of the flexible tensioning element 60 back around the first and second bone fragments to form the loop 67; (7) inserting the second end 162 of the flexible tensioning element 60 back into the second end 102 of the longitudinal passageway 104; (8) passing the second end 162 of the flexible tensioning element 60 through the tension chamber 113 such that the flexible tensioning element 60 is located between the tension chamber locking surface 114 and the taper bullet locking surface 402; (9) passing the second end 162 of the flexible tensioning element 60 back out of the first end 101 of the longitudinal passageway 104; and (10) applying the selected tension force 68 to the second end 162 of the flexible tensioning element 60, which will cause the tension locking mechanism 405 to lock and maintain the selected tension force 68 to preload the bone fracture 3 in compression and resist tensile force imparted across the bone fracture 3, thereby maintaining fixation of the first bone fragment 1 relative to the second bone fragment 2.

In some embodiments, a bone anchor 410 may also be implanted within the bone 10 to provide to provide a secondary lock to help maintain the selected tension force 68 applied to the flexible tensioning element 60, as shown in FIGS. 17 and 18.

In some embodiments, the bone anchor 410 may comprise a threaded bone/suture anchor, a compression bone/suture anchor, an anti-rotation bone anchor, a finned anti-rotation bone anchor, a transverse fastener or bone screw, etc.

In some embodiments, the bone anchor 410 may include an anchor body 411 having an anchor proximal end 412 and an anchor distal end 413, an anchor distal projection 414, an anchor helical thread 415, and an anchor torque connection interface 416.

In some embodiments, the bone anchor 410 or threaded suture anchor may comprise any suitable material, including but not limited to: a resorbable material (such as PEEK, hydroxyapatite, etc.), and/or any other biocompatible material such as titanium, stainless steel, polymer, etc.

In some embodiments, the bone anchor 410 may be threaded into one of the prepared intramedullary canals such that the anchor distal projection 414 is at least partially received within the tension chamber 113 and/or the anchor reception chamber 115 to further trap the flexible tensioning element 60 therein (and/or compress the flexible tensioning element 60 against the bone tunnel wall) to provide a secondary lock to maintain the selected tension force 68.

FIGS. 19A-29 illustrate example devices and systems for a bone fixation assembly, according to another embodiment of the present disclosure. Specifically, FIGS. 19A-19D show various views of an elongate fixation member 320, according to another embodiment of the present disclosure, FIGS. 20-23 show various views of a bone fixation assembly utilizing the elongate fixation member 320, and FIGS. 24-29 show various views of the bone fixation assembly implanted in a bone 10.

In some embodiments, the elongate fixation member 320 may include a proximal end, first end, or first portion 101, a distal end, second end, or second portion 102, a central longitudinal axis 103, a longitudinal passageway 104, a torque connection feature 108, a proximal helical thread 109 (or a plurality of anti-rotation fins, splines, etc.), an anchor reception chamber 115 comprising a first transverse notch 111, a second transverse notch 112, and an anchor reception chamber chamfered edge 116.

In some embodiments, the elongate fixation member 320 may also include at least a portion of the tension locking mechanism 405 (similar to the embodiment shown in FIGS. 12A-18), comprising a tension chamber 113, a tension chamber locking surface 114, and a taper bullet 400 disposable therein having a taper bullet body 401 and a taper bullet locking surface 402. Thus, the tension locking mechanism 405 for the embodiment shown in FIGS. 19A-29 may operate similarly to the tension locking mechanism 405 already shown and described for the embodiment shown in FIGS. 12A-18, except the tension chamber 113 may be placed within the first portion 101 of the elongate fixation member 320 and the anchor reception chamber 115 may be placed within the second portion 102 of the elongate fixation member 320.

In some embodiments, a bone fixation assembly may include the elongate fixation member 320, the flexible tensioning element 60, the tension locking mechanism 405 configured to lock and maintain a selected tension force 68 applied to the flexible tensioning element 60, and a bone anchor 410 that may be configured to provide a secondary lock to maintain the selected tension force 68 applied to the flexible tensioning element 60.

In some embodiments, the first portion 101 of the elongate fixation member 320 may be couplable to the first bone fragment 1 of the bone 10, and the second portion 102 of the elongate fixation member 320 may be couplable to the second bone fragment 2 of the bone 10 to provide fixation of the second bone fragment 2 relative to the first bone fragment 1, as can be seen in FIGS. 24-29.

In some embodiments, the flexible tensioning element 60 may be configured to pass through the longitudinal passageway 104 formed through the elongate fixation member 320 and form the loop 67 spanning the bone fracture 3 and the first and second bone fragments to secure the elongate fixation member 320 to the bone 10, as previously described.

In some embodiments, the selected tension force 68 applied to the flexible tensioning element 60 may be locked and maintained by the tension locking mechanism 405 to preload the bone fracture 3 in compression to resist tensile force imparted across the bone fracture 3, thereby maintaining fixation of the first bone fragment 1 relative to the second bone fragment 2. In this manner, the flexible tensioning element 60 may provide additional fixation strength vs. the elongate fixation member 320 alone.

In some embodiments, the bone fixation assembly of FIGS. 19A-29 may be generally implanted within the bone 10 by performing one or more of the following steps: (1) drilling/reaming at least a portion of the intramedullary canals of the first bone fragment 1 and the second bone fragment 2; (2) inserting the elongate fixation member 320 into the prepared intramedullary canals to provisionally fix the first bone fragment 1 relative to the second bone fragment 2; (3) rotating (or pushing) the elongate fixation member 320 to thread the proximal helical thread 109 (or engage the plurality of anti-rotation fins, splines, etc.) into at least one of the prepared intramedullary canals (e.g., the elongate fixation member 320 may be placed into the first and second bone fragments from either a medial or lateral direction); (4) coupling the first end 161 of the flexible tensioning element 60 to the taper bullet 400 (or it may be pre-coupled); (5) threading the second end 162 of the flexible tensioning element 60 through the longitudinal passageway 104 (from the first end 101 to the second end 102), until the taper bullet 400 enters the tension chamber 113 (e.g., utilizing one or more retrieval wires 50, etc.); (6) wrapping the second end 162 of the flexible tensioning element 60 back around the first and second bone fragments to form the loop 67; (7) inserting the second end 162 of the flexible tensioning element 60 back into the first end 101 of the longitudinal passageway 104; (8) passing the second end 162 of the flexible tensioning element 60 through the tension chamber 113 such that the flexible tensioning element 60 is located between the tension chamber locking surface 114 and the taper bullet locking surface 402; (9) passing the second end 162 of the flexible tensioning element 60 back out of the second end 102 of the longitudinal passageway 104; and (10) applying the selected tension force 68 to the second end 162 of the flexible tensioning element 60, which will cause the tension locking mechanism 405 to lock and maintain the selected tension force 68 to preload the bone fracture 3 in compression and resist tensile force imparted across the bone fracture 3, thereby maintaining fixation of the first bone fragment 1 relative to the second bone fragment 2.

In some embodiments, the distal end of the elongate fixation member 320 comprises the anchor reception chamber 115 with the first transverse notch 111 and the second transverse notch 112 formed therethrough.

Figure 21:
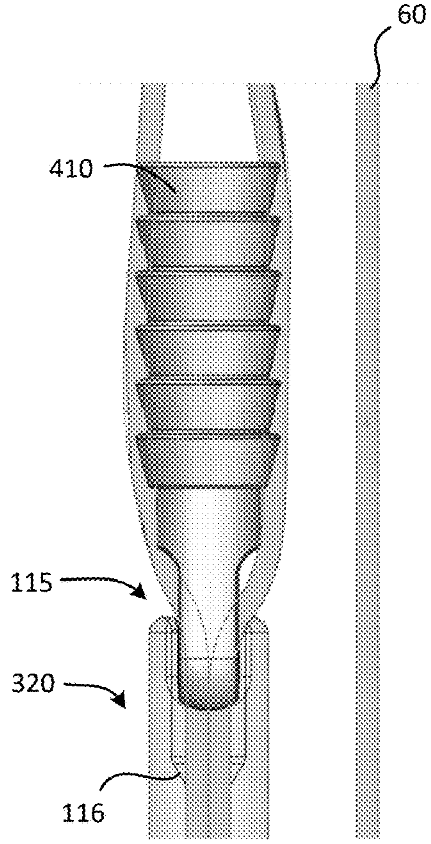
FIG. 21 illustrates a close up view of a distal end of the bone fixation assembly of FIG. 20.
Figure 22:
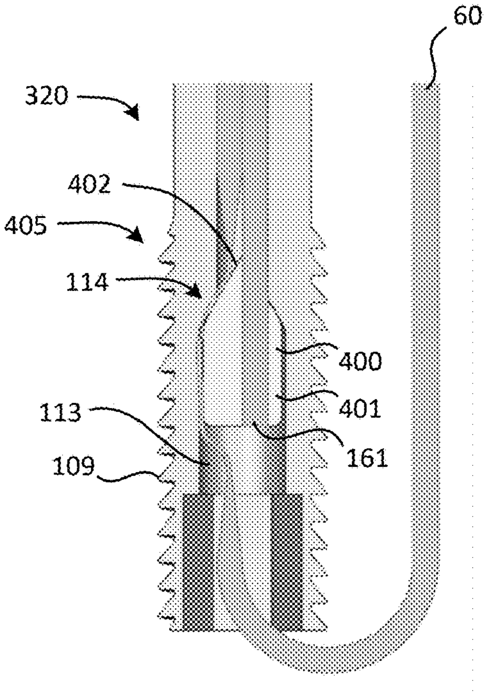
FIG. 22 illustrates a close up view of a proximal end of the bone fixation assembly of FIG. 20.
Figure 23:
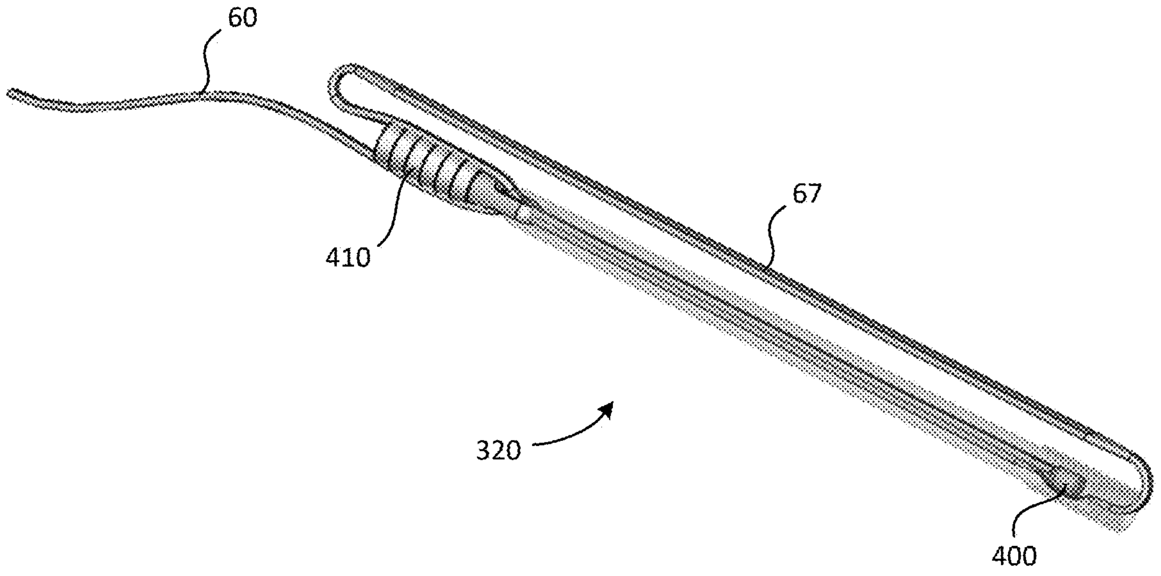
FIG. 23 illustrates a perspective view of the bone fixation assembly of FIG. 20.
Figure 24:
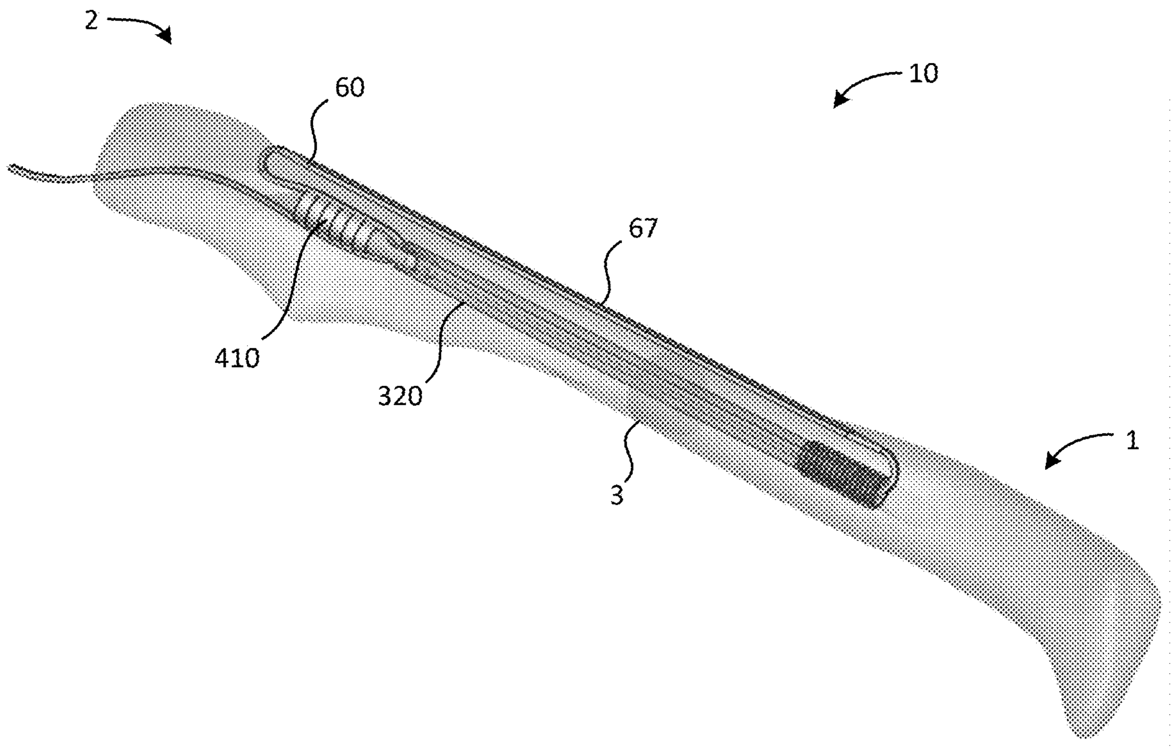
FIG. 24 illustrates a transparent anterior perspective view of the bone fixation assembly of FIG. 20 implanted in a bone.
Figure 25:
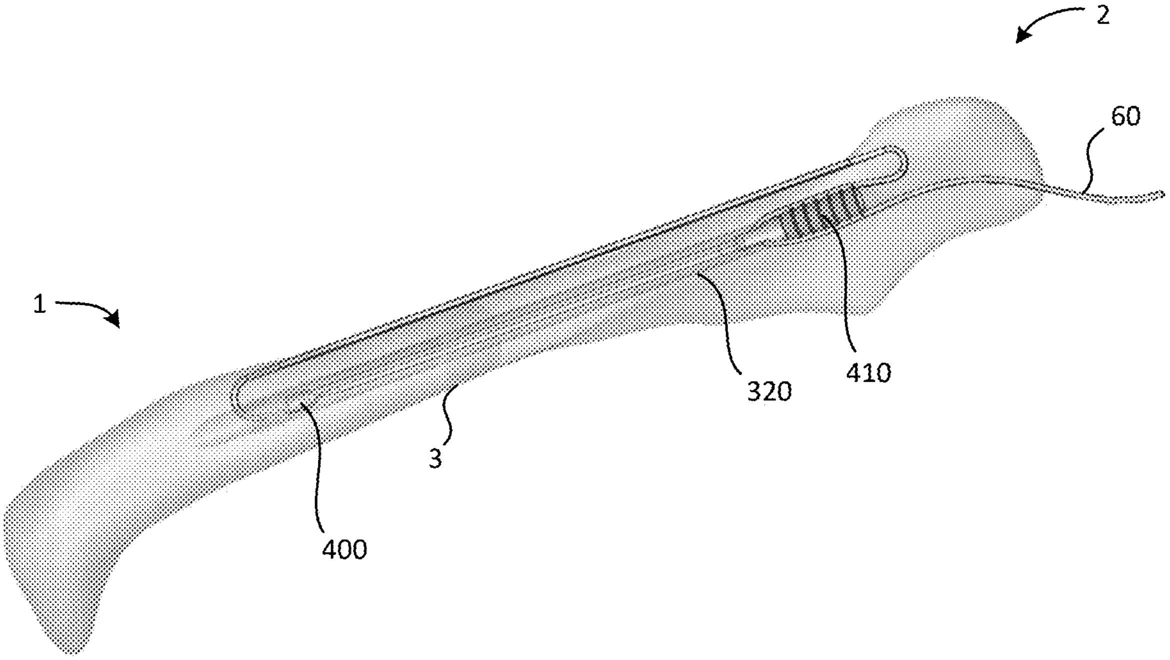
FIG. 25 illustrates a transparent posterior perspective view of the bone fixation assembly of FIG. 20 implanted in the bone.
Figure 26:
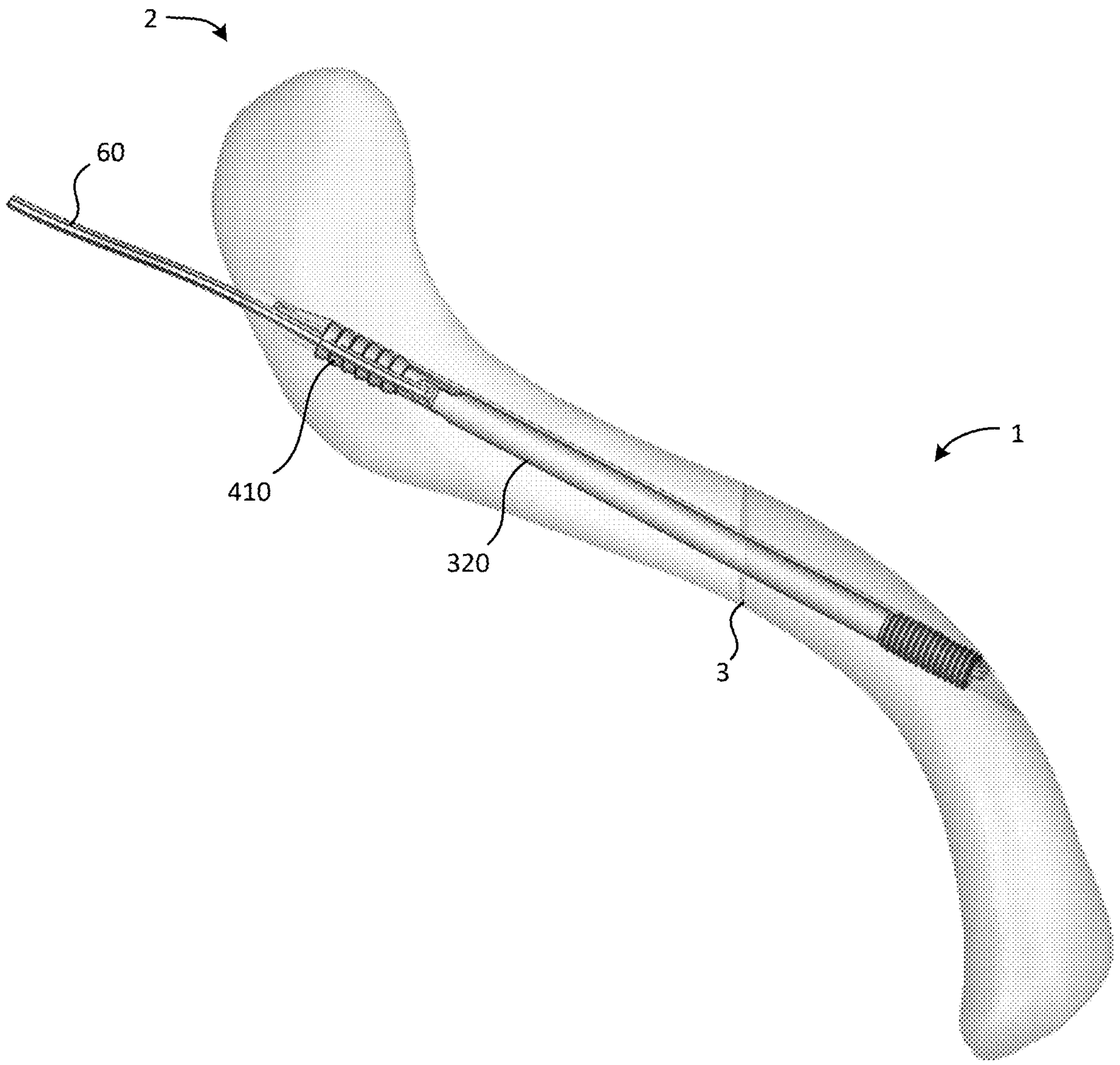
FIG. 26 illustrates a transparent distal perspective view of the bone fixation assembly of FIG. 20 implanted in the bone.
Figure 27:
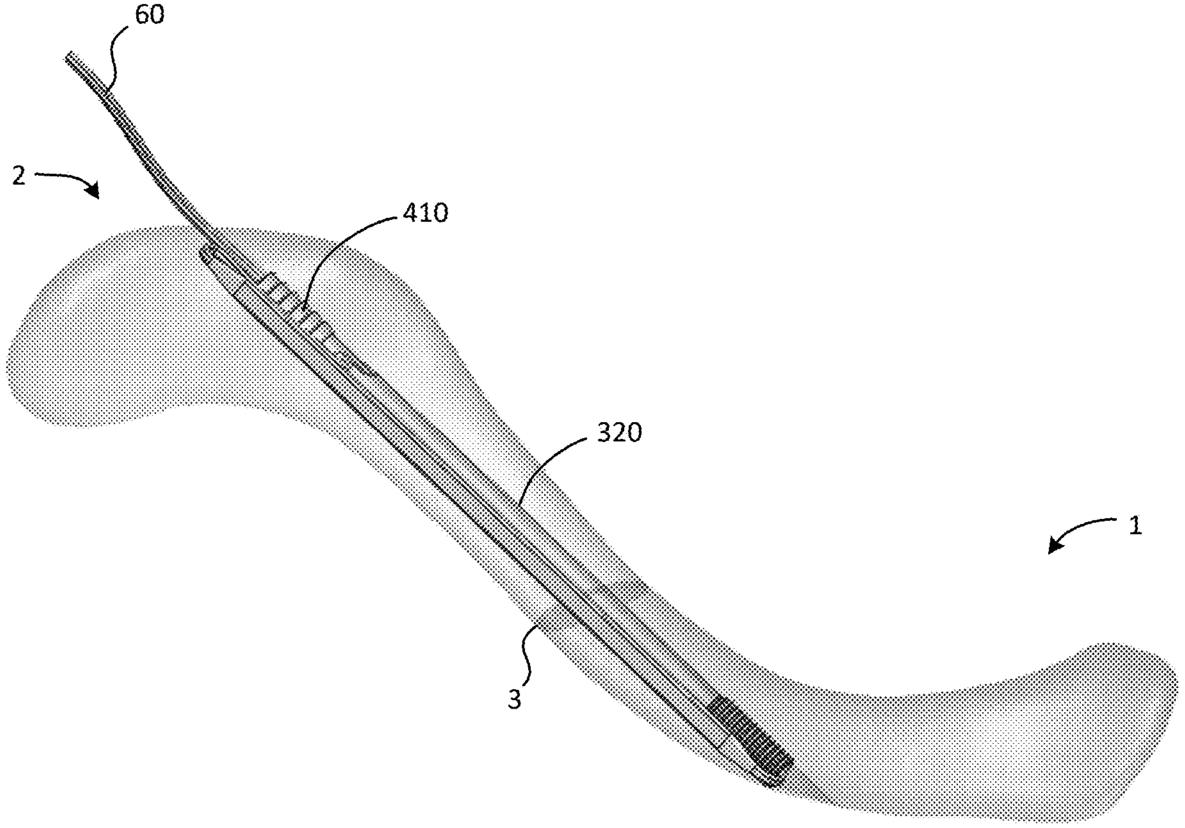
FIG. 27 illustrates a transparent proximal perspective view of the bone fixation assembly of FIG. 20 implanted in the bone.

In some embodiments, the anchor reception chamber 115 may be configured to receive at least a portion of a bone anchor 410 therein intermediate the first transverse notch 111 and the second transverse notch 112 to provide a secondary lock that maintains the selected tension force 68 applied to the flexible tensioning element 60 (e.g., see FIG. 21).

In some embodiments, the bone anchor 410 may comprise a compression style bone or suture anchor that may be pressed into one of the prepared intramedullary canals and at least partially received within the anchor reception chamber 115 of the elongate fixation member 320 to further trap the flexible tensioning element 60 and maintain the selected tension force 68 as a secondary lock.

Figure 28:
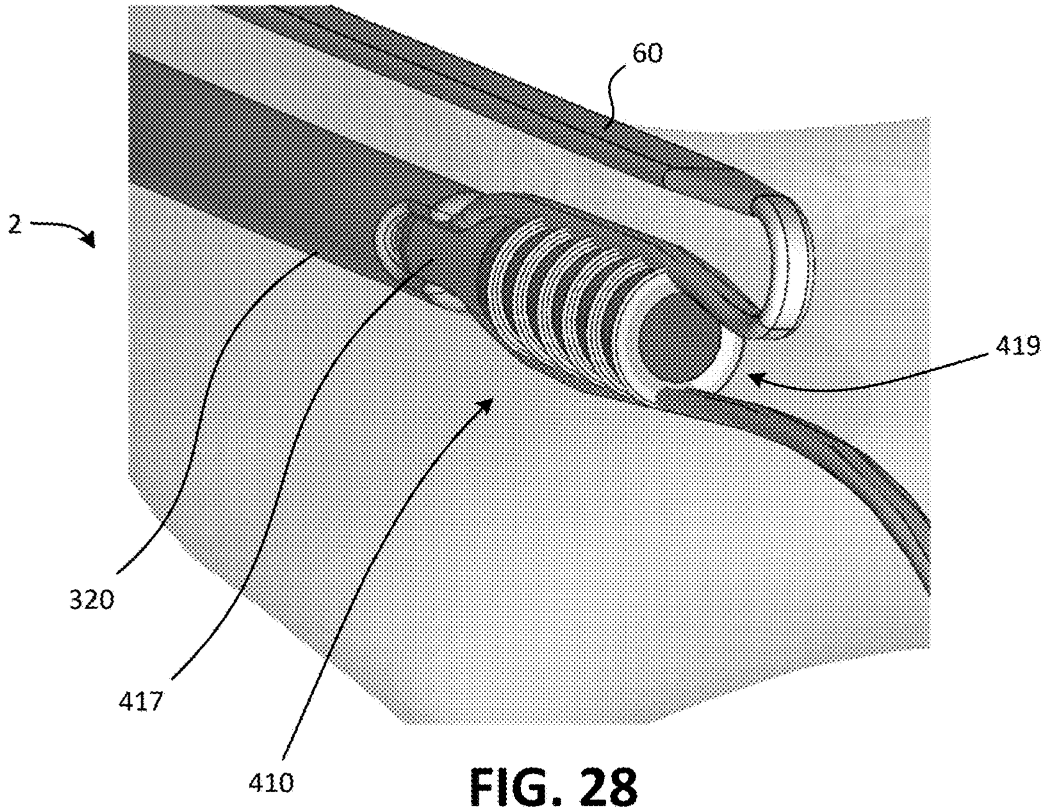
FIG. 28 illustrates a close up perspective view of a distal end of the bone fixation assembly of FIG. 20 in the bone with a compression suture anchor placed therein.
Figure 29:
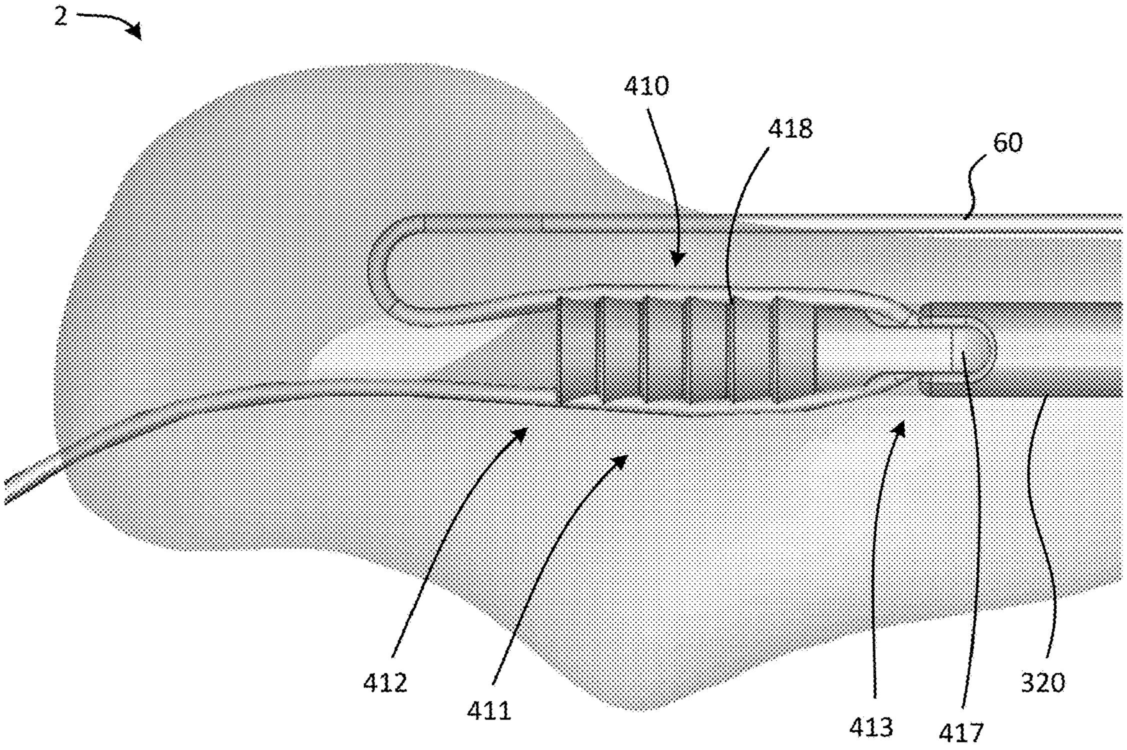
FIG. 29 illustrates a close up side view of the distal end of the bone fixation assembly of FIG. 28.
Figure 30A:
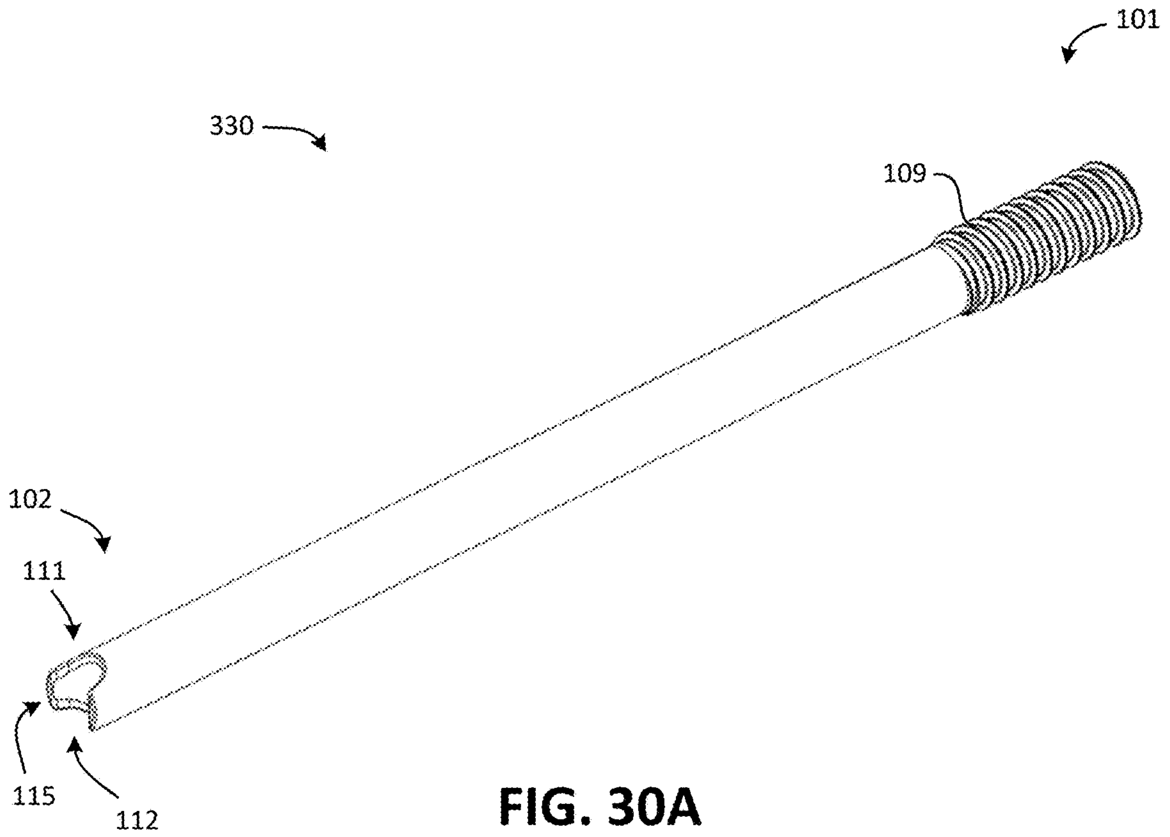
FIG. 30A illustrates a distal perspective view of an elongate fixation member, according to another embodiment of the present disclosure.
Figure 30B:
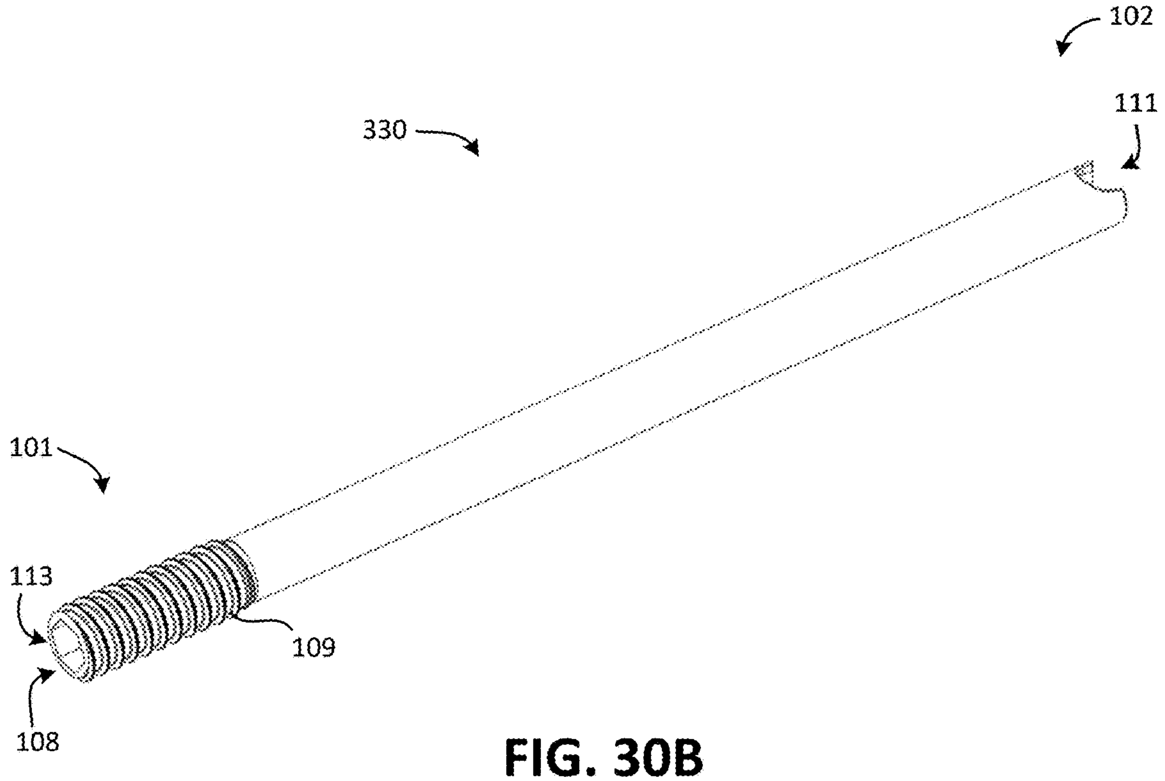
FIG. 30B illustrates a proximal perspective view of the elongate fixation member of FIG. 30A.
Figure 30C:
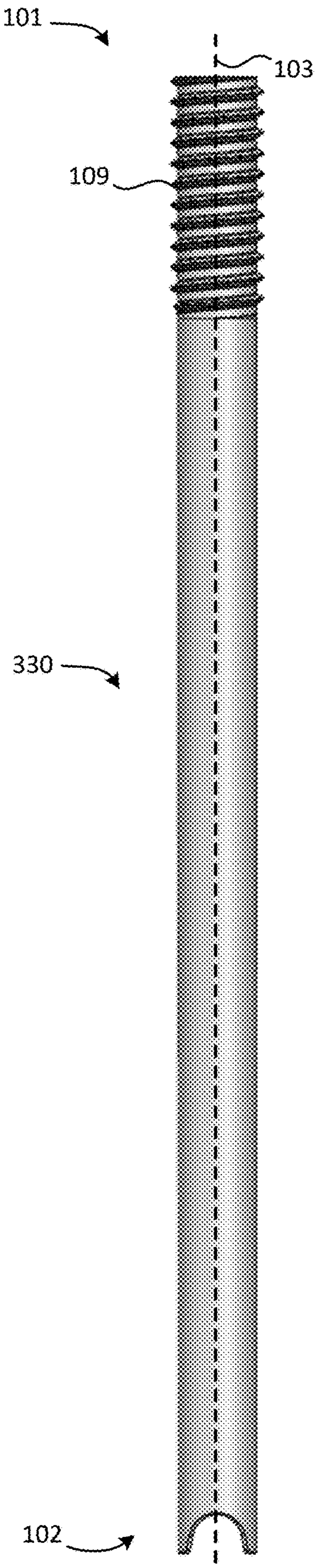
FIG. 30C illustrates a side view of the elongate fixation member of FIG. 30A.
Figure 30D:
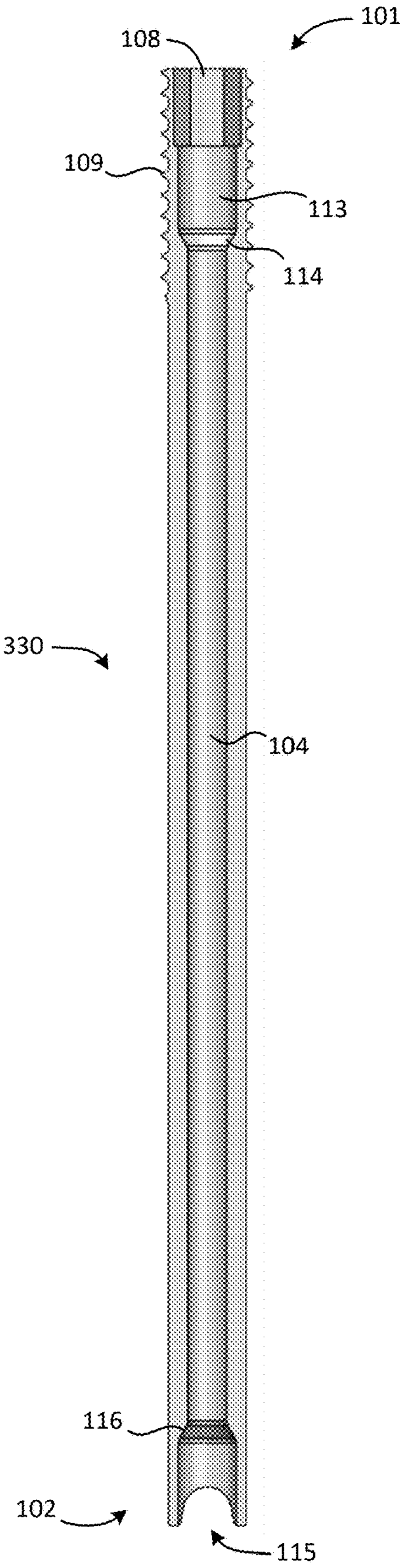
FIG. 30D illustrates a cross-sectional view of the elongate fixation member of FIG. 30C.

As shown in FIGS. 28 and 29, the bone anchor 410 may include an anchor body 411 having an anchor proximal end 412 and an anchor distal end 413, an anchor eyelet 417 configured to receive the flexible tensioning element 60 therethrough, a plurality of anti-backout fins 418, and an anchor impact interface 419 that may be configured to receive an impact force to drive the bone anchor 410 into the prepared bone tunnel and/or at least partially into the anchor reception chamber 115. In this manner, the bone anchor 410 may provide a secondary lock that maintains the selected tension force 68 by trapping the flexible tensioning element 60 between the plurality of anti-backout fins 418 and the walls of the prepared bone tunnel. The bone anchor 410 may also provide additional rotational stability between the first and second bone fragments by frictionally coupling with one of the bone fragments (e.g., via the plurality of anti-backout fins 418 pressed against the walls of the prepared bone tunnel) and the anchor eyelet 417 coupling within the anchor reception chamber 115 of the elongate fixation member 320 to rotationally stabilize the first bone fragment 1 relative to the second bone fragment 2.

In some embodiments, the bone anchor 410 or compression style bone or suture anchor may comprise any suitable material, including but not limited to: a resorbable material (such as PEEK, hydroxyapatite, etc.), and/or any other biocompatible material such as titanium, stainless steel, polymer, etc.

FIGS. 30A-38 illustrate example devices and systems for a bone fixation assembly, according to another embodiment of the present disclosure. Specifically, FIGS. 30A-30D show various views of an elongate fixation member 330, according to an embodiment of the present disclosure, FIGS. 31-34 show various views of a bone fixation assembly utilizing the elongate fixation member 330, and FIGS. 35-38 show various views of the bone fixation assembly implanted in a bone 10.

In some embodiments, the elongate fixation member 330 may similarly include a proximal end, first end, or first portion 101, a distal end, second end, or second portion 102, a central longitudinal axis 103, a longitudinal passageway 104, a torque connection feature 108, a proximal helical thread 109 (or a plurality of anti-rotation fins, splines, etc.), an anchor reception chamber 115 comprising a first transverse notch 111, a second transverse notch 112, and an anchor reception chamber chamfered edge 116.

In some embodiments, the elongate fixation member 330 may also include at least a portion of the tension locking mechanism 405 (similar to previous embodiments) comprising a tension chamber 113, a tension chamber locking surface 114, and a taper bullet 400 disposable therein having a taper bullet body 401 and a taper bullet locking surface 402. Thus, the tension locking mechanism 405 for the embodiment shown in FIGS. 30A-38 may operate similarly to the tension locking mechanism 405 previously described herein.

In some embodiments, a bone fixation assembly may include the elongate fixation member 330, the flexible tensioning element 60, the tension locking mechanism 405 configured to lock and maintain a selected tension force 68 applied to the flexible tensioning element 60, and a bone anchor 410 that may be configured to provide a secondary lock to maintain the selected tension force 68 applied to the flexible tensioning element 60.

In some embodiments, the first portion 101 of the elongate fixation member 330 may be couplable to the first bone fragment 1 of the bone 10, and the second portion 102 of the elongate fixation member 330 may be couplable to the second bone fragment 2 of the bone 10 to provide fixation of the second bone fragment 2 relative to the first bone fragment 1, as can be seen in FIGS. 35-38.

In some embodiments, the flexible tensioning element 60 may be configured to pass through the longitudinal passageway 104 formed through the elongate fixation member 330 and form the loop 67 spanning the bone fracture 3 and the first and second bone fragments to secure the elongate fixation member 330 to the bone 10, as previously described.

In some embodiments, the selected tension force 68 applied to the flexible tensioning element 60 may be locked and maintained by the tension locking mechanism 405 to preload the bone fracture 3 in compression to resist tensile force imparted across the bone fracture 3, thereby maintaining fixation of the first bone fragment 1 relative to the second bone fragment 2. In this manner, the flexible tensioning element 60 may provide additional fixation strength vs. the elongate fixation member 330 alone.

In some embodiments, the bone fixation assembly of FIGS. 30A-38 may be generally implanted within the bone 10 by performing one or more of the following steps: (1) drilling/reaming at least a portion of the intramedullary canals of the first bone fragment 1 and the second bone fragment 2; (2) inserting the elongate fixation member 330 into the prepared intramedullary canals to provisionally fix the first bone fragment 1 relative to the second bone fragment 2; (3) rotating (or pushing) the elongate fixation member 330 to thread the proximal helical thread 109 (or engage the plurality of anti-rotation fins, splines, etc.) into at least one of the prepared intramedullary canals (e.g., the elongate fixation member 330 may be placed into the first and second bone fragments from either a medial or lateral direction); (4) coupling the first end 161 of the flexible tensioning element 60 to the taper bullet 400 (or it may be pre-coupled); (5) threading the second end 162 of the flexible tensioning element 60 through the longitudinal passageway 104 (from the first end 101 to the second end 102), until the taper bullet 400 enters the tension chamber 113 (e.g., utilizing one or more retrieval wires 50, etc.); (6) wrapping the second end 162 of the flexible tensioning element 60 back around the first and second bone fragments to form the loop 67; (7) inserting the second end 162 of the flexible tensioning element 60 back into the first end 101 of the longitudinal passageway 104; (8) passing the second end 162 of the flexible tensioning element 60 through the tension chamber 113 such that the flexible tensioning element 60 is located between the tension chamber locking surface 114 and the taper bullet locking surface 402; (9) passing the second end 162 of the flexible tensioning element 60 back out of the second end 102 of the longitudinal passageway 104; and (10) applying the selected tension force 68 to the second end 162 of the flexible tensioning element 60, which will cause the tension locking mechanism 405 to lock and maintain the selected tension force 68 to preload the bone fracture 3 in compression and resist tensile force imparted across the bone fracture 3, thereby maintaining fixation of the first bone fragment 1 relative to the second bone fragment 2.

Figure 31:
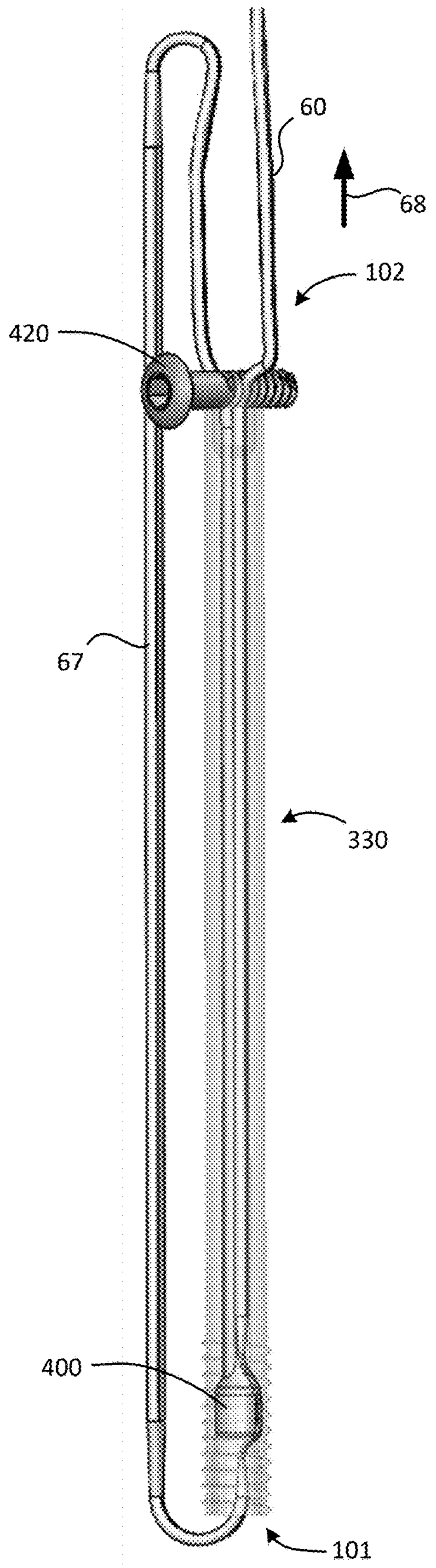
FIG. 31 illustrates a partially transparent side view of a bone fixation assembly, according to an embodiment of the present disclosure.
Figure 32:
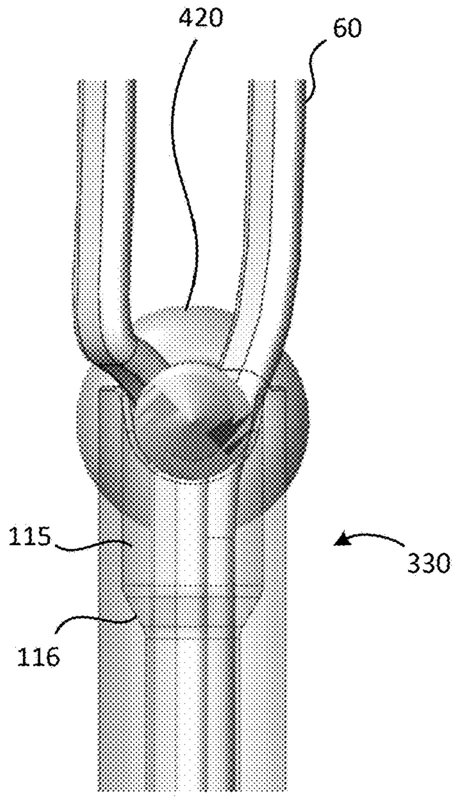
FIG. 32 illustrates a close up view of a distal end of the bone fixation assembly of FIG. 31.
Figure 33:
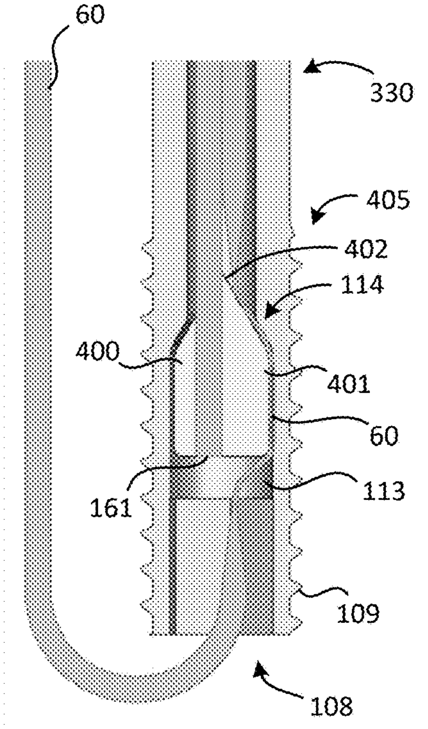
FIG. 33 illustrates a close up view of a proximal end of the bone fixation assembly of FIG. 31.
Figure 34:
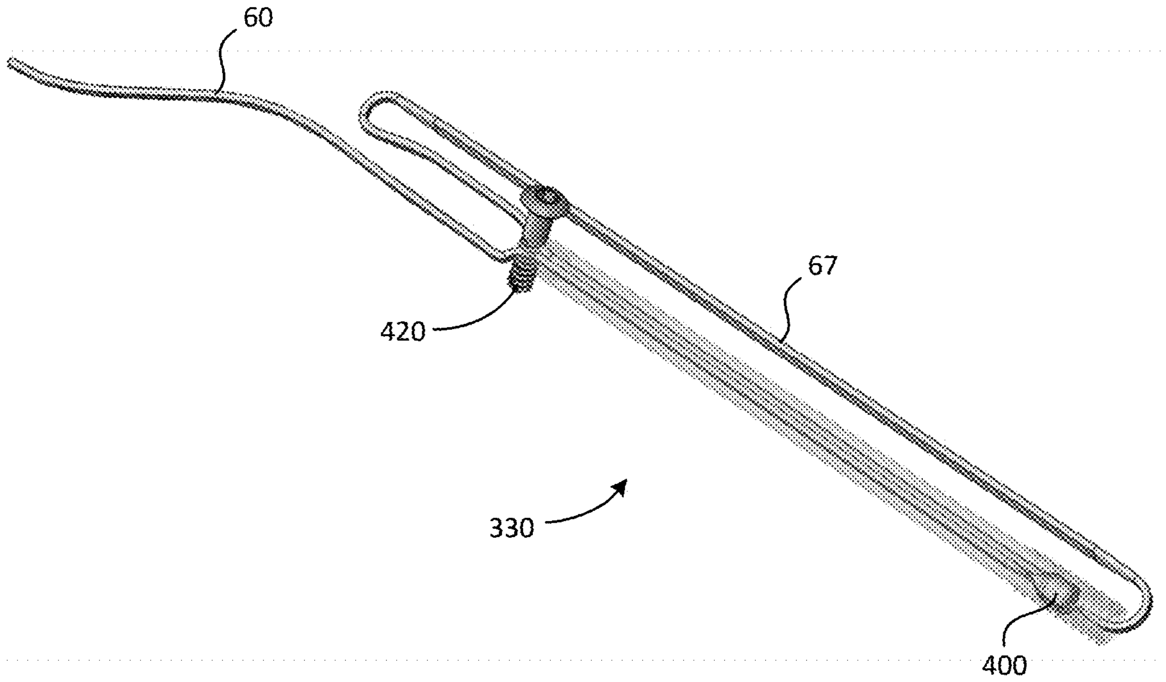
FIG. 34 illustrates a perspective view of the bone fixation assembly of FIG. 31.
Figure 35:
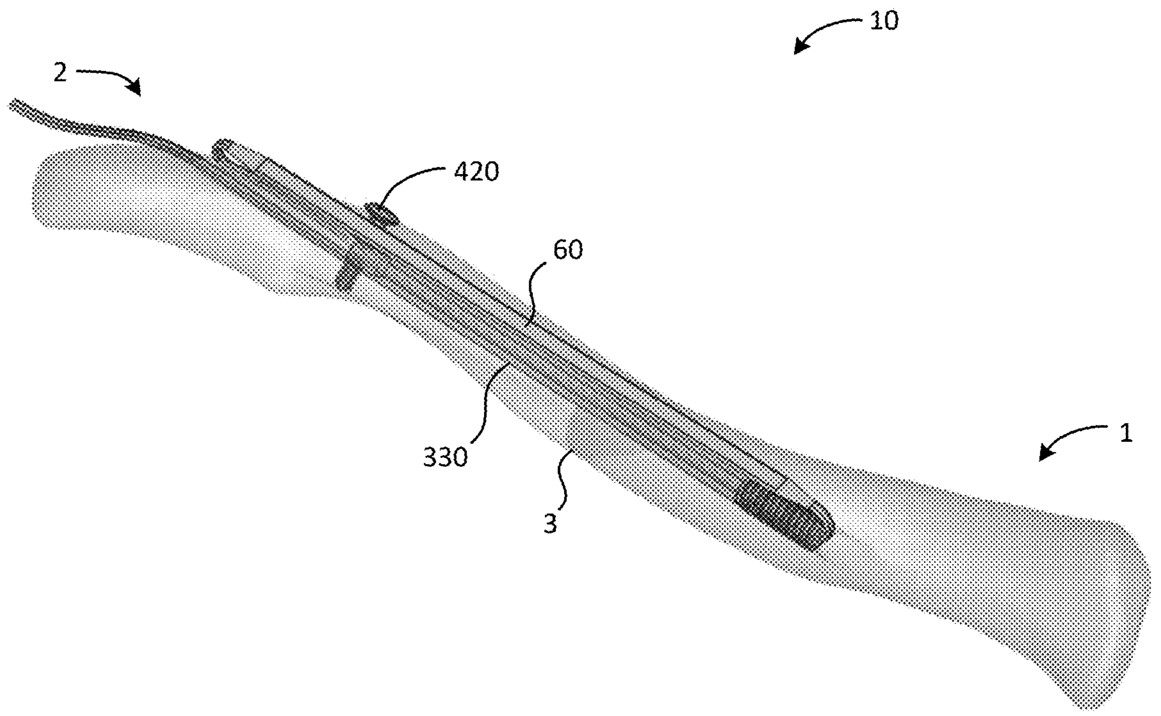
FIG. 35 illustrates a transparent anterior perspective view of the bone fixation assembly of FIG. 31 implanted in a bone.
Figure 36:
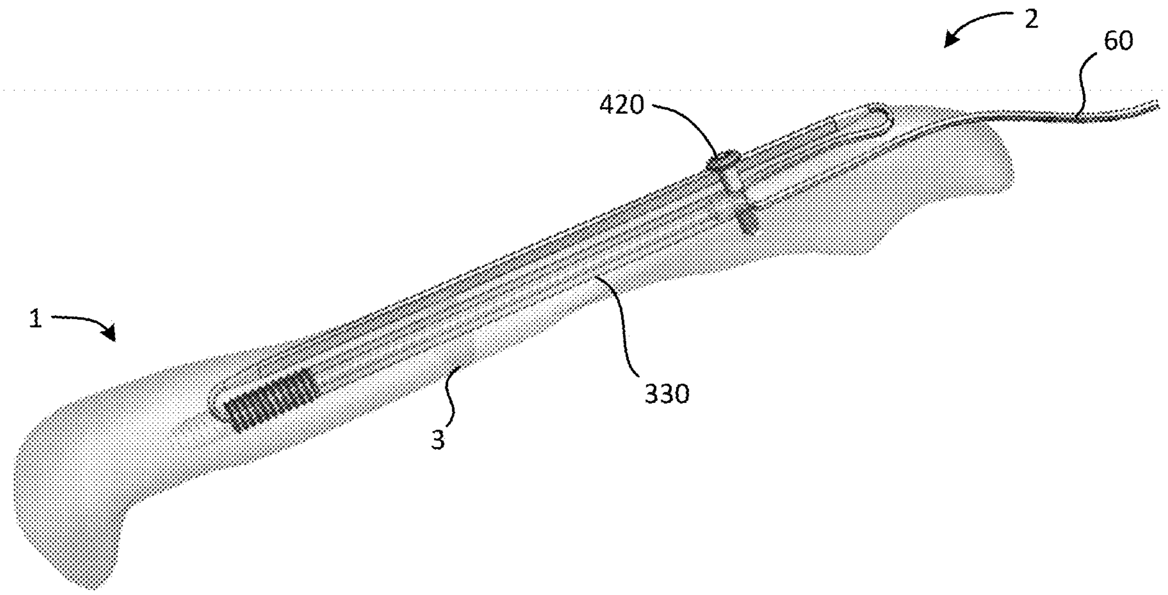
FIG. 36 illustrates a transparent posterior perspective view of the bone fixation assembly of FIG. 31 implanted in the bone.
Figure 37:
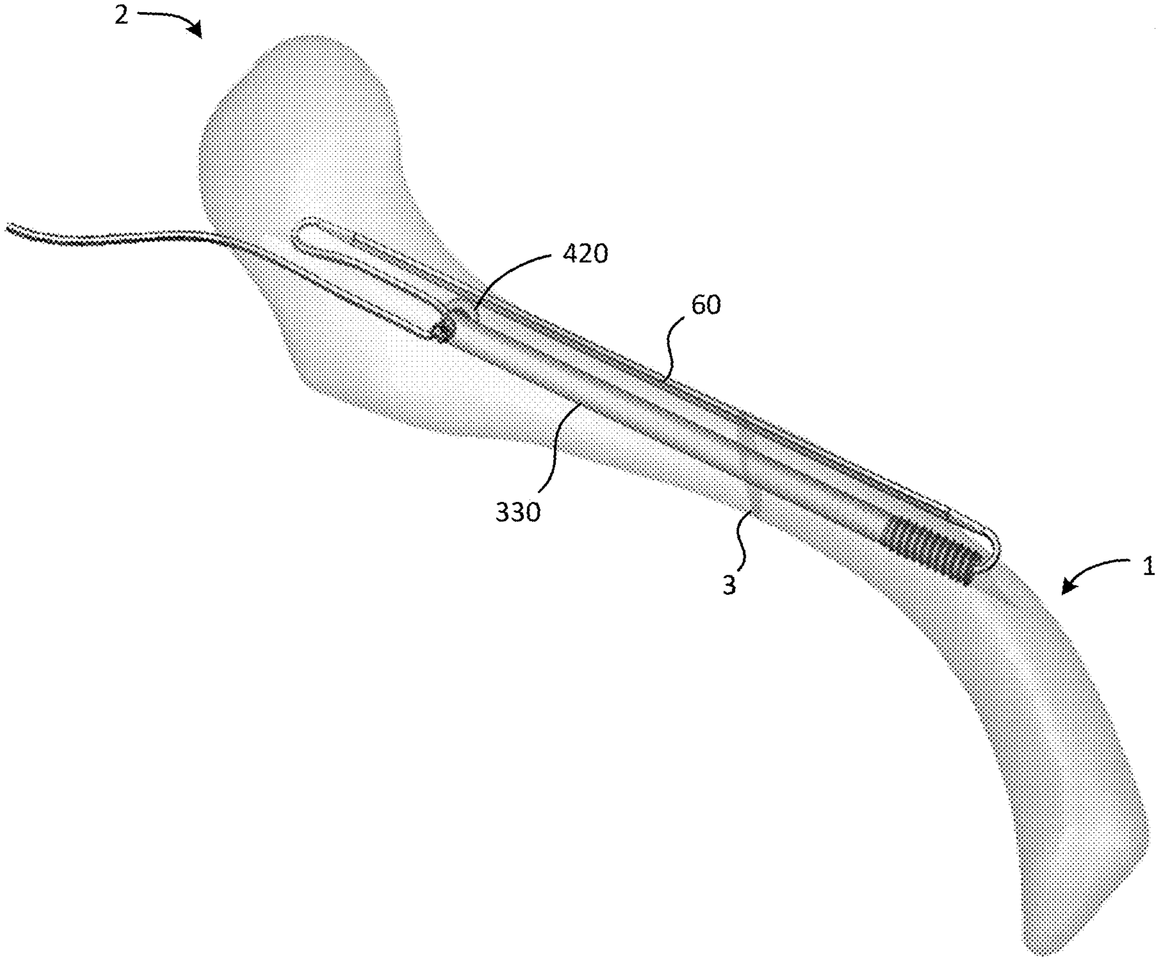
FIG. 37 illustrates a transparent distal perspective view of the bone fixation assembly of FIG. 31 implanted in the bone.
Figure 38:
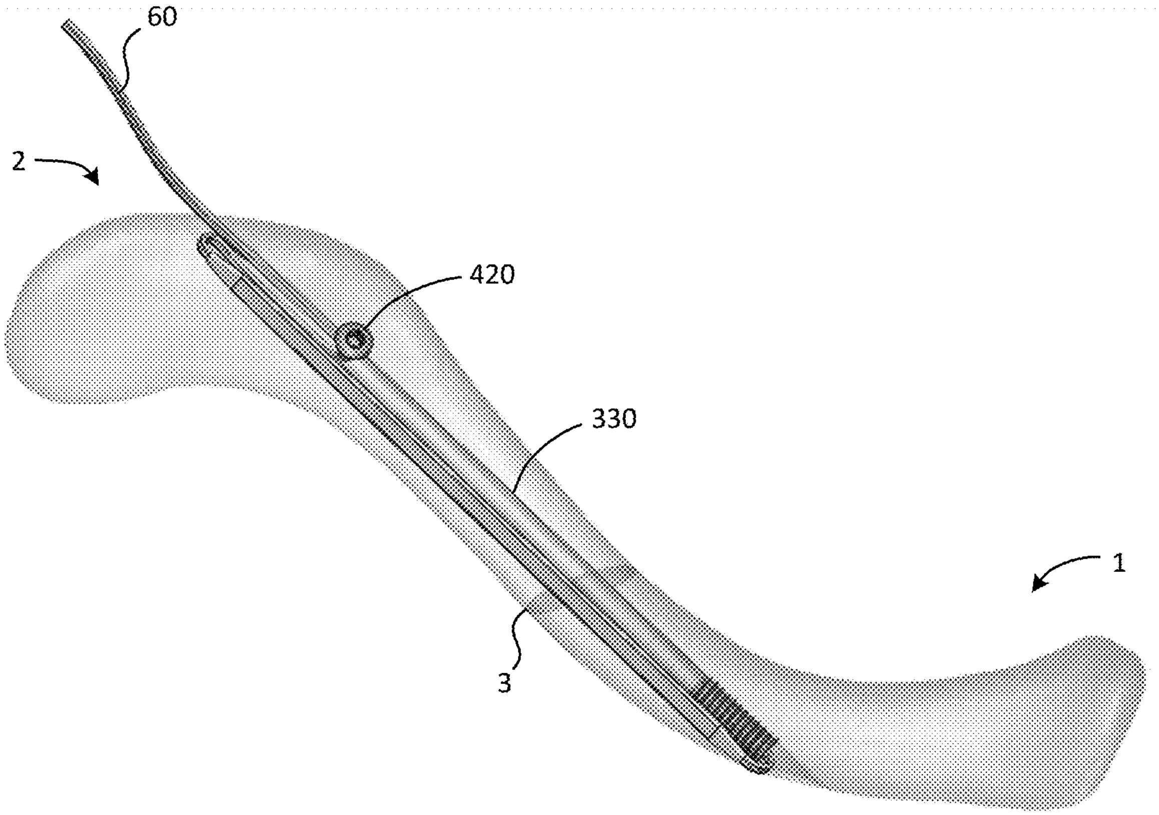
FIG. 38 illustrates a transparent proximal perspective view of the bone fixation assembly of FIG. 31 implanted in the bone.

In some embodiments, the anchor reception chamber 115 may be configured to receive at least a portion of a bone anchor 410 therein intermediate the first transverse notch 111 and the second transverse notch 112 to provide a secondary lock that maintains the selected tension force 68 applied to the flexible tensioning element 60 (e.g., see FIGS. 31 and 32).

In some embodiments, the bone anchor 410 may comprise a transverse bone screw that may be at least partially received within the anchor reception chamber 115 of the elongate fixation member 330 to further trap the flexible tensioning element 60 and maintain the selected tension force 68 as a secondary lock, as well as provide additional rotational stability between the first and second bone fragments.

FIGS. 39A-48 illustrate example devices and systems for a bone fixation assembly, according to another embodiment of the present disclosure. Specifically, FIGS. 39A-39D show various views of an elongate fixation member 340, FIGS. 40A-40D show various views of a finned anti-rotation bone anchor 430, FIGS. 41-44 show various views of a bone fixation assembly utilizing the elongate fixation member 340 and finned anti-rotation bone anchor 430, and FIGS. 45-48 show various views of the bone fixation assembly implanted in a bone 10.

In some embodiments, the elongate fixation member 340 may include a proximal end, first end, or first portion 101, a distal end, second end, or second portion 102, a central longitudinal axis 103, a longitudinal passageway 104, a torque connection feature 108, a proximal helical thread 109, an anchor reception chamber 115 comprising a first transverse notch 111, a second transverse notch 112, and an anchor reception chamber chamfered edge 116.

In some embodiments, the elongate fixation member 340 may also include at least a portion of the tension locking mechanism 405 (similar to previous embodiments) comprising a tension chamber 113, a tension chamber locking surface 114, and a taper bullet 400 disposable therein having a taper bullet body 401 and a taper bullet locking surface 402. Thus, the tension locking mechanism 405 for the embodiment shown in FIGS. 30A-38 may operate similarly to the tension locking mechanism 405 previously described herein.

In some embodiments, a bone fixation assembly may include the elongate fixation member 340, the flexible tensioning element 60, the tension locking mechanism 405 configured to lock and maintain a selected tension force 68 applied to the flexible tensioning element 60, and a finned anti-rotation bone anchor 430 that may be configured to provide a secondary lock to maintain the selected tension force 68 applied to the flexible tensioning element 60, and also provide rotational stability between the first and second bone fragments.

In some embodiments, the first portion 101 of the elongate fixation member 340 may be couplable to the first bone fragment 1 of the bone 10, and the second portion 102 of the elongate fixation member 340 may be couplable to the second bone fragment 2 of the bone 10 to provide fixation of the second bone fragment 2 relative to the first bone fragment 1, as can be seen in FIGS. 45-48.

In some embodiments, the flexible tensioning element 60 may be configured to pass through the longitudinal passageway 104 formed through the elongate fixation member 340 and form the loop 67 spanning the first and second bone fragments 1, 2 and the bone fracture 3 to secure the elongate fixation member 340 to the bone 10, as previously described.

In some embodiments, the selected tension force 68 applied to the flexible tensioning element 60 may be locked and maintained by the tension locking mechanism 405 to preload the bone fracture 3 in compression to resist tensile force imparted across the bone fracture 3, thereby maintaining fixation of the first bone fragment 1 relative to the second bone fragment 2. In this manner, the flexible tensioning element 60 may provide additional fixation strength vs. the elongate fixation member 340 alone.

In some embodiments, the bone fixation assembly of FIGS. 39A-48 may generally be implanted within the bone 10 by performing one or more of the following steps: (1) drilling/reaming at least a portion of the intramedullary canals of the first bone fragment 1 and the second bone fragment 2; (2) inserting the elongate fixation member 340 into the prepared intramedullary canals to provisionally fix the first bone fragment 1 relative to the second bone fragment 2; (3) rotating (or pushing) the elongate fixation member 340 to thread the proximal helical thread 109 (or engage the plurality of anti-rotation fins, splines, etc.) into at least one of the prepared intramedullary canals (e.g., the elongate fixation member 340 may be placed into the first and second bone fragments 1, 2 from either a medial or lateral direction, etc.); (4) coupling the first end 161 of the flexible tensioning element 60 to the taper bullet 400 (or it may be pre-coupled); (5) threading the second end 162 of the flexible tensioning element 60 through the longitudinal passageway 104 (e.g., from the first end 101 to the second end 102) until the taper bullet 400 enters the tension chamber 113 (e.g., utilizing one or more retrieval wires 50, etc.); (6) wrapping the second end 162 of the flexible tensioning element 60 back around the first and second bone fragments 1, 2 to form the loop 67; (7) inserting the second end 162 of the flexible tensioning element 60 back into the first end 101 of the longitudinal passageway 104; (8) passing the second end 162 of the flexible tensioning element 60 through the tension chamber 113 such that the flexible tensioning element 60 is located between the tension chamber locking surface 114 and the taper bullet locking surface 402; (9) passing the second end 162 of the flexible tensioning element 60 back out of the second end 102 of the longitudinal passageway 104; and (10) applying the selected tension force 68 to the second end 162 of the flexible tensioning element 60, which will cause the tension locking mechanism 405 to automatically lock and maintain the selected tension force 68 to preload the bone fracture 3 in compression and resist tensile force imparted across the bone fracture 3, thereby maintaining fixation of the first bone fragment 1 relative to the second bone fragment 2.

In some embodiments, the finned anti-rotation bone anchor 430 may then be implanted to provide a secondary lock for the flexible tensioning element 60, as well as provide rotational stability/control of the first bone fragment 1 relative to the second bone fragment 2.

In some embodiments, the finned anti-rotation bone anchor 430 may include a body 431, a proximal end 432, a distal end 433, a transverse passageway 434, at least one anti-rotation fin 435, an impact surface 436, and at least one flexible tensioning element guide surface 437.

Figure 42:
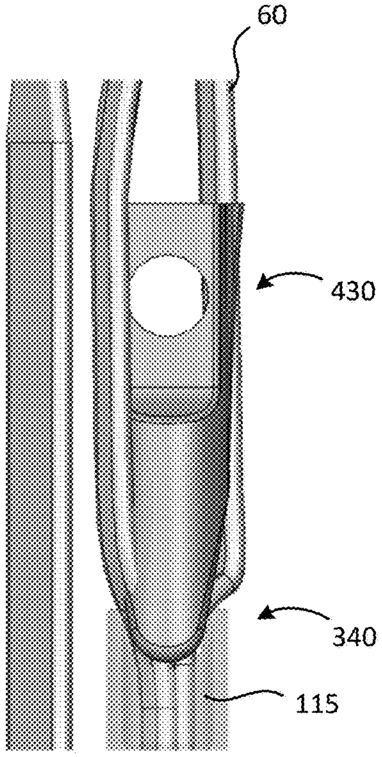
Figure 43:
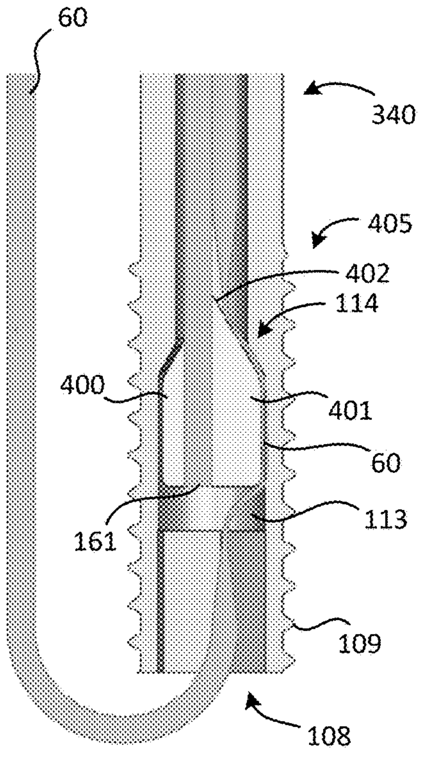

In some embodiments, the finned anti-rotation bone anchor 430 may be pressed or impacted into place via the impact surface 436 with the flexible tensioning element 60 in tension and/or engaging against the at least one flexible tensioning element guide surface 437 on either side of the finned anti-rotation bone anchor 430 (e.g., see FIGS. 41 and 42).

In some embodiments, the at least one anti-rotation fin 435 may be pressed into the walls of the prepared bone tunnel as the finned anti-rotation bone anchor 430 is pressed into place to provide additional rotational stability for the finned anti-rotation bone anchor 430 relative to the bone.

In some embodiments, the distal end 433 of the finned anti-rotation bone anchor 430 may be shaped to be received within the anchor reception chamber 115 of the elongate fixation member 340. In this manner, the distal end 433 of the finned anti-rotation bone anchor 430 that is coupled to the anchor reception chamber 115 may provide a secondary lock to maintain the selected tension force 68 by trapping the flexible tensioning element 60 therein, as well as provide additional rotational stability between the first and second bone fragments via the at least one anti-rotation fin 435.

In some embodiments, the finned anti-rotation bone anchor 430 may comprise any suitable material, including but not limited to: a resorbable material (such as PEEK, hydroxyapatite, etc.), and/or any other biocompatible material such as titanium, stainless steel, polymer, etc.

FIGS. 49-55 illustrate example devices and systems for a bone fixation assembly, according to another embodiment of the present disclosure. Specifically, FIGS. 49-51 show various views of the elongate fixation member 340 coupled to the finned anti-rotation bone anchor 430 with the transverse fastener 420 placed therethrough to provide additional rotational stability over the finned anti-rotation bone anchor 430 alone, and FIGS. 52-55 show various views of the modified bone fixation assembly implanted in a bone 10.

Accordingly, the modified bone fixation assembly shown in FIGS. 49-55 may operate in a similar fashion to the bone fixation assembly previously described herein with respect to FIGS. 39A-48, except for the additional inclusion of the transverse fastener 420 that is placed through the bone 10 and transverse passageway 434 of the finned anti-rotation bone anchor 430 to provide additional rotational stability for the finned anti-rotation bone anchor 430, and thus provide additional rotational stability/control of the first bone fragment 1 relative to the second bone fragment 2.

In some embodiments, a transverse bone tunnel 438 may be formed in the bone 10 to receive the transverse fastener 420 therein.

FIGS. 56-58 illustrate a ratcheting bone fixation assembly, according to another embodiment of the present disclosure. The ratcheting bone fixation assembly may include an elongate fixation member 350, a flexible tensioning element 60 that may be threaded through a longitudinal passageway of the elongate fixation member 350, and a rotating ratchet member 440.

In some embodiments, the rotating ratchet member 440 may be configured to: (1) couple with an end of the elongate fixation member 350 via a ratcheting mechanism (not shown); (2) couple with the flexible tensioning element 60; (3) receive a rotational force to rotate the rotating ratchet member 440 in a first or tensioning direction; and (4) wrap the flexible tensioning element 60 around the rotating ratchet member 440 as it is rotated to apply the selected tension force 68 to the flexible tensioning element 60.

In some embodiments, the ratcheting mechanism may be configured to lock and maintain the selected tension force 68 applied to the flexible tensioning element 60. For example, in at least some embodiments the ratcheting mechanism may include a plurality of ratcheting teeth (not shown) that intermesh with each other to form a one-way ratcheting mechanism that locks and maintains the selected tension force 68 that is applied to the flexible tensioning element 60. However, it will also be understood that the ratcheting mechanism may include any suitable ratcheting structure(s) that can form a one-way ratcheting mechanism capable of locking and maintaining a selected tension force 68 applied to the flexible tensioning element 60.

In some embodiments, a length of the rotating ratchet member 440 may also be extended such that the ends of the rotating ratchet member 440 may transversely extend through the bone 10 to provide additional rotational stability/control of the first bone fragment 1 relative to the second bone fragment 2. In this manner, the rotating ratchet member 440 may act as a pin or bone fastener that is oriented transversely with respect to the elongate fixation member 350 to provide additional rotational stability/control for the first and second bone fragments.

In some embodiments, the ratcheting bone fixation assembly of FIGS. 56-58 may be implanted within a bone 10 by performing one or more of the following steps: (1) drilling/reaming at least a portion of the intramedullary canals of the first bone fragment 1 and the second bone fragment 2; (2) inserting the elongate fixation member 350 into the prepared intramedullary canals to provisionally fix the first bone fragment 1 relative to the second bone fragment 2; (3) rotating (or pushing) the elongate fixation member 350 to thread the proximal helical thread 109 (or engage the plurality of anti-rotation fins, splines, etc.) into at least one of the prepared intramedullary canals (e.g., the elongate fixation member 350 may be placed into the first and second bone fragments from either a medial or lateral direction); (4) coupling the first end 161 of the flexible tensioning element 60 to the taper bullet 400 (or it may be pre-coupled); (5) threading the second end 162 of the flexible tensioning element 60 through the longitudinal passageway 104 (from the first end 101 to the second end 102) until the taper bullet 400 enters the tension chamber 113 (e.g., utilizing one or more retrieval wires 50, etc.); (6) wrapping the second end 162 of the flexible tensioning element 60 back around the first and second bone fragments to form the loop 67; (7) inserting the second end 162 of the flexible tensioning element 60 back into the first end 101 of the longitudinal passageway 104; (8) passing the second end 162 of the flexible tensioning element 60 through the tension chamber 113 such that the flexible tensioning element 60 is located between the tension chamber locking surface 114 and the taper bullet locking surface 402; (9) passing the second end 162 of the flexible tensioning element 60 back out of the second end 102 of the longitudinal passageway 104; (10) utilizing a bone cutting device (e.g., an awl, an oscillating bone saw, a drill, etc.) to cut a bone slot for the rotating ratchet member 440; (11) coupling the flexible tensioning element 60 to the rotating ratchet member 440; (12) sliding the rotating ratchet member 440 into the bone slot and the distal end of the elongate fixation member 350 to couple the rotating ratchet member 440 to the distal end of the elongate fixation member 350 with the ends of the rotating ratchet member 440 protruding through the bone transverse to the elongate fixation member 350; and (13) applying the selected tension force 68 to the second end 162 of the flexible tensioning element 60 via rotation of the rotating ratchet member 440, which will lock and maintain the selected tension force 68 via the ratcheting mechanism to preload the bone fracture 3 in compression and resist tensile force imparted across the bone fracture 3, thereby maintaining fixation of the first bone fragment 1 relative to the second bone fragment 2.

FIGS. 59A-70 illustrate example devices and systems for a bone fixation assembly, according to another embodiment of the present disclosure. Specifically, FIGS. 59A-59D show various views of an elongate fixation member 360; FIGS. 60A-60D show various views of an anti-rotation bone anchor 450; FIGS. 61-66 show various views of a bone fixation assembly utilizing the elongate fixation member 360, the anti-rotation bone anchor 450, and/or the transverse fastener 420; and FIGS. 67-70 show various views of the bone fixation assembly implanted in a bone 10.

In some embodiments, the elongate fixation member 360 may include a proximal end, first end, or first portion 101, a distal end, second end, or second portion 102, a central longitudinal axis 103, a longitudinal passageway 104, a torque connection feature 108, a proximal helical thread 109, and at least one anchor reception chamber, first anchor reception chamber, or anchor reception chamber 115 comprising a first transverse notch 111, a second transverse notch 112, and an anchor reception chamber chamfered edge 116.

In some embodiments, the elongate fixation member 360 may also include a second anchor reception chamber 119 comprising a third transverse notch 117 and a fourth transverse notch 118. In these embodiments, the second anchor reception chamber 119 may function similarly to the anchor reception chamber 115, and may likewise receive at least a portion of a bone anchor 410 therein to further trap the flexible tensioning element 60 (and/or compress the flexible tensioning element 60 against the bone tunnel wall) to provide a secondary (or tertiary) lock to maintain the selected tension force 68. In these embodiments, any style of bone anchor 410 may also be utilized with the second anchor reception chamber 119 (e.g., a threaded bone/suture anchor, a compression bone/suture anchor, an anti-rotation bone anchor, a finned anti-rotation bone anchor, a transverse fastener or bone screw, etc.). Moreover, the second anchor reception chamber 119 may also be adapted for use with an insertion tool (not shown) which may be shaped to interface with the second anchor reception chamber 119 to provide rotational torque to the elongate fixation member 360 to thread the proximal helical thread 109 of the elongate fixation member 360 into a bone 10. In this manner, the second anchor reception chamber 119 may also serve as a torque connection feature 108.

In some embodiments, the elongate fixation member 360 may also include at least a portion of the tension locking mechanism 405 (similar to previous embodiments) comprising a tension chamber 113, a tension chamber locking surface 114, and a taper bullet 400 disposable therein having a taper bullet body 401 and a taper bullet locking surface 402. Thus, the tension locking mechanism 405 for the embodiment shown in FIGS. 30A-38 may operate similarly to the tension locking mechanism 405 previously described herein.

In some embodiments, a bone fixation assembly may include the elongate fixation member 360, the flexible tensioning element 60, the tension locking mechanism 405 configured to lock and maintain a selected tension force 68 applied to the flexible tensioning element 60, and the anti-rotation bone anchor 450 that may be configured to provide a secondary lock to maintain the selected tension force 68 applied to the flexible tensioning element 60, and also provide rotational stability between the first and second bone fragments 1, 2.

In some embodiments, the first portion 101 of the elongate fixation member 360 may be couplable to the first bone fragment 1 of the bone 10, and the second portion 102 of the elongate fixation member 360 may be couplable to the second bone fragment 2 of the bone 10 to provide fixation of the second bone fragment 2 relative to the first bone fragment 1, as can be seen in FIGS. 67-70.

In some embodiments, the flexible tensioning element 60 may be configured to pass through the longitudinal passageway 104 formed through the elongate fixation member 360 and form the loop 67 spanning the bone fracture 3 and the first and second bone fragments 1, 2 to secure the elongate fixation member 360 to the bone 10, as previously described.

In some embodiments, the selected tension force 68 applied to the flexible tensioning element 60 may be locked and maintained by the tension locking mechanism 405 to preload the bone fracture 3 in compression to resist tensile force imparted across the bone fracture 3, thereby maintaining fixation of the first bone fragment 1 relative to the second bone fragment 2. In this manner, the flexible tensioning element 60 may provide additional fixation strength vs. the elongate fixation member 360 alone.

In some embodiments, the bone fixation assembly of FIGS. 59A-70 may generally be implanted within the bone 10 by performing one or more of the following steps: (1) drilling/reaming at least a portion of the intramedullary canals of the first bone fragment 1 and the second bone fragment 2; (2) inserting the elongate fixation member 360 into the prepared intramedullary canals to provisionally fix the first bone fragment 1 relative to the second bone fragment 2; (3) rotating (or pushing) the elongate fixation member 360 to thread the proximal helical thread 109 (or engage the plurality of anti-rotation fins, splines, etc.) into at least one of the prepared intramedullary canals (e.g., the elongate fixation member 360 may be placed into the first and second bone fragments from either a medial or lateral direction, etc.); (4) coupling the first end 161 of the flexible tensioning element 60 to the taper bullet 400 (or it may be pre-coupled); (5) threading the second end 162 of the flexible tensioning element 60 through the longitudinal passageway 104 (e.g., from the first end 101 to the second end 102, or vice versa) until the taper bullet 400 enters the tension chamber 113 (e.g., utilizing one or more retrieval wires 50, etc.); (6) wrapping the second end 162 of the flexible tensioning element 60 back around the first and second bone fragments 1, 2 to form the loop 67; (7) inserting the second end 162 of the flexible tensioning element 60 back into the first end 101 of the longitudinal passageway 104; (8) passing the second end 162 of the flexible tensioning element 60 through the tension chamber 113 such that the flexible tensioning element 60 is located between the tension chamber locking surface 114 and the taper bullet locking surface 402; (9) passing the second end 162 of the flexible tensioning element 60 back out of the second end 102 of the longitudinal passageway 104; and (10) applying the selected tension force 68 to the second end 162 of the flexible tensioning element 60, which will cause the tension locking mechanism 405 to automatically lock and maintain the selected tension force 68 to preload the bone fracture 3 in compression and resist tensile force imparted across the bone fracture 3, thereby maintaining fixation of the first bone fragment 1 relative to the second bone fragment 2.

In some embodiments, the anti-rotation bone anchor 450 may then be implanted to provide a secondary lock for the flexible tensioning element 60, as well as provide rotational stability/control of the first bone fragment 1 relative to the second bone fragment 2.

In some embodiments, the anti-rotation bone anchor 450 may include an anchor body 451, an anchor proximal end 452, an anchor distal end 453, an anchor transverse passageway 454, an anchor impact surface 456, and at least one anchor flexible tensioning element guide surface 457.

In some embodiments, the anti-rotation bone anchor 450 may be pressed or impacted into place via the anchor impact surface 456 with the flexible tensioning element 60 in tension and/or engaging against the at least one anchor flexible tensioning element guide surface 457 on either side of the anti-rotation bone anchor 450 (e.g., see FIGS. 61 and 62).

In some embodiments, the anchor distal end 453 may be shaped to be received within the anchor reception chamber 115 (and/or the second anchor reception chamber 119) of the elongate fixation member 360. In this manner, the anchor distal end 453 that is coupled to the anchor reception chamber 115 (and/or the second anchor reception chamber 119) may provide a secondary (or tertiary) lock to maintain the selected tension force 68 by trapping the flexible tensioning element 60 therein, as well as provide additional rotational stability between the first and second bone fragments 1, 2.

In some embodiments, the anti-rotation bone anchor 450 may comprise any suitable material, including but not limited to: a resorbable material (such as PEEK, hydroxyapatite, etc.), and/or any other biocompatible material such as titanium, stainless steel, polymer, etc.

In some embodiments, the anti-rotation bone anchor 450 may also include a transverse fastener 420 placed through the anchor transverse passageway 454 (e.g., see FIGS. 62 and 64-70) to provide additional rotational stability for the anti-rotation bone anchor 450, and thus provide additional rotational stability/control of the first bone fragment 1 relative to the second bone fragment 2.

FIGS. 71A-83 illustrate example devices and systems for a bone fixation assembly, according to another embodiment of the present disclosure. Specifically, FIGS. 71A-71D show various views of an elongate fixation member 370; FIGS. 72A-72D show various views of a first button or first cortical fixation element 460; FIGS. 73A-73D show various views of a second button or second cortical fixation element 470; FIGS. 74-79 show various views of a bone fixation assembly utilizing the elongate fixation member 370, the first cortical fixation element 460, and the second cortical fixation element 470; and FIGS. 80-83 show various views of the bone fixation assembly implanted in a bone 10.

In some embodiments, the elongate fixation member 370 may include a proximal end, first end, or first portion 101, a distal end, second end, or second portion 102, a central longitudinal axis 103, a longitudinal passageway 104, a torque connection feature 108, a proximal helical thread 109, an angled surface 371, an impact surface 373, and a fixation element dock 372 formed on the distal or second portion 102 of the elongate fixation member 370.

In some embodiments, the first cortical fixation element 460 may include a first bone-facing side 467, a first reverse side 464, as well as a first hole 461, a second hole 462, and a third hole 463 formed through the first cortical fixation element 460 between the first bone-facing side 467 and the first reverse side 464 which may be configured to receive the flexible tensioning element 60 therethrough, as will be discussed in more detail below.

In some embodiments, the first bone-facing side 467 of the first cortical fixation element 460 may comprise a concave shape that may conform to a first cortical surface 481 on the first bone fragment 1.

In some embodiments, the second cortical fixation element 470 may include a second bone-facing side 477, a second reverse side 474, as well as a first passageway 471 and a second passageway 472 formed through the second cortical fixation element 470 between the second bone-facing side 477 and the second reverse side 474 which may be configured to receive the flexible tensioning element 60 therethrough, as will be discussed in more detail below.

In some embodiments, the second bone-facing side 477 of the second cortical fixation element 470 may comprise a concave shape that may conform to a second cortical surface 482 on the second bone fragment 2.

In some embodiments, the second cortical fixation element 470 may also include a channel 475 formed thereon (intermediate the first passageway 471 and the second passageway 472) which may be shaped to receive a portion of the flexible tensioning element 60 therein.

In some embodiments, the second cortical fixation element 470 may also include a docking surface 476 that may be shaped for reception on the fixation element dock 372 on the distal end of the elongate fixation member 370 (e.g., see FIGS. 85-88).

In some embodiments, the docking surface 476 on the second cortical fixation element 470 may comprise a convex shape that may conform to a concave surface 374 formed on the fixation element dock 372, as shown in FIGS. 85-88. However, it will be understood that the docking surface 476 and/or the fixation element dock 372 may comprise any surface shape(s) which may (or may not) conform to each other in order to place the second cortical fixation element 470 on the fixation element dock 372. In this manner, the second cortical fixation element 470 may be initially placed on the fixation element dock 372 to facilitate insertion of the second cortical fixation element 470 through the bone tunnels formed in the bone 10, whereupon the second cortical fixation element 470 may be separated from the fixation element dock 372 (after exiting from the bone tunnels) in order to engage the second cortical surface 482 of the second bone fragment 2, as shown in FIGS. 80-83 and 90-93.

In some embodiments, a bone fixation assembly may include the elongate fixation member 370, the first cortical fixation element 460, the second cortical fixation element 470, and the flexible tensioning element 60.

In some embodiments, the proximal portion of the elongate fixation member 370 may rotatably couple within the first bone fragment 1 of the bone 10, and the distal portion of the elongate fixation member 370 may couple within the second bone fragment 2 of the bone 10 to provide fixation of the second bone fragment 2 relative to the first bone fragment 1.

In some embodiments, the proximal portion of the elongate fixation member 370 may include the proximal helical thread 109 that may rotatably couple the proximal portion of the elongate fixation member 370 within the first bone fragment 1 during rotation.

In some embodiments, the distal portion of the elongate fixation member 370 may include a distal helical thread (not shown) that may rotatably couple the distal portion of the elongate fixation member 370 within the second bone fragment 2 during rotation.

In some embodiments, the torque connection feature 108 may be configured to receive a torque force to rotatably couple the elongate fixation member 370 within the first bone fragment 1.

In some embodiments, the first cortical fixation element 460 may be configured to engage the first cortical surface 481 on the first bone fragment 1 adjacent the proximal portion of the elongate fixation member 370, and the second cortical fixation element 470 may be configured to engage the second cortical surface 482 on the second bone fragment 2 adjacent the distal portion of the elongate fixation member 370.

In some embodiments, the flexible tensioning element 60 may be configured to pass through the longitudinal passageway 104 of the elongate fixation member 370 and couple intermediate the first and second cortical fixation elements 460, 470 to provide a compression force therebetween. The flexible tensioning element 60 passing through the longitudinal passageway 104 of the elongate fixation member 370 may span a bone fracture 3 intermediate the first and second bone fragments 1, 2. The flexible tensioning element 60 coupled intermediate the first and second cortical fixation elements 460, 470 may also be configured to preload the bone fracture 3 in compression to resist tensile force imparted across the bone fracture 3, thereby maintaining fixation of the first bone fragment relative to the second bone fragment.

In some embodiments, the flexible tensioning element 60 passing through the holes of the first cortical fixation element 460 may be configured to form a tension locking mechanism 405 that locks and maintains a selected tension force 68 applied to the flexible tensioning element 60. In this manner, the selected tension force 68 applied to the flexible tensioning element 60 may be locked and maintained by the tension locking mechanism 405 to preload the bone fracture 3 in compression to resist tensile force imparted across the bone fracture 3, thereby maintaining fixation of the first bone fragment 1 relative to the second bone fragment 2. In this manner, the flexible tensioning element 60 may provide additional fixation strength vs. the elongate fixation member 360 alone.

In some embodiments, the bone fixation assembly of FIGS. 59A-83 may generally be implanted within the bone 10 by performing one or more of the following steps: (1) drilling/reaming at least a portion of the intramedullary canals of the first bone fragment 1 and the second bone fragment 2; (2) inserting the elongate fixation member 370 into the prepared intramedullary canals to provisionally fix the first bone fragment 1 relative to the second bone fragment 2; (3) rotating the elongate fixation member 370 to thread the proximal helical thread 109 into at least one of the prepared intramedullary canals (e.g., the elongate fixation member 370 may be placed into the first and second bone fragments 1, 2 from either a medial or lateral direction, etc.); (4) deploying the second cortical fixation element 470 from the fixation element dock 372 to engage the second cortical surface 482 on the second bone fragment (note: the flexible tensioning element 60 may be pre-inserted through the passageways of second cortical fixation element 470 and through the longitudinal passageway 104 before the elongate fixation member 370 is inserted through the bone tunnels); (5) tying the flexible tensioning element 60 to the first cortical fixation element 460 (as will be discussed in more detail below) and engaging the first cortical fixation element 460 with the first cortical surface 481 on the second bone fragment 2; and (6) applying the selected tension force 68 to the flexible tensioning element 60, which will cause the tension locking mechanism 405 of the first cortical fixation element 460 to automatically lock and maintain the selected tension force 68 to preload the bone fracture 3 in compression and resist tensile force imparted across the bone fracture 3, thereby maintaining fixation of the first bone fragment 1 relative to the second bone fragment 2.

In some embodiments, the flexible tensioning element 60 may be assembled to the bone fixation assembly by performing one or more of the following steps: (1) passing the first end 161 of the flexible tensioning element 60 through the third hole 463 of the first cortical fixation element 460, into the proximal end of the longitudinal passageway 104, and out of the distal end of the longitudinal passageway 104; (2) passing the first end 161 of the flexible tensioning element 60 through the first passageway 471 of the second cortical fixation element 470, into the channel 475, and back through the second passageway 472 of the second cortical fixation element 470; (3) passing the first end 161 of the flexible tensioning element 60 back through the distal end of the longitudinal passageway 104, out of the proximal end of the longitudinal passageway 104, and through the first hole 461 of the first cortical fixation element 460; (4) passing the first end 161 of the flexible tensioning element 60 back through the second hole 462 of the first cortical fixation element 460, around the flexible tensioning element 60 (e.g., see FIG. 78), back through the second hole 462 of the first cortical fixation element 460, over the ends of the flexible tensioning element 60 (e.g., see FIG. 77), and then back through the first hole 461 of the first cortical fixation element 460; (5) passing the first end 161 of the flexible tensioning element 60 back through the proximal end of the longitudinal passageway 104, out of the distal end of the longitudinal passageway 104, through the second passageway 472 of the second cortical fixation element 470, into the channel 475, and back through the first passageway 471 of the second cortical fixation element 470; (6) passing the first end 161 of the flexible tensioning element 60 back through the distal end of the longitudinal passageway 104, out of the proximal end of the longitudinal passageway 104, and through the third hole 463 of the first cortical fixation element 460, such that the first end 161 of the flexible tensioning element 60 and the second end 162 of the flexible tensioning element 60 are trapped by the portions of the flexible tensioning element 60 that loop between the first hole 461 and the second hole 462 of the first cortical fixation element 460 (e.g., see FIG. 77).

FIGS. 84A-93 illustrate example devices and systems for a bone fixation assembly, according to another embodiment of the present disclosure. Specifically, FIGS. 84A-84F show various views of an elongate fixation member 380; FIGS. 85-88 show various views of the second cortical fixation element 470 docking to the fixation element dock 372; FIG. 89 shows a bone fixation assembly utilizing the elongate fixation member 380, the first cortical fixation element 460, and the second cortical fixation element 470; and FIGS. 90-93 show various views of the bone fixation assembly implanted in a bone 10.

The bone fixation assembly shown in FIGS. 84A-93 may include similar features/functions to the bone fixation assembly shown in FIGS. 71A-83, except the elongate fixation member 380 may include one or more anti-rotation features 383 in place of the proximal helical thread 109 (and/or a distal helical thread, if any).

In some embodiments, the one or more anti-rotation features 383 may comprise one or more splines, ribs, grooves, channels, protrusions, etc., which may be shaped or otherwise configured to resist rotational movement of the elongate fixation member 380 within the bone 10. In this manner, the one or more anti-rotation features 383 may be configured to translatably couple within the first bone fragment 1 and/or the second bone fragment 2 to resist/prevent rotational movement between the first bone fragment 1 and the second bone fragment 2 and provide additional rotational fixation of the first bone fragment 1 relative to the second bone fragment 2.

In some embodiments, the proximal portion of the elongate fixation member 380 may include one or more proximal anti-rotation features configured to translatably couple the proximal portion of the elongate fixation member 380 within the first bone fragment 1 to provide rotational fixation of the first bone fragment 1 relative to the second bone fragment 2.

In some embodiments, the distal portion of the elongate fixation member 380 comprises one or more distal anti-rotation features configured to translatably couple the distal portion of the elongate fixation member 380 within the second bone fragment 2 to provide rotational fixation of the second bone fragment 2 relative to the first bone fragment 1.

In some embodiments, the impact surface 373 may be configured to receive an impact force from a driver tool (not shown) to translatably couple the elongate fixation member 380 within the bone 10.

In some embodiments, the angled surface 371 may be formed with any angle (e.g., 45 degrees, 30 degrees, 60 degrees, etc.) to prevent unwanted protrusion of the proximal end (and/or the distal end) of the elongate fixation member 380 from the bone 10.

Any procedures or methods disclosed herein may comprise one or more steps or actions for performing the described procedures or methods. The method steps and/or actions may be interchanged with one another. In other words, unless a specific order of steps or actions is required for proper operation of the embodiment, the order and/or use of specific steps and/or actions may be modified.

Reference throughout this specification to "an embodiment" or "the embodiment" means that a particular feature, structure, or characteristic described in connection with that embodiment is included in at least one embodiment. Thus, the quoted phrases, or variations thereof, as recited throughout this specification are not necessarily all referring to the same embodiment.

Similarly, it should be appreciated that in the above description of embodiments, various features are sometimes grouped together in a single embodiment, drawing, or description thereof for the purpose of streamlining the present disclosure. This method of disclosure, however, is not to be interpreted as reflecting an intention that any embodiment requires more features than those expressly recited in that embodiment. Rather, inventive aspects lie in a combination of fewer than all features of any single embodiment disclosed herein.

Recitation of the term "first" with respect to a feature or element does not necessarily imply the existence of a second or additional such feature or element. Elements recited in means-plus-function format are intended to be construed in accordance with 35 U.S.C. § 112(f). It will be apparent to those having skill in the art that changes may be made to the details of the above-described embodiments without departing from the underlying principles set forth herein.

The phrases "connected to," "coupled to," and "in communication with" refer to any form of interaction between two or more entities, including mechanical, electrical, magnetic, electromagnetic, fluid, and thermal interaction. The phrase "fluid communication" refers to two or more features that are connected such that a fluid within one feature is able to pass into another feature. Moreover, as defined herein the term "substantially" means within +/−20% of a target value, measurement, or desired characteristic.

While specific embodiments and applications of the present disclosure have been illustrated and described herein, it is to be understood that the scope of this disclosure is not limited to the precise configuration and components disclosed herein. Various modifications, changes, and variations which will be apparent to those skilled in the art may be made in the arrangement, operation, and details of the devices, systems, and methods disclosed herein.

What is claimed is:

1. A bone fixation assembly comprising:

an elongate fixation member comprising:

a longitudinal passageway formed through the elongate fixation member;

a proximal portion configured to rotatably couple within a first bone fragment of a bone; and a distal portion configured to couple within a second bone fragment of the bone to provide fixation of the second bone fragment relative to the first bone fragment;

a first cortical fixation element configured to engage a first cortical surface on the first bone fragment adjacent the proximal portion of the elongate fixation member;

a second cortical fixation element configured to engage a second cortical surface on the second bone fragment adjacent the distal portion of the elongate fixation member; and a flexible tensioning element configured to pass through the longitudinal passageway of the elongate fixation member and couple intermediate the first and second cortical fixation elements to provide a compression force therebetween, wherein:

the flexible tensioning element passing through the longitudinal passageway of the elongate fixation member spans a bone fracture intermediate the first and second bone fragments; and the flexible tensioning element coupled intermediate the first and second cortical fixation elements is configured to preload the bone fracture in compression to resist tensile force imparted across the bone fracture, thereby maintaining fixation of the first bone fragment relative to the second bone fragment.

2. The bone fixation assembly of claim 1, wherein the proximal portion of the elongate fixation member comprises a proximal helical thread that rotatably couples the proximal portion of the elongate fixation member within the first bone fragment.

3. The bone fixation assembly of claim 2, wherein the proximal portion of the elongate fixation member comprises a torque connection feature configured to receive a torque force to rotatably couple the proximal portion of the elongate fixation member within the first bone fragment.

4. The bone fixation assembly of claim 1, wherein the first cortical fixation element comprises:

a first bone-facing side;

a first reverse side opposite the first bone-facing side;

a first hole formed through the first cortical fixation element between the first bone-facing side and the first reverse side configured to receive the flexible tensioning element therethrough;

a second hole formed through the first cortical fixation element between the first bone-facing side and the first reverse side configured to receive the flexible tensioning element therethrough; and a third hole formed through the first cortical fixation element between the first bone-facing side and the first reverse side configured to receive the flexible tensioning element therethrough.

5. The bone fixation assembly of claim 1, wherein the second cortical fixation element comprises:
- a second bone-facing side;
- a second reverse side opposite the second bone-facing side;
- a first passageway formed through the second cortical fixation element between the second bone-facing side and the second reverse side configured to receive the flexible tensioning element therethrough; and
- a second passageway formed through the second cortical fixation element between the second bone-facing side and the second reverse side configured to receive the flexible tensioning element therethrough.

6. The bone fixation assembly of claim 5, wherein the second cortical fixation element comprises a channel formed thereon intermediate the first passageway and the second passageway that is configured to receive the flexible tensioning element therein.

7. The bone fixation assembly of claim 5, wherein:
- the elongate fixation member comprises a fixation element dock formed on the distal portion of the elongate fixation member; and
- the second cortical fixation element comprises a docking surface shaped to be received on the fixation element dock.

8. A bone fixation assembly comprising:
- an elongate fixation member comprising:
  - a longitudinal passageway formed through the elongate fixation member;
  - a proximal portion configured to translatably couple within a first bone fragment of a bone; and
  - a distal portion configured to couple within a second bone fragment of the bone to provide fixation of the second bone fragment relative to the first bone fragment;
- a first cortical fixation element configured to engage a first cortical surface on the first bone fragment adjacent the proximal portion of the elongate fixation member;
- a second cortical fixation element configured to engage a second cortical surface on the second bone fragment adjacent the distal portion of the elongate fixation member; and
- a flexible tensioning element configured to pass through the longitudinal passageway of the elongate fixation member and couple intermediate the first and second cortical fixation elements to provide a compression force therebetween, wherein:
- the flexible tensioning element passing through the longitudinal passageway of the elongate fixation member spans a bone fracture intermediate the first and second bone fragments; and
- the flexible tensioning element coupled intermediate the first and second cortical fixation elements is configured to preload the bone fracture in compression to resist tensile force imparted across the bone fracture, thereby maintaining fixation of the first bone fragment relative to the second bone fragment.

9. The bone fixation assembly of claim 8, wherein the proximal portion of the elongate fixation member comprises one or more proximal anti-rotation features configured to translatably couple the proximal portion of the elongate fixation member within the first bone fragment to provide rotational fixation of the first bone fragment relative to the second bone fragment.

10. The bone fixation assembly of claim 8, wherein the proximal portion of the elongate fixation member comprises an impact surface configured to receive an impact force to translatably couple the elongate fixation member within the bone.

11. The bone fixation assembly of claim 8, wherein the distal portion of the elongate fixation member comprises one or more distal anti-rotation features configured to translatably couple the distal portion of the elongate fixation member within the second bone fragment to provide rotational fixation of the second bone fragment relative to the first bone fragment.

12. The bone fixation assembly of claim 8, wherein the first cortical fixation element comprises:
- a first bone-facing side;
- a first reverse side opposite the first bone-facing side;
- a first hole formed through the first cortical fixation element between the first bone-facing side and the first reverse side configured to receive the flexible tensioning element therethrough;
- a second hole formed through the first cortical fixation element between the first bone-facing side and the first reverse side configured to receive the flexible tensioning element therethrough; and
- a third hole formed through the first cortical fixation element between the first bone-facing side and the first reverse side configured to receive the flexible tensioning element therethrough.

13. The bone fixation assembly of claim 8, wherein the second cortical fixation element comprises:
- a second bone-facing side;
- a second reverse side opposite the second bone-facing side;
- a first passageway formed through the second cortical fixation element between the second bone-facing side and the second reverse side configured to receive the flexible tensioning element therethrough; and
- a second passageway formed through the second cortical fixation element between the second bone-facing side and the second reverse side configured to receive the flexible tensioning element therethrough.

14. The bone fixation assembly of claim 13, wherein:
- the elongate fixation member comprises a fixation element dock formed on the distal portion of the elongate fixation member; and
- the second cortical fixation element comprises a docking surface shaped to be received on the fixation element dock.

15. A bone fixation assembly comprising:
- an elongate fixation member comprising:
  - a longitudinal passageway formed through the elongate fixation member;
  - a proximal portion couplable to a first bone fragment of a bone; and
  - a distal portion couplable to a second bone fragment of the bone to provide fixation of the second bone fragment relative to the first bone fragment;
- a flexible tensioning element configured to pass through the longitudinal passageway and form a loop that spans the first and second bone fragments to secure the elongate fixation member to the bone; and
- a tension locking mechanism configured to lock and maintain a selected tension force applied to the flexible tensioning element, the tension locking mechanism comprising:
  - a tension chamber formed within the elongate fixation member;
  - a tension chamber locking surface positioned within the tension chamber;

a taper bullet receivable within the tension chamber; and a taper bullet locking surface shaped to engage the tension chamber locking surface;

wherein:

the loop spanning the first and second bone fragments spans a bone fracture intermediate the first and second bone fragments;

the selected tension force applied to the flexible tensioning element is locked and maintained by the tension locking mechanism to preload the bone fracture in compression to resist tensile force imparted across the bone fracture, thereby maintaining fixation of the first bone fragment relative to the second bone fragment;

a first end of the flexible tensioning element is configured to couple with the taper bullet; and a second end of the flexible tensioning element is configured to:

exit the longitudinal passageway at a distal end of the elongate fixation member;

wrap back around the first and second bone fragments to form the loop spanning the first and second bone fragments;

enter back into the longitudinal passageway at a proximal end of the elongate fixation member;

pass through the tension chamber formed within the elongate fixation member such that the flexible tensioning element becomes trapped between the tension chamber locking surface and the taper bullet locking surface; and exit the longitudinal passageway at the distal end of the elongate fixation member.

16. The bone fixation assembly of claim 15, wherein:

the second end of the flexible tensioning element is configured to receive the selected tension force;

the first end of the flexible tensioning element is configured to pull the taper bullet within the tension chamber toward the second end of the elongate fixation member in response to the selected tension force applied to the second end of the flexible tensioning element; and the taper bullet locking surface is configured to compress the flexible tensioning element against the tension chamber locking surface to lock and maintain the selected tension force applied to the flexible tensioning element.

17. The bone fixation assembly of claim 15, wherein the tension chamber is formed within at least one of:

the proximal portion of the elongate fixation member;

the distal portion of the elongate fixation member; and an intermediate portion of the elongate fixation member.

18. The bone fixation assembly of claim 15, wherein:

the elongate fixation member further comprises at least one anchor reception chamber configured to receive at least a portion of a bone anchor therein to provide a secondary lock that maintains the selected tension force applied to the flexible tensioning element, wherein the bone anchor comprises at least one of:

a threaded bone anchor;

a compression bone anchor;

an anti-rotation bone anchor;

a finned anti-rotation bone anchor; and a transverse fastener.

19. The bone fixation assembly of claim 18, wherein the at least one anchor reception chamber is formed within at least one of:

the proximal portion of the elongate fixation member; and the distal portion of the elongate fixation member.

* * * * *